United States Patent
Hoveyda et al.

(10) Patent No.: US 9,446,394 B2
(45) Date of Patent: Sep. 20, 2016

(54) Z-SELECTIVE RING-CLOSING METATHESIS REACTIONS

(71) Applicants: Massachusetts Institute of Technology, Cambridge, MA (US); Trustees of Boston College, Chestnut Hill, MA (US)

(72) Inventors: Amir H. Hoveyda, Lincoln, MA (US); Miao Yu, West Roxbury, MA (US); Chenbo Wang, Chestnut Hill, MA (US); Richard R. Schrock, Winchester, MA (US)

(73) Assignees: Trustees of Boston College, Chestnut Hill, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/641,293

(22) Filed: Mar. 6, 2015

(65) Prior Publication Data
US 2015/0246348 A1   Sep. 3, 2015

Related U.S. Application Data

(62) Division of application No. 13/487,067, filed on Jun. 1, 2012, now Pat. No. 9,073,801.

(60) Provisional application No. 61/492,996, filed on Jun. 3, 2011, provisional application No. 61/598,307, filed on Feb. 13, 2012.

(51) Int. Cl.
*B01J 31/22*     (2006.01)
*C07F 11/00*    (2006.01)
*C07D 417/06*  (2006.01)

*C07D 313/00*  (2006.01)
*C07D 225/02*  (2006.01)
(Continued)

(52) U.S. Cl.
CPC ......... *B01J 31/2295* (2013.01); *B01J 31/2208* (2013.01); *C07B 37/10* (2013.01); *C07D 225/02* (2013.01); *C07D 245/02* (2013.01); *C07D 267/00* (2013.01); *C07D 313/00* (2013.01); *C07D 417/06* (2013.01); *C07D 491/18* (2013.01); *C07D 491/22* (2013.01); *C07F 11/00* (2013.01); *B01J 2231/543* (2013.01); *B01J 2531/64* (2013.01); *B01J 2531/66* (2013.01)

(58) Field of Classification Search
CPC .. C07F 11/00; B01J 31/2295; B01J 31/2208; C07D 417/06; C07D 313/00; C07D 491/22; C07D 245/02; C07D 225/02; C07B 37/10
USPC ............... 502/155; 548/402; 556/10, 12, 58; 585/5, 646
See application file for complete search history.

(56) References Cited

U.S. PATENT DOCUMENTS 5,055,628 A   10/1991   Lin et al.
5,889,128 A    3/1999   Schrock et al.
(Continued)

OTHER PUBLICATIONS

Ackermann, L. et al., Ruthenium carbene complexes with imidazols-ylidene ligands; syntheses of conduritol derivatives reveals superior RCM activity. Tetrahedron 56:2195-2202 (2000).
(Continued)

*Primary Examiner* — Porfirio Nazario Gonzalez
(74) *Attorney, Agent, or Firm* — Stoel Rives LLP

(57) ABSTRACT

The present invention relates generally to olefin metathesis. In some embodiments, the present invention provides methods for Z-selective ring-closing metathesis.

28 Claims, 7 Drawing Sheets

(51) Int. Cl.
  C07B 37/10    (2006.01)
  C07D 245/02   (2006.01)
  C07D 267/00   (2006.01)
  C07D 491/18   (2006.01)
  C07D 491/22   (2006.01)

(56) References Cited

U.S. PATENT DOCUMENTS

| | | | |
|---|---|---|---|
| 6,121,473 | A | 9/2000 | Schrock et al. |
| 6,271,325 | B1 | 8/2001 | McConville et al. |
| 6,306,988 | B1 | 10/2001 | Grubbs et al. |
| 6,316,555 | B1 | 11/2001 | Schrock et al. |
| 6,346,652 | B1 | 2/2002 | Schrock et al. |
| 6,414,097 | B1 | 7/2002 | Grubbs et al. |
| 6,610,806 | B2 | 8/2003 | Schrock et al. |
| 6,855,839 | B2 | 2/2005 | McConville et al. |
| 7,135,544 | B2 | 11/2006 | Schrock et al. |
| 7,932,397 | B2 | 4/2011 | Hock et al. |
| 8,222,469 | B2 | 7/2012 | Schrock et al. |
| 8,350,073 | B2 | 1/2013 | Hock et al. |
| 8,362,311 | B2 | 1/2013 | Schrock et al. |
| 8,546,500 | B2 | 10/2013 | Hoveyda et al. |
| 8,598,400 | B2 | 12/2013 | Hoveyda et al. |
| 8,829,219 | B2 | 9/2014 | Hock et al. |
| 9,073,801 | B2 | 7/2015 | Hoveyda et al. |
| 9,079,173 | B2 | 7/2015 | Schrock et al. |
| 9,085,595 | B2 | 7/2015 | Schrock et al. |
| 9,206,211 | B2 | 12/2015 | Schrock et al. |
| 9,242,240 | B2 | 1/2016 | Hock et al. |
| 2008/0119678 | A1 | 5/2008 | Hock et al. |
| 2011/0015430 | A1 | 1/2011 | Schrock et al. |
| 2011/0065915 | A1 | 3/2011 | Malcolmson et al. |
| 2011/0077421 | A1 | 3/2011 | Schrock et al. |
| 2011/0237815 | A1 | 9/2011 | Hock et al. |
| 2011/0245477 | A1 | 10/2011 | Hoveyda et al. |
| 2012/0323000 | A1 | 12/2012 | Hoveyda et al. |
| 2013/0116434 | A1 | 5/2013 | Schrock et al. |
| 2013/0274482 | A1 | 10/2013 | Schrock et al. |
| 2013/0281706 | A1 | 10/2013 | Hock et al. |
| 2014/0309388 | A1 | 10/2014 | Schrock et al. |
| 2014/0316088 | A1 | 10/2014 | Schrock et al. |
| 2014/0330018 | A1 | 11/2014 | Czirok et al. |
| 2014/0378637 | A1 | 12/2014 | Schrock et al. |
| 2015/0065723 | A1 | 3/2015 | Hock et al. |
| 2015/0240008 | A1 | 8/2015 | Schrock et al. |

OTHER PUBLICATIONS

Aeilts et al., A readily available and user-friendly chiral catalyst for efficient enantioselective olefin metathesis. Angew Chem Int Ed. 40(8):1452-6 (2001).

Agbossou et al., Synthesis and reactivity of chiral rhenium alcohol complexes of the formula [(μ5-C$_5$H$_5$)Re(NO)(PPh$_3$)(ROH)] ⊕ BF4⊖. Chem Berichte.123(6):1293-9 (1990).

Al Obaidi, N. et al., Steric and Electronic Effects on the Chemistry of Molybdenum Octahedral Co-ordinated by Six Nitrogen Atoms. The Molecular Structure of [Mo{HB(3,5-Me2C3N2H)3)(NO)(pyrrollide)2]. J. Chem. Soc., Chem. Commun. 690-692 (1984).

Altmann, K. H. et al., The chemistry and biology of epothilones—The wheel keeps turning. ChemMedChem. 2:396-423 (2007).

Anderson et al., Kinetic selectivity of olefin metathesis catalysts bearing cyclic (alkyl)(amino)carbenes. Organometallics 27(4):563-6 (2008).

Arisawa, M. et al., Selective isomerization of a terminal olefin catalyzed by a ruthenium complex: the synthesis of indoles through ring-closing metathesis. Angew. Chem. Int. Ed. 41:4732-4734 (2002).

Ascenso et al., Synthesis and characterization of [W(NC4Me4)2Cl2] and [W(NC4Me4)2(CH3)2], the first azametallocene tungsten complexes with pyrrolyl ligands. Electronic structure and bonding of tungsten bispyrrolyl complexes. Inorg Chem Acta. 356:249-58 (2003).

Bailey et al., Evaluation of molybdenum and tungsten metathesis catalysts for homogeneous tandem alkane metathesis. Organometallics 28(1):355-60 (2009).

Balog, A., et al., A novel aldol condensation with 2-methyl-4-pentenal and Its application to an Improved total synthesis of epothilone B**. Angew. Chem., Int. Ed. 37:2675-2678 (1998).

Barluenga et al., Zirconium-mediated coupling reactions of amines and enol or allyl ethers: Synthesis of allyl-and homoallylamines. Chemistry—A European Journal 10(1):109-116 (Abstract) (2004).

Barrett, A.G.M. et al., Tandem ireland-claisen rearrangement ring-closing alkene metathesis in the construction of bicyclic β-lactam carboxylic esters. J. Org. Chem. 65:3716-3721 (2000).

Bazan et al., Living ring-opening metathesis polymerization of 2,3-difunctionalized 7-oxanorbornenes and 7-oxanorbornadienes by Mo(CHCMe$_2$R)(N-2,6-C$_6$H$_3$-iso-Pr$_2$)(O-tert-Bu)$_2$ and Mo(CHCMe$_2$R)(N-2,6-C$_6$H$_3$-iso-Pr$_2$)(OCMe$_2$CF$_3$)$_2$. J Am Chem Soc. 113(18):6899-907 (1991).

Bei et al., Highly efficient olefin-metathesis catalysts. Pharm Technol. 2008:s18.

Blackwell et al., New approaches to olefin cross-metathesis. J Am Chem Soc. 122:58-71 (2000).

Blackwell, J. et al., Enediynes via sequential acetylide reductive coupling and alkyne metathesis: Easy access to well-defined molybdenum initiators for alkyne metathesis. Organometallics 22:3351-3353 (2003).

Blanc, F. et al., Dramatic improvements of well-defined silica supported Mo-based olefin metathesis catalysts by tuning the N-containing ligands. J. Am. Chem. Soc.129(27):8434-8435 (2007).

Blanc, F. et al., Highly active, stable, and selective well defined silica supported Mo imido olefin metathesis catalysts. J. Am. Chem. Soc. 129(17):1044-1045 (2007).

Blanc, F. et al., Surface versus molecular siloxy ligands in well-defined olefin metathesis catalysis: [{(RO)$_3$SiO}Mo(=NAr)(=CH$_t$Bu)(CH$_2$tBu)]. Angew. Chem. Int. Ed. 45:1216-1220 (2006).

Borer, B.C. et al., The first synthesis of the ABCD ring system of manzamine A. Construction of the macrocyclic ring D, Tetrahedron Letters 35 (19):3191-3194 (1994).

Bornand et al., Mechanism-based design of a ROMP catalyst for sequence-selective copolymerization. Angew Chem Int Ed. 44(48):7909-11 (2005).

Bourgeois, D. et al., Synthesis of BC ring-systems of taxol by ring-closing metathesis, Synthesis 869-882 (2000).

Bourgeois, D. et al., Synthesis of highly functionalized cyclooctenes by ring-closing metathesis: unexpected formation of a trans isomer. Angew. Chem. Int. Ed. 39 (4):726-728 (2000).

Brunner et al., Catalytic hydrosilylation or hydrogenation at one coordination site of Cp'Fe(CO)(X)] fragments. Angew Chem Intl Ed. 29(10):1131-2 (1990).

Brunner et al., Optisch aktive Übergangsmetall-Komplexe, LI: P-Liganden als optisch aktive Hilfsstoffe in den Komplexen C$_5$H$_5$M(CO)(NO)L, M=Cr, Mo, W. Chem Ber. 11:673-91.—Abstract only (1978).

Brunner, Optical activity at an asymmetrical manganese atom. Angew. Chem. Int Ed. 8:382-3 (1969).

Brunner, Optically active organometallic compounds of transition elements with chiral metal atoms. Angew Chem Intl Ed. 38(9):1194-1208 (1999).

Brunner, Stability of the metal configuration in chiral-at-metal half-sandwich compounds. Eur J Inorg Chem. 905-12 (2001).

Burdett et al., Renewable monomer feedstocks via olefin metathesis: fundamental mechanistic studies of methyl oleate ethenolysis with the first-generation Grubbs catalyst. Organometallics. 23(9):2027-47 (2004).

Cadot, C. et al., Olefin isomerization by a ruthenium carbenoid complex. Cleavage of allyl and homoallyl groups. Tetrahedron Lett. 43:1839-1841 (2002).

Cantrell et al., Ring-Opening Metathesis of a Cyclic Imine. Organometallics 19:3562-3568 (2000).

Chatterjee et al., Olefin Cross-Metathesis. Handbook Metathesis 2:246-95 (2003).

(56) References Cited

OTHER PUBLICATIONS

Chen, Y. et al., Regioselective substitution of fluorine in F8BINOL as a versatile route to new ligands with axial chirality. Org. Lett. 2:3433-3436 (2000).

Clark, J.S. et al., Enantioselective synthesis of medium-ring sub-units of brevetoxin A by ring-closing metathesis. Tetrahedron Lett. 38:127-130 (1997).

Clark, J.S. et al., Synthesis of brevetoxin sub-units by sequential ring-closing metathesis and hydroboration. Tetrahedron Lett. 38:123-126 (1997).

Clark, J.S. et al., Synthesis of medium-sized cyclic allylic ethers by ring-closing metathesis and subsequent elaboration to sub-units found in the brevetoxins and ciguatoxins. Tetrahedron Lett. 39:8321-8324 (1998).

Clark, J.S. et al., Synthesis of polycyclic ethers by two-directional double ring-closing metathesis. Angew. Chem. Int. Ed. 39:372-374 (2000).

Clark, J.S. et al., Synthesis of sub-units of marine polycyclic ethers by ring-closing metathesis and hydroboration of enol ethers. Tetrahedron Lett. 55:8231-8248 (1999).

Connon et al., Recent developments in olefin cross-metathesis. Angew Chem Int Ed. 42(17):1900-23(2003).

Corma et al., Chemical routes for the transformation of biomass into chemicals. Chem Rev. 107(6):2411-502. (2007).

Coutelier, O. et al., Terminal alkyne metathesis: A further step towards selectivity. Adv. Synth. Catal. 348:2038-2042 (2006).

Deiter, A. et al., Synthesis of oxygen- and nitrogen-containing heterocycles by ring-closing metathesis. Chem. Rev. 104:2199-2238 (2004).

Dias, A. et al., Synthesis, characterisation, crystal structure, reactivity and bonding in titanium complexes containing 2,3,4,5-tetramethylpyrrolyl. J. Chem. Soc., Dalton Trans.1055-1061 (1997).

Dinger et al., High turnover numbers with ruthenium-based metathesis catalysts. Adv Synth Catal. 344(6-7):671-7 (2002).

Dolman et al., Efficient catalytic enantioselective synthesis of unsaturated amines: preparation of small- and medium-ring cyclic amines through Mo-catalyzed asymmetric ring-closing metathesis in the absence of solvent. J Am Chem Soc. 124(24):6991-7 (2002).

Dolman, New chiral molybdenum metathesis catalysts; application of the enantioselective preparation of cyclic amines, Ph.D. Thesis. MIT. 234 pages. (Jun. 2004).

Duarte, M. et al., Chlorobis(dimethylamido)(η5-2,5-dimethylpyrrolyl)titanium(IV), [Ti(NMe$_2$)$_2$(DMP)Cl]. Acta Cryst. C.61:104-106 (2005).

Feldman, J. et al., Recent advances in thes chemistry of "d0" alkylidene metallacyclobutane complexes. Prog. Inorg. Chem. 39:1-74 (1991).

Fellows, I.M. et al., Application of ring-closing metathesis to the formal total synthesis of (+)?FR900482. J. Am. Chem. Soc. 122:10781-10787 (2000).

Flook et al., Z-selective olefin metathesis processes catalyzed by a molybdenum hexaisopropylterphenoxide monopyrrolide complex. J. Am Chem Soc. 131(23):7962-3 (2009).

Fontecave et al., Chiral-at-metal complexes as asymmetric catalysts, in chiral diazaligands for asymmetric synthesis. Top Organometallic Chem. 15:271-88 (2005).

Forman et al., A stable ruthenium catalyst for productive olefin metathesis. Organometallics 23(21):4824-7 (2004).

Fujimura, O. et al., Hydroxyl-directed, stereoselective olefination of ketones by transition metal alkylidenes. J. Am. Chem. Soc. 117:2355-2356 (1995).

Fuwa, H. et al., A concise total synthesis of (+)-Neopeltolide, Angew Chem Int Ed 49:3041-3044 (2010).

Fürstner et al., Cationic ruthenium allenylidene complexes as catalysts for ring closing olefin metathesis. Chemistry 6(10):1847-57 (2000).

Fürstner, A., A concise total synthesis of dactylol via ring closing metathesis. J. Org. Chem. 61:8746-8749 (1996).

Fürstner, A. et al., Alkyne metathesis: Development of a novel molybdenum-based catalyst system and its application to the total synthesis of Epothilone A and C. Chem. Eur. J. 7(24):5299-5317 (2001).

Fürstner, A. et al., Conformationally unbiased macrocyclization reactions by ring closing metathesis. J. Org. Chem. 61:3942-3943 (1996).

Fürstner, A. et al., Formal total synthesis of (−)-balanol: Concise approach to the hexahydroazepine segment based on RCM. J. Org. Chem. 65:1738-1742 (2000).

Fürstner, A. et al., Macrocycles by ring-closing metathesis. Synthesis 792-803 (1997).

Fürstner, A. et al., Mo[N(t-Bu)(Ar)]$_3$ complexes as catalyst precursors: in situ activation and application to metathesis reactions of alkynes and diynes. J. Am. Chem. Soc. 121:9453-9454 (1999).

Fürstner, A. et al., Ring closing alkyne metathesis. Comparative investigation of two different catalyst systems and application to the stereoselective synthesis of olfactory lactones, azamacrolides, and the macrocyclic perimeter of the marine alkaloid nakadomarin A. J. Am. Chem. Soc. 121:11108-11113 (1999).

Fürstner, A. et al., Total syntheses of (+)-ricinelaidic acid lactone and of (−)-gloeosporone based on transition-metal-catalyzed C—C bond formations. J. Am. Chem. Soc. 119:9130-9136 (1997).

Fürstner, A. et al., Total synthesis of the turrianes and evaluation of their DNA-cleaving properties. Che. Eur. J. 8:1856-1871 (2002).

Ganter, Chiral organometallic half-sandwich complexes with defined metal configuration. Chem Soc Rev. 32(3):130-8 (2003).

Garber, S. B. et al., Efficient and recyclable monomeric and dendritic Ru-based metathesis catalysts. J. Am. Chem. Soc. 122:8168-8179 (2000).

Giessert et al., Intermolecular enol ether-alkyne metathesis. Org Lett. 5(10):1793-6 (2003).

Gillingham et al., Chiral N-heterocyclic carbenes in natural product synthesis: application of Ru-catalyzed asymmetric ring-opening/cross-metathesis and Cu-catalyzed allylic alkylation to total synthesis of baconipyrone C. Angew Chem Int Ed. 46(21):3860-4 (2007).

Giudici et al., Directed catalytic asymmetric olefin metathesis. Selectivity control by enoate and ynoate groups in Ru-catalyzed asymmetric ring-opening/cross-metathesis. J Am Chem Soc. 129(13):3824-5 (2007).

Gosh, A.K. et al., Ring-closing metathesis strategy to unsaturated γ- and δ-lactones: Synthesis of hydroxyethylene isostere for protease inhibitors. Tetrahedron Lett. 39:4651-4654 (1998).

Gradillas, A. et al., In Metathesis in natural product synthesis (eds Cossy, J., Arseniyadis, S., Meyer, C.)—(Wiley-VCH, 2010).

Gradillas, A. et al., Macrocyclization by ring-closing metathesis in the total synthesis of natural products: reaction conditions and limitations. Angew. Chem. Int. Ed. 45:6086-6101 (2006).

Gurjar, M. et al., Temperature-dependent isomerisation versus net fragmentation of secondary allylic alcohols with Grubbs' catalyst. Tetrahedron Lett. 42:3633-3636 (2001).

Hadlington, Catalyst flexes for extra control. Chemistry World. Nov. 17, 2008. Last accessed online. Dec. 1, 2008.

Herrmann et al., Methyltrioxorhenium als Katalysator für die Olefin-Metathese. Angew Chem 103:1704-1706 (1991).

Herrmann et al., Methyltrioxorhenium as catalyst for olefin metathesis. Angew Chem Int. Ed. 103:1636-1638 (1991).

Hesek et al., The first asymmetric synthesis of chiral ruthenium tris(bipyridine) from racemic ruthenium bis(bipyridine) complexes. Tetrahedron Lett. 41(15):2617-20 (2000).

Hock, A. et al., Dipyrrolyl Precursors to Bisalkoxide Molybdenum Olefin Metathesis Catalysts. J. Am. Chem. Soc. 128(50):16373-16375 (2006).

Houri, A.F. et al., Cascade catalysis in synthesis. An enantioselective route to Sch 38516 (and Fluvirucin B1) Aglycon Macrolactam. J. Am. Chem. Soc. 117:2943-2944 (1995).

Hoveyda, A. et al., The remarkable metal-catalyzed olefin metathesis reaction. Nature 450:243-251 (2007).

Humphrey, J.M. et al., Enantioselective total syntheses of manzamine A and related alkaloids. J. Am. Chem. Soc. 124:8584-8592 (2002).

(56) References Cited

OTHER PUBLICATIONS

Ibrahem et al., Highly Z- and enantioselective ring-opening/cross-metathesis reactions catalyzed by stereogenic-at-Mo adamantylimido complexes. J Am Chem Soc. 131(11):3844-5 (2009).
International Preliminary Report on Patentability for PCT/US2007/024318, mailed May 26, 2009.
International Preliminary Report on Patentability for PCT/US2009/000465, issued Jul. 27, 2010.
International Preliminary Report on Patentability for PCT/US2010/002644, issued Apr. 3, 2012.
International Preliminary Report on Patentability for PCT/US2011/024100, issued Aug. 14, 2012.
International Search Report and Written Opinion for PCT/US2007/024318, mailed on May 7, 2008.
International Search Report and Written Opinion for PCT/US2009/000465, mailed Jul. 13, 2009.
International Search Report and Written Opinion for PCT/US2011/024100, mailed on Apr. 23, 2011.
International Search Report for PCT/US12/40574, 3 pages (Sep. 5, 2012).
International Search Report for PCT/US2010/002644, mailed Mar. 7, 2011.
Jakubec, P. et al., Total synthesis of (−)-nakadomarin A. J. Am. Chem. Soc. 131:16632-16633 (2009).
Jiang et al., Fundamental studies of tungsten alkylidene imido monoalkoxidepyrrolide complexes. J Am Chem Soc. 131(22):7770-80 (2009).
Jiang et al., Highly Z-selective metathesis homocoupling of terminal olefins. J Am Chem Soc. 131(46):16630-1 (2009).
Jiang, A. J. et al., Fundamental studies of tungsten alkylidene imido monoalkoxidepyrrolide complexes. J. Am. Chem. Soc. 131:7770-7780 (2009).
Joe, D. et al., An unexpected product arising from metal alkylidene mediated ring-closing diene metathesis, Tetrahedron Lett. 38:8635-8638 (1997).
Kershner, D. et al., η5-Heterocyclic Metal Carbonyls. Coord. Chem. Rev. 79:279-92 (1987).
Kiely et al., Enantioselective synthesis of medium-ring heterocycles, tertiary ethers, and tertiary alcohols by Mo-catalyzed ring-closing metathesis. J Am Chem Soc. 124(12):2868-9 (2002).
Knof et al., Predetermined chirality at metal centers. Angew Chem Intl Ed. 38(3):302-22 (1999).
Kreickmann, T. et al., Imido alkylidene bispyrrolyl complexes of tungsten. Organometallics 26:5702-5711 (2007).
Lacour et al., Recent developments in chiral anion mediated asymmetric chemistry. Chem Soc Rev. 32(6):373-82 (2003).
Lee et al., Enantioselective synthesis of cyclic enol ethers and all-carbon quaternary stereogenic centers through catalytic asymmetric ring-closing metathesis. J Am Chem Soc. 128(15):5153-7 (2006).
Lee et al., Endo-selective enyne ring-closing metathesis promoted by stereogenic-at-Mo monoalkoxide and monoaryloxide complexes. Efficient synthesis of cyclic dienes not accessible through reactions with Ru carbenes. J Am Chem Soc. 131(30):10652-61 (2009).
Liu et al., Regioselective ring-opening/cross-metathesis reactions of norbornene derivatives with electron-rich olefins. Org Lett. 7(I):131-3 (2005).
Lokare et al., Synthesis, properties, and structure of tethered molybdenum alkylidenes. Organometallics 27(19):5130-8 (2008).
Malcolmson et al., Highly efficient molybdenum-based catalysts for enantioselective alkene metathesis. Nature 456(7224):933-7 (2008).
Marinescu et al., Ethenolysis reactions catalyzed by imido alkylidene monoaryloxide monopyrrolide (MAP) complexes of molybdenum. J Am Chem Soc. 131(31):10840-1 (2009).
Marinescu et al., Inversion of configuration at the metal in diastereomeric imido alkylidene monoaryloxide monopyrrolide complexes of molybdenum. J Am Chem Soc.131 (1):58-9 (2009).
Marinescu, S. C. et al., Room-temperature Z-selective homocoupling of α-olefins by tungsten catalysts. Organometallics 30:1780-1782 (2011).
Marsella, N.J. et al., Template-directed ring-closing metathesis: synthesis and polymerization of unsaturated crown ether analogs. Angew. Chem. Int. Ed. 36:1101-1103 (1997).
Martin, S.F. et al., A novel approach to the asymmetric synthesis of manzamine A. Construction of the tetracyclic ABCE ring system. Tetrahedron Lett. 35:691-694 (1994).
Martin, S.F. et al., Ring-closing olefin meta thesis for the synthesis of fused nitrogen heterocycles. Tetrahedron 52:7251-7264 (1996).
Maruoka et al., Efficient synthesis of sterically hindered chiral binaphthol derivatives. Bull Chem Soc Jpn. 61(8):2975-6 (1988).
May, S. A. et al., Total synthesis of (−)-epothilone B. Chem. Commun. 1597-1598 (1998).
McDougal et al., Asymmetric Morita-Baylis-Hillman reactions catalyzed by chiral Brønsted acids. J Am Chem Soc. 125(40):12094-5 (2003).
McDougal et al., The development of the asymmetric Morita-Baylis-Hillman reaction catalyzed by chiral Brønsted acids. Adv Synth Cat. 346:1231-40 (2004).
Meek et al., The significance of degenerate processes to enantioselective olefin metathesis reactions promoted by stereogenic-at-Mo complexes. J Am Chem Soc. 131(45):16407-9 (2009).
Meek, S. J., et al., Catalytic Z-selective olefin cross-metathesis for natural product synthesis. Nature 471:461-466 (2011).
Meng, D. et al., Total syntheses of epothilones A and B. J. Am. Chem. Soc. 119:10073-10092 (1997).
Miller, S.J. et al., Application of ring-closing metathesis to the synthesis of rigidified amino acids and peptides. J. Am. Chem. Soc. 118:9606-9614 (1996).
Monchaud et al., Ion-pair-mediated asymmetric synthesis of a configurationally stable mononuclear tris(diimine)-iron(II) complex. Angew Chem Int Ed. 41(13):2317-9 (2002).
Morrison, D. J. et al., 2,2'-Disubstiuted F12binaphthyl derivatives: stannanes, boranes, and (R)-F12BINOL. Chem. Commun. 2875-2877 (2006).
Nagata, T. et al., The first total synthesis of nakadomarin A. J. Am. Chem. Soc. 125:7484-7485 (2003).
Nakashima, K. et al., Total synthesis and absolute configuration of liverwort diterpenes, (−)-13(15)E, 16E-3β,4β-epoxy-18-hydroxysphenoloba-13(15),16-diene and (−)-13(15)Z,16E-3β,4β-epoxy-18-hydroxysphenoloba-13(15),16-diene, by use of the ring closing metathesis reaction applied to seven-membered carbocycles with a trisubstituted double bond. J. Org. Chem. 67:6034-6040 (2002).
Nicolaou et al,, Metathesis reactions in total synthesis. Angew Chem Int Ed. 44(29):4490-527 (2005).
Nicolaou, K. C. et al. The olefin metathesis approach to epothilone A and its analogues. J. Am. Chem. Soc. 119:7960-7973 (1997).
Nicolaou, K. C. et al., Chemical biology of epothilones. Angew. Chem. Int. Ed. 37:2014-2045 (1998).
Nicolaou, K. C. et al., Synthesis of epothilones A and B in solid and solution phase. Nature 387:268-272 (1997).
Nicolaou, K. C. et al., Total syntheses of Epothilones A and B via a macrolactonization-based strategy. J. Am. Chem. Soc. 119:7974-7991 (1997).
Nicolaou, K.C. et al., Model studies towards diazonamide a: synthesis of the heterocyclic core. Angew Chem. Int. Ed. 39:3473-3478 (2000).
Nilson, M. G. et al., Total synthesis of (−)-nakadomarin A. Org. Lett. 12:4912-4915 (2010).
Ono, K. et al., Asymmetric total synthesis of (−)-nakadomarin A. Angew. Chem. Int. Ed. 43:2020-2023 (2004).
Paquette, L.A. et al., Teubrevin g and teubrevin h: The first total syntheses of rearranged *neo*-clerodanes including solutions to the problems of chirality merger and furan ring assembly. J. Am. Chem. Soc. 123:4492-4501 (2001).
Pezet et al., Highly diastereoselective preparation of ruthenium bis(diimine) sulfoxide complexes: new concept in the preparation of optically active octahedral ruthenium complexes. Organometallics 19(20):4008-15 (2000).

(56) References Cited

OTHER PUBLICATIONS

Poater et al., Understanding d(0)-olefin metathesis catalysts: which metal, which ligands? J Am Chem Soc. 129(26):8207-16 (2007).

Quintard, D. et al., Synthesis and conformational analysis of macrocycles related to 10-Oxa-epothilone. Eur. J. Org. Chem. 4762-4770 (2004).

Rhers, B. et al., A well-defined, silica-supported tungsten imido alkylidene olefin metathesis catalyst. Organometallics 25:3554-3557 (2006).

Rivkin, A. et al., On the remarkable antitumor properties of fludelone: How we got there. Angew. Chem., Int. Ed. 44:2838-2850 (2005).

Sattely et al., Design and stereoselective preparation of a new class of chiral olefin metathesis catalysts and application to enantioselective synthesis of quebrachamine: catalyst development inspired by natural product synthesis. J Am Chem Soc. 131(3):943-53 (2009).

Sattely et al., Enantioselective synthesis of cyclic amides and amines through mo-catalyzed asymmetric ring-closing metathesis. J Am Chem Soc. 127(23):8526-33 (2005).

Sattely, Cyclic amines and amides through molybdenum-catalyzed asymmetric olefin metathesis: A total synthesis of quebrachamine. Boston College Dissertations and Theses. Paper AAI3256831. http://escholarship.bc.edu/dissertations/AAI3256831. 340 pages. (Jan. 1, 2007).

Schinzer, D. et al., Syntheses of (−)-Epothilone B. Chem. Eur. J. 5:2492-2500 (1999).

Schinzer, D. et al., Synthesis of (−)-Epothilone A. Angew. Chem., Int. Ed. 36:523-524 (1997).

Schinzer, D. et al., Synthesis of (−)-Epothilone A. Chem. Eur. J. 5:2483-2491 (1999).

Scholl, M. et al., Synthesis and activity of a new generation of ruthenium-based olefin metathesis catalysts coordinated with 1,3-dimesityl-4,5-dihydroimidazol-2-ylidine ligands. Org. Lett. 1:953-956 (1999).

Schrock et al., Further studies of imido alkylidene complexes of tungsten, well-characterized olefin metathesis catalysts with controllable activity, Organometallics 9(8):2262-2275 (1990).

Schrock et al., Thousands of catalysts for olefin metathesis: variability, longevity and asymmetry at the metal. Abstract. Presented at Technical University of Berlin (Oct. 24, 2008).

Schrock, R. et al., Molybdenum alkylidyne complexes that contain 3,3'-di-t-butyl-5,5', 6,6'-tetramethyl-1,1', 11-biphenyl-2, 2'-diolate ([Biphen]$^2$-) ligand. J. Organomet, Chem. 684:56-67 (2003).

Schrock, R. et al., Molybdenum and tungsten imido alkylidene complexes as efficient olefinmetathesis catalysts. Angew. Chem. Int. Ed. 42:4592-4633 (2003).

Schrock, R. et al., Preparation of molybdenum and tungsten neopentylidyne complexes of the type $M(CCMe_3)(O_2CR)_3$, their reactions with acetylenes, and the X-ray structure of the $\mu^3$-cyclopropenyl complex $W[C_3(CMe_3)Et_2]O_2CCH_3)_3$. Organometallics 5:25-33 (1986).

Schrock, R. et al., Synthesis of molybdenum imido alkylidene complexes and some reactions involving acyclic olefins. J. Am. Chem. Soc. 112:3875-3886 (1990).

Schrock, R., High oxidation state multiple metal-carbon bonds. Chem. Rev. 102:145-179 (2002).

Schrock, Recent advances in high oxidation state Mo and W imido alkylidene chemistry. Chem Rev. 109(8):3211-26 (2009).

Schrodi et al., Ruthenium olefin metathesis catalysts for the ethenolysis of renewable feedstocks. Clean: Soil, Air, Water. 36:669-673 (2008).

Science Daily, New catalysts promise faster, cleaner, and more efficient research platform, 1-2, (2008).

She, J. et al., Examination of the olefin-olefin ring-closing metathesis to prepare latrunculin B, Tetrahedron Lett. 50:298-301 (2009).

Singh, R. et al., Molybdenum imido alkylidene metathesis catalysts that contain electron-withdrawing biphenolates or binaphtholates. Organometallics 26(10):2528-2539 (2007).

Singh, R. et al., Synthesis of monoalkoxide monopyrrolyl complexes Mo(NR)(CHR')(OR")(pyrrolyl): Enyne metathesis with high oxidation state catalysts. J. Am. Chem. Soc.129(42):12654-12655 (2007).

Sinha, A. et al., Diphenylamido precursors to bisalkoxide molybdenum olefin metathesis catalysts. Organometallics 25:4621-4626 (2006).

Sinha, A. et al., Reactions of $M(N-2,6-i-Pr_2C_6H_3)(CHR')(CH_2R')_2$(M=Mo, W) complexes with alcohols to give olefin metathesis catalysts of the type $M(N-2,6-i-Pr_2C_6H_3)(CHR')(CH_2R')(OR")$. Organometallics 25:1412-23 (2006).

Sinha, S. C. et al., Catalytic antibody route to the naturally occurring epothilones: Total synthesis of epothilones A-F. Chem. Eur. J. 7:1691-1702 (2001).

Smith, A.B. et al., Total synthesis of (−)-cylindrocyclophanes A and F exploiting the reversible nature of the olefin cross metathesis reaction. J. Am. Chem. Soc. 123:5925-5937 (2001).

Smith, B. J. et al., Total synthesis of (±)-haliclonacyclamine C. Angew. Chem. Int. Ed. 49:1599-1602 (2010).

Smith, J. et al., Assembly of (−)-cylindrocyclophanes A and F via remarkable olefin metathesis dimerizations. J. Am. Chem. Soc. 122:4984-4985 (2000).

Smith, J. et al., On the reversible nature of the olefin cross metathesis reaction. J. Am. Chem. Soc. 123:990-991 (2001).

Solans-Monfort et al., d0 Re-based olefin metathesis catalysts, Re(=CR)(=CHR)(X)(Y): The key role of X and Y ligands for efficient active sites. J Am Chem Soc. 127(40):14015-25 (2005).

Sutton, A.E. et al., New tandem catalysis: Preparation of cyclic enol ethers through a ruthenium-catalyzed ring-closing metathesis-olefin isomerization sequence. J. Am. Chem. Soc. 124:13390-13391 (2002).

Takano et al., Enantioselective route to both (+)- and (−)-enantiomers of quebrachamine using a single chiral synthon. J Chem Soc Chem Commun. 1153-5 (1981).

Takemura et al., Stereochemical aspects of asymmetric Diels-Alder reaction catalyzed by chiral alkoxyaluminum dichlorides. Tetrahedron Lett. 28(46):5687-90 (1987).

Tallarico et al., Selectivity in ring-opening metatheses. Tetrahedron 53(48):16511-20 (1997).

Tayama et al., Activation of ether functionality of allyl vinyl ethers by chiral bis(organoaluminum) Lewis acids: application to asymmetric Claisen rearrangement. Tetrahedron 58(41):8307-12 (2002).

Tonzetich, Z. et al., Reaction of phosphoranes with $Mo(N-2,6-Pr_2C_6H_3)(CHCMe_3)[OCMe(CF_3)_2]_2$: synthesis and reactivity of an anionic imido alkylidyne complex. Organometallics 25:4301-4306 (2006).

Toró, A. et al., Furanophane transannular Diels-Adler approach to (+)-chatancin: An asymmetric total synthesis of (+)-anhydrochatancin. J. Org. Chem. 68:6847-6852 (2003).

Tsai, Y. et al, Facile synthesis of trialkoxymolybdenum(VI) alkylidyne complexes for alkyne metathesis. Organometallics 19:5260-5262 (2000).

Van Veldhuizen et al., A readily available chiral Ag-based N-heterocyclic carbene complex for use in efficient and highly enantioselective Ru-catalyzed olefin metathesis and Cu-catalyzed allylic alkylation reactions. J Am Chem Soc. 127(18):6877-82 (2005).

Van Veldhuizen et al., A recyclable chiral Ru catalyst for enantioselective olefin metathesis. Efficient catalytic asymmetric ring-opening/cross metathesis in air. J Am Chem Soc. 124(18):4954-5 (2002). Erratum in: J Am Chem Soc. 125(41):12666 (2003).

Walls et al., Alkaloids from stemmadenia species-I : The alkaloids of S. Donnell-Smithii and S. Galeottiana. Tetrahedron 2(3-4):173-82 (1958).

Wang, Y. et al., Control of olefin geometry in macrocyclic ring-closing metathesis using a removable silyl group. J. Am. Chem. Soc. 133:9196-9199 (2011).

Weatherhead et al., Mo-catalyzed asymmetric olefin metathesis in target-oriented synthesis: enantioselective synthesis of (+)-africanol. Proc Natl Acad Sci U S A. 101(16):5805-9 (2004).

(56) References Cited

OTHER PUBLICATIONS

Werner et al., Bur Kennfnie dee asymmetrimhen Kobaltatoms. I. Ber Dtsch Chem Ges. 44:1887-98. German. (1911).

Written Opinion for PCT/US12/040574, 10 pages (Sep. 5, 2012).

Written Opinion for PCT/US2010/002644, mailed Mar. 7, 2011.

Xie, J. et al., Total synthesis of the proposed structure of iriomoteolide-1a. Chem. Commun. 46:4770-4772 (2010).

Xu, Z. et al., Applications of Zr-catalyzed carbomagnesation and Mo-catalyzed macrocyclic ring-closing metathesis in asymmetric synthesis. Enantioselective total synthesis of Sch 38516 (fluvirucin B). J. Am. Chem. Soc. 119:10302-10316 (1997).

Xu, Z. et al., Enantioselective total synthesis of antifungal agent Sch 38516. J. Am Chem. Soc. 118:10926-10927 (1996).

Yang, Z. et al., Total synthesis of epothilone A: The olefin metathesis approach. Angew. Chem., Int. Ed. 36:166-168 (1997).

Yashiro et al., Efficient stereochemical regulation of octahedral cobalt(III) complexes by a chiral bidentate ligand. Part 2. Remarkable effect of the chelate-ring size in the stereoselective formation of sym-cis-(ethylenediamine-N,N'-diacetato)(pentane-2,4-diamine)cobalt(III). J Chem Soc. Dalton Trans. 10:1511-6 (1994).

Yashiro et al., Efficient stereochemical regulation of octahedral cobalt(III) complexes by a chiral bidentate ligand. Part I. Effect of N-alkyl substitutions. J Chem Soc, Dalton Trans. 7:1073-7 (1994).

Yi et al., The ruthenium acetylide catalyzed cross-coupling reaction of terminal and internal alkynes: isolation of a catalytically active β-agostic intermediate species. Organometallics 17(15):3158-60 (1998).

Young, I. et al., Total synthesis of (+)-nakadomarin A. J. Am. Chem. Soc. 129:1465-1469 (2007).

Yu, M. et al., Enol ethers as substrates for efficient Z- and enantioselective ring-opening/cross-metathesis reactions promoted by stereogenic-at-Mo complexes: Utility in chemical synthesis and mechanistic attributes. J. Am. Chem. Soc. 134:2788-2799 (2012).

Yu, M. et al., Synthesis of macrocyclic natural products by catalyst-controlled stereoselective ring-closing metathesis. Nature 479:88-93 (2011).

Yudin, A. K. et al., F8BINOL, an electronically perturbed version of BINOL with remarkable configurational stability. Org. Lett. 2:41-44 (2000).

Zhang, W. et al., A reductive recycle strategy for the facile synthesis of molybdenum(VI) alkylidyne catalysts for alkyne metathesis. Chem. Commun. 832-833 (2003).

Zhao, Y. et al., Endo-selective enyne ring-closing metathesis promoted by stereogenic-at-W mono-pyrrolide complexes. Org. Lett. 13:784-787 (2011).

Zhou et al., Synthesis and reactivity of chiral rhenium indenyl complexes of the formula [(η5-C9H7)Re(NO)(PPh3)(X)]n+. Organometallics 12(10):3918-23 (1993).

Zhu et al., Chiral Mo-Binol complexes: activity, synthesis, and structure. Efficient enantioselective six-membered ring synthesis through catalytic metathesis. J Am Chem Soc. 121:8251-9 (1999).

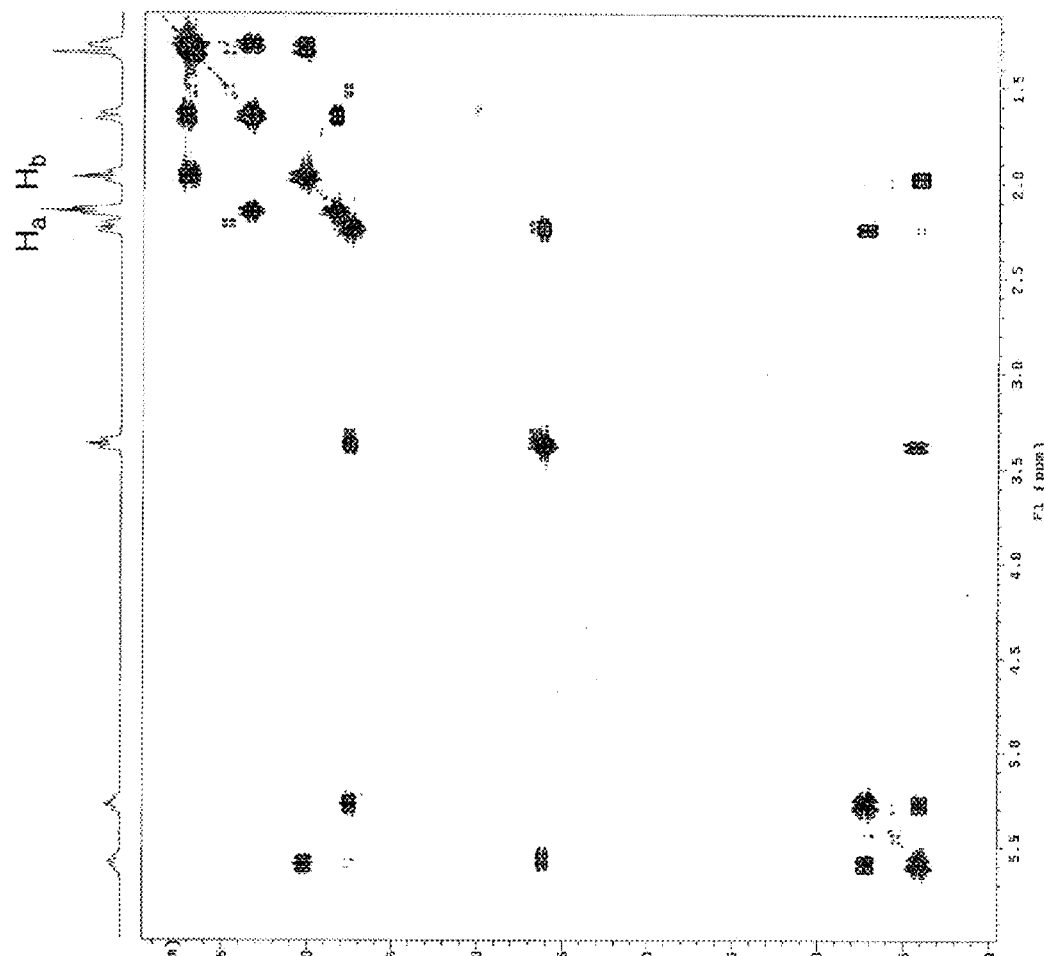
FIG. 3A
DQCOSY of 16:
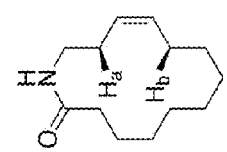

Z-SELECTIVE RING-CLOSING METATHESIS REACTIONS

CROSS-REFERENCE TO RELATED APPLICATIONS

This application is a Division of U.S. patent application Ser. No. 13/487,067, filed Jun. 1, 2012, which claims priority to U.S. Provisional Application Ser. No. 61/492,996, filed Jun. 3, 2011, and 61/598,307, filed Feb. 13, 2012, the entirety of each of which is incorporated herein by reference.

STATEMENT REGARDING FEDERALLY SPONSORED RESEARCH OR DEVELOPMENT

This invention was made with the support under the following government contracts: GM59426 and GM52496, both awarded by the National Institute of Health. The government has certain rights in the invention.

FIELD OF THE INVENTION

The present invention generally relates to Z-selective ring-closing metathesis reactions.

BACKGROUND

Catalytic olefin metathesis has transformed chemical synthesis and offers exceptionally efficient pathways for synthesis of alkenes. Many biologically active molecules are macrocycles that contain alkenes or other commonly occurring functional groups, such as an epoxide, diol or cyclopropane, which can be accessed via the carbon-carbon double bond. One of the most widely utilized protocols for synthesis of large rings is catalytic ring-closing metathesis (RCM). In most cases, however, macrocyclic RCM proceeds with minimal control of alkene stereoselectivity; this shortcoming is particularly costly in the case of complex molecules, since ring closure is typically performed after a long sequence of transformations.

Catalytic ring-closing metathesis (RCM) is an indispensable method for the preparation of cyclic structures of various sizes (Hoveyda, A. H. & Zhugralin, A. R. The remarkable metal-catalyzed olefin metathesis reaction. *Nature* 450, 243-251 (2007)); it is one of the most popular strategies used in the total synthesis of a large number of biologically active natural products (Deiters, A. & Martin, S. F. Synthesis of oxygen- and nitrogen-containing heterocycles by ring-closing metathesis. *Chem. Rev.* 104, 2199-2238 (2004); Nicolaou, K. C., Bulger, P. G. & Sarlah, D. Metathesis reactions in total synthesis. *Angew. Chem. Int. Edn* 44, 4490-4527 (2005); Gradillas, A. & Perez-Castells, J. Macrocyclization by ring-closing metathesis in the total synthesis of natural products: reaction conditions and limitations. *Angew. Chem. Int. Edn* 45, 6086-6101 (2006); Gradillas, A. & Pérez-Castells, J. in *Metathesis in Natural Product Synthesis* (eds Cossy, J., Arsenyadis, S., Meyer, C.)—(Wiley-VCH, 2010)).

However, the stereochemical outcome in RCM reactions is typically not subject to catalyst control; instead, selectivity is based on energetic attributes of the stereoisomers of the product molecules. In the case of small- or medium-ring structures, Z alkenes are strongly favored. With larger rings, on the other hand, the energy difference between the two alkene isomers is often not sufficiently large to allow for high stereoselectivity through thermodynamic control, or the E isomer is strongly preferred. Furthermore, since olefin metathesis is reversible, as the reaction moves towards completion, the higher energy Z isomer might be converted to the lower energy E form through post-RCM isomerization. Accordingly, there remains a need for reliable methods for highly selective synthesis of Z macrocyclic alkenes through RCM.

SUMMARY

The present invention provides new methods for the synthesis of Z macrocyclic alkenes through ring-closing metathesis. In some embodiments, the present invention provides new methods for use in the synthesis of natural products comprising Z macrocyclic alkenes and/or natural products comprising functionality which can be accessed via transformation of a Z-macrocyclic alkene intermediate. By way of non-limiting example, such natural products include epothilone A, epothilone B, epothilone C, epothilone D, epilachnene, nakadomarin A, yuzu lactone, ambrettolide, etc. In certain embodiments, a provided method is useful in the synthesis of a compound from the same class and/or from a similar class as any one of epothilone A, epothilone B, epothilone C, epothilone D, epilachnene, nakadomarin A, yuzu lactone, and/or ambrettolide.

The present invention also provides novel metal complexes which are useful in Z-selective stereogenic-at-metal ring-closing metathesis reactions. In some embodiments, a provided metal complex provides novel metal complexes which are useful in Z-selective ring-closing metathesis reactions but is not stereogenic-at-metal. In some embodiments, a provided metal complex is useful in the synthesis of natural products comprising Z macrocyclic alkenes and/or natural products comprising functionality which can be accessed via transformation of a Z-macrocyclic alkene intermediate. In some embodiments, a provided metal complex is useful in the synthesis of natural products comprising Z macrocyclic alkenes and/or natural products comprising functionality which can be accessed via transformation of a Z macrocyclic alkene intermediate, wherein the Z macrocyclic alkenes are tri-substituted. As noted above, exemplary such natural products include, but are not limited to, epothilone A, epothilone B, epothilone C, epothilone D, epilachnene, nakadomarin A, yuzu lactone, ambrettolide, etc. In certain embodiments, a provided metal complex is useful in the synthesis of compounds from the same class and/or from a similar class as any one of epothilone A, epothilone B, epothilone C, epothilone D, epilachnene, nakadomarin A, yuzu lactone, and/or ambrettolide.

The present invention further provides compositions which comprise an alkene-containing macrocyclic compound enriched in the Z conformation. Exemplary such compositions include, e.g., compositions comprising epothilone C, epothilone D, epilachnene, nakadomarin A, yuzu lactone, ambrettolide, and/or compositions comprising compounds from the same class and/or from a similar class of any one of epothilone C, epothilone D, epilachnene, nakadomarin A, yuzu lactone, and/or ambrettolide.

BRIEF DESCRIPTION OF THE DRAWING

FIGS. 3a-3b. Proof of stereochemistry for macrocycle 16. FIG. 3a: DQCOSY NMR spectra of 16. FIG. 3b: nOe study of 16.

DETAILED DESCRIPTION OF CERTAIN EMBODIMENTS

1. General Description of Certain Embodiments of the Invention

The present invention provides methods for the synthesis of macrocyclic alkenes through catalytic RCM reactions, which proceed with high efficiency and stereoselectivity, in some embodiments delivering up to 97% of the Z isomer, as the result of effective control by molybdenum- or tungsten-based catalysts. Utility is demonstrated by applications to preparation of several biologically active molecules, including anti-cancer epothilone A and anti-microbial nakadomarin A—syntheses of which have been marred by late-stage non-selective RCM. It is demonstrated herein that a complex derived from tungsten or molybdenum delivers high efficiency and stereoselectivity, even at relatively high concentrations. Reactions proceed through the desired pathway in preference to undesired alternatives: efficient RCM and cross-metathesis between adventitiously formed homo-coupling product and ethylene to regenerate the substrate but minimal macrocyclic Z-alkene isomerization.

It was surprisingly found that stereogenic-at-metal (Attygalle, A. B., McCormick, K. D., Blankespoor, C. L., Eisner, T. & Meinwald, J. Azamacrolides: A family of alkaloids from the pupal defensive secretion of a ladybird beetle (*Epilachna varivestis*). *Proc. Natl. Acad. Sci. USA* 90, 5204-5208 (1993)) catalysts promote efficient and highly Z-selective olefin formation through ring-closing metathesis reactions, described in detail below. It was surprisingly found that non-stereogenic-at-metal catalysts promote efficient and highly Z-selective tri-substituted macrocyclic olefin formation through ring-closing metathesis reactions, described in detail below. It was surprisingly found that stereogenic-at-metal catalysts promote efficient and highly Z-selective tri-substituted macrocyclic olefin formation through ring-closing metathesis reactions, described in detail below.

Methods of the present invention are useful in the synthesis of macrocyclic alkenes enriched in the Z configuration. In some embodiments, the present invention provides methods which are useful in the synthesis of a large assortment of biologically active compounds comprising Z-alkenes. In some embodiments, the present invention provides methods which are useful in the synthesis of a large assortment of compounds comprising Z-alkenes which serve as intermediates to biologically active compounds. Exemplary such biologically active natural products and/or intermediates thereto are described below and herein.

Case Studies: Epilachnene, Epothilone A & Nakadomarin A

Figure 1A:
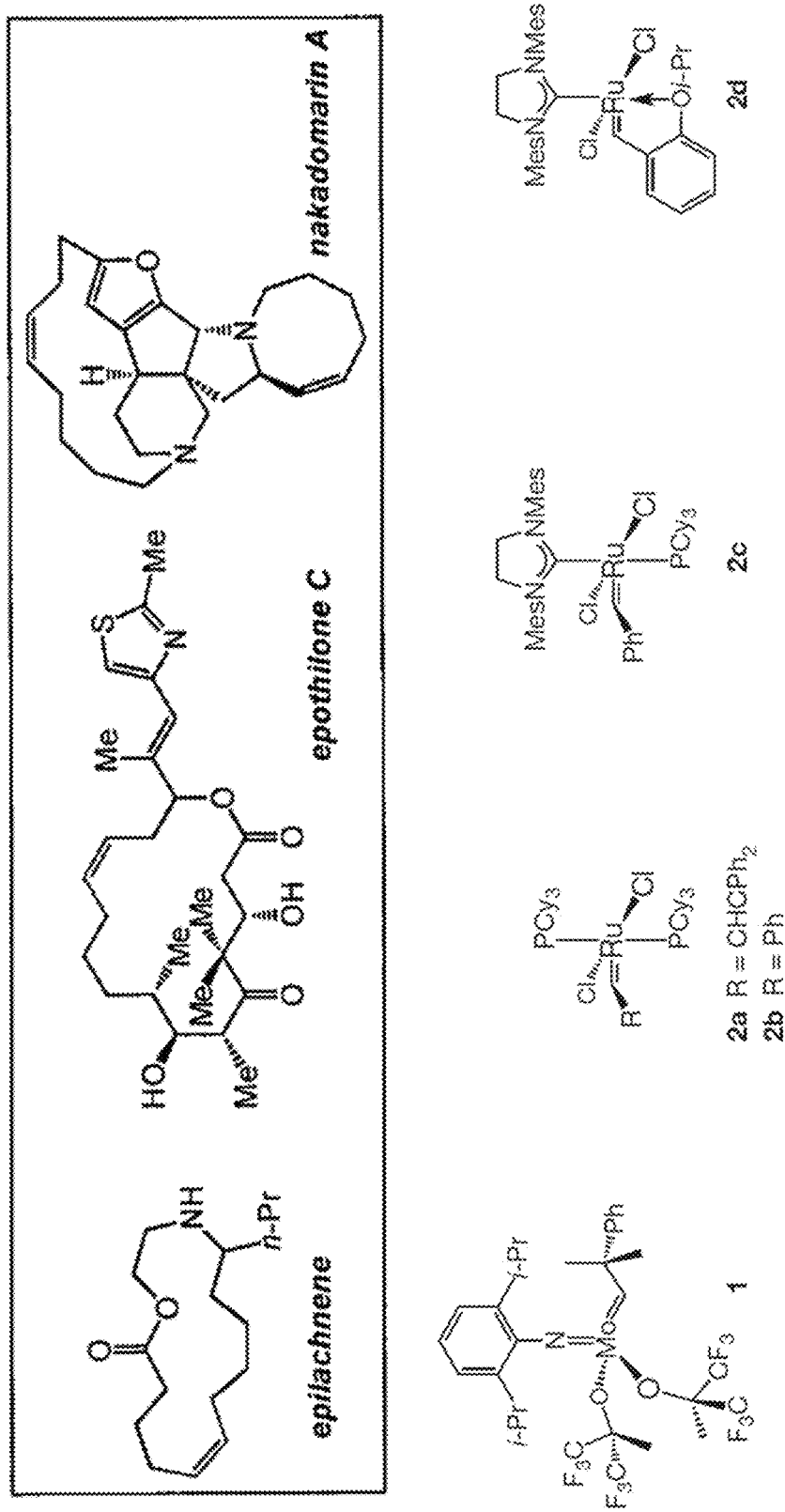
FIGS. 1a-1b. Three cases in natural product synthesis where catalytic ring-closing metathesis (RCM), promoted by some of the most commonly used catalysts (1, 2a-d) (FIG. 1a), affords the macrocyclic alkene but minimal stereoselectivity and often with a preference for generation of the undesired E isomer (FIG. 1b).
Figure 1B:
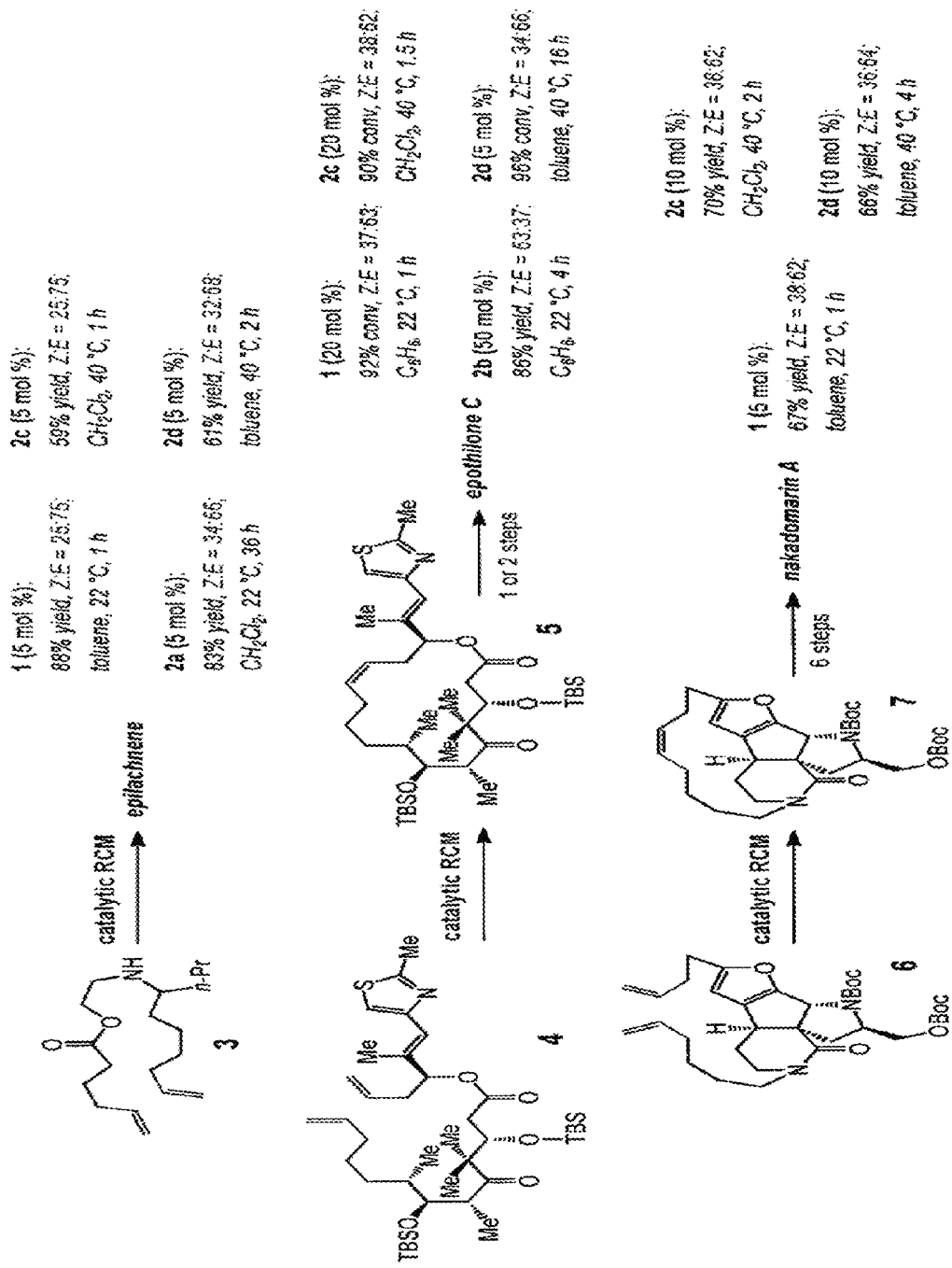

The three sets of non-selective catalytic RCM reactions shown in FIG. 1, performed to access macrocyclic natural products epilachnene (Höfle, G. et al. Epothilone A and B—novel 16-membered macrolides with cytotoxic activity: Isolation, crystal structure, and conformation in solution. *Angew. Chem. Int. Edn* 35, 1567-1569 (1996)), epothilone C (Kowalski, R. J., Giannakakou, P. & Hamel, E. Activities of the microtubule-stabilizing agents epothilones A and B with purified tubulin and in cells resistant to paclitaxel (taxol). *J. Biol. Chem.* 272, 2534-2541 (1997); Bollag, D. M., et al. Epothilones, a new class of microtubule-stabilizing agents with a taxol-like mechanism of action. *Cancer Res.* 55, 2325-2333 (1995); Kobayashi, J., Watanabe, D., Kawasaki, N. & Tsuda, M. Nakadomarin A, a novel hexacyclic manzamine-related alkaloid from Amphimedon Sponge. *J. Org. Chem.* 62, 9236-9239 (1997)) and nakadomarin A (Schrock, R. R.& Hoveyda, A. H. Molybdenum and tungsten imido alkylidene complexes as efficient olefin metathesis catalysts. *Angew. Chem. Int. Edn* 42, 4592-4633 (2003)), with four commonly used metal complexes illustrate the severe shortcomings of the state-of-the art. Efforts from a number of leading laboratories have involved catalytic RCM as the means to synthesize the requisite macrocyclic moiety of various members of the epothilone family; use of popular catalysts, such as complexes 1 (Scholl, M., Ding, S., Lee, C. W. & Grubbs, R. H. Synthesis and activity of a new generation of ruthenium-based olefin metathesis catalysts coordinated with 1,3-dimesityl-4,5-dihydroimidazol-2-ylidine ligands. *Org. Lett.* 1, 953-956 (1999)) and 2a-c (Garber, S. B., Kingsbury, J. S., Gray, B. L. & Hoveyda, A. H. Efficient and recyclable monomeric and dendritic Ru-based metathesis catalysts. *J. Am. Chem. Soc.* 122, 8168-8179 (2000); Nicolaou, K. C., et al. Synthesis of epothilones A and B in solid and solution phase. *Nature* 387, 268-272 (1997)) (FIG. 1), results in little or no stereoselectivity (see the Exemplification for details of reactions with 2b-c) (Nicolaou, K. C. et al. The olefin metathesis approach to epothilone A and its analogues. *J. Am. Chem. Soc.* 119, 7960-7973 (1997); Meng, D. et al. Total synthesis of epothilones A and B. *J. Am. Chem. Soc.* 119, 10073-10092 (1997); Nagata, T., Nakagawa, M. & Nishida, A. The first total synthesis of nakadomarin A. *J. Am. Chem. Soc.* 125, 7484-7485 (2003)). More recent initiatives regarding nakadomarin A, consisting of four different routes that involve catalytic macrocyclic RCM, have been equally discouraging (Ono, K., Nakagawa, M. & Nishida, A. Asymmetric total synthesis of (−)-nakadomarin A. *Angew. Chem. Int. Edn*, 43, 2020-2023 (2004); Young, I. S. & Kerr, M. A. Total synthesis of (+)-nakadomarin A. *J. Am. Chem. Soc.* 129, 1465-1469 (2007); Jakubec, P., Cockfield, D. M. & Dixon, D. J. Total synthesis of (−)-nakadomarin A. *J. Am. Chem. Soc.* 131, 16632-16633 (2009); Fürstner, A. & Langemann, K. Macrocycles by ring-closing metathesis. *Synthesis* 792-803 (1997)).

A catalytic Z-selective RCM that affords epilachnene would represent a more efficient approach than those previously outlined (Xu, Z. et al. Applications of Zr-catalyzed carbomagnesation and Mo-catalyzed macrocyclic ring-closing metathesis in asymmetric synthesis. Enantioselective total synthesis of Sch 38516 (fluvirucin B). *J. Am. Chem. Soc.* 119, 10302-10316 (1997)), allowing access to other sparingly substituted macrocycles. Reactions of more complex dienes, such as 4 and 6 (FIG. 1), constitute a particularly compelling objective for several reasons. First, epothilone C, as well as nakadomarin A, belong to important classes of natural products, which exhibit exceptional biological activity (e.g., anticancer and antimicrobial, respectively). An effective method for laboratory synthesis of such targets would furnish larger quantities of these molecules and their analogs. Second, since regardless of the protocol employed, formation of the large ring in such targets involves highly functionalized substrates and occurs late in a long multi-step route, a non-selective transformation inflicts a costly diminution in overall efficiency. It might be envisioned that with more complex substrates, such as 4 or 6, preliminary modeling studies involving simpler analogs could be used to establish the feasibility of an RCM strategy (Nagata, T., Nakagawa, M. & Nishida, A. The first total synthesis of nakadomarin A. *J. Am. Chem. Soc.* 125, 7484-7485 (2003)). Such a tactic is unadvisable, however, as specific substituents and their stereochemical identities play an important role in the efficiency and stereoselectivity of the catalytic ring closure and their absence often has a major influence on an RCM reaction (Meng, D. et al. Total synthesis of epothilones A and B. *J. Am. Chem. Soc.* 119, 10073-10092 (1997); Fürstner, A., Mathes, C. & Lehmann, C. W. Alkyne metathesis: development of a novel molybdenum-based catalyst system and its application to the total synthesis of epothilone A and C. *Chem. Eur. J.* 7, 5299-5317 (2001)).

Such difficulties in stereoselective ring closure are particularly damaging since the catalytic RCM takes place late in the synthesis route and inflict substantial loss in efficiency. For example, diene precursor 4, used in the total synthesis of anti-cancer agent epothilone C is prepared by a 16-step sequence. A catalyst controlled Z-selective RCM would be less susceptible to the attributes of the substrate structure.

There have been attempts to find solutions for the above-mentioned complications by the more common but less effective stratagem of altering a substrate's structure (vs. identification of a catalyst that delivers the desired alkene stereochemistry). In one case, a two-step procedure, involving Mo-catalyzed alkyne metathesis followed by unmasking of the alkene by controlled Pd-catalyzed hydrogenation has been developed to access macrocyclic Z alkenes (Nilson, M. G. & Funk, R. L. Total synthesis of (−)-nakadomarin A. *Org. Lett.* 12, 4912-4915 (2010); Coutelier, O. & Mortreux, A. Terminal alkyne metathesis: A further step towards selectivity. *Adv. Synth. Catal.* 348, 2038-2042 (2006)). Thus, one catalytic process affords the ring system and another adjusts the oxidation state, furnishing the desired stereochemistry. However, syntheses of the requisite alkyne precursors, which must be internal (methyl-substituted, so as to enhance catalyst longevity and avoid oligomerization) (Wang, Y. et al. Control of olefin geometry in macrocyclic ring-closing metathesis using a removable silyl group. *J. Am. Chem. Soc.* 133, ASAP), require additional manipulations. Moreover, alkyne reductions are performed with catalysts containing palladium salts and poisonous lead additives; over-reduction can lead to complications, particularly since separation of the undesired alkane side product from the desired alkenes can be difficult. Most recently, macrocyclic RCM reactions between an internal vinylsilane and a terminal alkene have been disclosed (Malcolmson, S. J., Meek, S. J., Sattely, E. S., Schrock, R. R.& Hoveyda, A. H. Highly efficient molybdenum-based catalysts for alkene metathesis. *Nature* 456, 933-937 (2008)). Two additional steps are again used to address the problem: (1) the requisite vinylsilanes is first prepared by a Ru-catalyzed hydrosilylation of a terminal alkyne; and (2) the resulting trisubstituted silyl-substituted alkenes are protodesilylated through treatment with a mixture of an ammonium fluoride, silver fluoride salt and acetic acid to unmask the Z alkenes.

Stereogenic-at-Mo (Ibrahem, I., Yu, M., Schrock, R. R.& Hoveyda, A. H. Highly Z- and enantioselective ring-opening/cross-metathesis reactions catalyzed by stereogenic-at-Mo adamantylimido complexes. *J. Am. Chem. Soc.* 131, 3844-3845 (2009)) catalysts promote efficient and highly Z-selective olefin formation through ring-opening/cross-metathesis (Meek, S. J., O'Brien, R. V., Llaveria, J., Schrock, R. R. & Hoveyda, A. H. Catalytic Z-selective olefin cross-metathesis for natural product synthesis. *Nature* 471, 461-466 (2011)), homocoupling and cross-metathesis (Jiang, A. J., Zhao, Y., Schrock, R. R. & Hoveyda, A. H. Highly Z-selective metathesis homocoupling of terminal olefins. *J. Am. Chem. Soc.* 131, 16630-16631 (2009)); the molybdenum complexes as well as the related tungsten alkylidenes have been effective in homocoupling processes (Rossini, C., González, A., Farmer, J., Meinwald J. & Eisner, T. Antiinsectan activity of epilachnene, a defensive alkaloid from pupae of Mexican bean beetles (*Epilachna varivestis*). *J. Chem. Ecol.* 26, 391-397 (2000)). In the above transformations, two alkene-containing substrates react to afford an acyclic 1,2-disubstituted internal carbon-carbon double bond, which is less prone towards further reaction with the catalyst, causing equilibration and formation of the often energetically more favored E isomers. In instances where olefin metathesis involves two relatively unhindered alkenes (e.g., lacking allylic substituents), stereoisomeric purities tend to be more fragile, since the initial Z alkene product can undergo isomerization more readily (Jiang, A. J., Zhao, Y., Schrock, R. R. & Hoveyda, A. H. Highly Z-selective metathesis homocoupling of terminal olefins. *J. Am. Chem. Soc.* 131, 16630-16631 (2009)). In many applications, such as those depicted in FIG. 1, there is no allylic substituent to discourage association of the macrocyclic Z alkene with the catalyst, retard the rate of the equilibration process. Effective control of stereoselectivity therefore demands a catalyst that strikes the subtle balance in reactivity, such that there is efficient RCM but minimal ring-opening/RCM to cause E alkene formation. The sensitive interplay between ring closure and equilibration by ring-opening underlines another complicating factor. Ring strain does not apply to cross-metathesis but renders the cyclic alkene prone to post-RCM transformations. In further contrast, a crucial strategy in a catalytic cross-metathesis involves the use of excess amounts of one cross partner to favor formation of the desired product (vs. homocoupling or isomerization); the latter approach is not feasible in an RCM process where the two reacting alkenes can only be present at precisely the same concentration.

In some embodiments, the present invention provides a method for forming a macrocyclic ring having a cis double bond, comprising reacting a suitable diene with a stereogenic-at-metal catalyst. In some embodiments, the present invention provides a method comprising reacting a suitable diene with a stereogenic-at-metal catalyst to form a compound of formula I:

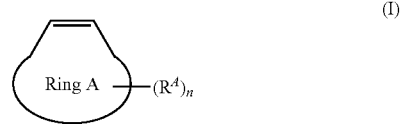

wherein the double bond depicted therein is in the cis configuration, and wherein:

Ring A is an optionally substituted 8-30 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^1$-, wherein:

each -Cy$^1$- is independently:

a bivalent optionally substituted monocyclic ring independently selected from phenylene, a 3-8 membered saturated or partially unsaturated carbocyclylene, a 5-6 membered heteroarylene having 1-4 heteroatoms independently selected from nitrogen, oxygen, or sulfur, or a 3-8 membered saturated or partially unsaturated heterocyclylene having 1-4 heteroatoms independently selected from nitrogen, oxygen, or sulfur; or a bivalent optionally substituted bicyclic ring independently selected from an 8-10 membered arylene, a 7-10 membered saturated or partially unsaturated carbocyclylene, an 8-10 membered heteroarylene having 1-5 heteroatoms independently selected from nitrogen, oxygen, or sulfur, or a 7-10 membered saturated or partially unsaturated heterocyclylene having 1-5 heteroatoms selected from nitrogen, oxygen, or sulfur; or a bivalent optionally substituted tricyclic ring independently selected from 14 membered arylene, a 9-20 membered saturated or partially unsaturated carbocyclylene, a 9-14 membered heteroarylene having 1-8 heteroatoms independently selected from nitrogen, oxygen, or sulfur, or a 9-20 membered saturated or partially unsaturated heterocyclylene having 1-8 heteroatoms independently selected from nitrogen, oxygen, or sulfur; or a bivalent optionally substituted tetracyclic ring independently selected from a 16-18 membered arylene, an 11-30 membered saturated or partially unsaturated carbocyclylene, a 15-18 membered heteroarylene having 1-8 heteroatoms independently selected from nitrogen, oxygen, or sulfur, or an 11-30 membered saturated or partially unsaturated heterocyclylene having 1-12 heteroatoms independently selected from nitrogen, oxygen, or sulfur;

n is 0-20;

each R is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or two R groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur; or two R groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur;

each R$^A$ is independently selected from —R, -QR, —OR, a suitably protected hydroxyl group, —SR, a suitably protected thiol group, —S(O)R, —SO$_2$R, —OSO$_2$R, —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$, wherein:

two R$^A$ on the same carbon atom are optionally taken together to form an oxo moiety, an oxime, an optionally substituted hydrazone, an optionally substituted imine, an optionally substituted C$_{2-6}$ alkylidene, or an optionally substituted 3-8 membered saturated or partially unsaturated spirocycle having 0-4 heteroatoms independently selected from nitrogen, oxygen, or sulfur, or:

two R$^A$ on adjacent atoms are optionally taken together to form an optionally substituted 3-8 membered, saturated, partially unsaturated, or aryl ring having 0-4 heteroatoms independently selected from nitrogen, oxygen, or sulfur;

each Q is independently an optionally substituted bivalent C$_{1-10}$ hydrocarbon chain wherein one, two, or three methylene units of Q are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^2$-; and each -Cy$^2$- is independently a bivalent optionally substituted ring selected from phenylene, a 3-8 membered saturated or partially unsaturated monocyclic carbocyclylene, a 5-6 membered monocyclic heteroarylene having 1-4 heteroatoms independently selected from nitrogen, oxygen, or sulfur, or a 3-8 membered saturated or unsaturated monocyclic heterocyclylene having 1-4 heteroatoms independently selected from nitrogen, oxygen, or sulfur, an 8-10 membered bicyclic arylene, a 7-10 membered saturated or partially unsaturated bicyclic carbocyclylene, an 8-10 membered bicyclic heteroarylene having 1-5 heteroatoms independently selected from nitrogen, oxygen, or sulfur, or a 7-10 membered saturated or partially unsaturated bicyclic heterocyclylene having 1-5 heteroatoms independently selected from nitrogen, oxygen, or sulfur.

In some embodiments, the present invention provides a method for forming a macrocyclic ring having a Z double bond, comprising reacting a suitable diene with a catalyst, wherein the Z double bond is tri-substituted. In some embodiments, the present invention provides a method for forming a macrocyclic ring having a Z double bond, comprising reacting a suitable diene with a sterogenic-at-metal catalyst, wherein the Z double bond is tri-substituted. In some embodiments, the present invention provides a method for forming a macrocyclic ring having a Z double bond, comprising reacting a suitable diene with a non-stereogenic-at-metal catalyst, wherein the Z double bond is tri-substituted. In some embodiments, the present invention provides a method comprising reacting a suitable diene with a catalyst to form a compound of formula I-a:

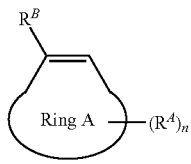

wherein the double bond depicted therein is in the Z configuration, and wherein:
Ring A is an optionally substituted 8-30 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^1$-, wherein:
each -Cy$^1$- is independently:
a bivalent optionally substituted monocyclic ring independently selected from phenylene, a 3-8 membered saturated or partially unsaturated carbocyclylene, a 5-6 membered heteroarylene having 1-4 heteroatoms independently selected from nitrogen, oxygen, or sulfur, or a 3-8 membered saturated or partially unsaturated heterocyclylene having 1-4 heteroatoms independently selected from nitrogen, oxygen, or sulfur; or
a bivalent optionally substituted bicyclic ring independently selected from an 8-10 membered arylene, a 7-10 membered saturated or partially unsaturated carbocyclylene, an 8-10 membered heteroarylene having 1-5 heteroatoms independently selected from nitrogen, oxygen, or sulfur, or a 7-10 membered saturated or partially unsaturated heterocyclylene having 1-5 heteroatoms selected from nitrogen, oxygen, or sulfur; or
a bivalent optionally substituted tricyclic ring independently selected from 14 membered arylene, a 9-20 membered saturated or partially unsaturated carbocyclylene, a 9-14 membered heteroarylene having 1-8 heteroatoms independently selected from nitrogen, oxygen, or sulfur, or a 9-20 membered saturated or partially unsaturated heterocyclylene having 1-8 heteroatoms independently selected from nitrogen, oxygen, or sulfur; or
a bivalent optionally substituted tetracyclic ring independently selected from a 16-18 membered arylene, an 11-30 membered saturated or partially unsaturated carbocyclylene, a 15-18 membered heteroarylene having 1-8 heteroatoms independently selected from nitrogen, oxygen, or sulfur, or an 11-30 membered saturated or partially unsaturated heterocyclylene having 1-12 heteroatoms independently selected from nitrogen, oxygen, or sulfur;
n is 0-20;
each R is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:
two R groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; or
two R groups on the same carbon atom are optionally taken together with their intervening atoms to form an optionally substituted 3-8 membered saturated or partially unsaturated spirocycle ring having 0-4 heteroatoms independently selected from nitrogen, oxygen, or sulfur; or
two R groups on adjacent atoms are optionally taken together with their intervening atoms form an optionally substituted 3-8 membered, saturated, partially unsaturated, or aryl ring having 0-4 heteroatoms independently selected from nitrogen, oxygen, or sulfur;
each R$^A$ is independently selected from —R, -QR, —OR, a suitably protected hydroxyl group, —SR, a suitably protected thiol group, —S(O)R, —SO$_2$R, —OSO$_2$R, —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$, wherein:
two R$^A$ on the same carbon atom are optionally taken together to form an oxo moiety, an oxime, an optionally substituted hydrazone, an optionally substituted imine, an optionally substituted C$_{2-6}$ alkylidene, or an optionally substituted 3-8 membered saturated or partially unsaturated spirocycle having 0-4 heteroatoms independently selected from nitrogen, oxygen, or sulfur, or:
two R$^A$ on adjacent atoms are optionally taken together to form an optionally substituted 3-8 membered, saturated, partially unsaturated, or aryl ring having 0-4 heteroatoms independently selected from nitrogen, oxygen, or sulfur;
R$^B$ is —R, -QR, —OR, a suitably protected hydroxyl group, —SR, a suitably protected thiol group, —S(O)R, —SO$_2$R, —OSO$_2$R, —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$;
each Q is independently an optionally substituted bivalent C$_{1-10}$ hydrocarbon chain wherein one, two, or three methylene units of Q are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^2$-; and
each -Cy$^2$- is independently a bivalent optionally substituted ring selected from phenylene, a 3-8 membered saturated or partially unsaturated monocyclic carbocyclylene, a 5-6 membered monocyclic heteroarylene having 1-4 heteroatoms independently selected from nitrogen, oxygen, or sulfur, or a 3-8 membered saturated or unsaturated monocyclic heterocyclylene having 1-4 heteroatoms independently selected from nitrogen, oxygen, or sulfur, an 8-10 membered bicyclic arylene, a 7-10 membered saturated or partially unsaturated bicyclic carbocyclylene, an 8-10 membered bicyclic heteroarylene having 1-5 heteroatoms independently selected from nitrogen, oxygen, or sulfur, or a 7-10 membered saturated or partially unsaturated bicyclic heterocyclylene having 1-5 heteroatoms independently selected from nitrogen, oxygen, or sulfur.

As used herein, the phrase "suitable diene" refers to any diene that can undergo a provided ring-closing metathesis reaction to form a compound of formula I. Exemplary such dienes are described herein and depicted in the Exemplification section herein.

As used herein, unless otherwise designated, when determining the E/Z configuration of tri-substituted double bond in a ring, ring atoms of the said ring are given higher priority over atoms that are not part of the said ring. Unless otherwise designated, no matter what $R^A$ and $R^B$ are, the double bond illustrated in Formula I-a, below, is a Z double bond in Ring A, wherein each variable is independently as defined above and described herein.

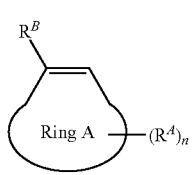

I-a

In some embodiments, the Z-macrocyclic alkene comprises an ester or an amide. Further aspects of compounds of formula I are described in detail, infra.

In some embodiments, the present invention provides a method for forming a compound of formula I or I-a, comprising reacting a suitable diene under suitable conditions with a metal complex of formula II-a:

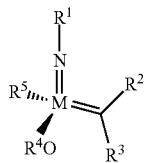

II-a wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;

$R^4$ is an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

Ar is of the following formula:

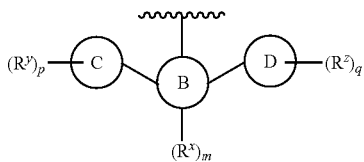

wherein:

m is 0-3;

Ring B is an optionally substituted group selected from phenyl or a 5-6 membered monocyclic heteroaryl ring having 1-4 heteroatoms independently selected from nitrogen, oxygen, or sulfur;

p and q are independently 0-6;

each of Ring C and Ring D are independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each $R^x$, $R^y$, and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur;

$R^5$ is halogen, —OR$^6$, —N(R')$_2$, —NR'C(O)R', —NR'C(O)OR', —NR'C(O)N(R')$_2$, —NR'SO$_2$R', —NR'SO$_2$N(R')$_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

$R^6$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides a method for forming a compound of formula I or I-a, comprising reacting a suitable diene under suitable conditions with a metal complex of formula II-b:

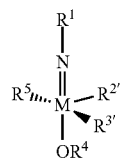

wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^{2'}$ and $R^{3'}$ are taken together with their intervening metal atoms to form an optionally substituted 3-8 membered saturated or partially unsaturated ring having, in addition to the intervening metal atom, 0-4 heteroatoms independently selected from nitrogen, oxygen, or sulfur;

$R^4$ is an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; wherein:

Ar is of the following formula:

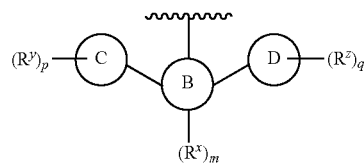

wherein:

m is 0-3;

Ring B is an optionally substituted group selected from phenyl or a 5-6 membered monocyclic heteroaryl ring having 1-4 heteroatoms independently selected from nitrogen, oxygen, or sulfur;

each of Ring C and Ring D are independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

p and q are independently 0-6;

each $R^x$, $R^y$, and $R^z$ is independently halogen, —OR$^6$, —N(R')$_2$, —NR'C(O)R', —NR'C(O)OR', —NR'C(O)

N(R')$_2$, —NR'SO$_2$R', —NR'SO$_2$N(R')$_2$, —NR'OR', or an optionally substituted group selected from C$_{1-20}$ aliphatic, C$_{1-20}$ heteroaliphatic having 1-3 heteroatoms independently selected from nitrogen, oxygen, or sulfur;

R$^5$ is halogen, —OR$^6$, —N(R')$_2$, —NR'C(O)R', —NR'C(O)OR', —NR'C(O)N(R')$_2$, —NR'SO$_2$R', —NR'SO$_2$N(R')$_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

R$^6$ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides a method for forming a compound of formula I or I-a, comprising reacting a suitable diene under suitable conditions with a metal complex of formula II-c:

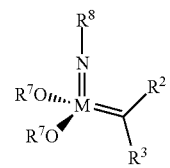

wherein:
M is molybdenum or tungsten;
R$^8$ is R$^1$, or phenyl optionally substituted with one to five R$^9$;
each R$^9$ is independently halogen or R$^1$;
R$^1$ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of R$^2$ and R$^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that R$^2$ and R$^3$ are not simultaneously hydrogen;
each R$^7$ is independently an optionally substituted group selected from —Ar', C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two R$^7$ are optionally taken together with the oxygen atoms they are bound to form a bidentate ligand;
Ar' is of the following formula:

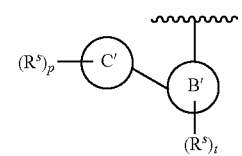

wherein:
t is 0-4;
p is 0-6;

each Ring B' and Ring C' is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR';

each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, the present invention provides a metal complex of formula II-c:

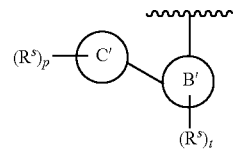

II-c wherein:
M is molybdenum or tungsten;
$R^8$ is $R^1$, or phenyl optionally substituted with one to five $R^9$;
each $R^9$ is independently halogen or $R^1$;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;

each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand;

Ar' is of the following formula:

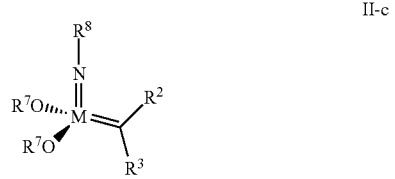

wherein:
t is 0-4;
p is 0-6;
each Ring B' and Ring C' is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR';

each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

Further aspects of metal complexes of formula II-a, II-b, and II-c useful in methods provided herein are described in detail, infra.

In some embodiments, the present invention provides metal complexes for use in the synthesis of Z macrocyclic alkenes. In particular, provided metal complexes are useful in Z-selective ring-closing metathesis reactions. In certain embodiments, a provided metal complex is of either of formula III-a or III-b:

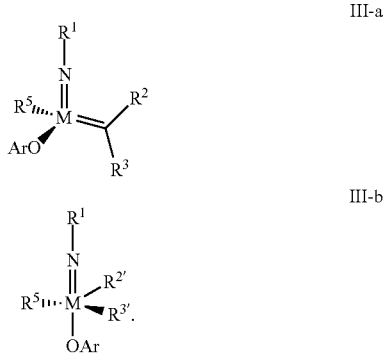

In some embodiments, a provided metal complex of formula III-a is other than:

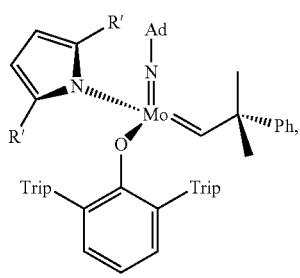

wherein Ad is adamantly, Ph is phenyl, Trip is 2,4,6-i-PrC$_6$H$_2$, and wherein R' is hydrogen or methyl.

Further aspects of complexes of formula III-a and III-b are described in detail, infra.

In some embodiments, the present invention provides a composition comprising an alkene-containing macrocyclic compound, wherein the composition is enriched in the Z configuration of that compound. Further aspects of such compositions are described in detail, infra.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic C$_3$-C$_6$ hydrocarbon, or a C$_8$-C$_{10}$ bicyclic hydrocarbon that is completely saturated or that contains one or more units of unsaturation, but which is not aromatic, that has a single point of attachment to the rest of the molecule, or a C$_9$-C$_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrol), NH (as in pyrrolidinyl) or NR' (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —(CH$_2$)$_{0-4}$SR°; —(CH$_2$)$_{0-4}$S(O)R°; —(CH$_2$)$_{0-4}$S(O)$_2$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —PR°$_2$; —OPR°$_2$; —SiR°$_3$; —OSiR°$_3$; —(C$_{1-4}$ straight or branched alkylene)O—N(R°$_2$; or —(C$_{1-4}$ straight or branched)alkylene)C(O)O—N(R°$_2$; wherein each R° may be substituted as defined below and is independently hydrogen, C$_{1-6}$aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-6 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR'$_3$, —OSiR'$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this invention. Such compounds are useful, for example, as analytical tools or probes in biological assays.

Protected hydroxyl groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, 0-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise designated, when determining the E/Z configuration of tri-substituted double bond in a ring, ring atoms of the said ring are given higher priority over atoms that are not part of the said ring. Therefore, unless otherwise designated, no matter what $R^A$ and $R^B$ are, the double bond illustrated in Formula I-a, below, is a Z double bond in Ring A, wherein each variable is independently as defined above and described herein.

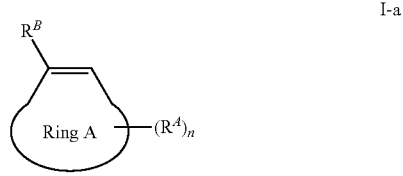

I-a

3. Description of Certain Embodiments of the Invention

Methods of the Present Invention

Methods of the present invention are useful in the synthesis of macrocyclic alkenes enriched in the Z configuration. In some embodiments, methods of the present invention are useful in Z-selective ring-closing metathesis reactions to generate compounds of formula I, as described in detail above and herein. In some embodiments, methods of the present invention are useful in Z-selective ring-closing metathesis reactions to generate compounds of formula I-a, as described in detail above and herein.

As used herein, the term "metathesis reaction" is given its ordinary meaning in the art and refers to a chemical reaction in which two reacting species exchange partners in the presence of a transition-metal catalyst. In some cases, a byproduct of a metathesis reaction may be ethylene. A metathesis reaction may involve reaction between species comprising, for example, olefins and/or alkynes. Examples of different kinds of metathesis reactions include cross metathesis, ring-closing metathesis, ring-opening metathesis, acyclic diene metathesis, alkyne metathesis, enyne metathesis, and the like. A metathesis reaction may occur between two substrates which are not joined by a bond (e.g., intermolecular metathesis reaction) or between two portions of a single substrate (e.g., intramolecular metathesis reaction).

As described generally above, the present invention provides a method for forming a compound of formula I:

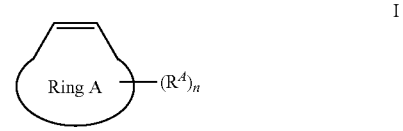

I wherein the double bond depicted therein is in the cis configuration, and wherein each of Ring A, n, and $R^A$ are as defined above and described in embodiments herein, both singly and in combination.

As described generally above, the present invention provides a method for forming a compound of formula I-a:

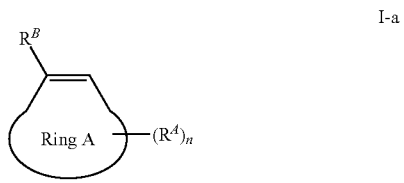

I-a wherein the double bond depicted therein is in the Z configuration, and wherein each of Ring A, n, and $R^A$ are as defined above and described in embodiments herein, both singly and in combination.

In some embodiments, a compound of formula I is the final product. In some embodiments, a compound of formula I is an intermediate useful in the synthesis of the final product. In some embodiments, a compound of formula I-a is the final product. In some embodiments, a compound of formula I-a is an intermediate useful in the synthesis of the final product. One of ordinary skill in the art would recognize that such intermediates are useful in a variety of transformations to which alkenes are generally susceptible, such as, e.g., oxidation reactions, reduction reactions, etc.

In some embodiments, Ring A is an optionally substituted 8-30 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-.

In some embodiments, Ring A is an optionally substituted 9-12 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 9-12 membered saturated or partially unsaturated ring wherein 1-5 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 9-12 membered saturated or partially unsaturated ring wherein 2-4 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 9-12 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In certain embodiments, Ring A forms nakadomarin A or a derivative thereof. In some embodiments, Ring A is an optionally substituted 9 membered saturated or partially unsaturated ring wherein 1-6 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In certain embodiments, Ring A is an optionally substituted 9 membered saturated or partially unsaturated ring wherein 1 methylene unit of Ring A is replaced by -Cy¹-.

In some embodiments, Ring A is an optionally substituted 12-18 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 12-18 membered saturated or partially unsaturated ring wherein 1-5 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 12-18 membered saturated or partially unsaturated ring wherein 2-4 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 12-18 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-.

In some embodiments, Ring A is an optionally substituted 12-14 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is a yuzu lactone, or derivative thereof. In certain embodiments, Ring A is an optionally substituted 12-14 membered saturated or partially unsaturated ring wherein 1-5 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 12-14 membered saturated or partially unsaturated ring wherein 2-4 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is an optionally substituted 12-14 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-.

In some embodiments, Ring A is an optionally substituted 12-14 membered saturated or partially unsaturated ring wherein 2-3 methylene units of Ring A are optionally and independently replaced by —O—, —N(R)—, —S—, —C(O)—, —OC(O)—, —C(O)O—, or —OC(O)O—.

In some embodiments, Ring A is an optionally substituted 12 membered saturated or partially unsaturated ring wherein 2 methylene units of Ring A are optionally and independently replaced by —O—, —N(R)—, or —C(O)—.

In some embodiments, Ring A is an optionally substituted 13 membered saturated or partially unsaturated ring wherein 2 methylene units of Ring A are optionally and independently replaced by —O—, —N(R)—, or —C(O)—.

In some embodiments, Ring A is an optionally substituted 14 membered saturated or partially unsaturated ring wherein 2 methylene units of Ring A are optionally and independently replaced by —O—, —N(R)—, or —C(O)—.

In some embodiments, Ring A is an optionally substituted 15-17 membered saturated or partially unsaturated ring wherein 0-6 methylene units of Ring A are optionally and independently replaced by —O—, —N(R)—, —S—, —C(O)—, —OC(O)—, —C(O)O—, —OC(O)O—, —S(O)—, —S(O)₂—, —OSO₂O—, —N(R)C(O)—, —C(O)N(R)—, —N(R)C(O)O—, —OC(O)NR—, —N(R)C(O)NR—, or -Cy¹-. In some embodiments, Ring A is a epilachnene, or a derivative thereof. In certain embodiments, Ring A is an optionally substituted 15-17 membered saturated or partially unsaturated ring wherein 1-5 methylene units of Ring A are optionally and independently replaced by —O—, —N(R)—, —S—, —C(O)—, —OC(O)—, —C(O)

O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-. In some embodiments, Ring A is an optionally substituted 15-17 membered saturated or partially unsaturated ring wherein 2-4 methylene units of Ring A are optionally and independently replaced by —O—, —N(R)—, —S—, —C(O)—, —OC(O)—, —C(O)O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-. In some embodiments, Ring A is an optionally substituted 15-17 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-.

In some embodiments, Ring A is an optionally substituted 15 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-. In some embodiments, Ring A is an optionally substituted 15 membered saturated or partially unsaturated ring wherein 3 methylene units of Ring A are optionally and independently replaced by —O—, —N(R)—, —S—, —C(O)—, —OC(O)—, —C(O)O—, or —OC(O)O—. In some embodiments, Ring A is an optionally substituted 15 membered saturated or partially unsaturated ring wherein 3 methylene units of Ring A are optionally and independently replaced by —O—, —N(R)—, or —C(O)—.

In some embodiments, Ring A is an optionally substituted 16 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-. In some embodiments, Ring A is an optionally substituted 16 membered saturated or partially unsaturated ring wherein 2 methylene units of Ring A are optionally and independently replaced by —O— or —C(O)—.

In some embodiments, Ring A is an optionally substituted 17 membered saturated or partially unsaturated ring wherein 1, 2, or 3 methylene units of Ring A are optionally and independently replaced by —O—, —N(R)—, —S—, —C(O)—, —OC(O)—, —C(O)O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-. In some embodiments, Ring A is ambrettolide or a derivative thereof. In certain embodiments, Ring A is an optionally substituted 17 membered saturated or partially unsaturated ring wherein 2 methylene units of Ring A are optionally and independently replaced by —O—, —N(R)—, —S—, —C(O)—, —OC(O)—, —C(O)O—, —OC(O)O—, —S(O)—, —S(O)$_2$—, —OSO$_2$O—, —N(R)C(O)—, —C(O)N(R)—, —N(R)C(O)O—, —OC(O)NR—, —N(R)C(O)NR—, or -Cy$^1$-. In some embodiments, Ring A is an optionally substituted 17 membered saturated or partially unsaturated ring wherein 2 methylene units of Ring A are optionally and independently replaced by —O— or —C(O)—.

As defined above and described herein, each -Cy$^1$- is independently:

a bivalent optionally substituted monocyclic ring independently selected from phenylene, a 3-8 membered saturated or partially unsaturated carbocyclylene, a 5-6 membered heteroarylene having 1-4 heteroatoms independently selected from nitrogen, oxygen, or sulfur, or a 3-8 membered saturated or unsaturated heterocyclylene having 1-4 heteroatoms independently selected from nitrogen, oxygen, or sulfur; or a bivalent optionally substituted bicyclic ring independently selected from a 10 membered arylene, a 7-10 membered saturated or partially unsaturated carbocyclylene, an 8-10 membered heteroarylene having 1-5 heteroatoms independently selected from nitrogen, oxygen, or sulfur, or a 7-10 membered saturated or partially unsaturated heterocyclylene having 1-5 heteroatoms selected from nitrogen, oxygen, or sulfur; or a bivalent optionally substituted tricyclic ring independently selected from a 14 membered arylene, a 9-20 membered saturated or partially unsaturated carbocyclylene, a 9-14 membered heteroarylene having 1-8 heteroatoms independently selected from nitrogen, oxygen, or sulfur, or a 9-20 membered saturated or partially unsaturated heterocyclylene having 1-8 heteroatoms independently selected from nitrogen, oxygen, or sulfur; or a bivalent optionally substituted tetracyclic ring independently selected from a 16-18 membered arylene, an 11-30 membered saturated or partially unsaturated carbocyclylene, a 15-18 membered heteroarylene having 1-8 heteroatoms independently selected from nitrogen, oxygen, or sulfur, or an 11-30 membered saturated or partially unsaturated heterocyclylene having 1-12 heteroatoms independently selected from nitrogen, oxygen, or sulfur.

One of skill in the art will appreciate that when Ring A comprises one or more optionally substituted -Cy$^1$- groups, the present invention contemplates the substitution of any substitutable atom or atoms of the one or more optionally substituted -Cy$^1$- groups with one or more R$^A$, as valency permits.

In some embodiments, -Cy$^1$- is a bivalent optionally substituted monocyclic ring.

In certain embodiments, -Cy$^1$- is bivalent optionally substituted phenylene.

In certain embodiments, -Cy$^1$- is a bivalent optionally substituted 3-8 membered saturated carbocyclylene. In certain embodiments, -Cy$^1$- is a bivalent optionally substituted 3-8 membered partially unsaturated carbocyclylene. In certain embodiments, -Cy$^1$- is a bivalent optionally substituted 5-6 membered saturated carbocyclylene. In certain embodiments, -Cy$^1$- is a bivalent optionally substituted 5-6 membered partially unsaturated carbocyclylene.

In certain embodiments, -Cy$^1$- is a bivalent optionally substituted 5 membered heteroarylene having 1-4 heteroatoms independently selected from nitrogen, oxygen, or sulfur. In certain embodiments, -Cy$^1$- is a bivalent optionally substituted 5 membered heteroarylene having 1-2 heteroatoms independently selected from nitrogen, oxygen, or sulfur. In certain embodiments, -Cy$^1$- is a bivalent optionally substituted 6 membered heteroarylene having 1-4 heteroatoms independently selected from nitrogen, oxygen, or sulfur. In certain embodiments, -Cy$^1$- is a bivalent optionally substituted 6 membered heteroarylene having 1-2 heteroatoms independently selected from nitrogen, oxygen, or sulfur.

In certain embodiments, -Cy$^1$- is a bivalent optionally substituted 3-8 membered saturated heterocyclylene having 1-4 heteroatoms independently selected from nitrogen, oxygen, or sulfur. In certain embodiments, -Cy$^1$- is a bivalent optionally substituted 3-8 membered saturated heterocyclylene having 1-2 heteroatoms independently selected from nitrogen, oxygen, or sulfur. In certain embodiments, -Cy$^1$- is a bivalent optionally substituted 5-6 membered saturated heterocyclylene having 1-4 heteroatoms independently selected from nitrogen, oxygen, or sulfur. In certain embodiments, -Cy$^1$- is a bivalent optionally substituted 5-6 membered saturated heterocyclylene having 1-2 heteroatoms independently selected from nitrogen, oxygen, or sulfur. In certain embodiments, -Cy$^1$- is a bivalent optionally substituted 5 membered saturated heterocyclylene having 1-2 heteroatoms independently selected from nitrogen, oxygen, or sulfur. In certain embodiments, -Cy$^1$- is a bivalent optionally substituted 6 membered saturated heterocyclylene having 1-2 heteroatoms independently selected from nitrogen, oxygen, or sulfur.

In certain embodiments, -Cy$^1$- is a bivalent optionally substituted 3-8 membered unsaturated heterocyclylene having 1-4 heteroatoms independently selected from nitrogen, oxygen, or sulfur. In certain embodiments, -Cy$^1$- is a bivalent optionally substituted 3-8 membered unsaturated heterocyclylene having 1-2 heteroatoms independently selected from nitrogen, oxygen, or sulfur. In certain embodiments, -Cy$^1$- is a bivalent optionally substituted 5-6 membered unsaturated heterocyclylene having 1-4 heteroatoms independently selected from nitrogen, oxygen, or sulfur. In certain embodiments, -Cy$^1$- is a bivalent optionally substituted 5-6 membered unsaturated heterocyclylene having 1-2 heteroatoms independently selected from nitrogen, oxygen, or sulfur. In certain embodiments, -Cy$^1$- is a bivalent optionally substituted 5 membered unsaturated heterocyclylene having 1-2 heteroatoms independently selected from nitrogen, oxygen, or sulfur. In certain embodiments, -Cy$^1$- is a bivalent optionally substituted 6 membered unsaturated heterocyclylene having 1-2 heteroatoms independently selected from nitrogen, oxygen, or sulfur.

In some embodiments, -Cy$^1$- is bivalent optionally substituted naphthylene.

In some embodiments, -Cy$^1$- is a bivalent optionally substituted bicyclic 7-10 membered saturated carbocyclylene. In some embodiments, -Cy$^1$- is a bivalent optionally substituted bicyclic 7 membered saturated carbocyclylene. In some embodiments, -Cy$^1$- is a bivalent optionally substituted bicyclic 8 membered saturated carbocyclylene. In some embodiments, -Cy$^1$- is a bivalent optionally substituted bicyclic 9 membered saturated carbocyclylene. In some embodiments, -Cy$^1$- is a bivalent optionally substituted bicyclic 10 membered saturated carbocyclylene.

In some embodiments, -Cy$^1$- is a bivalent optionally substituted bicyclic 7-10 membered partially unsaturated carbocyclylene. In some embodiments, -Cy$^1$- is a bivalent optionally substituted bicyclic 7 membered partially unsaturated carbocyclylene. In some embodiments, -Cy$^1$- is a bivalent optionally substituted bicyclic 8 membered partially unsaturated carbocyclylene. In some embodiments, -Cy$^1$- is a bivalent optionally substituted bicyclic 9 membered partially unsaturated carbocyclylene. In some embodiments, -Cy$^1$- is a bivalent optionally substituted bicyclic 10 membered partially unsaturated carbocyclylene.

In some embodiments, -Cy$^1$- is a bivalent optionally substituted bicyclic 8-10 membered heteroarylene having 1-5 heteroatoms independently selected from nitrogen, oxygen, or sulfur. In some embodiments, -Cy$^1$- is a bivalent optionally substituted bicyclic 8-10 membered heteroarylene having 1-2 heteroatoms independently selected from nitrogen, oxygen, or sulfur. In some embodiments, -Cy$^1$- is a bivalent optionally substituted bicyclic 8 membered heteroarylene having 1-5 heteroatoms independently selected from nitrogen, oxygen, or sulfur. In some embodiments, -Cy$^1$- is a bivalent optionally substituted bicyclic 8 membered heteroarylene having 1-2 heteroatoms independently selected from nitrogen, oxygen, or sulfur. In some embodiments, -Cy$^1$- is a bivalent optionally substituted bicyclic 9 membered heteroarylene having 1-5 heteroatoms independently selected from nitrogen, oxygen, or sulfur. In some embodiments, -Cy$^1$- is a bivalent optionally substituted bicyclic 9 membered heteroarylene having 1-2 heteroatoms independently selected from nitrogen, oxygen, or sulfur. In some embodiments, -Cy$^1$- is a bivalent optionally substituted bicyclic 10 membered heteroarylene having 1-5 heteroatoms independently selected from nitrogen, oxygen, or sulfur. In some embodiments, -Cy$^1$- is a bivalent optionally substituted bicyclic 10 membered heteroarylene having 1-2 heteroatoms independently selected from nitrogen, oxygen, or sulfur.

In some embodiments, -Cy$^1$- is a bivalent optionally substituted bicyclic 7-10 membered saturated heterocyclylene having 1-5 heteroatoms selected from nitrogen, oxygen, or sulfur. In some embodiments, -Cy$^1$- is a bivalent optionally substituted bicyclic 7-10 membered saturated heterocyclylene having 1-2 heteroatoms selected from nitrogen, oxygen, or sulfur. In some embodiments, -Cy$^1$- is a bivalent optionally substituted bicyclic 7 membered saturated heterocyclylene having 1-5 heteroatoms selected from nitrogen, oxygen, or sulfur. In some embodiments, -Cy$^1$- is a bivalent optionally substituted bicyclic 7 membered saturated heterocyclylene having 1-2 heteroatoms selected from nitrogen, oxygen, or sulfur. In some embodiments, -Cy$^1$- is a bivalent optionally substituted bicyclic 8 membered saturated heterocyclylene having 1-5 heteroatoms selected from nitrogen, oxygen, or sulfur. In some embodiments, -Cy$^1$- is a bivalent optionally substituted bicyclic 8 membered saturated heterocyclylene having 1-2 heteroatoms selected from nitrogen, oxygen, or sulfur. In some embodiments, -Cy$^1$- is a bivalent optionally substituted bicyclic 9 membered saturated heterocyclylene having 1-5 heteroatoms selected from nitrogen, oxygen, or sulfur. In some embodiments, -Cy$^1$- is a bivalent optionally substituted bicyclic 9 membered saturated heterocyclylene having 1-2 heteroatoms selected from nitrogen, oxygen, or sulfur. In some embodiments, -Cy$^1$- is a bivalent optionally substituted bicyclic 10 membered saturated heterocyclylene having 1-5 heteroatoms selected from nitrogen, oxygen, or sulfur. In some embodiments, -Cy$^1$- is a bivalent optionally substituted bicyclic 10 membered saturated heterocyclylene having 1-2 heteroatoms selected from nitrogen, oxygen, or sulfur.

In some embodiments, -Cy$^1$- is a bivalent optionally substituted bicyclic 7-10 membered partially unsaturated heterocyclylene having 1-5 heteroatoms selected from nitrogen, oxygen, or sulfur. In some embodiments, -Cy$^1$- is a bivalent optionally substituted bicyclic 7-10 membered partially unsaturated heterocyclylene having 1-2 heteroatoms selected from nitrogen, oxygen, or sulfur. In some embodiments, -Cy$^1$- is a bivalent optionally substituted bicyclic 7 membered partially unsaturated heterocyclylene having 1-5 heteroatoms selected from nitrogen, oxygen, or sulfur. In some embodiments, -Cy$^1$- is a bivalent optionally substituted bicyclic 7 membered partially unsaturated heterocyclylene having 1-2 heteroatoms selected from nitrogen, oxygen, or sulfur. In some embodiments, -Cy$^1$- is a bivalent optionally substituted bicyclic 8 membered partially unsaturated heterocyclylene having 1-5 heteroatoms selected from nitrogen, oxygen, or sulfur. In some embodiments, -Cy$^1$- is a bivalent optionally substituted bicyclic 8 membered partially unsaturated heterocyclylene having 1-2 heteroatoms selected from nitrogen, oxygen, or sulfur. In some embodiments, -Cy$^1$- is a bivalent optionally substituted bicyclic 9 membered partially unsaturated heterocyclylene having 1-5 heteroatoms selected from nitrogen, oxygen, or sulfur. In some embodiments, -Cy$^1$- is a bivalent optionally substituted bicyclic 9 membered partially unsaturated heterocyclylene having 1-2 heteroatoms selected from nitrogen, oxygen, or sulfur. In some embodiments, -Cy$^1$- is a bivalent optionally substituted bicyclic 10 membered partially unsaturated heterocyclylene having 1-5 heteroatoms selected from nitrogen, oxygen, or sulfur. In some embodiments, -Cy$^1$- is a bivalent optionally substituted bicyclic 10 membered partially unsaturated heterocyclylene having 1-2 heteroatoms selected from nitrogen, oxygen, or sulfur.

In some embodiments, -Cy$^1$- is a bivalent optionally substituted tricyclic 14 membered arylene.

In some embodiments, -Cy$^1$- is a bivalent optionally substituted tricyclic 9-20 membered saturated carbocyclylene. In some embodiments, -Cy$^1$- is a bivalent optionally substituted tricyclic 10-20 membered saturated carbocyclylene. In some embodiments, -Cy$^1$- is a bivalent optionally substituted tricyclic 12-20 membered saturated carbocyclylene. In some embodiments, -Cy$^1$- is a bivalent optionally substituted tricyclic 12-18 membered saturated carbocyclylene. In some embodiments, -Cy$^1$- is a bivalent optionally substituted tricyclic 12-14 membered saturated carbocyclylene. In some embodiments, -Cy$^1$- is a bivalent optionally substituted tricyclic 14-16 membered saturated carbocyclylene. In some embodiments, -Cy$^1$- is a bivalent optionally substituted tricyclic 16-18 membered saturated carbocyclylene.

In some embodiments, -Cy$^1$- is a bivalent optionally substituted tricyclic 9-20 membered partially unsaturated carbocyclylene. In some embodiments, -Cy$^1$- is a bivalent optionally substituted tricyclic 10-20 membered partially unsaturated carbocyclylene. In some embodiments, -Cy$^1$- is a bivalent optionally substituted tricyclic 12-20 membered partially unsaturated carbocyclylene. In some embodiments, -Cy$^1$- is a bivalent optionally substituted tricyclic 12-18 membered partially unsaturated carbocyclylene. In some embodiments, -Cy$^1$- is a bivalent optionally substituted tricyclic 12-14 membered partially unsaturated carbocyclylene. In some embodiments, -Cy$^1$- is a bivalent optionally substituted tricyclic 14-16 membered partially unsaturated carbocyclylene. In some embodiments, -Cy$^1$- is a bivalent optionally substituted tricyclic 16-18 membered partially unsaturated carbocyclylene.

In some embodiments, -Cy$^1$- is a bivalent optionally substituted tricyclic 9-14 membered heteroarylene having 1-8 heteroatoms independently selected from nitrogen, oxygen, or sulfur. In some embodiments, -Cy$^1$- is a bivalent optionally substituted tricyclic 9-14 membered heteroarylene having 1-6 heteroatoms independently selected from nitrogen, oxygen, or sulfur. In some embodiments, -Cy$^1$- is a bivalent optionally substituted tricyclic 9-14 membered heteroarylene having 1-4 heteroatoms independently selected from nitrogen, oxygen, or sulfur. In some embodiments, -Cy$^1$- is a bivalent optionally substituted tricyclic 9-14 membered heteroarylene having 1-3 heteroatoms independently selected from nitrogen, oxygen, or sulfur. In some embodiments, -Cy$^1$- is a bivalent optionally substituted tricyclic 9-14 membered heteroarylene having 2-4 heteroatoms independently selected from nitrogen, oxygen, or sulfur. In some embodiments, -Cy$^1$- is a bivalent optionally substituted tricyclic 9-14 membered heteroarylene having 4-6 heteroatoms independently selected from nitrogen, oxygen, or sulfur.

In some embodiments, -Cy$^1$- is a bivalent optionally substituted tricyclic 10-14 membered heteroarylene having 1-8 heteroatoms independently selected from nitrogen, oxygen, or sulfur. In some embodiments, -Cy$^1$- is a bivalent optionally substituted tricyclic 10-14 membered heteroarylene having 1-6 heteroatoms independently selected from nitrogen, oxygen, or sulfur. In some embodiments, -Cy$^1$- is a bivalent optionally substituted tricyclic 10-14 membered heteroarylene having 1-4 heteroatoms independently selected from nitrogen, oxygen, or sulfur. In some embodiments, -Cy$^1$- is a bivalent optionally substituted tricyclic 10-14 membered heteroarylene having 1-3 heteroatoms independently selected from nitrogen, oxygen, or sulfur. In some embodiments, -Cy$^1$- is a bivalent optionally substituted tricyclic 10-14 membered heteroarylene having 2-4 heteroatoms independently selected from nitrogen, oxygen, or sulfur. In some embodiments, -Cy$^1$- is a bivalent optionally substituted tricyclic 10-14 membered heteroarylene having 4-6 heteroatoms independently selected from nitrogen, oxygen, or sulfur.

In some embodiments, -Cy$^1$- is a bivalent optionally substituted tricyclic 12-14 membered heteroarylene having 1-8 heteroatoms independently selected from nitrogen, oxygen, or sulfur. In some embodiments, -Cy$^1$- is a bivalent optionally substituted tricyclic 12-14 membered heteroarylene having 1-6 heteroatoms independently selected from nitrogen, oxygen, or sulfur. In some embodiments, -Cy$^1$- is a bivalent optionally substituted tricyclic 12-14 membered heteroarylene having 1-4 heteroatoms independently selected from nitrogen, oxygen, or sulfur. In some embodiments, -Cy$^1$- is a bivalent optionally substituted tricyclic 12-14 membered heteroarylene having 1-3 heteroatoms independently selected from nitrogen, oxygen, or sulfur. In some embodiments, -Cy$^1$- is a bivalent optionally substituted tricyclic 12-14 membered heteroarylene having 2-4 heteroatoms independently selected from nitrogen, oxygen, or sulfur. In some embodiments, -Cy$^1$- is a bivalent optionally substituted tricyclic 12-14 membered heteroarylene having 4-6 heteroatoms independently selected from nitrogen, oxygen, or sulfur.

In some embodiments, -Cy$^1$- is a bivalent optionally substituted tricyclic 9-20 membered saturated heterocyclylene having 1-8 heteroatoms independently selected from nitrogen, oxygen, or sulfur. In some embodiments, -Cy$^1$- is a bivalent optionally substituted tricyclic 9-20 membered saturated heterocyclylene having 1-6 heteroatoms independently selected from nitrogen, oxygen, or sulfur. In some embodiments, -Cy$^1$- is a bivalent optionally substituted tricyclic 9-20 membered saturated heterocyclylene having 1-4 heteroatoms independently selected from nitrogen, oxygen, or sulfur. In some embodiments, -Cy$^1$- is a bivalent optionally substituted tricyclic 9-20 membered saturated heterocyclylene having 1-3 heteroatoms independently selected from nitrogen, oxygen, or sulfur. In some embodiments, -Cy$^1$- is a bivalent optionally substituted tricyclic 9-20 membered saturated heterocyclylene having 2-4 heteroatoms independently selected from nitrogen, oxygen, or sulfur. In some embodiments, -Cy$^1$- is a bivalent optionally substituted tricyclic 9-20 membered saturated heterocyclylene having 4-6 heteroatoms independently selected from nitrogen, oxygen, or sulfur.

In some embodiments, -Cy$^1$- is a bivalent optionally substituted tricyclic 12-20 membered saturated heterocyclylene having 1-8 heteroatoms independently selected from nitrogen, oxygen, or sulfur. In some embodiments, -Cy$^1$- is a bivalent optionally substituted tricyclic 12-20 membered saturated heterocyclylene having 1-6 heteroatoms independently selected from nitrogen, oxygen, or sulfur. In some embodiments, -Cy$^1$- is a bivalent optionally substituted tricyclic 12-20 membered saturated heterocyclylene having 1-4 heteroatoms independently selected from nitrogen, oxygen, or sulfur. In some embodiments, -Cy$^1$- is a bivalent optionally substituted tricyclic 12-20 membered saturated heterocyclylene having 1-3 heteroatoms independently selected from nitrogen, oxygen, or sulfur. In some embodiments, -Cy$^1$- is a bivalent optionally substituted tricyclic 12-20 membered saturated heterocyclylene having 2-4 heteroatoms independently selected from nitrogen, oxygen, or sulfur. In some embodiments, -Cy$^1$- is a bivalent optionally substituted tricyclic 12-20 membered saturated heterocyclylene having 4-6 heteroatoms independently selected from nitrogen, oxygen, or sulfur.

In some embodiments, -Cy$^1$- is a bivalent optionally substituted tricyclic 12-18 membered saturated heterocyclylene having 1-8 heteroatoms independently selected from nitrogen, oxygen, or sulfur. In some embodiments, -Cy$^1$- is a bivalent optionally substituted tricyclic 12-18 membered saturated heterocyclylene having 1-6 heteroatoms independently selected from nitrogen, oxygen, or sulfur. In some embodiments, -Cy$^1$- is a bivalent optionally substituted tricyclic 12-18 membered saturated heterocyclylene having 1-4 heteroatoms independently selected from nitrogen, oxygen, or sulfur. In some embodiments, -Cy$^1$- is a bivalent optionally substituted tricyclic 12-18 membered saturated heterocyclylene having 1-3 heteroatoms independently selected from nitrogen, oxygen, or sulfur. In some embodiments, -Cy$^1$- is a bivalent optionally substituted tricyclic 12-18 membered saturated heterocyclylene having 2-4 heteroatoms independently selected from nitrogen, oxygen, or sulfur. In some embodiments, -Cy$^1$- is a bivalent optionally substituted tricyclic 12-18 membered saturated heterocyclylene having 4-6 heteroatoms independently selected from nitrogen, oxygen, or sulfur.

In some embodiments, -Cy$^1$- is a bivalent optionally substituted tricyclic 12-14 membered saturated heterocyclylene having 1-8 heteroatoms independently selected from nitrogen, oxygen, or sulfur. In some embodiments, -Cy$^1$- is a bivalent optionally substituted tricyclic 12-14 membered saturated heterocyclylene having 1-6 heteroatoms independently selected from nitrogen, oxygen, or sulfur. In some embodiments, -Cy$^1$- is a bivalent optionally substituted tricyclic 12-14 membered saturated heterocyclylene having 1-4 heteroatoms independently selected from nitrogen, oxygen, or sulfur. In some embodiments, -Cy$^1$- is a bivalent optionally substituted tricyclic 12-14 membered saturated heterocyclylene having 1-3 heteroatoms independently selected from nitrogen, oxygen, or sulfur. In some embodiments, -Cy$^1$- is a bivalent optionally substituted tricyclic 12-14 membered saturated heterocyclylene having 2-4 heteroatoms independently selected from nitrogen, oxygen, or sulfur. In some embodiments, -Cy$^1$- is a bivalent optionally substituted tricyclic 12-14 membered saturated heterocyclylene having 4-6 heteroatoms independently selected from nitrogen, oxygen, or sulfur.

In some embodiments, -Cy$^1$- is a bivalent optionally substituted tricyclic 14-16 membered saturated heterocyclylene having 1-8 heteroatoms independently selected from nitrogen, oxygen, or sulfur. In some embodiments, -Cy$^1$- is a bivalent optionally substituted tricyclic 14-16 membered saturated heterocyclylene having 1-6 heteroatoms independently selected from nitrogen, oxygen, or sulfur. In some embodiments, -Cy$^1$- is a bivalent optionally substituted tricyclic 14-16 membered saturated heterocyclylene having 1-4 heteroatoms independently selected from nitrogen, oxygen, or sulfur. In some embodiments, -Cy$^1$- is a bivalent optionally substituted tricyclic 14-16 membered saturated heterocyclylene having 1-3 heteroatoms independently selected from nitrogen, oxygen, or sulfur. In some embodiments, -Cy$^1$- is a bivalent optionally substituted tricyclic 14-16 membered saturated heterocyclylene having 2-4 heteroatoms independently selected from nitrogen, oxygen, or sulfur. In some embodiments, -Cy$^1$- is a bivalent optionally substituted tricyclic 14-16 membered saturated heterocyclylene having 4-6 heteroatoms independently selected from nitrogen, oxygen, or sulfur.

In some embodiments, -Cy$^1$- is a bivalent optionally substituted tricyclic 16-18 membered saturated heterocyclylene having 1-8 heteroatoms independently selected from nitrogen, oxygen, or sulfur. In some embodiments, -Cy$^1$- is a bivalent optionally substituted tricyclic 16-18 membered saturated heterocyclylene having 1-6 heteroatoms independently selected from nitrogen, oxygen, or sulfur. In some embodiments, -Cy$^1$- is a bivalent optionally substituted tricyclic 16-18 membered saturated heterocyclylene having 1-4 heteroatoms independently selected from nitrogen, oxygen, or sulfur. In some embodiments, -Cy$^1$- is a bivalent optionally substituted tricyclic 16-18 membered saturated heterocyclylene having 1-3 heteroatoms independently selected from nitrogen, oxygen, or sulfur. In some embodiments, -Cy$^1$- is a bivalent optionally substituted tricyclic 16-18 membered saturated heterocyclylene having 2-4 heteroatoms independently selected from nitrogen, oxygen, or sulfur. In some embodiments, -Cy$^1$- is a bivalent optionally substituted tricyclic 16-18 membered saturated heterocyclylene having 4-6 heteroatoms independently selected from nitrogen, oxygen, or sulfur.

In some embodiments, -Cy$^1$- is a bivalent optionally substituted tricyclic 9-20 membered partially unsaturated heterocyclylene having 1-8 heteroatoms independently selected from nitrogen, oxygen, or sulfur. In some embodiments, -Cy$^1$- is a bivalent optionally substituted tricyclic 9-20 membered partially unsaturated heterocyclylene having 1-6 heteroatoms independently selected from nitrogen, oxygen, or sulfur. In some embodiments, -Cy$^1$- is a bivalent optionally substituted tricyclic 9-20 membered partially unsaturated heterocyclylene having 1-4 heteroatoms independently selected from nitrogen, oxygen, or sulfur. In some embodiments, -Cy$^1$- is a bivalent optionally substituted tricyclic 9-20 membered partially unsaturated heterocyclylene having 1-3 heteroatoms independently selected from nitrogen, oxygen, or sulfur. In some embodiments, -Cy$^1$- is a bivalent optionally substituted tricyclic 9-20 membered partially unsaturated heterocyclylene having 2-4 heteroatoms independently selected from nitrogen, oxygen, or sulfur. In some embodiments, -Cy$^1$- is a bivalent optionally substituted tricyclic 9-20 membered partially unsaturated heterocyclylene having 4-6 heteroatoms independently selected from nitrogen, oxygen, or sulfur.

In some embodiments, -Cy$^1$- is a bivalent optionally substituted tricyclic 12-20 membered partially unsaturated heterocyclylene having 1-8 heteroatoms independently selected from nitrogen, oxygen, or sulfur. In some embodiments, -Cy$^1$- is a bivalent optionally substituted tricyclic 12-20 membered partially unsaturated heterocyclylene having 1-6 heteroatoms independently selected from nitrogen, oxygen, or sulfur. In some embodiments, -Cy$^1$- is a bivalent optionally substituted tricyclic 12-20 membered partially unsaturated heterocyclylene having 1-4 heteroatoms independently selected from nitrogen, oxygen, or sulfur. In some embodiments, -Cy$^1$- is a bivalent optionally substituted tricyclic 12-20 membered partially unsaturated heterocyclylene having 1-3 heteroatoms independently selected from nitrogen, oxygen, or sulfur. In some embodiments, -Cy$^1$- is a bivalent optionally substituted tricyclic 12-20 membered partially unsaturated heterocyclylene having 2-4 heteroatoms independently selected from nitrogen, oxygen, or sulfur. In some embodiments, -Cy$^1$- is a bivalent optionally substituted tricyclic 12-20 membered partially unsaturated heterocyclylene having 4-6 heteroatoms independently selected from nitrogen, oxygen, or sulfur.

In some embodiments, -Cy$^1$- is a bivalent optionally substituted tricyclic 12-18 membered partially unsaturated heterocyclylene having 1-8 heteroatoms independently selected from nitrogen, oxygen, or sulfur. In some embodiments, -Cy$^1$- is a bivalent optionally substituted tricyclic 12-18 membered partially unsaturated heterocyclylene having 1-6 heteroatoms independently selected from nitrogen, oxygen, or sulfur. In some embodiments, -Cy$^1$- is a bivalent optionally substituted tricyclic 12-18 membered partially unsaturated heterocyclylene having 1-4 heteroatoms independently selected from nitrogen, oxygen, or sulfur. In some embodiments, -Cy$^1$- is a bivalent optionally substituted tricyclic 12-18 membered partially unsaturated heterocyclylene having 1-3 heteroatoms independently selected from nitrogen, oxygen, or sulfur. In some embodiments, -Cy$^1$- is a bivalent optionally substituted tricyclic 12-18 membered partially unsaturated heterocyclylene having 2-4 heteroatoms independently selected from nitrogen, oxygen, or sulfur. In some embodiments, -Cy$^1$- is a bivalent optionally substituted tricyclic 12-18 membered partially unsaturated heterocyclylene having 4-6 heteroatoms independently selected from nitrogen, oxygen, or sulfur.

In some embodiments, -Cy$^1$- is a bivalent optionally substituted tricyclic 12-14 membered partially unsaturated heterocyclylene having 1-8 heteroatoms independently selected from nitrogen, oxygen, or sulfur. In some embodiments, -Cy$^1$- is a bivalent optionally substituted tricyclic 12-14 membered partially unsaturated heterocyclylene having 1-6 heteroatoms independently selected from nitrogen, oxygen, or sulfur. In some embodiments, -Cy$^1$- is a bivalent optionally substituted tricyclic 12-14 membered partially unsaturated heterocyclylene having 1-4 heteroatoms independently selected from nitrogen, oxygen, or sulfur. In some embodiments, -Cy$^1$- is a bivalent optionally substituted tricyclic 12-14 membered partially unsaturated heterocyclylene having 1-3 heteroatoms independently selected from nitrogen, oxygen, or sulfur. In some embodiments, -Cy$^1$- is a bivalent optionally substituted tricyclic 12-14 membered partially unsaturated heterocyclylene having 2-4 heteroatoms independently selected from nitrogen, oxygen, or sulfur. In some embodiments, -Cy$^1$- is a bivalent optionally substituted tricyclic 12-14 membered partially unsaturated heterocyclylene having 4-6 heteroatoms independently selected from nitrogen, oxygen, or sulfur.

In some embodiments, -Cy$^1$- is a bivalent optionally substituted tricyclic 14-16 membered partially unsaturated heterocyclylene having 1-8 heteroatoms independently selected from nitrogen, oxygen, or sulfur. In some embodiments, -Cy$^1$- is a bivalent optionally substituted tricyclic 14-16 membered partially unsaturated heterocyclylene having 1-6 heteroatoms independently selected from nitrogen, oxygen, or sulfur. In some embodiments, -Cy$^1$- is a bivalent optionally substituted tricyclic 14-16 membered partially unsaturated heterocyclylene having 1-4 heteroatoms independently selected from nitrogen, oxygen, or sulfur. In some embodiments, -Cy$^1$- is a bivalent optionally substituted tricyclic 14-16 membered partially unsaturated heterocyclylene having 1-3 heteroatoms independently selected from nitrogen, oxygen, or sulfur. In some embodiments, -Cy$^1$- is a bivalent optionally substituted tricyclic 14-16 membered partially unsaturated heterocyclylene having 2-4 heteroatoms independently selected from nitrogen, oxygen, or sulfur. In some embodiments, -Cy$^1$- is a bivalent optionally substituted tricyclic 14-16 membered partially unsaturated heterocyclylene having 4-6 heteroatoms independently selected from nitrogen, oxygen, or sulfur.

In some embodiments, -Cy$^1$- is a bivalent optionally substituted tricyclic 16-18 membered partially unsaturated heterocyclylene having 1-8 heteroatoms independently selected from nitrogen, oxygen, or sulfur. In some embodiments, -Cy$^1$- is a bivalent optionally substituted tricyclic 16-18 membered partially unsaturated heterocyclylene having 1-6 heteroatoms independently selected from nitrogen, oxygen, or sulfur. In some embodiments, -Cy$^1$- is a bivalent optionally substituted tricyclic 16-18 membered partially unsaturated heterocyclylene having 1-4 heteroatoms independently selected from nitrogen, oxygen, or sulfur. In some embodiments, -Cy$^1$- is a bivalent optionally substituted tricyclic 16-18 membered partially unsaturated heterocyclylene having 1-3 heteroatoms independently selected from nitrogen, oxygen, or sulfur. In some embodiments, -Cy$^1$- is a bivalent optionally substituted tricyclic 16-18 membered partially unsaturated heterocyclylene having 2-4 heteroatoms independently selected from nitrogen, oxygen, or sulfur. In some embodiments, -Cy$^1$- is a bivalent optionally substituted tricyclic 16-18 membered partially unsaturated heterocyclylene having 4-6 heteroatoms independently selected from nitrogen, oxygen, or sulfur.

In some embodiments, -Cy$^1$- is a bivalent optionally substituted tetracyclic 16-18 membered arylene.

In some embodiments, -Cy$^1$- is a bivalent optionally substituted tetracyclic 11-30 membered saturated carbocyclylene. In some embodiments, -Cy$^1$- is a bivalent optionally substituted tetracyclic 11-25 membered saturated carbocyclylene. In some embodiments, -Cy$^1$- is a bivalent optionally substituted tetracyclic 12-24 membered saturated carbocyclylene. In some embodiments, -Cy$^1$- is a bivalent optionally substituted tetracyclic 14-24 membered saturated carbocyclylene. In some embodiments, -Cy$^1$- is a bivalent optionally substituted tetracyclic 15-20 membered saturated carbocyclylene. In some embodiments, -Cy$^1$- is a bivalent optionally substituted tetracyclic 20-24 membered saturated carbocyclylene.

In some embodiments, -Cy$^1$- is a bivalent optionally substituted tetracyclic 11-30 membered partially unsaturated carbocyclylene. In some embodiments, -Cy$^1$- is a bivalent optionally substituted tetracyclic 11-25 membered partially unsaturated carbocyclylene. In some embodiments, -Cy$^1$- is a bivalent optionally substituted tetracyclic 12-24 membered partially unsaturated carbocyclylene. In some embodiments, -Cy$^1$- is a bivalent optionally substituted tetracyclic 14-24 membered partially unsaturated carbocyclylene. In some embodiments, -Cy$^1$- is a bivalent optionally substituted tetracyclic 15-20 membered partially unsaturated carbocyclylene. In some embodiments, -Cy$^1$- is a bivalent optionally substituted tetracyclic 20-24 membered partially unsaturated carbocyclylene.

In some embodiments, -Cy$^1$- is a bivalent optionally substituted tetracyclic 15-18 membered heteroarylene having 1-8 heteroatoms independently selected from nitrogen, oxygen, or sulfur. In some embodiments, -Cy$^1$- is a bivalent optionally substituted tetracyclic 15-18 membered heteroarylene having 1-6 heteroatoms independently selected from nitrogen, oxygen, or sulfur. In some embodiments, -$Cy^1$- is a bivalent optionally substituted tetracyclic 15-18 membered heteroarylene having 1-4 heteroatoms independently selected from nitrogen, oxygen, or sulfur. In some embodiments, -$Cy^1$- is a bivalent optionally substituted tetracyclic 15-18 membered heteroarylene having 1-3 heteroatoms independently selected from nitrogen, oxygen, or sulfur. In some embodiments, -$Cy^1$- is a bivalent optionally substituted tetracyclic 15-18 membered heteroarylene having 2-4 heteroatoms independently selected from nitrogen, oxygen, or sulfur. In some embodiments, -$Cy^1$- is a bivalent optionally substituted tetracyclic 15-18 membered heteroarylene having 4-8 heteroatoms independently selected from nitrogen, oxygen, or sulfur.

In certain embodiments, -$Cy^1$- is a bivalent optionally substituted tetracyclic 15-18 membered heteroarylene having 3 heteroatoms independently selected from nitrogen, oxygen, or sulfur. In certain embodiments, -$Cy^1$- is a bivalent optionally substituted tetracyclic 15 membered heteroarylene having 3 heteroatoms independently selected from nitrogen, oxygen, or sulfur. In certain embodiments, -$Cy^1$- is a bivalent tetracyclic 15 membered heteroarylene having 3 heteroatoms independently selected from nitrogen, oxygen, or sulfur, wherein -$Cy^1$- is substituted with at least two R groups. In certain embodiments, -$Cy^1$- is a bivalent tetracyclic 15 membered heteroarylene having 3 heteroatoms independently selected from oxygen and nitrogen, wherein -$Cy^1$- is substituted with at least two R groups, and wherein the at least two R groups are on adjacent atoms and are taken together with their intervening atoms to form an optionally substituted 3-8 membered saturated, partially unsaturated, or aryl ring having 0-4 heteroatoms independently selected from nitrogen, oxygen, or sulfur. In certain embodiments, -$Cy^1$- is a bivalent tetracyclic 15 membered heteroarylene having 3 heteroatoms independently selected from oxygen or nitrogen, wherein -$Cy^1$- is substituted with at least two R groups, and wherein the at least two R groups are on adjacent atoms and are taken together with their intervening atoms to form an optionally substituted 8 membered partially unsaturated ring having 1 heteroatom independently selected from nitrogen, oxygen, or sulfur. In certain embodiments, the one heteroatom of the above described optionally substituted 8 membered partially unsaturated ring is nitrogen.

In some embodiments, -$Cy^1$- is a bivalent optionally substituted tetracyclic 11-30 membered saturated heterocyclylene having 1-12 heteroatoms independently selected from nitrogen, oxygen, or sulfur. In some embodiments, -$Cy^1$- is a bivalent optionally substituted tetracyclic 11-30 membered saturated heterocyclylene having 1-10 heteroatoms independently selected from nitrogen, oxygen, or sulfur. In some embodiments, -$Cy^1$- is a bivalent optionally substituted tetracyclic 11-30 membered saturated heterocyclylene having 1-8 heteroatoms independently selected from nitrogen, oxygen, or sulfur. In some embodiments, -$Cy^1$- is a bivalent optionally substituted tetracyclic 11-30 membered saturated heterocyclylene having 1-6 heteroatoms independently selected from nitrogen, oxygen, or sulfur. In some embodiments, -$Cy^1$- is a bivalent optionally substituted tetracyclic 11-30 membered saturated heterocyclylene having 1-4 heteroatoms independently selected from nitrogen, oxygen, or sulfur. In some embodiments, -$Cy^1$- is a bivalent optionally substituted tetracyclic 11-30 membered saturated heterocyclylene having 1-3 heteroatoms independently selected from nitrogen, oxygen, or sulfur. In some embodiments, -$Cy^1$- is a bivalent optionally substituted tetracyclic 11-30 membered saturated heterocyclylene having 4-6 heteroatoms independently selected from nitrogen, oxygen, or sulfur. In some embodiments, -$Cy^1$- is a bivalent optionally substituted tetracyclic 11-30 membered saturated heterocyclylene having 4-8 heteroatoms independently selected from nitrogen, oxygen, or sulfur. In some embodiments, -$Cy^1$- is a bivalent optionally substituted tetracyclic 11-30 membered saturated heterocyclylene having 6-8 heteroatoms independently selected from nitrogen, oxygen, or sulfur.

In some embodiments, -$Cy^1$- is a bivalent optionally substituted tetracyclic 11-25 membered saturated heterocyclylene having 1-12 heteroatoms independently selected from nitrogen, oxygen, or sulfur. In some embodiments, -$Cy^1$- is a bivalent optionally substituted tetracyclic 11-25 membered saturated heterocyclylene having 1-10 heteroatoms independently selected from nitrogen, oxygen, or sulfur. In some embodiments, -$Cy^1$- is a bivalent optionally substituted tetracyclic 11-25 membered saturated heterocyclylene having 1-8 heteroatoms independently selected from nitrogen, oxygen, or sulfur. In some embodiments, -$Cy^1$- is a bivalent optionally substituted tetracyclic 11-25 membered saturated heterocyclylene having 1-6 heteroatoms independently selected from nitrogen, oxygen, or sulfur. In some embodiments, -$Cy^1$- is a bivalent optionally substituted tetracyclic 11-25 membered saturated heterocyclylene having 1-4 heteroatoms independently selected from nitrogen, oxygen, or sulfur. In some embodiments, -$Cy^1$- is a bivalent optionally substituted tetracyclic 11-25 membered saturated heterocyclylene having 1-3 heteroatoms independently selected from nitrogen, oxygen, or sulfur. In some embodiments, -$Cy^1$- is a bivalent optionally substituted tetracyclic 11-25 membered saturated heterocyclylene having 4-6 heteroatoms independently selected from nitrogen, oxygen, or sulfur. In some embodiments, -$Cy^1$- is a bivalent optionally substituted tetracyclic 11-25 membered saturated heterocyclylene having 4-8 heteroatoms independently selected from nitrogen, oxygen, or sulfur. In some embodiments, -$Cy^1$- is a bivalent optionally substituted tetracyclic 11-25 membered saturated heterocyclylene having 6-8 heteroatoms independently selected from nitrogen, oxygen, or sulfur.

In some embodiments, -$Cy^1$- is a bivalent optionally substituted tetracyclic 12-24 membered saturated heterocyclylene having 1-12 heteroatoms independently selected from nitrogen, oxygen, or sulfur. In some embodiments, -$Cy^1$- is a bivalent optionally substituted tetracyclic 12-24 membered saturated heterocyclylene having 1-10 heteroatoms independently selected from nitrogen, oxygen, or sulfur. In some embodiments, -$Cy^1$- is a bivalent optionally substituted tetracyclic 12-24 membered saturated heterocyclylene having 1-8 heteroatoms independently selected from nitrogen, oxygen, or sulfur. In some embodiments, -$Cy^1$- is a bivalent optionally substituted tetracyclic 12-24 membered saturated heterocyclylene having 1-6 heteroatoms independently selected from nitrogen, oxygen, or sulfur. In some embodiments, -$Cy^1$- is a bivalent optionally substituted tetracyclic 12-24 membered saturated heterocyclylene having 1-4 heteroatoms independently selected from nitrogen, oxygen, or sulfur. In some embodiments, -$Cy^1$- is a bivalent optionally substituted tetracyclic 12-24 membered saturated heterocyclylene having 1-3 heteroatoms independently selected from nitrogen, oxygen, or sulfur. In some embodiments, -$Cy^1$- is a bivalent optionally substituted tetracyclic 12-24 membered saturated heterocyclylene having 4-6 heteroatoms independently selected from nitrogen, oxygen, or sulfur. In some embodiments, -$Cy^1$- is a bivalent optionally substituted tetracyclic 12-24 membered saturated heterocyclylene having 4-8 heteroatoms independently selected from nitrogen, oxygen, or sulfur. In some embodiments, -Cy$^1$- is a bivalent optionally substituted tetracyclic 12-24 membered saturated heterocyclylene having 6-8 heteroatoms independently selected from nitrogen, oxygen, or sulfur.

In some embodiments, -Cy$^1$- is a bivalent optionally substituted tetracyclic 15-20 membered saturated heterocyclylene having 1-12 heteroatoms independently selected from nitrogen, oxygen, or sulfur. In some embodiments, -Cy$^1$- is a bivalent optionally substituted tetracyclic 15-20 membered saturated heterocyclylene having 1-10 heteroatoms independently selected from nitrogen, oxygen, or sulfur. In some embodiments, -Cy$^1$- is a bivalent optionally substituted tetracyclic 15-20 membered saturated heterocyclylene having 1-8 heteroatoms independently selected from nitrogen, oxygen, or sulfur. In some embodiments, -Cy$^1$- is a bivalent optionally substituted tetracyclic 15-20 membered saturated heterocyclylene having 1-6 heteroatoms independently selected from nitrogen, oxygen, or sulfur. In some embodiments, -Cy$^1$- is a bivalent optionally substituted tetracyclic 15-20 membered saturated heterocyclylene having 1-4 heteroatoms independently selected from nitrogen, oxygen, or sulfur. In some embodiments, -Cy$^1$- is a bivalent optionally substituted tetracyclic 15-20 membered saturated heterocyclylene having 1-3 heteroatoms independently selected from nitrogen, oxygen, or sulfur. In some embodiments, -Cy$^1$- is a bivalent optionally substituted tetracyclic 15-20 membered saturated heterocyclylene having 4-6 heteroatoms independently selected from nitrogen, oxygen, or sulfur. In some embodiments, -Cy$^1$- is a bivalent optionally substituted tetracyclic 15-20 membered saturated heterocyclylene having 4-8 heteroatoms independently selected from nitrogen, oxygen, or sulfur. In some embodiments, -Cy$^1$- is a bivalent optionally substituted tetracyclic 15-20 membered saturated heterocyclylene having 6-8 heteroatoms independently selected from nitrogen, oxygen, or sulfur.

In some embodiments, -Cy$^1$- is a bivalent optionally substituted tetracyclic 20-24 membered saturated heterocyclylene having 1-12 heteroatoms independently selected from nitrogen, oxygen, or sulfur. In some embodiments, -Cy$^1$- is a bivalent optionally substituted tetracyclic 20-24 membered saturated heterocyclylene having 1-10 heteroatoms independently selected from nitrogen, oxygen, or sulfur. In some embodiments, -Cy$^1$- is a bivalent optionally substituted tetracyclic 20-24 membered saturated heterocyclylene having 1-8 heteroatoms independently selected from nitrogen, oxygen, or sulfur. In some embodiments, -Cy$^1$- is a bivalent optionally substituted tetracyclic 20-24 membered saturated heterocyclylene having 1-6 heteroatoms independently selected from nitrogen, oxygen, or sulfur. In some embodiments, -Cy$^1$- is a bivalent optionally substituted tetracyclic 20-24 membered saturated heterocyclylene having 1-4 heteroatoms independently selected from nitrogen, oxygen, or sulfur. In some embodiments, -Cy$^1$- is a bivalent optionally substituted tetracyclic 20-24 membered saturated heterocyclylene having 1-3 heteroatoms independently selected from nitrogen, oxygen, or sulfur. In some embodiments, -Cy$^1$- is a bivalent optionally substituted tetracyclic 20-24 membered saturated heterocyclylene having 4-6 heteroatoms independently selected from nitrogen, oxygen, or sulfur. In some embodiments, -Cy$^1$- is a bivalent optionally substituted tetracyclic 20-24 membered saturated heterocyclylene having 4-8 heteroatoms independently selected from nitrogen, oxygen, or sulfur. In some embodiments, -Cy$^1$- is a bivalent optionally substituted tetracyclic 20-24 membered saturated heterocyclylene having 6-8 heteroatoms independently selected from nitrogen, oxygen, or sulfur.

In some embodiments, -Cy$^1$- is a bivalent optionally substituted tetracyclic 11-30 membered partially unsaturated heterocyclylene having 1-12 heteroatoms independently selected from nitrogen, oxygen, or sulfur. In some embodiments, -Cy$^1$- is a bivalent optionally substituted tetracyclic 11-30 membered partially unsaturated heterocyclylene having 1-10 heteroatoms independently selected from nitrogen, oxygen, or sulfur. In some embodiments, -Cy$^1$- is a bivalent optionally substituted tetracyclic 11-30 membered partially unsaturated heterocyclylene having 1-8 heteroatoms independently selected from nitrogen, oxygen, or sulfur. In some embodiments, -Cy$^1$- is a bivalent optionally substituted tetracyclic 11-30 membered partially unsaturated heterocyclylene having 1-6 heteroatoms independently selected from nitrogen, oxygen, or sulfur. In some embodiments, -Cy$^1$- is a bivalent optionally substituted tetracyclic 11-30 membered partially unsaturated heterocyclylene having 1-4 heteroatoms independently selected from nitrogen, oxygen, or sulfur. In some embodiments, -Cy$^1$- is a bivalent optionally substituted tetracyclic 11-30 membered partially unsaturated heterocyclylene having 1-3 heteroatoms independently selected from nitrogen, oxygen, or sulfur. In some embodiments, -Cy$^1$- is a bivalent optionally substituted tetracyclic 11-30 membered partially unsaturated heterocyclylene having 4-6 heteroatoms independently selected from nitrogen, oxygen, or sulfur. In some embodiments, -Cy$^1$- is a bivalent optionally substituted tetracyclic 11-30 membered partially unsaturated heterocyclylene having 4-8 heteroatoms independently selected from nitrogen, oxygen, or sulfur. In some embodiments, -Cy$^1$- is a bivalent optionally substituted tetracyclic 11-30 membered partially unsaturated heterocyclylene having 6-8 heteroatoms independently selected from nitrogen, oxygen, or sulfur.

In some embodiments, -Cy$^1$- is a bivalent optionally substituted tetracyclic 11-25 membered partially unsaturated heterocyclylene having 1-12 heteroatoms independently selected from nitrogen, oxygen, or sulfur. In some embodiments, -Cy$^1$- is a bivalent optionally substituted tetracyclic 11-25 membered partially unsaturated heterocyclylene having 1-10 heteroatoms independently selected from nitrogen, oxygen, or sulfur. In some embodiments, -Cy$^1$- is a bivalent optionally substituted tetracyclic 11-25 membered partially unsaturated heterocyclylene having 1-8 heteroatoms independently selected from nitrogen, oxygen, or sulfur. In some embodiments, -Cy$^1$- is a bivalent optionally substituted tetracyclic 11-25 membered partially unsaturated heterocyclylene having 1-6 heteroatoms independently selected from nitrogen, oxygen, or sulfur. In some embodiments, -Cy$^1$- is a bivalent optionally substituted tetracyclic 11-25 membered partially unsaturated heterocyclylene having 1-4 heteroatoms independently selected from nitrogen, oxygen, or sulfur. In some embodiments, -Cy$^1$- is a bivalent optionally substituted tetracyclic 11-25 membered partially unsaturated heterocyclylene having 1-3 heteroatoms independently selected from nitrogen, oxygen, or sulfur. In some embodiments, -Cy$^1$- is a bivalent optionally substituted tetracyclic 11-25 membered partially unsaturated heterocyclylene having 4-6 heteroatoms independently selected from nitrogen, oxygen, or sulfur. In some embodiments, -Cy$^1$- is a bivalent optionally substituted tetracyclic 11-25 membered partially unsaturated heterocyclylene having 4-8 heteroatoms independently selected from nitrogen, oxygen, or sulfur. In some embodiments, -Cy$^1$- is a bivalent optionally substituted tetracyclic 11-25 membered partially unsaturated heterocyclylene having 6-8 heteroatoms independently selected from nitrogen, oxygen, or sulfur.

In some embodiments, -Cy$^1$- is a bivalent optionally substituted tetracyclic 12-24 membered partially unsaturated heterocyclylene having 1-12 heteroatoms independently selected from nitrogen, oxygen, or sulfur. In some embodiments, -Cy$^1$- is a bivalent optionally substituted tetracyclic 12-24 membered partially unsaturated heterocyclylene having 1-10 heteroatoms independently selected from nitrogen, oxygen, or sulfur. In some embodiments, -Cy$^1$- is a bivalent optionally substituted tetracyclic 12-24 membered partially unsaturated heterocyclylene having 1-8 heteroatoms independently selected from nitrogen, oxygen, or sulfur. In some embodiments, -Cy$^1$- is a bivalent optionally substituted tetracyclic 12-24 membered partially unsaturated heterocyclylene having 1-6 heteroatoms independently selected from nitrogen, oxygen, or sulfur. In some embodiments, -Cy$^1$- is a bivalent optionally substituted tetracyclic 12-24 membered partially unsaturated heterocyclylene having 1-4 heteroatoms independently selected from nitrogen, oxygen, or sulfur. In some embodiments, -Cy$^1$- is a bivalent optionally substituted tetracyclic 12-24 membered partially unsaturated heterocyclylene having 1-3 heteroatoms independently selected from nitrogen, oxygen, or sulfur. In some embodiments, -Cy$^1$- is a bivalent optionally substituted tetracyclic 12-24 membered partially unsaturated heterocyclylene having 4-6 heteroatoms independently selected from nitrogen, oxygen, or sulfur. In some embodiments, -Cy$^1$- is a bivalent optionally substituted tetracyclic 12-24 membered partially unsaturated heterocyclylene having 4-8 heteroatoms independently selected from nitrogen, oxygen, or sulfur. In some embodiments, -Cy$^1$- is a bivalent optionally substituted tetracyclic 12-24 membered partially unsaturated heterocyclylene having 6-8 heteroatoms independently selected from nitrogen, oxygen, or sulfur.

In some embodiments, -Cy$^1$- is a bivalent optionally substituted tetracyclic 15-20 membered partially unsaturated heterocyclylene having 1-12 heteroatoms independently selected from nitrogen, oxygen, or sulfur. In some embodiments, -Cy$^1$- is a bivalent optionally substituted tetracyclic 15-20 membered partially unsaturated heterocyclylene having 1-10 heteroatoms independently selected from nitrogen, oxygen, or sulfur. In some embodiments, -Cy$^1$- is a bivalent optionally substituted tetracyclic 15-20 membered partially unsaturated heterocyclylene having 1-8 heteroatoms independently selected from nitrogen, oxygen, or sulfur. In some embodiments, -Cy$^1$- is a bivalent optionally substituted tetracyclic 15-20 membered partially unsaturated heterocyclylene having 1-6 heteroatoms independently selected from nitrogen, oxygen, or sulfur. In some embodiments, -Cy$^1$- is a bivalent optionally substituted tetracyclic 15-20 membered partially unsaturated heterocyclylene having 1-4 heteroatoms independently selected from nitrogen, oxygen, or sulfur. In some embodiments, -Cy$^1$- is a bivalent optionally substituted tetracyclic 15-20 membered partially unsaturated heterocyclylene having 1-3 heteroatoms independently selected from nitrogen, oxygen, or sulfur. In some embodiments, -Cy$^1$- is a bivalent optionally substituted tetracyclic 15-20 membered partially unsaturated heterocyclylene having 4-6 heteroatoms independently selected from nitrogen, oxygen, or sulfur. In some embodiments, -Cy$^1$- is a bivalent optionally substituted tetracyclic 15-20 membered partially unsaturated heterocyclylene having 4-8 heteroatoms independently selected from nitrogen, oxygen, or sulfur. In some embodiments, -Cy$^1$- is a bivalent optionally substituted tetracyclic 15-20 membered partially unsaturated heterocyclylene having 6-8 heteroatoms independently selected from nitrogen, oxygen, or sulfur.

In some embodiments, -Cy$^1$- is a bivalent optionally substituted tetracyclic 20-24 membered partially unsaturated heterocyclylene having 1-12 heteroatoms independently selected from nitrogen, oxygen, or sulfur. In some embodiments, -Cy$^1$- is a bivalent optionally substituted tetracyclic 20-24 membered partially unsaturated heterocyclylene having 1-10 heteroatoms independently selected from nitrogen, oxygen, or sulfur. In some embodiments, -Cy$^1$- is a bivalent optionally substituted tetracyclic 20-24 membered partially unsaturated heterocyclylene having 1-8 heteroatoms independently selected from nitrogen, oxygen, or sulfur. In some embodiments, -Cy$^1$- is a bivalent optionally substituted tetracyclic 20-24 membered partially unsaturated heterocyclylene having 1-6 heteroatoms independently selected from nitrogen, oxygen, or sulfur. In some embodiments, -Cy$^1$- is a bivalent optionally substituted tetracyclic 20-24 membered partially unsaturated heterocyclylene having 1-4 heteroatoms independently selected from nitrogen, oxygen, or sulfur. In some embodiments, -Cy$^1$- is a bivalent optionally substituted tetracyclic 20-24 membered partially unsaturated heterocyclylene having 1-3 heteroatoms independently selected from nitrogen, oxygen, or sulfur. In some embodiments, -Cy$^1$- is a bivalent optionally substituted tetracyclic 20-24 membered partially unsaturated heterocyclylene having 4-6 heteroatoms independently selected from nitrogen, oxygen, or sulfur. In some embodiments, -Cy$^1$- is a bivalent optionally substituted tetracyclic 20-24 membered partially unsaturated heterocyclylene having 4-8 heteroatoms independently selected from nitrogen, oxygen, or sulfur. In some embodiments, -Cy$^1$- is a bivalent optionally substituted tetracyclic 20-24 membered partially unsaturated heterocyclylene having 6-8 heteroatoms independently selected from nitrogen, oxygen, or sulfur.

In some embodiments, -Cy$^1$- is optionally substituted and is any one of the following formulae:

wherein each of R$^4$, R, and n is as defined above and described herein. In some embodiments, -Cy$^1$- is as depicted above, wherein two R$^4$ on the same carbon atom are taken together to form an oxo moiety, an oxime, an optionally substituted hydrazone, an optionally substituted imine, or an optionally substituted C$_{2-6}$ alkylidene. In certain embodiments, -Cy$^1$- is as depicted above, wherein two R$^4$ on the same carbon atom are taken together to form an oxo moiety. In some embodiments, -Cy$^1$- is as depicted above, wherein two R$^4$ on adjacent atoms are taken together to form an optionally substituted 3-8 membered saturated, partially unsaturated, or aryl ring having 0-4 heteroatoms independently selected from nitrogen, oxygen, or sulfur. In certain embodiments, -Cy$^1$- is as depicted above, wherein two R$^A$ on adjacent atoms are taken together to form an optionally substituted 5-6 membered saturated, partially unsaturated, or aryl ring having 0-4 heteroatoms independently selected from nitrogen, oxygen, or sulfur. In certain embodiments, -Cy$^1$- is as depicted above, wherein two R$^A$ on adjacent atoms are taken together to form an optionally substituted 5 membered saturated or partially unsaturated ring having 0-4 heteroatoms independently selected from nitrogen, oxygen, or sulfur.

In certain embodiments, -Cy$^1$- is optionally substituted and is of any one of the following formulae:

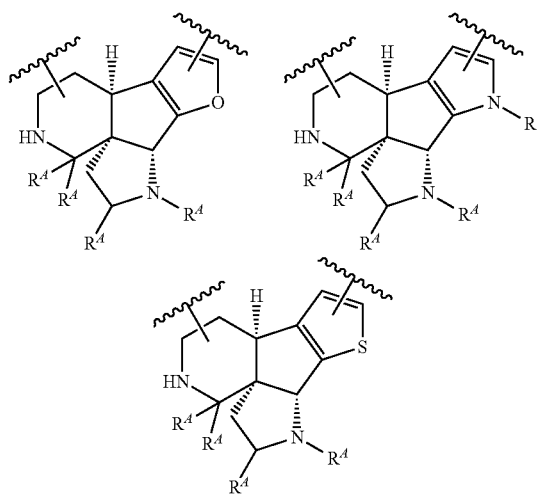

wherein each R and R$^A$ is as defined above and described herein. In some embodiments, -Cy$^1$- is as depicted above, wherein two R$^A$ on the same carbon atom are taken together to form an oxo moiety, an oxime, an optionally substituted hydrazone, an optionally substituted imine, or an optionally substituted C$_{2-6}$ alkylidene. In certain embodiments, -Cy$^1$- is as depicted above, wherein two R$^A$ on the same carbon atom are taken together to form an oxo moiety. In certain embodiments, -Cy$^1$- is as depicted above, wherein at least one R$^A$ is independently —C(O)OR. In certain embodiments, -Cy$^1$- is as depicted above, wherein at least one R$^A$ is independently —C(O)OR, wherein R is an optionally substituted C$_{1-6}$ aliphatic group. In certain embodiments, -Cy$^1$- is as depicted above, wherein at least one R$^A$ is independently —C(O)OR, wherein R is t-butyl. In certain embodiments, -Cy$^1$- is as depicted above, wherein at least one R$^A$ is independently -QR. In certain embodiments, -Cy$^1$- is as depicted above, wherein at least one R$^A$ is independently -QR, wherein Q is an optionally substituted bivalent C$_{1-10}$ hydrocarbon chain wherein one, two, or three methylene units of Q are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^2$-. In certain embodiments, -Cy$^1$- is as depicted above, wherein at least one R$^A$ is independently -QR, wherein Q is an optionally substituted bivalent C$_{1-10}$ hydrocarbon chain wherein one or two methylene units of Q are optionally and independently replaced by —O—, —N(R)—, —S—, —C(O)—, —OC(O)—, —C(O)O—, —OC(O)O—, and wherein R is hydrogen or C$_{1-6}$ aliphatic. In some embodiments, -Cy$^1$- is as depicted above, wherein two R$^A$ on adjacent atoms are taken together to form an optionally substituted 3-8 membered saturated, partially saturated, or aryl ring having 0-4 heteroaroms independently selected from nitrogen, oxygen, or sulfur. In some embodiments, -Cy$^1$- is as depicted above, wherein two R$^A$ on adjacent atoms are taken together to form an optionally substituted 5-6 membered saturated, partially saturated, or aryl ring having 0-4 heteroaroms independently selected from nitrogen, oxygen, or sulfur. In some embodiments, -Cy$^1$- is as depicted above, wherein two R$^A$ on adjacent atoms are taken together to form an optionally substituted 3-8 membered saturated, partially saturated, or aryl carbocycle. In some embodiments, -Cy$^1$- is as depicted above, wherein two R$^A$ on adjacent atoms are taken together to form an optionally substituted 3-8 membered saturated, partially saturated, or aryl ring having 1-4 heteroaroms independently selected from nitrogen, oxygen, or sulfur.

In certain embodiments, -Cy$^1$- is optionally substituted and is of any one of the following formulae:

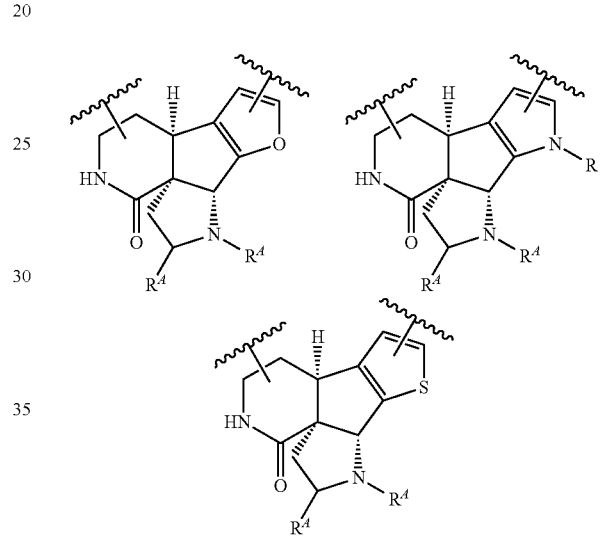

wherein each R and R$^A$ is as defined above and described herein.

In certain embodiments, -Cy$^1$- is optionally substituted and is of any one of the following formulae:

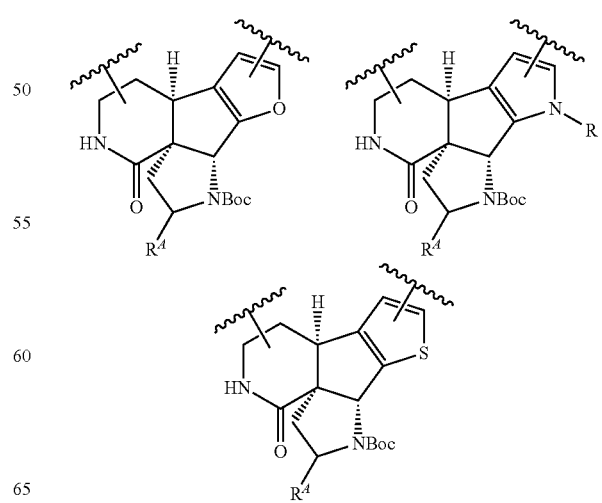

wherein each R and $R^A$ is as defined above and described herein.

In certain embodiments, -$Cy^1$- is optionally substituted and is of any one of the following formulae:

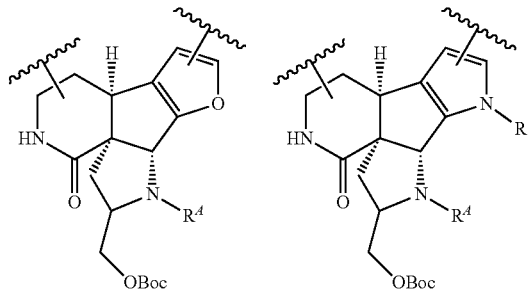

wherein each R and $R^A$ is as defined above and described herein.

In certain embodiments, -$Cy^1$- is optionally substituted and is of the following formula:

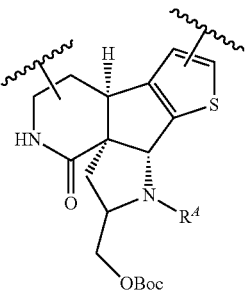

wherein each R and $R^A$ is as defined above and described herein.

In certain embodiments, -$Cy^1$- is optionally substituted and is of any of the following formulae:

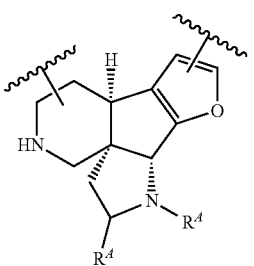

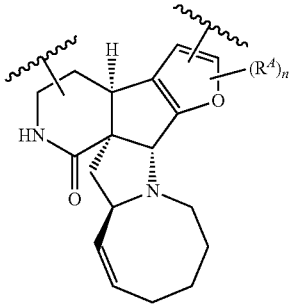

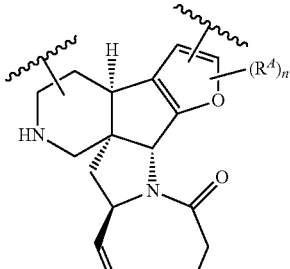

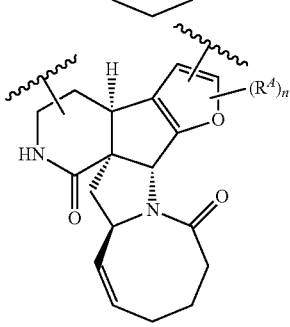

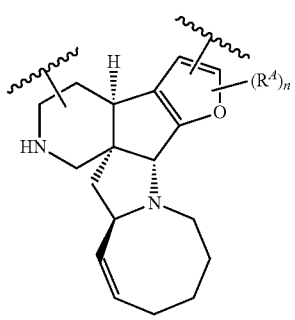

As defined above and described herein, n is 0-20. In some embodiments, n is 0-15. In some embodiments, n is 0-10. In some embodiments, n is 0-5. In some embodiments, n is 1-2. In some embodiments, n is 1-5. In some embodiments, n is 5-10. In some embodiments, n is 5-15. In some embodiments, n is 10-15. In some embodiments, n is 1, 2, 3, 4, 5, 6, 7, 8, 9, or 10. In some embodiments, n is 11, 12, 13, 14, 15, 16, 17, 18, 19, or 20.

In certain embodiments, n is 0.
In certain embodiments, n is 1.
In certain embodiments, n is 2.
In certain embodiments, n is 3.
In certain embodiments, n is 4.
In certain embodiments, n is 5
In certain embodiments, n is 6
In certain embodiments, n is 7.

As defined above and described herein, each $R^A$ is independently selected from —R, -QR, —OR, a suitably protected hydroxyl group, —SR, a suitably protected thiol group, —S(O)R, —$SO_2$R, —$OSO_2$R, —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$, or:

two $R^A$ on the same carbon atom are optionally taken together to form an oxo moiety, an oxime, an optionally substituted hydrazone, an optionally substituted imine, an optionally substituted $C_{2-6}$ alkylidene, or an optionally substituted 3-8 membered saturated or partially unsaturated spirocycle having 0-4 heteroatoms independently selected from nitrogen, oxygen, or sulfur, or:

two $R^A$ on adjacent atoms are optionally taken together to form an optionally substituted 3-8 membered, saturated, partially unsaturated, or aryl ring having 0-4 heteroatoms independently selected from nitrogen, oxygen, or sulfur.

In some embodiments, each $R^A$ is independently selected from R, -QR, —OR, a suitably protected hydroxyl group, —SR, a suitably protected thiol group, —S(O)R, —SO$_2$R, —OSO$_2$R, —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$.

In some embodiments, each $R^A$ is independently selected from R, -QR, —OR, a suitably protected hydroxyl group, —SR, a suitably protected thiol group, —N(R)$_2$, or a suitably protected amino group.

In some embodiments, each $R^A$ is independently selected from R, -QR, —OR, or a suitably protected hydroxyl group.

In certain embodiments, one or more $R^A$ is independently R, wherein R is methyl, ethyl, propyl, or butyl. In certain embodiments, one or more $R^A$ is independently methyl.

In certain embodiments, one or more $R^A$ is independently OR. In certain embodiments, one or more $R^A$ is independently OH. In certain embodiments, one or more $R^A$ is independently a suitably protected hydroxyl group.

In some embodiments, one or more $R^A$ is independently halogen.

In some embodiments, one or more $R^A$ is independently selected from —SR, a suitably protected thiol group, —S(O)R, —SO$_2$R, or —OSO$_2$R.

In some embodiments, one or more $R^A$ is independently selected from —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$.

In some embodiments, two $R^A$ on the same carbon atom are optionally taken together to form an oxo moiety, an oxime, an optionally substituted hydrazone, or an optionally substituted imine. In some embodiments, two $R^A$ on the same carbon atom are optionally taken together to form an optionally substituted $C_{2-6}$ alkylidene. In some embodiments, two $R^A$ on the same carbon atom are optionally taken together to form or an optionally substituted 3-8 membered saturated spirocycle having 0-4 heteroatoms independently selected from nitrogen, oxygen, or sulfur. In some embodiments, two $R^A$ on the same carbon atom are optionally taken together to form or an optionally substituted 5-6 membered saturated spirocycle having 0-4 heteroatoms independently selected from nitrogen, oxygen, or sulfur. In some embodiments, two $R^A$ on the same carbon atom are optionally taken together to form or an optionally substituted 3-8 membered saturated spirocycle having 1-2 heteroatoms independently selected from nitrogen, oxygen, or sulfur. In some embodiments, two $R^A$ on the same carbon atom are optionally taken together to form or an optionally substituted 5-6 membered saturated spirocycle having 1-2 heteroatoms independently selected from nitrogen, oxygen, or sulfur.

In some embodiments, two $R^A$ on the same carbon atom are optionally taken together to form or an optionally substituted 3-8 membered partially unsaturated spirocycle having 0-4 heteroatoms independently selected from nitrogen, oxygen, or sulfur. In some embodiments, two $R^A$ on the same carbon atom are optionally taken together to form or an optionally substituted 5-6 membered partially unsaturated spirocycle having 0-4 heteroatoms independently selected from nitrogen, oxygen, or sulfur. In some embodiments, two $R^A$ on the same carbon atom are optionally taken together to form or an optionally substituted 5-6 membered partially unsaturated spirocycle having 1-2 heteroatoms independently selected from nitrogen, oxygen, or sulfur.

In some embodiments, two $R^A$ on adjacent atoms are optionally taken together to form an optionally substituted 3-8 membered saturated ring having 0-4 heteroatoms independently selected from nitrogen, oxygen, or sulfur. In some embodiments, two $R^A$ on adjacent atoms are optionally taken together to form an optionally substituted 5-6 membered saturated ring having 0-4 heteroatoms independently selected from nitrogen, oxygen, or sulfur. In some embodiments, two $R^A$ on adjacent atoms are optionally taken together to form an optionally substituted 3-8 membered saturated ring having 1-2 heteroatoms independently selected from nitrogen, oxygen, or sulfur. In some embodiments, two $R^A$ on adjacent atoms are optionally taken together to form an optionally substituted 5-6 membered saturated ring having 1-2 heteroatoms independently selected from nitrogen, oxygen, or sulfur.

In some embodiments, two $R^A$ on adjacent atoms are optionally taken together to form an optionally substituted 3-8 membered partially unsaturated ring having 0-4 heteroatoms independently selected from nitrogen, oxygen, or sulfur. In some embodiments, two $R^A$ on adjacent atoms are optionally taken together to form an optionally substituted 5-6 membered partially unsaturated ring having 0-4 heteroatoms independently selected from nitrogen, oxygen, or sulfur. In some embodiments, two $R^A$ on adjacent atoms are optionally taken together to form an optionally substituted 3-8 membered partially unsaturated ring having 1-2 heteroatoms independently selected from nitrogen, oxygen, or sulfur. In some embodiments, two $R^A$ on adjacent atoms are optionally taken together to form an optionally substituted 5-6 membered partially unsaturated ring having 1-2 heteroatoms independently selected from nitrogen, oxygen, or sulfur.

In some embodiments, two $R^A$ on adjacent atoms are optionally taken together to form an optionally substituted 5-6 membered aryl ring having 0-4 heteroatoms independently selected from nitrogen, oxygen, or sulfur. In some embodiments, two $R^A$ on adjacent atoms are optionally taken together to form an optionally substituted 5 membered aryl ring having 1-4 heteroatoms independently selected from nitrogen, oxygen, or sulfur. In some embodiments, two $R^A$ on adjacent atoms are optionally taken together to form an optionally substituted 6 membered aryl ring having 1-4 heteroatoms independently selected from nitrogen, oxygen, or sulfur. In some embodiments, two $R^A$ on adjacent atoms are optionally taken together to form an optionally substituted 5 membered aryl ring having 1-2 heteroatoms independently selected from nitrogen, oxygen, or sulfur. In some embodiments, two $R^A$ on adjacent atoms are optionally taken together to form an optionally substituted 6 membered aryl ring having 1-2 heteroatoms independently selected from nitrogen, oxygen, or sulfur. In some embodiments, two $R^A$ on adjacent atoms are optionally taken together to form an optionally substituted phenyl.

In some embodiments, one or more $R^A$ is -QR.

As defined above and described herein, $R^B$ is —R, -QR, —OR, a suitably protected hydroxyl group, —SR, a suitably protected thiol group, —S(O)R, —SO$_2$R, —OSO$_2$R, —N(R)$_2$, a suitably protected amino group, —N(R)C(O)R, —N(R)C(O)C(O)R, —N(R)C(O)N(R)$_2$, —N(R)C(O)OR, —C(O)OR, —OC(O)R, —C(O)N(R)$_2$, or —OC(O)N(R)$_2$, wherein each R is independently as defined above and described herein. In some embodiments, $R^B$ is —R, -QR, —OR, a suitably protected hydroxyl group, —SR, a suitably protected thiol group, —S(O)R, —SO$_2$R, —OSO$_2$R, —N(R)₂, a suitably protected amino group, —N(R)C(O)R, —N(R)C(O)C(O)R, —N(R)C(O)N(R)₂, —N(R)C(O)OR, —C(O)OR, —OC(O)R, —C(O)N(R)₂, or —OC(O)N(R)₂ but not hydrogen, wherein each R is independently as defined above and described herein. In some embodiments, $R^B$ is —R, -QR, —OR, a suitably protected hydroxyl group, —SR, a suitably protected thiol group, —S(O)R, —SO₂R, —OSO₂R, —N(R)₂, a suitably protected amino group, —N(R)C(O)R, —N(R)C(O)C(O)R, —N(R)C(O)N(R)₂, —N(R)C(O)OR, —C(O)OR, —OC(O)R, —C(O)N(R)₂, or —OC(O)N(R)₂, wherein $R^B$ is not hydrogen, and wherein each R is independently as defined above and described herein.

In some embodiments, $R^B$ is R, wherein R is as defined above and described herein. In some embodiments, $R^B$ is or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^B$ is R, wherein R is as defined above and described herein. In some embodiments, $R^B$ is or an optionally substituted $C_{1-6}$ aliphatic. In some embodiments, $R^B$ is methyl. In some embodiments, $R^B$ is ethyl. In some embodiments, $R^B$ is or an optionally substituted phenyl. In some embodiments, $R^B$ is or an optionally substituted group selected from 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^B$ is -QR, —OR, a suitably protected hydroxyl group, —SR, a suitably protected thiol group, —S(O)R, —SO₂R, —OSO₂R, —N(R)₂, a suitably protected amino group, —N(R)C(O)R, —N(R)C(O)C(O)R, —N(R)C(O)N(R)₂, —N(R)C(O)OR, —C(O)OR, —OC(O)R, —C(O)N(R)₂, or —OC(O)N(R)₂, wherein each R is independently as defined above and described herein.

As defined above and described herein, each Q is independently an optionally substituted bivalent $C_{1-10}$ hydrocarbon chain wherein one, two, or three methylene units of Q are optionally and independently replaced by —O—, —N(R)—, —S—, —C(O)—, —OC(O)—, —C(O)O—, —S(O)—, or —S(O)₂—, —OSO₂O—, —N(R)C(O)—, —C(O)N(R)—, —N(R)C(O)O—, —OC(O)NR—, —N(R)C(O)NR—, or -Cy²-.

In some embodiments, each Q is independently an optionally substituted bivalent $C_{1-10}$ hydrocarbon chain, wherein the hydrocarbon chain is an aliphatic group comprising one or more units of unsaturation, and wherein one, two, or three methylene units of Q are optionally and independently replaced by —O—, —N(R)—, —S—, —C(O)—, —OC(O)—, —C(O)O—, —OC(O)O—, —S(O)—, or —S(O)₂—, —OSO₂O—, —N(R)C(O)—, —C(O)N(R)—, —N(R)C(O)O—, —OC(O)NR—, —N(R)C(O)NR—, or -Cy²-.

In some embodiments, each Q is independently an optionally substituted bivalent $C_{1-10}$ hydrocarbon chain, wherein the hydrocarbon chain is an aliphatic group comprising one or more units of unsaturation, and wherein one, two, or three methylene units of Q are optionally replaced -Cy²-. In certain embodiments, at least one Q is independently an optionally substituted bivalent $C_{1-5}$ hydrocarbon chain, wherein the hydrocarbon chain is an aliphatic group comprising one or more units of unsaturation, and wherein one methylene units of Q are optionally replaced -Cy²-.

As defined above and described herein, each -Cy²- is independently a bivalent optionally substituted ring selected from phenylene, a 3-8 membered saturated or partially unsaturated monocyclic carbocyclylene, a 5-6 membered monocyclic heteroarylene having 1-4 heteroatoms independently selected from nitrogen, oxygen, or sulfur, or a 3-8 membered saturated or unsaturated monocyclic heterocyclylene having 1-4 heteroatoms independently selected from nitrogen, oxygen, or sulfur, an 8-10 membered bicyclic arylene, a 7-10 membered saturated or partially unsaturated bicyclic carbocyclylene, an 8-10 membered bicyclic heteroarylene having 1-5 heteroatoms independently selected from nitrogen, oxygen, or sulfur, or a 7-10 membered saturated or partially unsaturated bicyclic heterocyclylene having 1-5 heteroatoms independently selected from nitrogen, oxygen, or sulfur.

In certain embodiments, a -Cy²- group is independently bivalent optionally substituted phenylene.

In certain embodiments, a -Cy²- group is independently an optionally substituted 3-8 membered saturated monocyclic carbocyclylene. In certain embodiments, a -Cy²- group is independently an optionally substituted 5-6 membered saturated monocyclic carbocyclylene.

In certain embodiments, a -Cy²- group is independently an optionally substituted 3-8 membered partially unsaturated monocyclic carbocyclylene. In certain embodiments, a -Cy²- group is independently an optionally substituted 5-6 membered partially unsaturated monocyclic carbocyclylene.

In certain embodiments, a -Cy²- group is independently an optionally substituted 5-6 membered monocyclic heteroarylene having 1-4 heteroatoms independently selected from nitrogen, oxygen, or sulfur. In certain embodiments, a -Cy²- group is independently an optionally substituted 5-6 membered monocyclic heteroarylene having 1-2 heteroatoms independently selected from nitrogen, oxygen, or sulfur.

In certain embodiments, a -Cy²- group is independently an optionally substituted 5 membered monocyclic heteroarylene having 1-4 heteroatoms independently selected from nitrogen, oxygen, or sulfur. In certain embodiments, a -Cy²- group is independently an optionally substituted 5 membered monocyclic heteroarylene having 1-2 heteroatoms independently selected from nitrogen, oxygen, or sulfur. In certain embodiments, a -Cy²- group is independently an optionally substituted 5 membered monocyclic heteroarylene having 2 heteroatoms independently selected from nitrogen or sulfur.

Exemplary optionally substituted -Cy²- heteroarylene groups include thienylene, furanylene, pyrrolylene, imidazolylene, pyrazolylene, triazolylene, tetrazolylene, oxazolylene, isoxazolylene, oxadiazolylene, thiazolylene, isothiazolylene, thiadiazolylene, pyridylene, pyridazinylene, pyrimidinylene, and pyrazinylene.

In certain embodiments, a -Cy$^2$- group is independently optionally substituted thiazolylene.

In certain embodiments, -Cy$^2$- is of the formula:

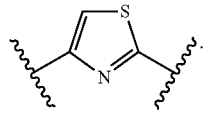 [SMILES: *c1csc(*)n1]

In certain embodiments, a -Cy$^2$- group is independently an optionally substituted 6 membered monocyclic heteroarylene having 1-4 heteroatoms independently selected from nitrogen, oxygen, or sulfur. In certain embodiments, a -Cy$^2$- group is independently an optionally substituted 6 membered monocyclic heteroarylene having 1-2 heteroatoms independently selected from nitrogen, oxygen, or sulfur.

In some embodiments, -QR is of the following formula:

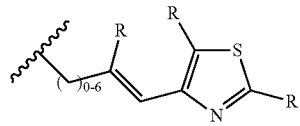

wherein each R is independently as defined above and described herein. In certain embodiments, -QR is as depicted above, wherein each R is independently selected from hydrogen or optionally substituted C$_{1-6}$ aliphatic. In certain embodiments, at least one R is independently methyl. In certain embodiments, two R are independently methyl.

In some embodiments, -QR is of the following formula:

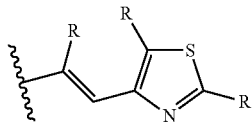

wherein each R is independently as defined above and described herein.

In certain embodiments, -QR is

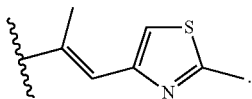 [SMILES: */C(C)=C/c1csc(C)n1]

Yuzu Lactone and Related Compounds

In some embodiments, a compound of formula I is of any one of the following formulae:

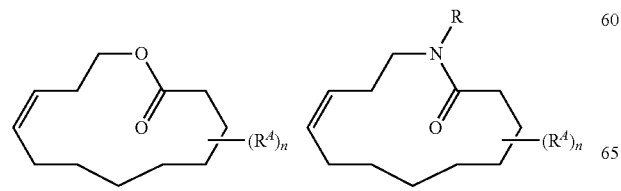

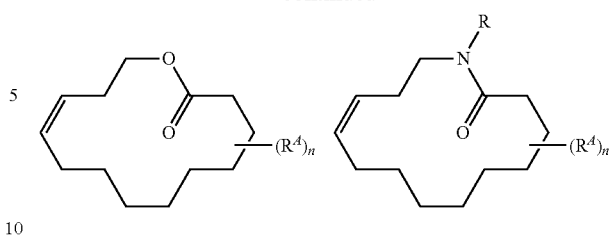

wherein each of R$^A$, R, and n are as defined above and described herein.

In some embodiments, a compound of formula I-a is of any one of the following formulae:

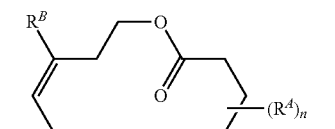

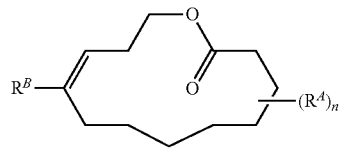

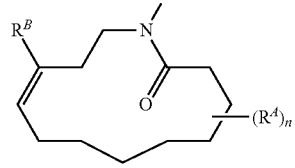

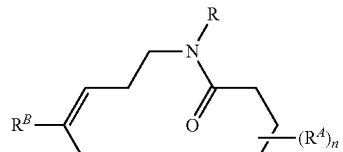

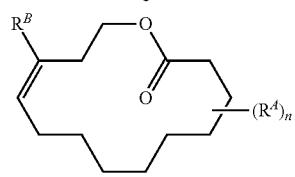

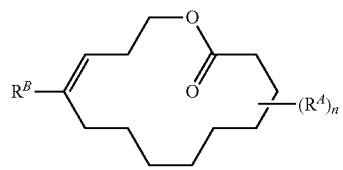

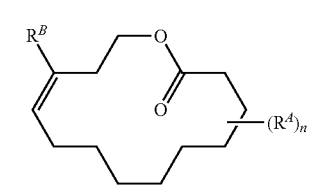

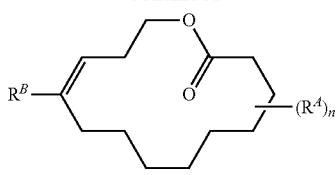

wherein each of $R^A$, $R^B$, R, and n are as defined above and described herein.

In certain embodiments, a compound of formula I is of any one of the following structures:

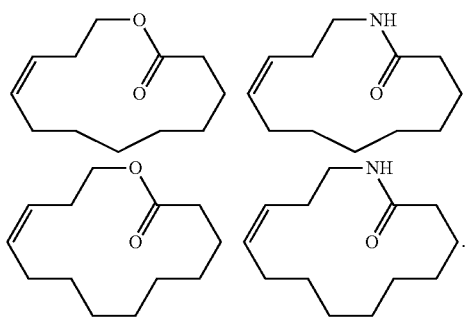

Epilachnene and Related Compounds

In some embodiments, a compound of formula I is of any one of the following formulae:

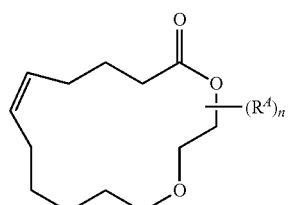

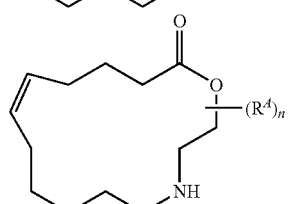

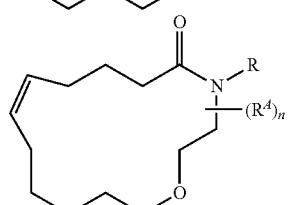

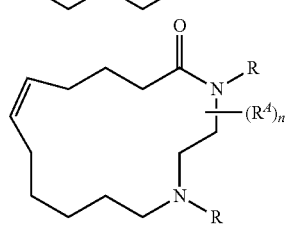

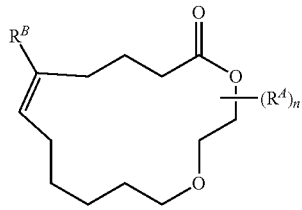

wherein each of $R^A$, R, and n are as defined above and described herein.

In some embodiments, a compound of formula I-a is of any one of the following formulae:

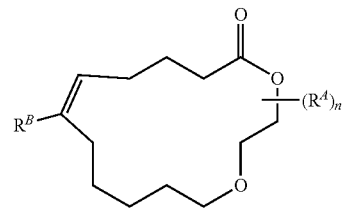

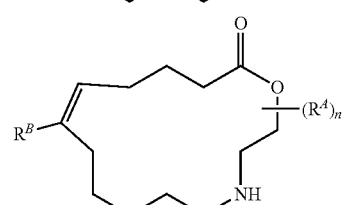

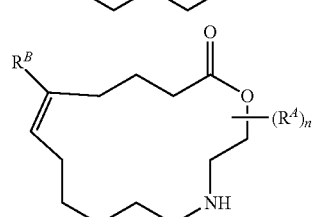

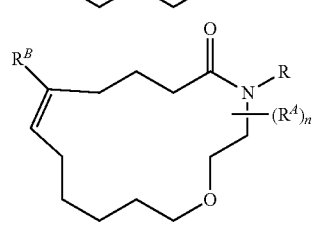

-continued
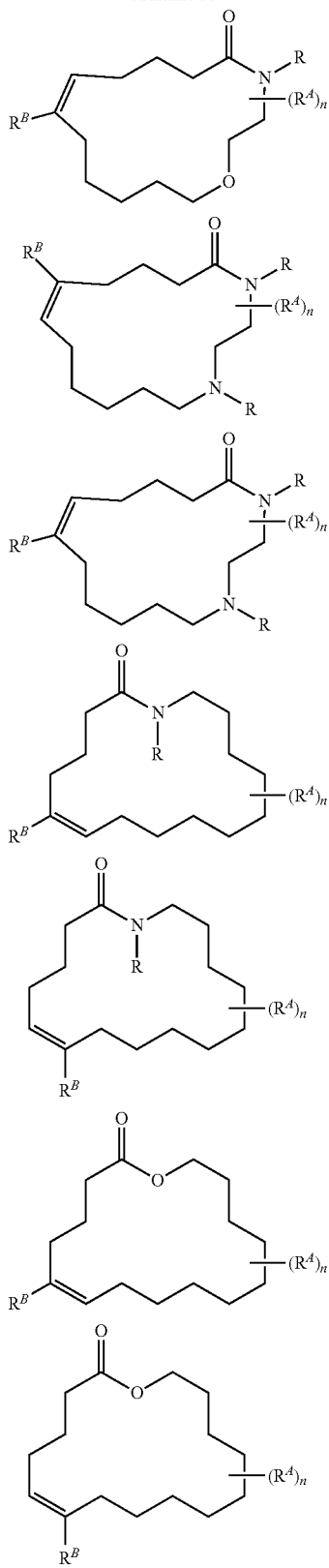
wherein each of $R^A$, $R^B$ and n is independently as defined above and described herein.
In some embodiments, a compound of formula I is of any one of the following formulae:
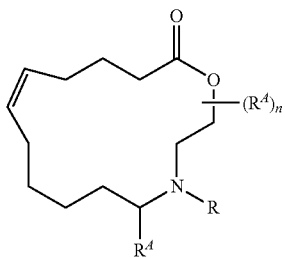
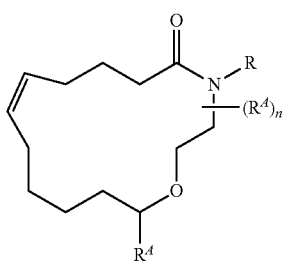
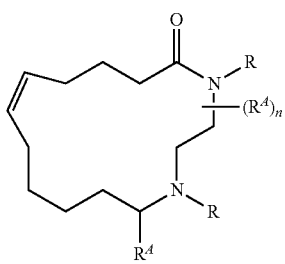
wherein each of $R^A$, R, and n is independently as defined above and described herein.
In some embodiments, a compound of formula I is of any one of the following formulae:
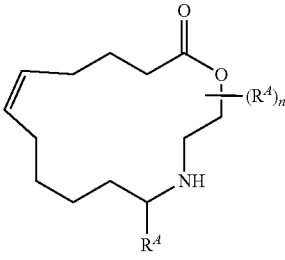
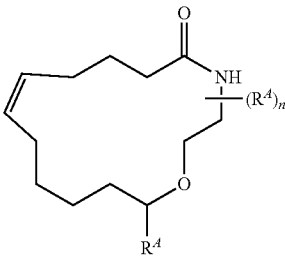

-continued

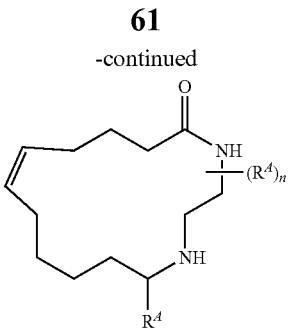

wherein each of $R^A$ and n is independently as defined above and described herein. In certain embodiments, a compound of formula I is as depicted above, wherein at least one $R^A$ is independently R. In certain embodiments, a compound of formula I is as depicted above, wherein at least one $R^A$ is independently R, wherein R is lower alkyl. In certain embodiments, a compound of formula I is as depicted above, wherein at least one $R^A$ is independently n-propyl.

In some embodiments, a compound of formula I is of any one of the following formulae:

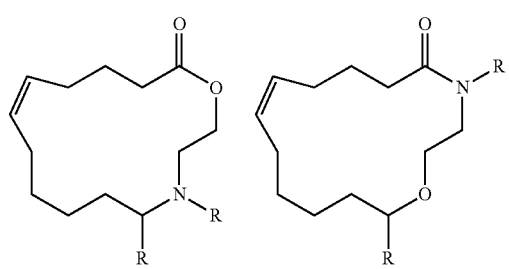

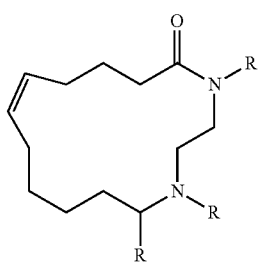

wherein R is as defined above and described herein.

In some embodiments, a compound of formula I is of any one of the following structures:

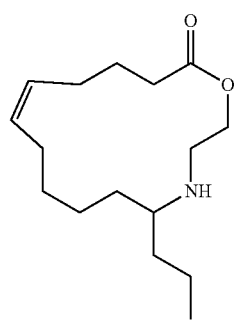

-continued

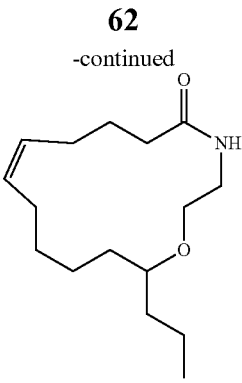

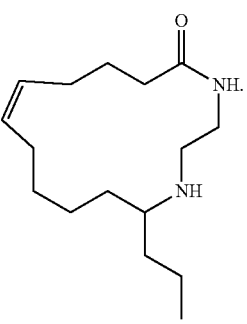

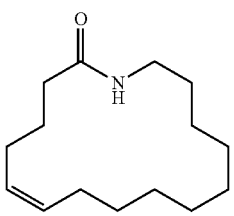

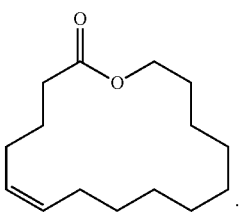

Ambrettolide and Related Compounds

In some embodiments, a compound of formula I is of the following formula:

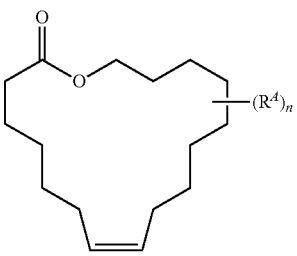

wherein each of $R^A$ and n are as defined above and described herein.

In some embodiments, a compound of formula I-a is of any of the following formula:

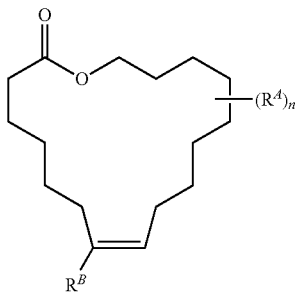

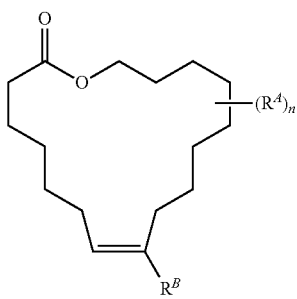

wherein each of $R^A$, $R^B$ and n is independently as defined above and described herein.

In some embodiments, a compound of formula I is of the following structure:

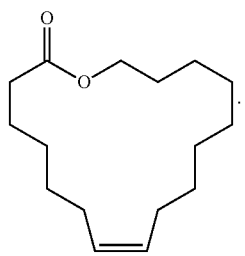 [SMILES: O=C1CCCCC/C=C\CCCCCCCCO1]

In some embodiments, a compound of formula I is of the following formula:

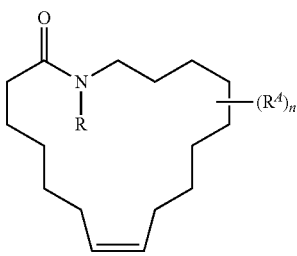

wherein each of $R^A$, R, and n is independently as defined above and described herein.

Epothilone C and Related Compounds

In some embodiments, a compound of formula I is of the following formula:

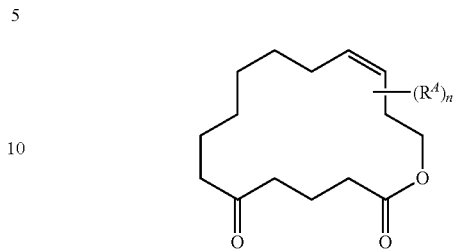

wherein each of $R^A$ and n are as defined above and described herein.

In some embodiments, a compound of formula I is of the following formula:

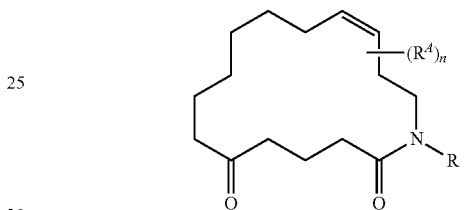

wherein each of $R^A$ and n are as defined above and described herein.

In some embodiments, a compound of formula I is of the following formula:

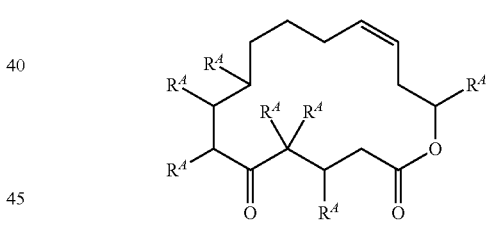

wherein each of $R^A$ and n are as defined above and described herein.

In some embodiments, a compound of formula I is of the following formula:

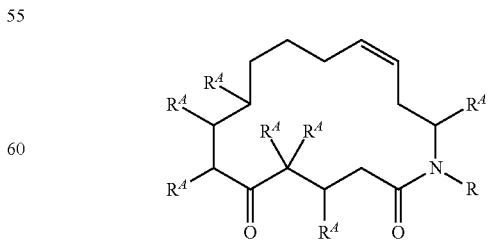

wherein each of $R^A$ and n are as defined above and described herein.

In some embodiments, a compound of formula I is of the following formula:

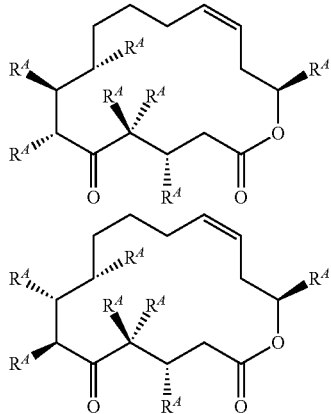

wherein each of $R^A$ and n are as defined above and described herein. In certain embodiments, a compound of formula I is as depicted above, wherein each $R^A$ is independently selected from R, -QR, —OR, or a suitably protected hydroxyl group.

In some embodiments, a compound of formula I is of the following formula:

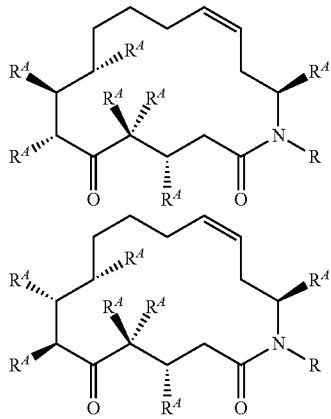

wherein each of $R^A$ and n are as defined above and described herein. In certain embodiments, a compound of formula I is as depicted above, wherein each $R^A$ is independently selected from R, -QR, —OR, or a suitably protected hydroxyl group.

In some embodiments, a compound of formula I is of any one of the following formulae:

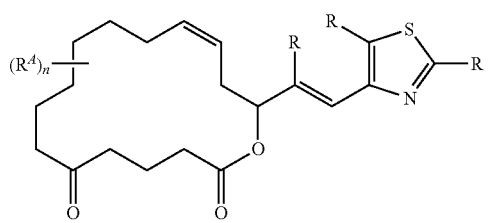

-continued

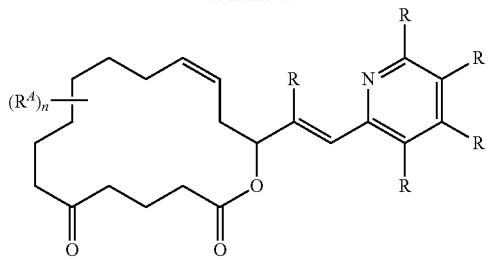

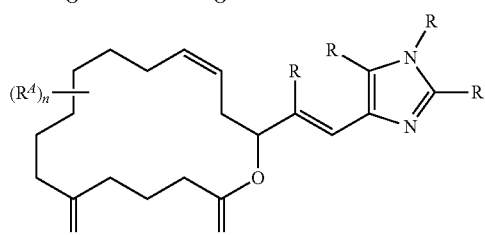

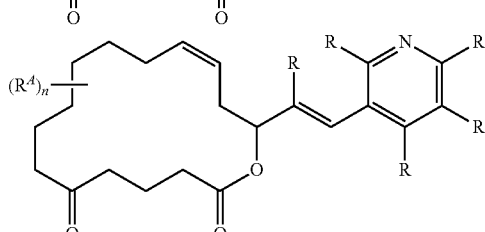

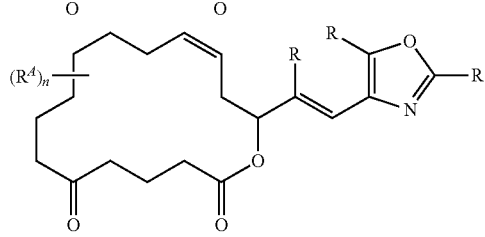

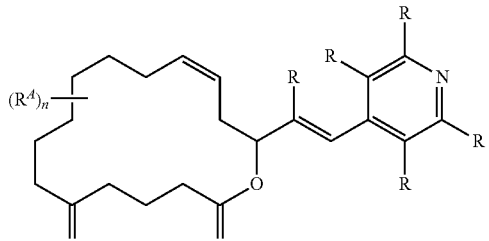

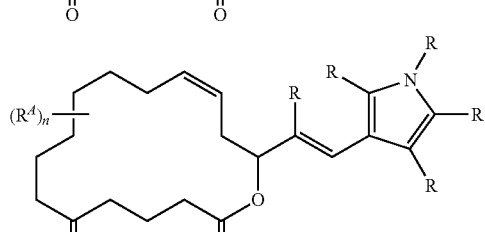

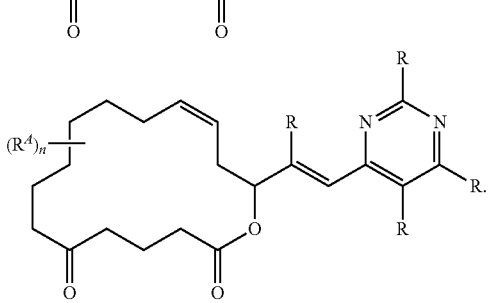

wherein each of $R^A$, R, and n are as defined above and described herein.

In some embodiments, a compound of formula I is of the following formula:

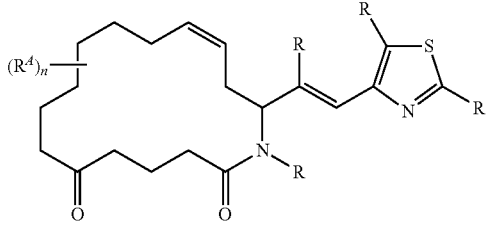

wherein each of $R^A$, R, and n are as defined above and described herein.

In some embodiments, a compound of formula I is of the following formula:

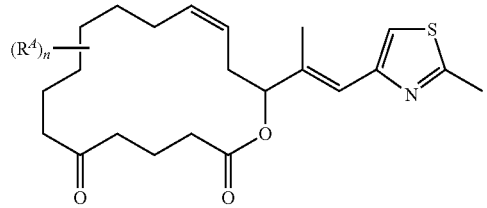

wherein each of $R^A$ and n are as defined above and described herein.

In some embodiments, a compound of formula I is of the following formula:

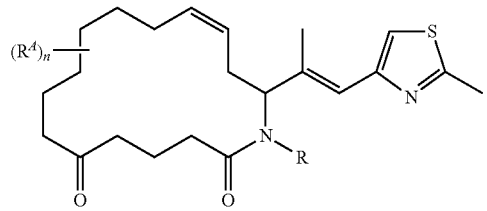

wherein each of $R^A$, R, and n are as defined above and described herein.

In some embodiments, a compound of formula I is of the following formula:

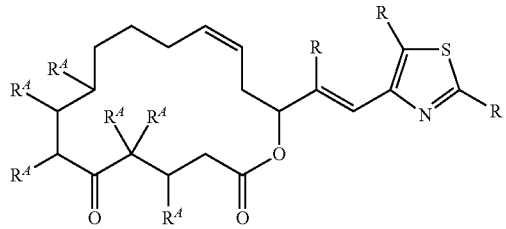

wherein each of $R^A$, R, and n are as defined above and described herein.

In some embodiments, a compound of formula I is of the following formula:

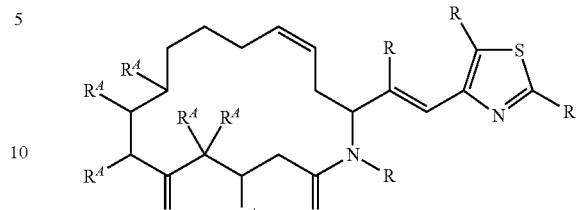

wherein each of $R^A$, R, and n are as defined above and described herein.

In some embodiments, a compound of formula I is of either of the following formulae:

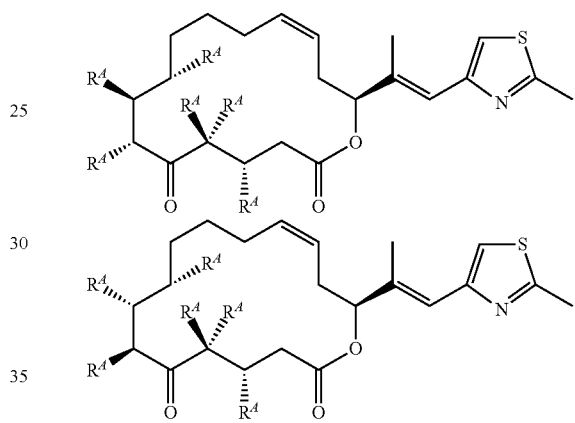

wherein each of $R^A$ and n are as defined above and described herein. In certain embodiments, a compound of formula I is as depicted above, wherein each $R^A$ is independently selected from R, —OR, or a suitably protected hydroxyl group.

In some embodiments, a compound of formula I is of either of the following formulae:

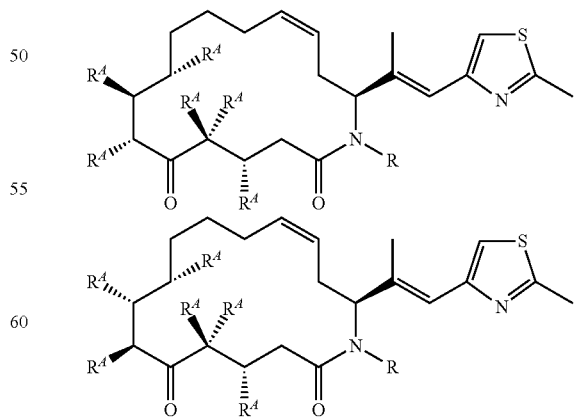

wherein each of $R^A$, R, and n are as defined above and described herein. In certain embodiments, a compound of formula I is as depicted above, wherein each $R^A$ is independently selected from R, —OR, or a suitably protected hydroxyl group.

In some embodiments, a compound of formula I is of either of the following structures:

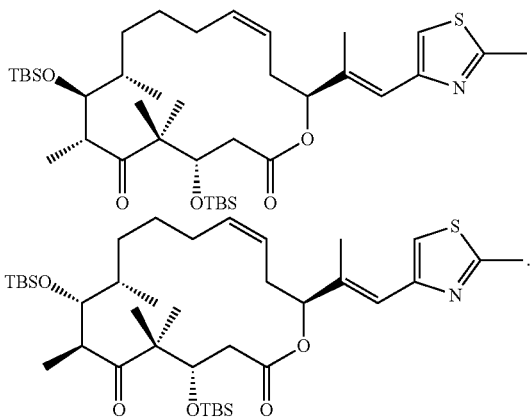

In some embodiments, a compound of formula I is of either of the following structures:

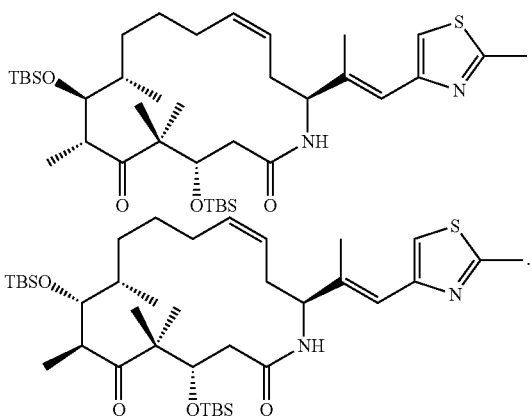

In some embodiments, a compound of formula I is of the following structure:

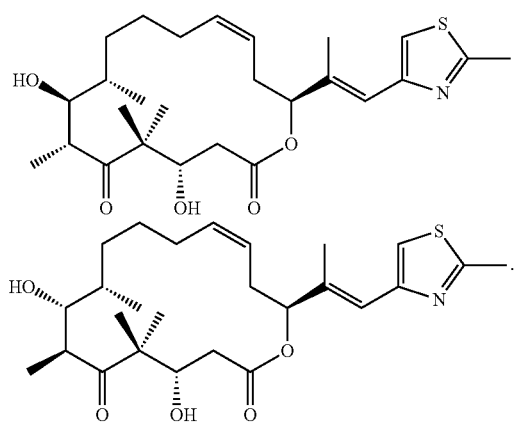

In some embodiments, a compound of formula I is of the following structure:

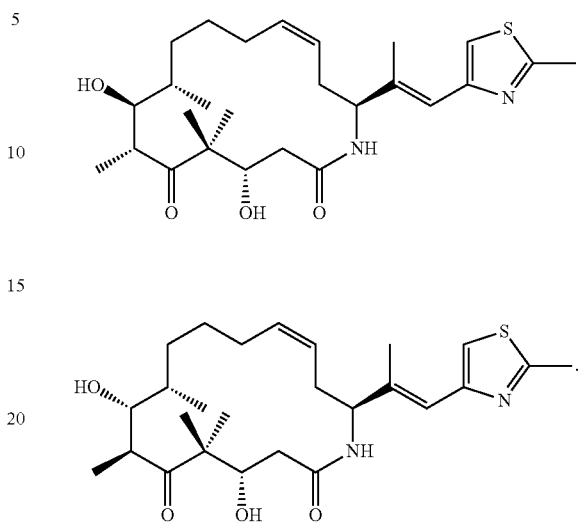

Epothilone D and Related Compounds

In some embodiments, a compound of formula I-a is of any one of the following formula:

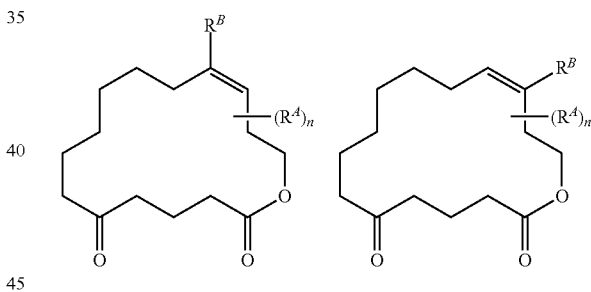

wherein each of $R^A$, $R^B$, and n is independently as defined above and described herein.

In some embodiments, a compound of formula I-a is of any one of the following formula:

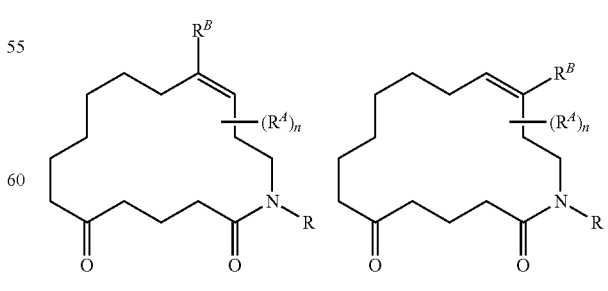

wherein each of $R^A$, $R^B$, R and n is independently as defined above and described herein.

In some embodiments, a compound of formula I-a is of any one of the following formula:

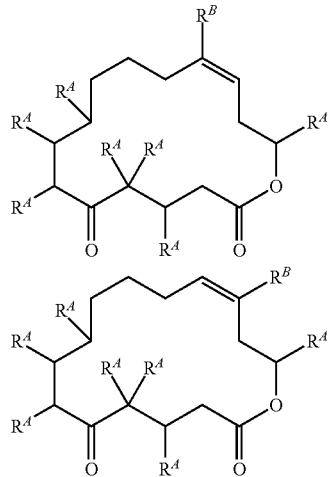

wherein each of $R^A$ and $R^B$ is independently as defined above and described herein.

In some embodiments, a compound of formula I-a is of any one of the following formula:

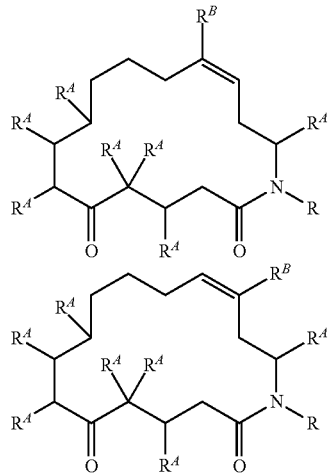

wherein each of $R^A$, $R^B$, and R is independently as defined above and described herein.

In some embodiments, a compound of formula I-a is of any one of the following formula:

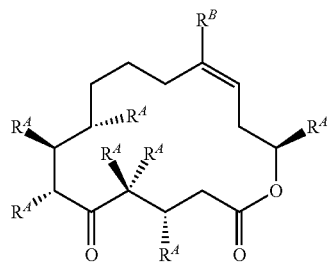

-continued

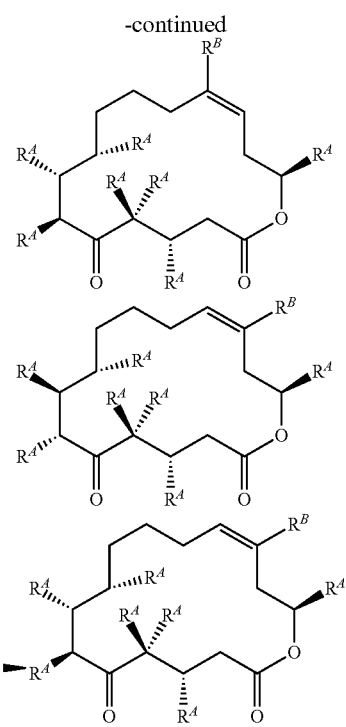

wherein each of $R^A$ and $R^B$ is independently as defined above and described herein. In certain embodiments, a compound of formula I-a is as depicted above, wherein each of $R^A$ and $R^B$ is independently selected from R, -QR, —OR, or a suitably protected hydroxyl group.

In some embodiments, a compound of formula I-a is of any one of the following formula:

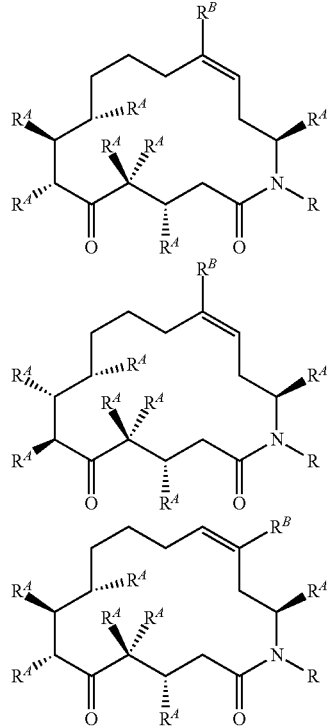

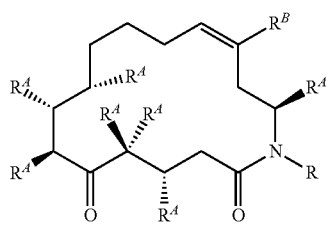
wherein each of $R^A$, $R^B$ and R is independently as defined above and described herein. In certain embodiments, a compound of formula I-a is as depicted above, wherein each $R^A$ is independently selected from R, -QR, —OR, or a suitably protected hydroxyl group.
In some embodiments, a compound of formula I-a is of any one of the following formulae:
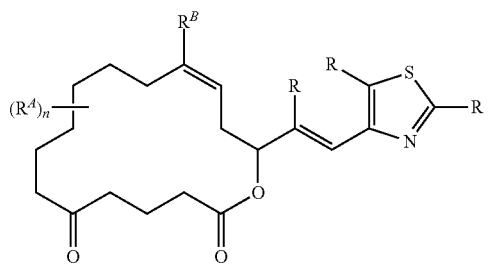
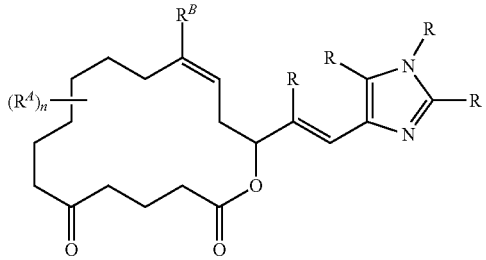
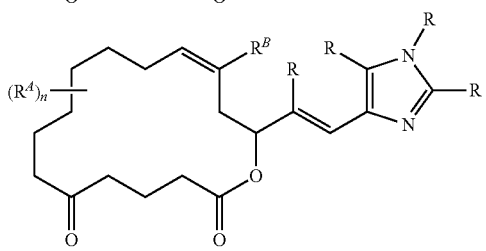
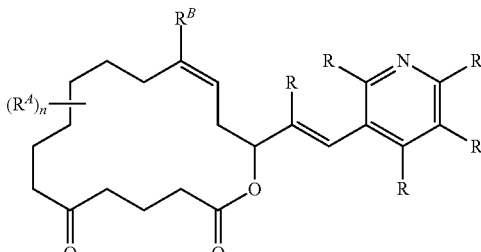
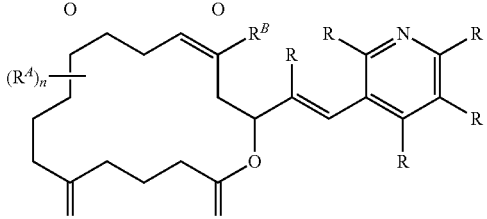
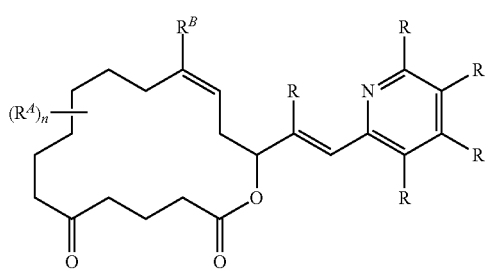
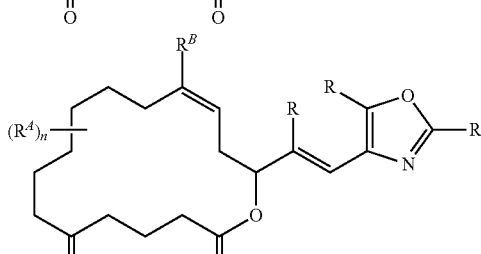
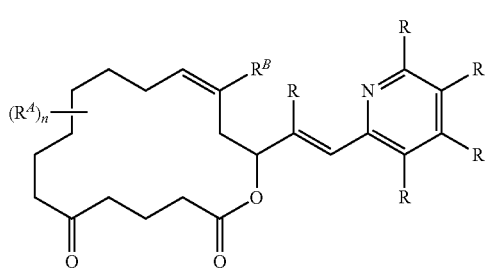
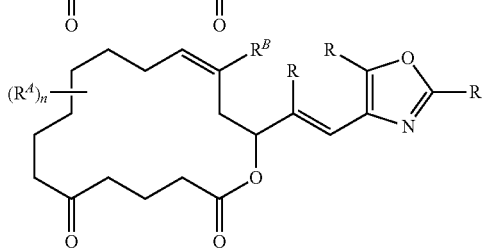
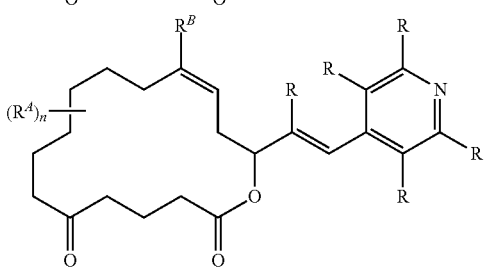

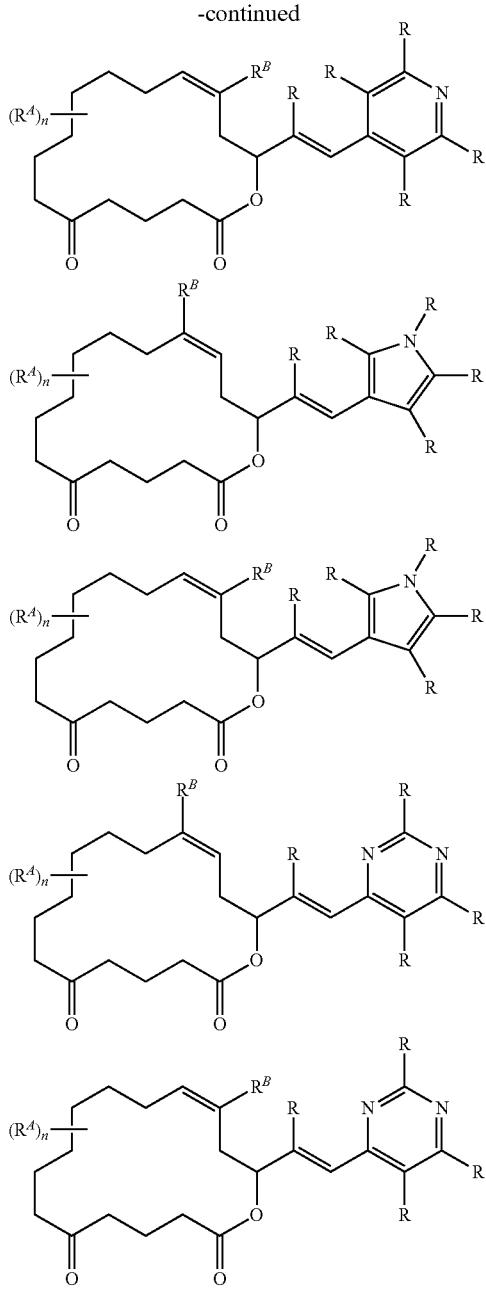

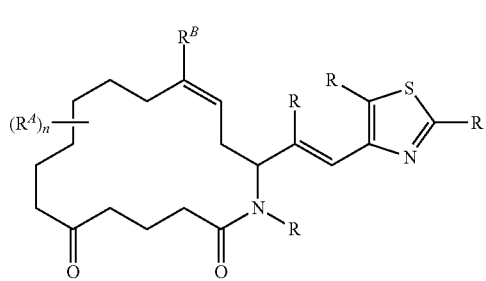

wherein each of $R^A$, $R^B$, R and n is independently as defined above and described herein.

In some embodiments, a compound of formula I-a is of any one of the following formula:

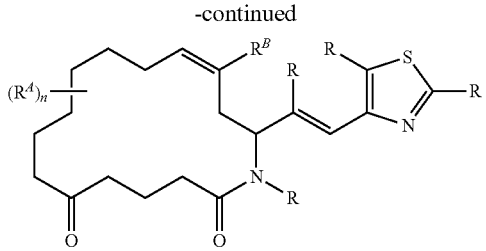

wherein each of $R^A$, $R^B$, R and n is independently as defined above and described herein.

In some embodiments, a compound of formula I-a is of any one of the following formula:

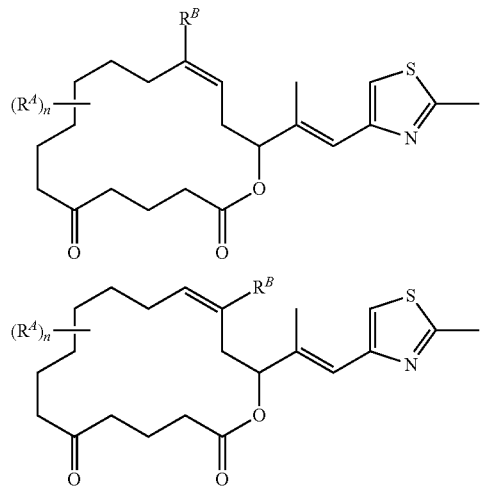

wherein each of $R^A$, $R^B$ and n is independently as defined above and described herein.

In some embodiments, a compound of formula I-a is of any one of the following formula:

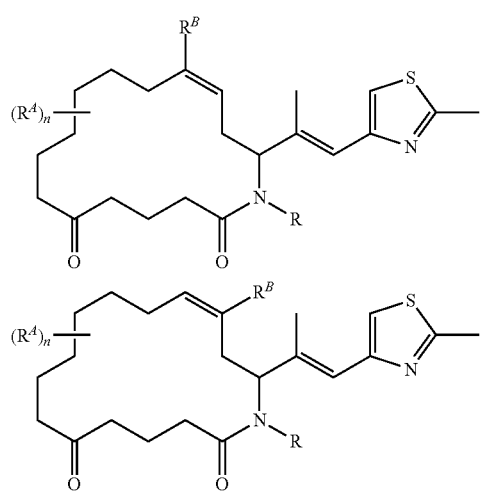

wherein each of $R^A$, $R^B$, and R is independently as defined above and described herein.

In some embodiments, a compound of formula I-a is of either of the following formula:

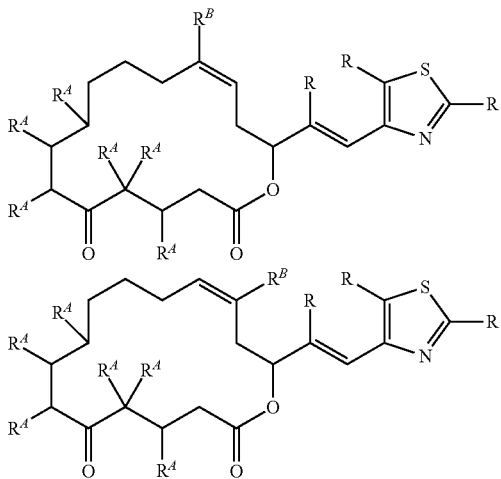

wherein each of $R^A$, $R^B$ and R is as defined above and described herein.

In some embodiments, a compound of formula I-a is of either of the following formula:

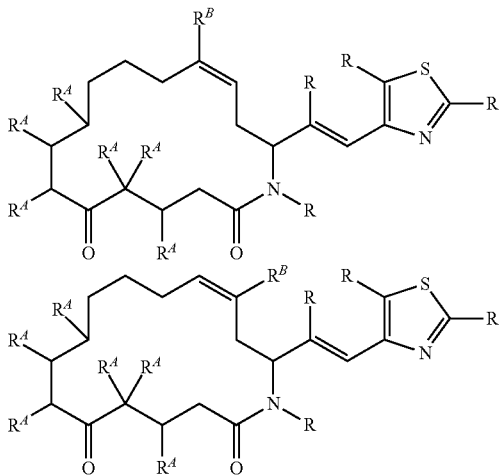

wherein each of $R^A$, $R^B$ and R is independently as defined above and described herein.

In some embodiments, a compound of formula I-a is of any one of the following formulae:

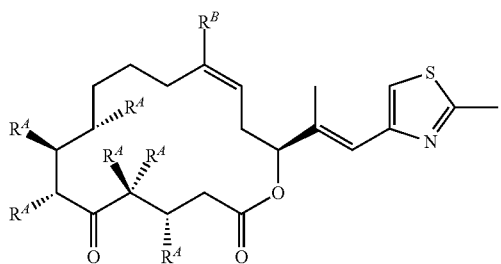

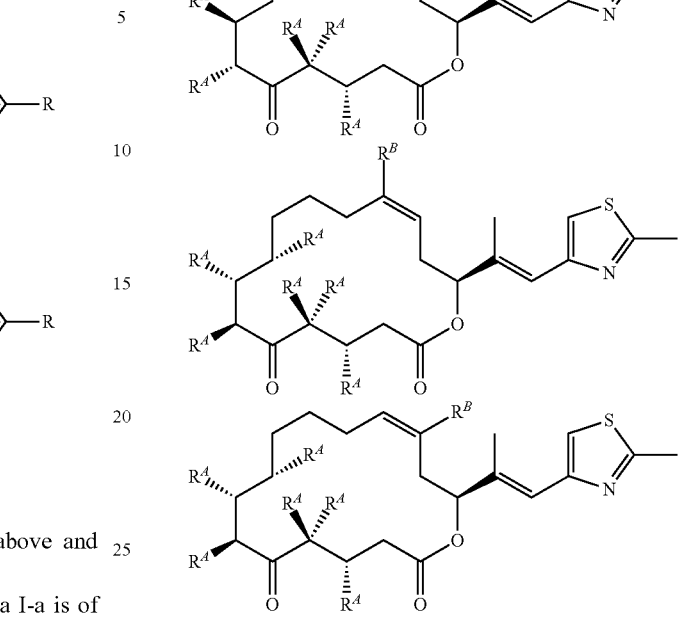

wherein each of $R^A$ and $R^B$ is independently as defined above and described herein. In certain embodiments, a compound of formula I-a is as depicted above, wherein each of $R^A$ and $R^B$ is independently selected from R, —OR, or a suitably protected hydroxyl group.

In some embodiments, a compound of formula I-a is of any one of the following formulae:

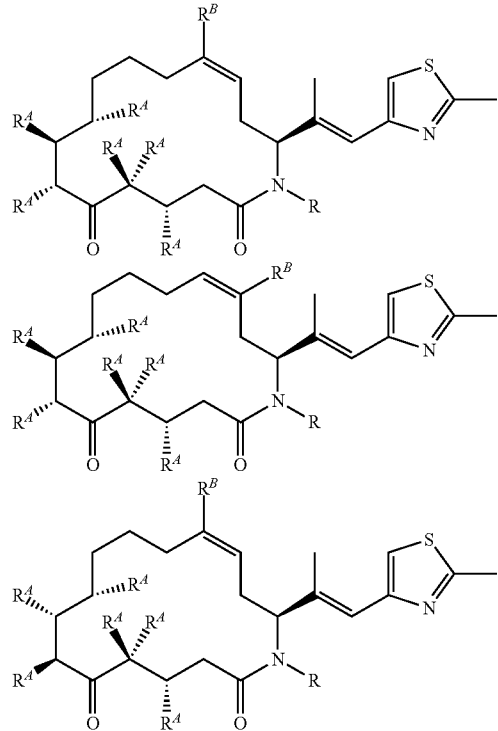

-continued

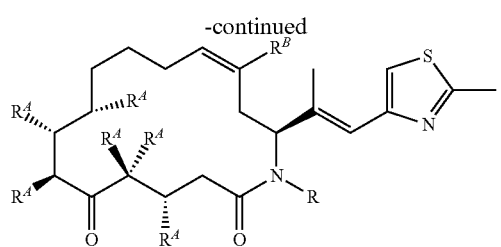

wherein each of $R^A$, $R^B$ and R is independently as defined above and described herein. In certain embodiments, a compound of formula I-a is as depicted above, wherein each of $R^A$ and $R^B$ is independently selected from R, —OR, or a suitably protected hydroxyl group.

In some embodiments, a compound of formula I-a is of any one of the following structures:

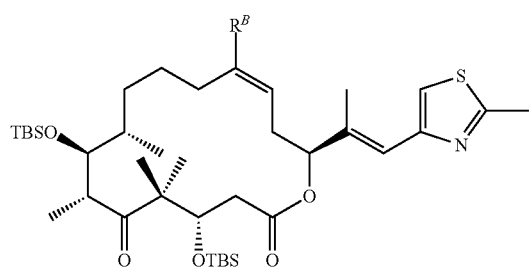

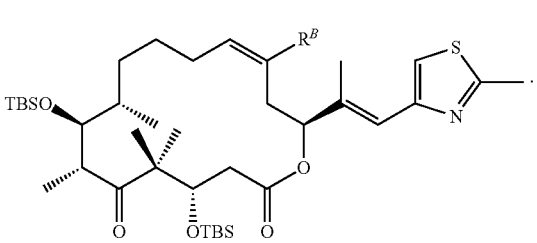

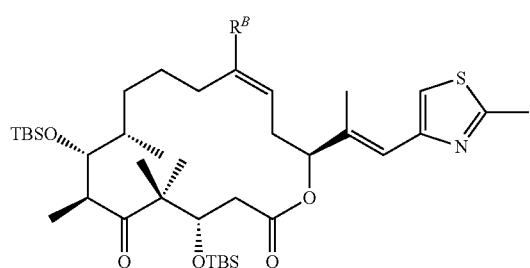

wherein each of $R^A$, $R^B$, and R is independently as defined above and described herein.

In some embodiments, a compound of formula I-a is of any one of the following structures:

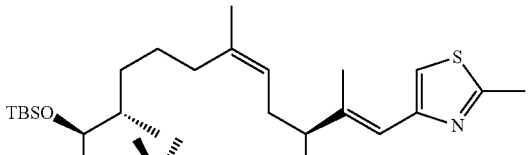

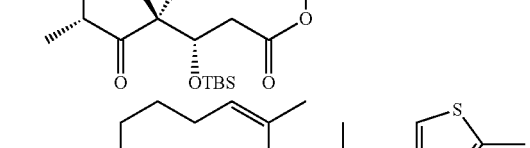

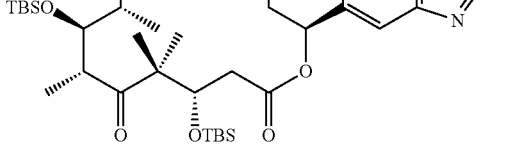

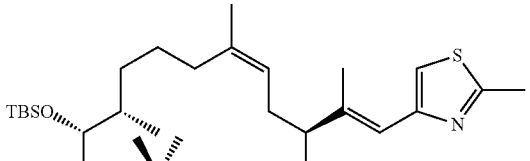

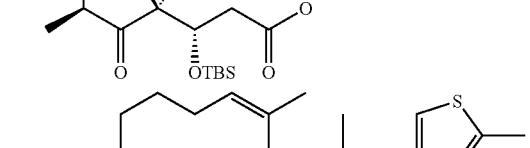

In some embodiments, a compound of formula I-a is of any one of the following structures:

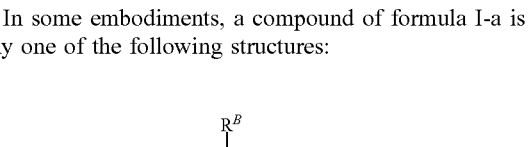

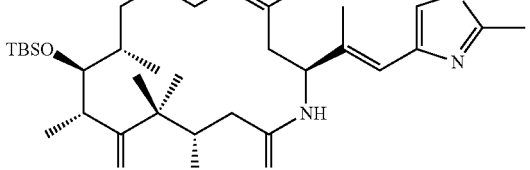

-continued
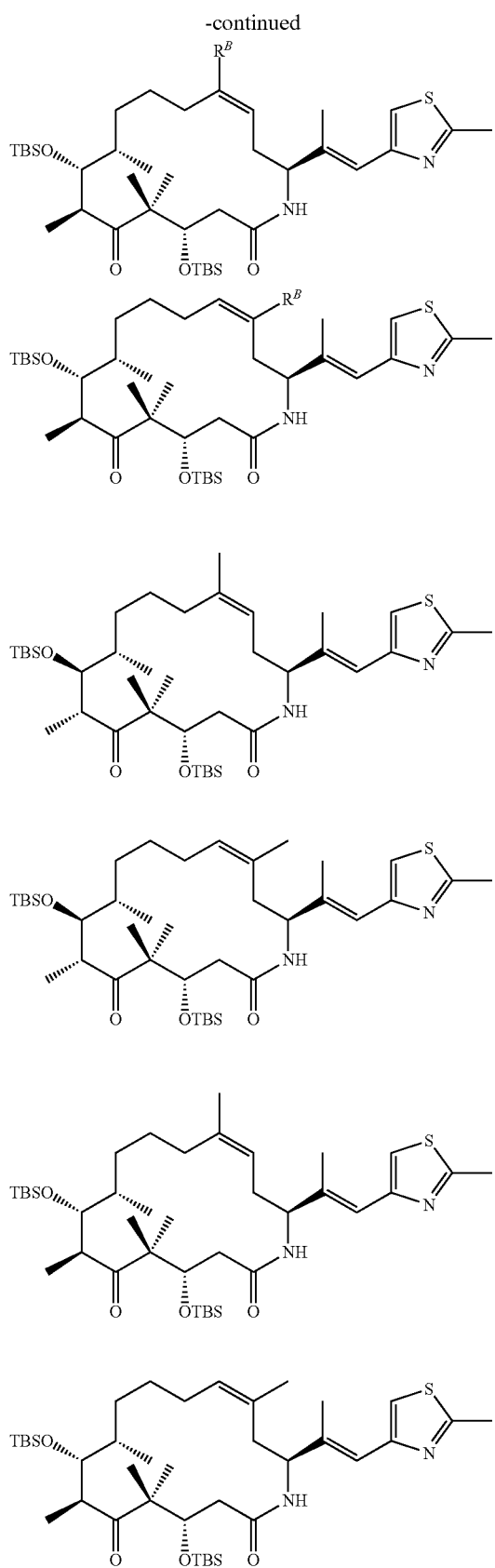
wherein each $R^B$ is independently as defined above and described herein.
In some embodiments, a compound of formula I-a is of the following structure:
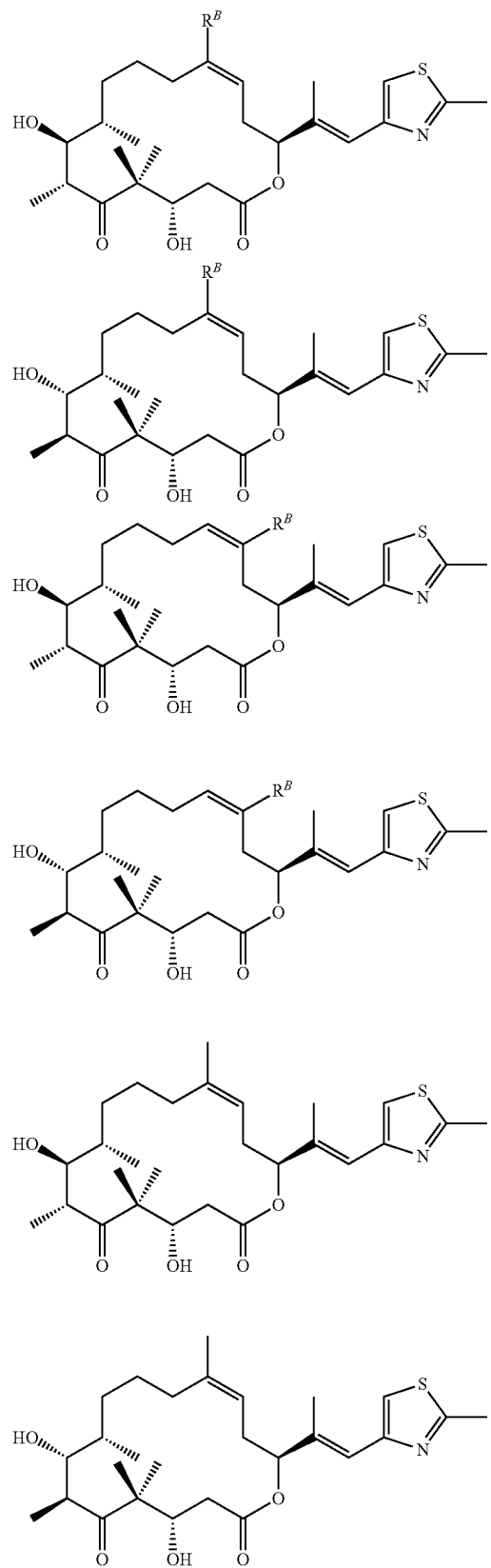

-continued

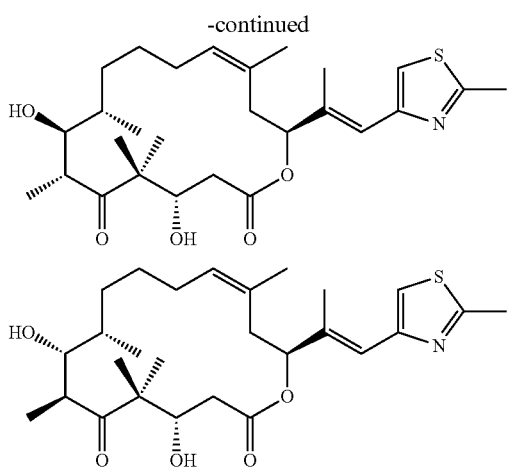

wherein each $R^B$ is independently as defined above and described herein.

In some embodiments, a compound of formula I-a is of the following structure:

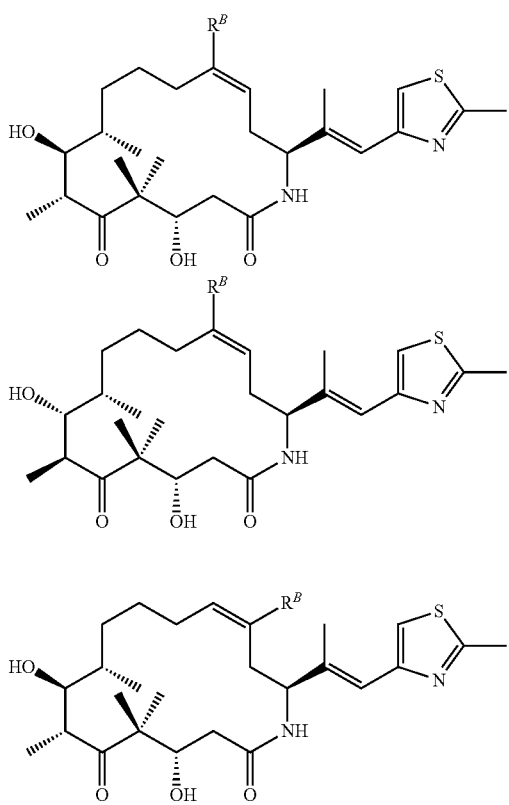

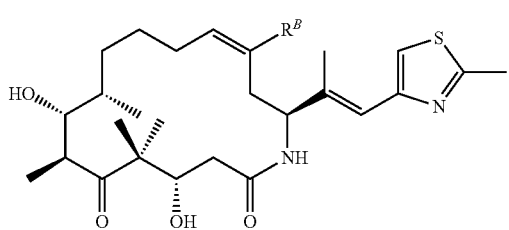

-continued

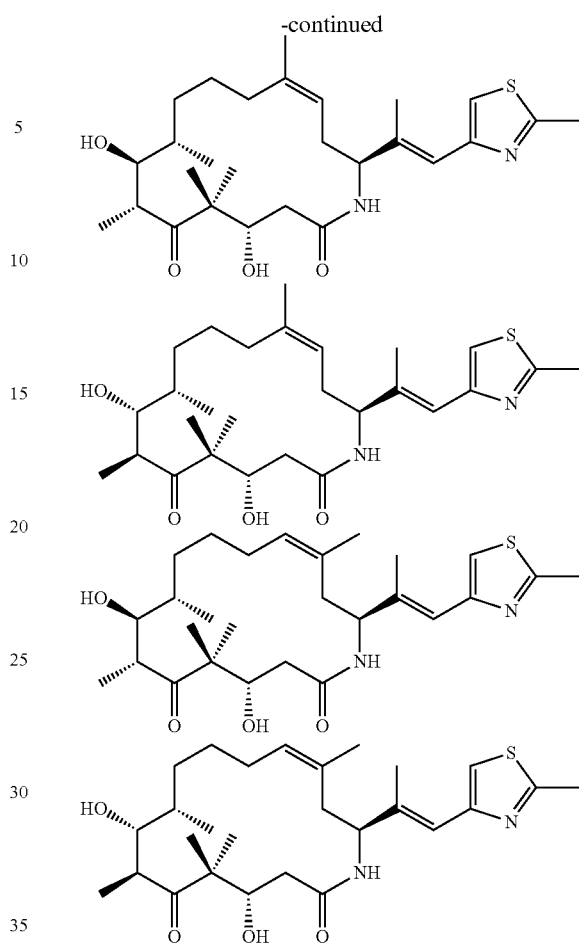

wherein each $R^B$ is independently as defined above and described herein.

In some embodiments, a compound of formula I-a is

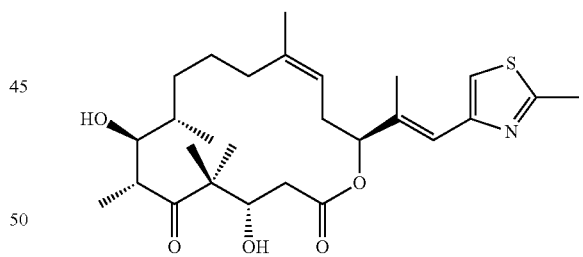

Nakadomarin a and Related Compounds

As described above, in certain embodiments Ring A of formula I comprises at least one -Cy$^1$- group, wherein the at least one -Cy$^1$- group is independently a bivalent tetracyclic 15 membered heteroarylene having 3 heteroatoms independently selected from nitrogen, oxygen, or sulfur. In some embodiments, the at least one -Cy$^1$- group is optionally substituted at any substitutable atom with one or more $R^A$ groups, as valency permits. In some embodiments, -Cy$^1$- is substituted with at least two R groups, wherein the at least two R groups are on adjacent atoms and are taken together with their intervening atoms to form an optionally substituted 3-8 membered saturated, partially unsaturated, or aryl ring having 0-4 heteroatoms independently selected from nitrogen, oxygen, or sulfur.

As described above, in certain embodiments Ring A of formula I-a comprises at least one -Cy$^1$- group, wherein the at least one -Cy$^1$- group is independently a bivalent tetracyclic 15 membered heteroarylene having 3 heteroatoms independently selected from nitrogen, oxygen, or sulfur. In some embodiments, the at least one -Cy$^1$- group is optionally substituted at any substitutable atom with one or more R$^A$ groups, as valency permits. In some embodiments, -Cy$^1$- is substituted with at least two R groups, wherein the at least two R groups are on adjacent atoms and are taken together with their intervening atoms to form an optionally substituted 3-8 membered saturated, partially unsaturated, or aryl ring having 0-4 heteroatoms independently selected from nitrogen, oxygen, or sulfur.

In some embodiments, Ring A of formula I is an optionally substituted 8-30 membered saturated or partially unsaturated ring wherein at least one methylene unit is replaced by -Cy$^1$-, wherein the at least one -Cy$^1$- group is optionally substituted and is of any one of the following formulae:

wherein each R and R$^A$ is as defined above and described herein.

In some embodiments, Ring A of formula I-a is an optionally substituted 8-30 membered saturated or partially unsaturated ring wherein at least one methylene unit is replaced by -Cy$^1$-, wherein the at least one -Cy$^1$- group is optionally substituted and is of any one of the following formulae:

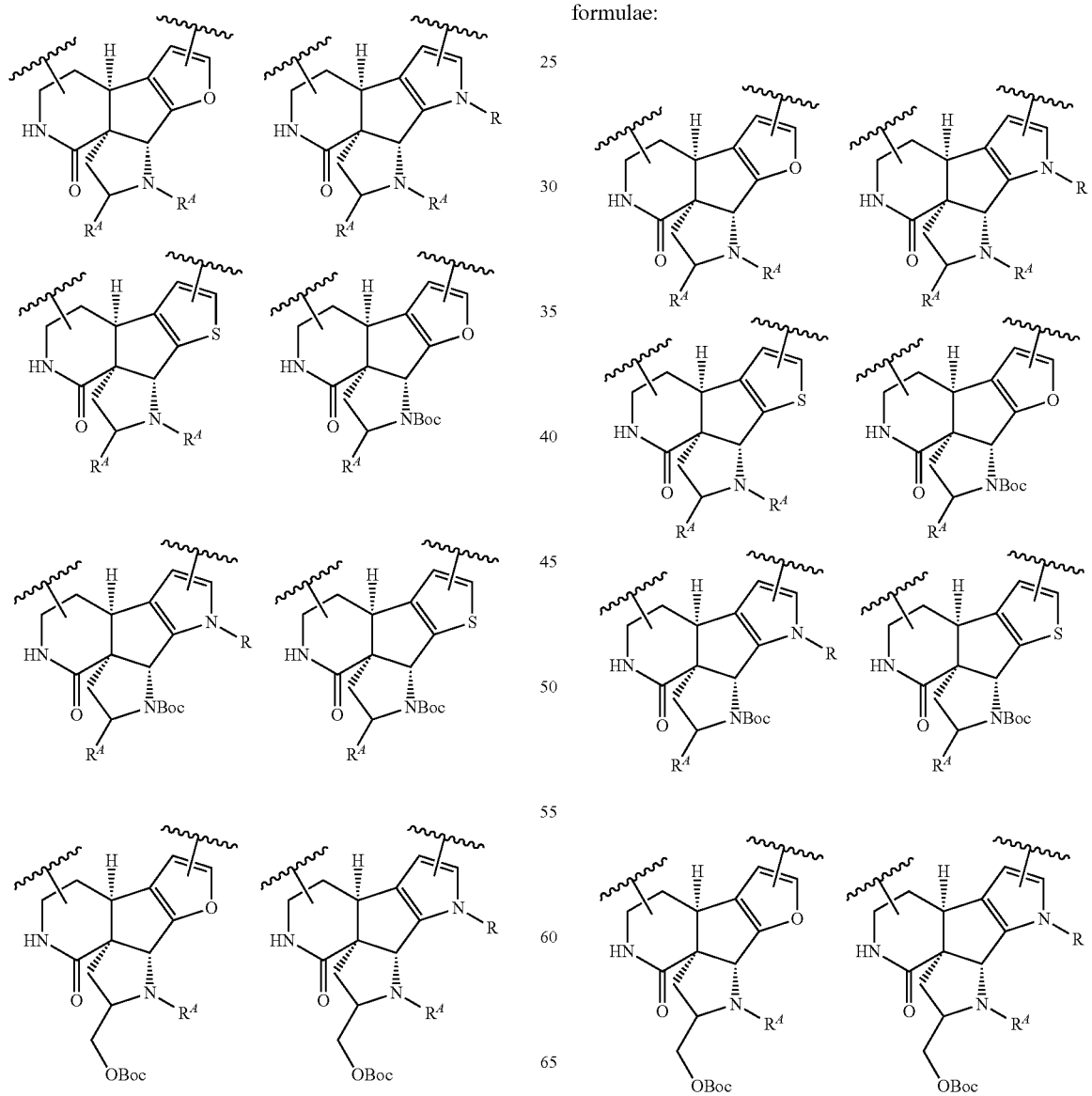

87

-continued

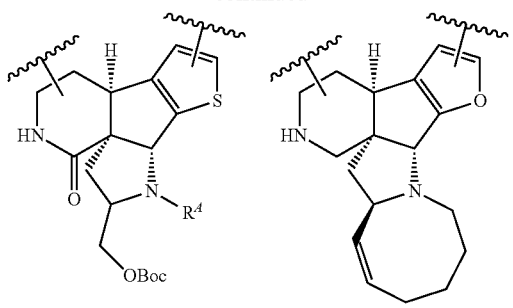

wherein each R and $R^A$ is as defined above and described herein.

In certain embodiments, a compound of formula I is as described and depicted above, wherein 1-5 additional methylene units are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^1$. In certain embodiments, a compound of formula I-a is as described and depicted above, wherein 1-5 additional methylene units are optionally and independently replaced by —O—, —N(R)—, —S—, —C(O)—, —OC(O)—, —C(O)O—, —OC(O)O—, —S(O)—, or —S(O)$_2$—, —OSO$_2$O—, —N(R)C(O)—, —C(O)N(R)—, —N(R)C(O)O—, —OC(O)NR—, —N(R)C(O)NR—, or -Cy$^1$.

In some embodiments, a compound of formula I is of any one of the following formulae:

88

-continued

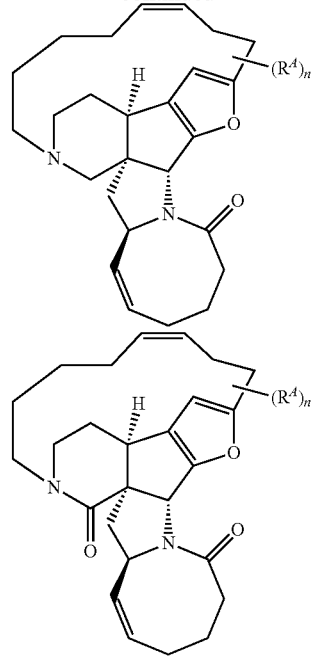

wherein $R^A$ and n are as defined above and described herein. One of skill in the art will recognize that $R^A$ can be present on any substitutable atom depicted in the above structures.

In certain embodiments, a compound of formula I is of either of the following structures:

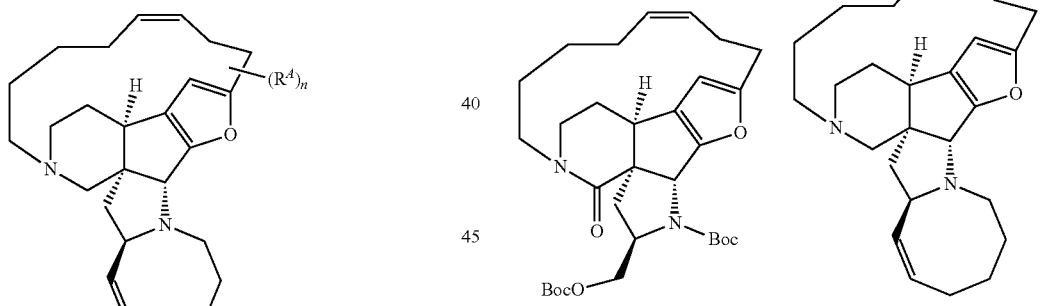

In some embodiments, a compound of formula I-a is of any one of the following formulae:

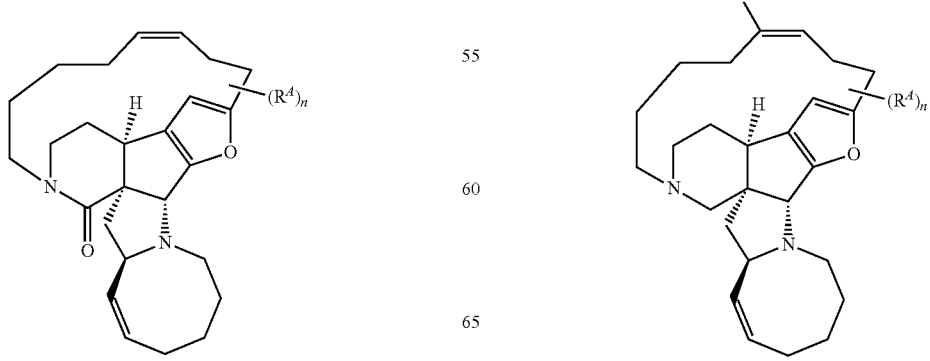

89
-continued
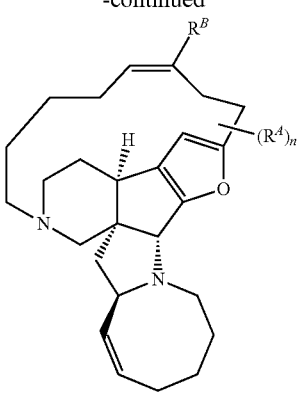
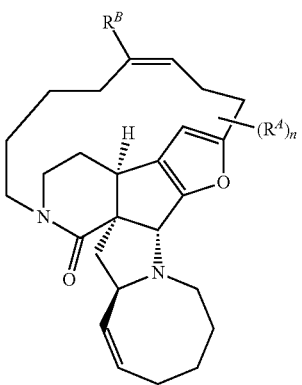
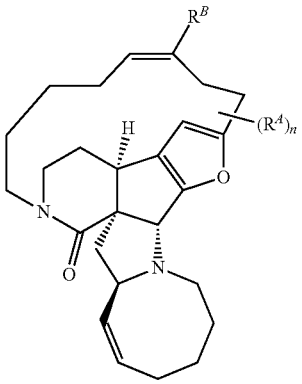
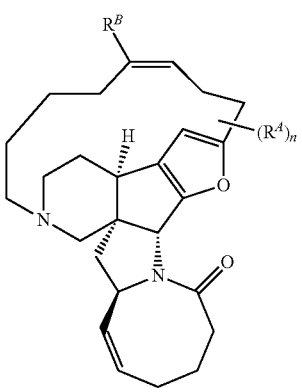
90
-continued
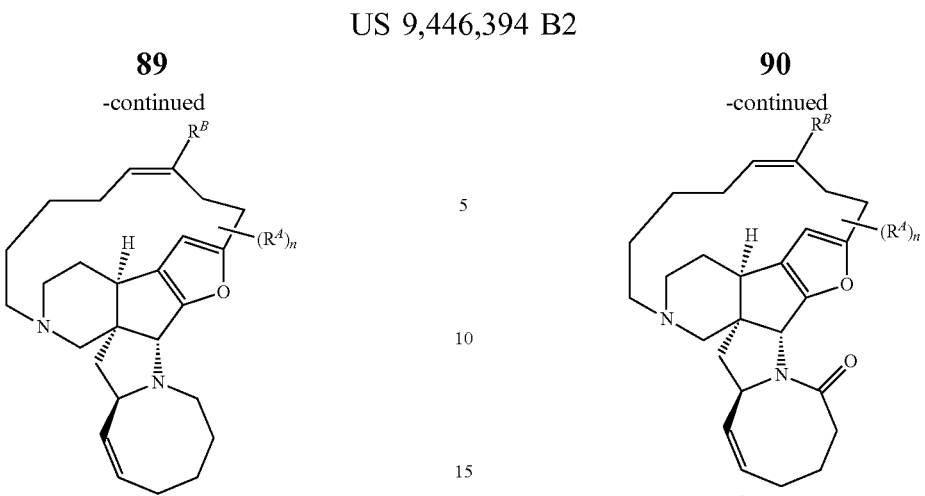
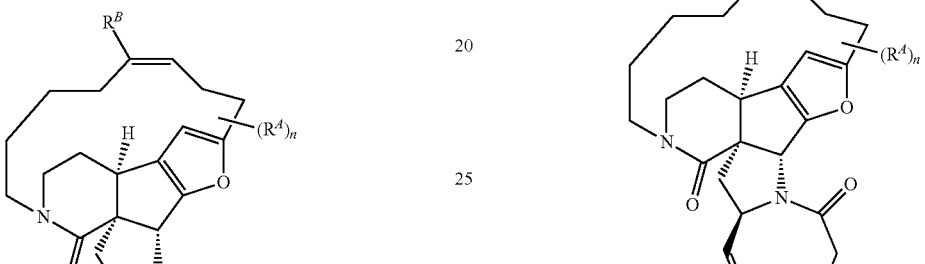
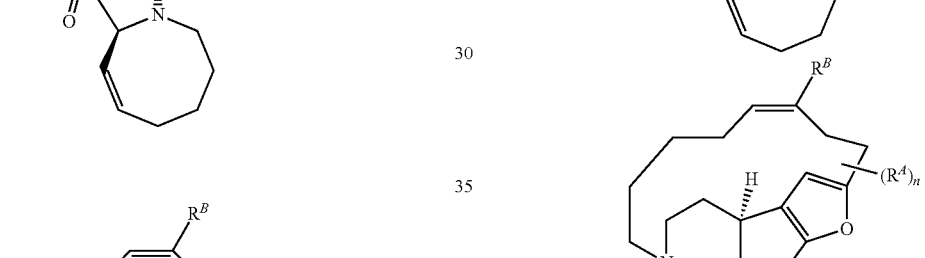
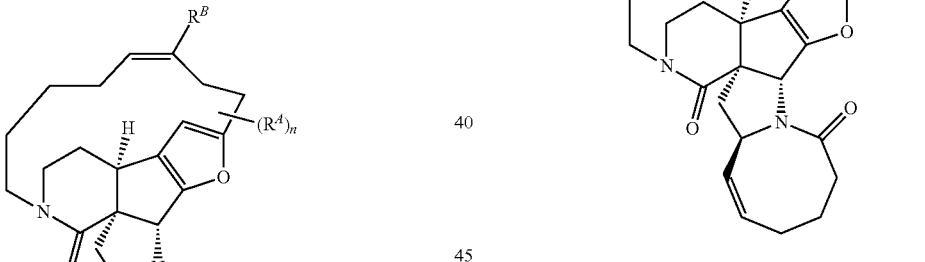
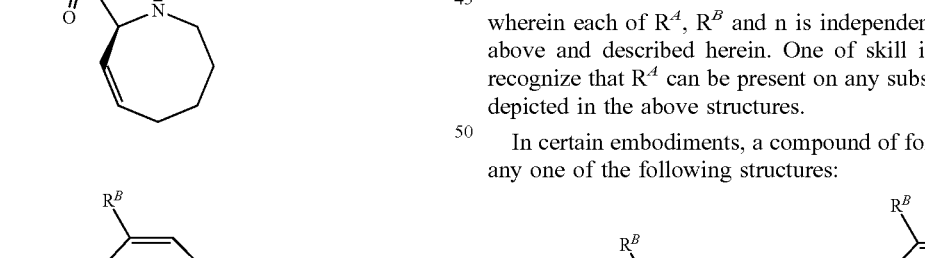
wherein each of $R^A$, $R^B$ and n is independently as defined above and described herein. One of skill in the art will recognize that $R^A$ can be present on any substitutable atom depicted in the above structures.
In certain embodiments, a compound of formula I-a is of any one of the following structures:
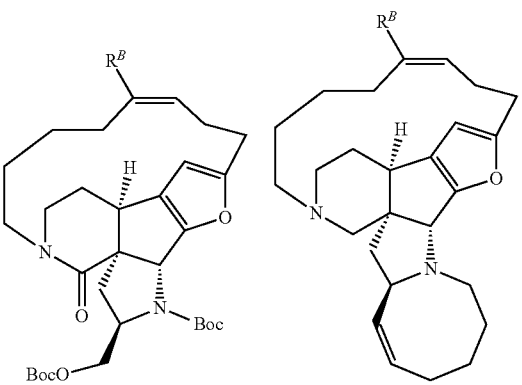

-continued

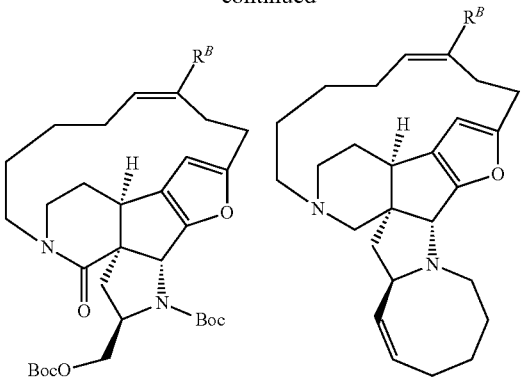

wherein each $R^B$ is independently as defined above and described herein.

Metal Complexes for Use in Methods of the Present Invention

In some embodiments, a provided method comprises use of a metal complex of formula II-a:

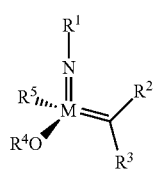
II-a to form a Z-alkene of formula I, wherein each of $R^1$, $R^2$, $R^3$, $R^4$, and $R^5$ of formula II-a are as defined above and described in embodiments herein, both singly and in combination.

In some embodiments, a provided method comprises use of a metal complex of formula II-b:

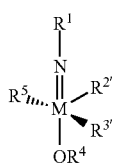
II-b to form a Z-alkene of formula I, wherein each of $R^1$, $R^{2'}$, $R^{3'}$, $R^4$, and $R^5$ of formula II-b are as defined above and described in embodiments herein, both singly and in combination.

In some embodiments, a provided method comprises use of a metal complex of formula II-a:

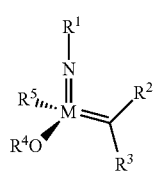
II-a to form a Z-alkene of formula I-a, wherein each of $R^1$, $R^2$, $R^3$, $R^4$, and $R^5$ of formula II-a are as defined above and described in embodiments herein, both singly and in combination.

In some embodiments, a provided method comprises use of a metal complex of formula II-b:

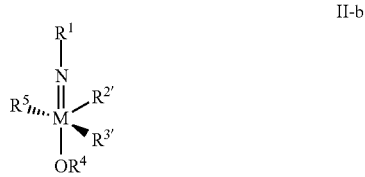
II-b to form a Z-alkene of formula I-a, wherein each of $R^1$, $R^{2'}$, $R^{3'}$, $R^4$, and $R^5$ of formula II-b are as defined above and described in embodiments herein, both singly and in combination.

In some embodiments, a provided method comprises use of a metal complex of formula II-c:

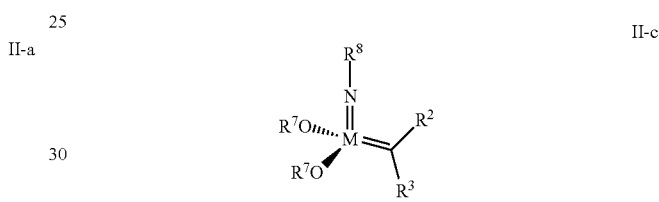
II-c to form a Z-alkene of formula I, wherein each of $R^8$, $R^2$, $R^3$, and $R^7$ of formula II-c is independently as defined above and described in embodiments herein, both singly and in combination.

In some embodiments, a provided method comprises use of a metal complex of formula II-c:

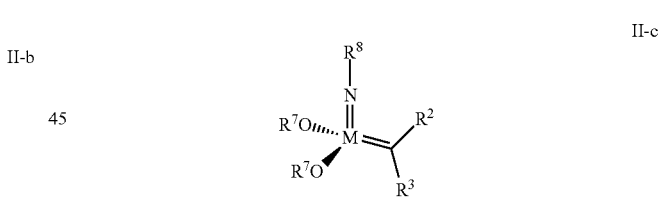
II-c to form a Z-alkene of formula I-a, wherein each of $R^8$, $R^2$, $R^3$, and $R^7$ of formula II-c is independently as defined above and described in embodiments herein, both singly and in combination.

As defined above, the M moiety of formula II-a, formula II-b, and formula II-c is a suitable metal. One of ordinary skill in the art would recognize that a suitable metal, M, is one that can achieve the appropriate valency and also result in a reactive metathesis catalyst. As defined above, M is molybdenum or tungsten. In some embodiments, M is molybdenum. In other embodiments, M is tungsten.

As defined generally above, the $R^1$ group of formula II-a, formula II-b, and formula II-c is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, the $R^1$ group of formula II-a, formula II-b, and formula II-c is an optionally substituted group selected from $C_{1-20}$ aliphatic, phenyl, a 3-7 membered saturated or partially unsaturated carbocyclic ring, or an 8-10 membered bicyclic saturated, partially unsaturated or aryl ring. In certain embodiments, $R^1$ is optionally substituted phenyl. In some embodiments, $R^1$ is substituted phenyl. In some embodiments, $R^1$ is mono-, di-, or tri-substituted phenyl. In certain embodiments, $R^1$ is 2,6-disubstituted phenyl. In some embodiments, $R^1$ is phenyl disubstituted with halogen or $C_{1-4}$ aliphatic. Such $R^1$ groups include 2,6-dichlorophenyl, 2,6-dibromophenyl, 2,6-dimethylphenyl, 2,6-di-tert-butylphenyl, and 2,6-diisopropylphenyl.

In certain embodiments, the $R^1$ group of formula II-a, formula II-b, and formula II-c is an optionally substituted group selected from $C_{1-20}$ aliphatic. In some embodiments, $R^1$ is an optionally substituted $C_{3-20}$ mono-, di-, or tri-cyclic aliphatic group. In some embodiments, $R^1$ is an optionally substituted bridged bicyclic or tricyclic aliphatic group. In certain embodiments, $R^1$ is an optionally substituted adamantyl group. In other embodiments, $R^1$ is an optionally substituted $C_{3-8}$ membered cycloalkyl group. In some embodiments, $R^1$ is selected from any of those $R^1$ groups depicted or described herein.

In some embodiments, $R^1$ is selected from:

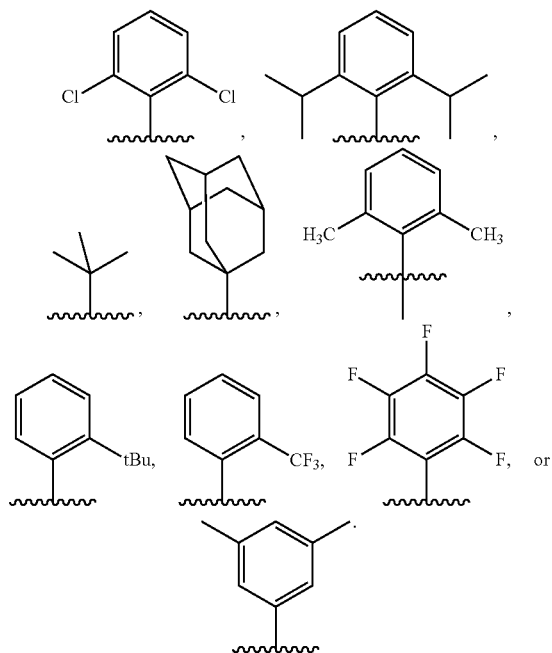

As defined generally above, each of $R^2$ and $R^3$ of formula II-a or II-c is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen, wherein R' is hydrogen, or an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, provided that $R^2$ and $R^3$ are not simultaneously hydrogen.

In some embodiments, one of $R^2$ and $R^3$ of formula II-a or II-c is hydrogen and the other is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, the $R^2$ group or the $R^3$ group of formula II-a or II-c is optionally substituted $C_{1-20}$ aliphatic. In some embodiments, $R^2$ or $R^3$ is optionally substituted $C_{1-20}$ alkyl. In certain embodiments, $R^2$ or $R^3$ is $C_{1-6}$ alkyl substituted with phenyl and one or two additional substituents. In certain embodiments, $R^2$ or $R^3$ is a lower alkyl group optionally substituted with one or two methyl groups and phenyl. In certain embodiments, $R^2$ or $R^3$ is —C(Me)$_2$Ph. In certain embodiments, $R^2$ or $R^3$ is C(Me)$_3$. In some embodiments, $R^2$ or $R^3$ is selected from any of those $R^2$ or $R^3$ groups depicted or described herein.

As defined above and described herein, $R^{2'}$ and $R^{3'}$ of formula II-b are taken together with the intervening metal atom to form an optionally substituted 3-8 membered saturated or partially unsaturated ring having, in addition to the intervening metal atom, 0-4 heteroatoms independently selected from nitrogen, oxygen, or sulfur.

In some embodiments, $R^{2'}$ and $R^{3'}$ of formula II-b are taken together with the intervening metal atom to form an optionally substituted 3-8 membered saturated ring having, in addition to the intervening metal atom, 0-4 heteroatoms independently selected from nitrogen, oxygen, or sulfur. In some embodiments, $R^{2'}$ and $R^{3'}$ of formula II-b are taken together with the intervening metal atom to form an optionally substituted 3-8 membered saturated ring having, in addition to the intervening metal atom, 0-2 heteroatoms independently selected from nitrogen, oxygen, or sulfur. In some embodiments, $R^{2'}$ and $R^{3'}$ of formula II-b are taken together with the intervening metal atom to form an optionally substituted 5-6 membered saturated ring having, in addition to the intervening metal atom, 0-4 heteroatoms independently selected from nitrogen, oxygen, or sulfur. In some embodiments, $R^{2'}$ and $R^{3'}$ of formula II-b are taken together with the intervening metal atom to form an optionally substituted 5-6 membered saturated ring having, in addition to the intervening metal atom, 0-2 heteroatoms independently selected from nitrogen, oxygen, or sulfur. In some embodiments, $R^{2'}$ and $R^{3'}$ of formula II-b are taken together with the intervening metal atom to form an optionally substituted 3-4 membered saturated ring having, in addition to the intervening metal atom, 0-4 heteroatoms independently selected from nitrogen, oxygen, or sulfur. In some embodiments, $R^{2'}$ and $R^{3'}$ of formula II-b are taken together with the intervening metal atom to form an optionally substituted 3-4 membered saturated ring having, in addition to the intervening metal atom, 0-2 heteroatoms independently selected from nitrogen, oxygen, or sulfur.

In certain embodiments, $R^{2'}$ and $R^{3'}$ of formula II-b are taken together with the intervening metal atom to form an optionally substituted 4 membered saturated ring. In certain embodiments, $R^{2'}$ and $R^{3'}$ of formula II-b are taken together with the intervening metal atom to form metallacyclobutane.

In some embodiments, $R^{2'}$ and $R^{3'}$ of formula II-b are taken together with the intervening metal atom to form an optionally substituted 3-8 membered partially unsaturated ring having, in addition to the intervening metal atom, 0-4 heteroatoms independently selected from nitrogen, oxygen, or sulfur. In some embodiments, $R^{2'}$ and $R^{3'}$ of formula II-b are taken together with the intervening metal atom to form an optionally substituted 3-8 membered partially unsaturated ring having, in addition to the intervening metal atom, 0-2 heteroatoms independently selected from nitrogen, oxygen, or sulfur. In some embodiments, $R^{2'}$ and $R^{3'}$ of formula II-b are taken together with the intervening metal atom to form an optionally substituted 5-6 membered partially unsaturated ring having, in addition to the intervening metal atom, 0-4 heteroatoms independently selected from nitrogen, oxygen, or sulfur. In some embodiments, $R^{2'}$ and $R^{3'}$ of formula II-b are taken together with the intervening metal atom to form an optionally substituted 5-6 membered partially unsaturated ring having, in addition to the intervening metal atom, 0-2 heteroatoms independently selected from nitrogen, oxygen, or sulfur. In some embodiments, $R^{2'}$ and $R^{3'}$ of formula II-b are taken together with the intervening metal atom to form an optionally substituted 3-4 membered partially unsaturated ring having, in addition to the intervening metal atom, 0-4 heteroatoms independently selected from nitrogen, oxygen, or sulfur. In some embodiments, $R^{2'}$ and $R^{3'}$ of formula II-b are taken together with the intervening metal atom to form an optionally substituted 3-4 membered partially unsaturated ring having, in addition to the intervening metal atom, 0-2 heteroatoms independently selected from nitrogen, oxygen, or sulfur.

As defined and described above and herein, $R^4$ is an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur.

In some embodiments, —$OR^4$ is a phenol.

In some embodiments, —$OR^4$ is an asymmetric ligand. In certain embodiments, —$OR^4$ is a silyl-protected BINOL derivative.

In some embodiments, —$OR^4$ is an optionally substituted group selected from:

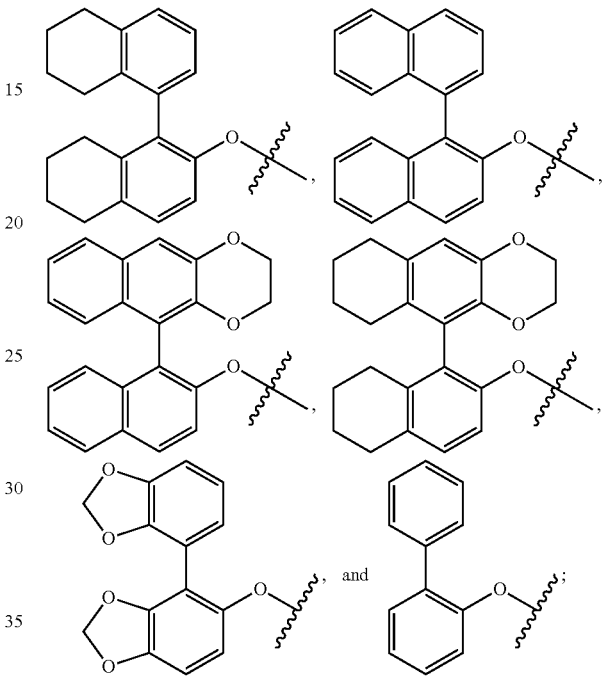

wherein each $\xi$ represents the point of attachment to the metal, M.

In certain embodiments, $R^4$ is optionally substituted —Ar.

As defined above and described herein, —Ar is of the following formula:

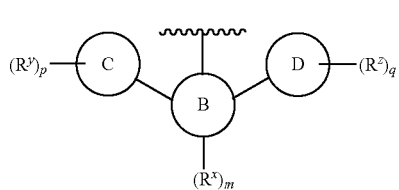

wherein:
m is 0-3;
Ring B is an optionally substituted group selected from phenyl or a 5-6 membered monocyclic heteroaryl ring having 1-4 heteroatoms independently selected from nitrogen, oxygen, or sulfur;
p and q are independently 0-6;
each of Ring C and Ring D are independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each $R^x$, $R^y$, and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur.

In some embodiments, m is 0. In some embodiments, m is 1. In some embodiments, m is 2. In some embodiments, m is 3.

In some embodiments, Ring B is an optionally substituted phenyl group. In some embodiments, Ring B is of the following structure:

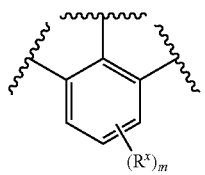

wherein $R^x$ and m are as defined above and described herein.

In certain embodiments, Ring B is of the following structure:

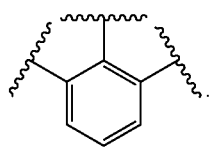 [SMILES: *c1cccc(*)c1*]

In some embodiments, Ring B is a 5-6 membered monocyclic heteroaryl ring having 1-4 heteroatoms independently selected from nitrogen, oxygen, or sulfur. In some embodiments, Ring B is a 5-6 membered monocyclic heteroaryl ring having 1-2 heteroatoms independently selected from nitrogen, oxygen, or sulfur.

In some embodiments, Ring B is a 5 membered monocyclic heteroaryl ring having 1-4 heteroatoms independently selected from nitrogen, oxygen, or sulfur. In some embodiments, Ring B is a 5 membered monocyclic heteroaryl ring having 1-2 heteroatoms independently selected from nitrogen, oxygen, or sulfur.

In some embodiments, Ring B is a 6 membered monocyclic heteroaryl ring having 1-4 heteroatoms independently selected from nitrogen, oxygen, or sulfur. In some embodiments, Ring B is a 6 membered monocyclic heteroaryl ring having 1-2 heteroatoms independently selected from nitrogen, oxygen, or sulfur.

Exemplary optionally substituted Ring B heteroaryl groups include thienylene, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and the like.

In some embodiments, each $R^x$ is independently halogen, —OR, —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur.

In certain embodiments, at least one $R^x$ is independently halogen.

In certain embodiments, at least one $R^x$ is independently selected from —OR, —N(R')$_2$, —NR'C(O)R', —NR'C(O)OR', —NR'C(O)N(R')$_2$, —NR'SO$_2$R', —NR'SO$_2$N(R')$_2$, or —NR'OR'.

In certain embodiments, each $R^x$ is independently optionally substituted $C_{1-20}$ aliphatic.

In certain embodiments, each $R^x$ is independently optionally substituted $C_{1-20}$ heteroaliphatic having 1-3 heteroatoms independently selected from nitrogen, oxygen, or sulfur.

In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, Ring C is optionally substituted phenyl.

In some embodiments, Ring C is of the following formula:

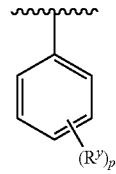

wherein $R^y$ and p are as defined above and described herein.

In certain embodiments, Ring C is of the following formula:

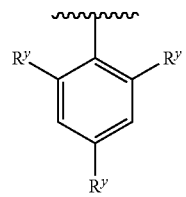

wherein $R^y$ is as defined above and described herein.

In certain embodiments, Ring C is of the following structure:

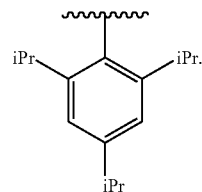 [SMILES: *c1c(C(C)C)cc(C(C)C)cc1C(C)C]

In some embodiments, Ring C is an optionally substituted a 3-7 membered saturated carbocyclic ring. In some embodiments, Ring C is an optionally substituted a 5-6 membered saturated carbocyclic ring. In some embodiments, Ring C is an optionally substituted a 3-7 membered partially unsaturated carbocyclic ring. In some embodiments, Ring C is an optionally substituted a 5-6 membered partially unsaturated carbocyclic ring.

In some embodiments, Ring C is an optionally substituted 8-10 membered bicyclic saturated carbocyclic ring. In some embodiments, Ring C is an optionally substituted 8-10 membered bicyclic partially unsaturated carbocyclic ring. In some embodiments, Ring C is an optionally substituted 10 membered bicyclic aryl ring.

In some embodiments, Ring C is an optionally substituted 5-6 membered monocyclic heteroaryl ring having 1-4 heteroatoms independently selected from nitrogen, oxygen, or sulfur. In some embodiments, Ring C is an optionally substituted 5-6 membered monocyclic heteroaryl ring having 1-2 heteroatoms independently selected from nitrogen, oxygen, or sulfur.

In some embodiments, Ring C is an optionally substituted 5 membered monocyclic heteroaryl ring having 1-4 heteroatoms independently selected from nitrogen, oxygen, or sulfur. In some embodiments, Ring C is an optionally substituted 5 membered monocyclic heteroaryl ring having 1-2 heteroatoms independently selected from nitrogen, oxygen, or sulfur.

In some embodiments, Ring C is an optionally substituted 6 membered monocyclic heteroaryl ring having 1-4 heteroatoms independently selected from nitrogen, oxygen, or sulfur. In some embodiments, Ring C is an optionally substituted 6 membered monocyclic heteroaryl ring having 1-2 heteroatoms independently selected from nitrogen, oxygen, or sulfur.

In some embodiments, Ring C is an optionally substituted 4-7 membered saturated heterocyclic ring having 1-3 heteroatoms independently selected from nitrogen, oxygen, or sulfur. In some embodiments, Ring C is an optionally substituted 5-6 membered saturated heterocyclic ring having 1-2 heteroatoms independently selected from nitrogen, oxygen, or sulfur.

In some embodiments, Ring C is an optionally substituted 4-7 membered partially unsaturated heterocyclic ring having 1-3 heteroatoms independently selected from nitrogen, oxygen, or sulfur. In some embodiments, Ring C is an optionally substituted 5-6 membered partially unsaturated heterocyclic ring having 1-2 heteroatoms independently selected from nitrogen, oxygen, or sulfur.

In some embodiments, Ring C is an optionally substituted 7-10 membered bicyclic saturated heterocyclic ring having 1-5 heteroatoms independently selected from nitrogen, oxygen, or sulfur. In some embodiments, Ring C is an optionally substituted 8-10 membered bicyclic saturated heterocyclic ring having 1-2 heteroatoms independently selected from nitrogen, oxygen, or sulfur.

In some embodiments, Ring C is an optionally substituted 7-10 membered bicyclic partially unsaturated heterocyclic ring having 1-5 heteroatoms independently selected from nitrogen, oxygen, or sulfur. In some embodiments, Ring C is an optionally substituted 8-10 membered bicyclic partially unsaturated heterocyclic ring having 1-2 heteroatoms independently selected from nitrogen, oxygen, or sulfur.

In some embodiments, Ring C is an optionally substituted 8-10 membered bicyclic heteroaryl ring having 1-5 heteroatoms independently selected from nitrogen, oxygen, or sulfur. In some embodiments, Ring C is an optionally substituted 8 membered bicyclic heteroaryl ring having 1-3 heteroatoms independently selected from nitrogen, oxygen, or sulfur. In some embodiments, Ring C is an optionally substituted 9 membered bicyclic heteroaryl ring having 1-3 heteroatoms independently selected from nitrogen, oxygen, or sulfur. In some embodiments, Ring C is an optionally substituted 10 membered bicyclic heteroaryl ring having 1-3 heteroatoms independently selected from nitrogen, oxygen, or sulfur.

In some embodiments, each $R^y$ is independently halogen, —OR, —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur.

In certain embodiments, at least one $R^y$ is independently halogen.

In certain embodiments, at least one $R^y$ is independently selected from —OR, —N(R')$_2$, —NR'C(O)R', —NR'C(O)OR', —NR'C(O)N(R')$_2$, —NR'SO$_2$R', —NR'SO$_2$N(R')$_2$, or —NR'OR'.

In certain embodiments, each $R^y$ is independently optionally substituted $C_{1-20}$ aliphatic. In certain embodiments, each $R^y$ is independently optionally substituted $C_{1-10}$ aliphatic. In certain embodiments, each $R^y$ is independently optionally substituted $C_{1-5}$ aliphatic. In certain embodiments, $R^y$ is alkyl. In certain embodiments, each $R^y$ is independently selected from methyl, ethyl, propyl, or butyl. In certain embodiments, each $R^y$ is isopropyl.

In certain embodiments, each $R^y$ is independently optionally substituted $C_{1-20}$ heteroaliphatic having 1-3 heteroatoms independently selected from nitrogen, oxygen, or sulfur.

In some embodiments, q is 0. In some embodiments, q is 1. In some embodiments, q is 2. In some embodiments, q is 3. In some embodiments, q is 4. In some embodiments, q is 5. In some embodiments, q is 6.

In some embodiments, Ring D is optionally substituted phenyl.

In some embodiments, Ring D is of the following formula:

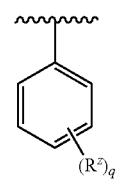

wherein $R^z$ and q are as defined above and described herein.

In certain embodiments, Ring D is of the following formula:

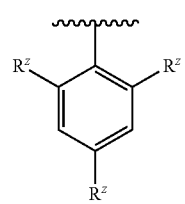

wherein $R^z$ is as defined above and described herein.

In certain embodiments, Ring D is of the following structure:

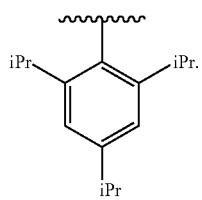 [SMILES: *c1c(C(C)C)cc(C(C)C)cc1C(C)C]

In some embodiments, Ring D is an optionally substituted a 3-7 membered saturated carbocyclic ring. In some embodiments, Ring D is an optionally substituted a 5-6 membered saturated carbocyclic ring. In some embodiments, Ring D is an optionally substituted a 3-7 membered partially unsaturated carbocyclic ring. In some embodiments, Ring D is an optionally substituted a 5-6 membered partially unsaturated carbocyclic ring.

In some embodiments, Ring D is an optionally substituted 8-10 membered bicyclic saturated carbocyclic ring. In some embodiments, Ring D is an optionally substituted 8-10 membered bicyclic partially unsaturated carbocyclic ring. In some embodiments, Ring D is an optionally substituted 10 membered bicyclic aryl ring.

In some embodiments, Ring D is an optionally substituted 5-6 membered monocyclic heteroaryl ring having 1-4 heteroatoms independently selected from nitrogen, oxygen, or sulfur. In some embodiments, Ring D is an optionally substituted 5-6 membered monocyclic heteroaryl ring having 1-2 heteroatoms independently selected from nitrogen, oxygen, or sulfur.

In some embodiments, Ring D is an optionally substituted 5 membered monocyclic heteroaryl ring having 1-4 heteroatoms independently selected from nitrogen, oxygen, or sulfur. In some embodiments, Ring D is an optionally substituted 5 membered monocyclic heteroaryl ring having 1-2 heteroatoms independently selected from nitrogen, oxygen, or sulfur.

In some embodiments, Ring D is an optionally substituted 6 membered monocyclic heteroaryl ring having 1-4 heteroatoms independently selected from nitrogen, oxygen, or sulfur. In some embodiments, Ring D is an optionally substituted 6 membered monocyclic heteroaryl ring having 1-2 heteroatoms independently selected from nitrogen, oxygen, or sulfur.

In some embodiments, Ring D is an optionally substituted 4-7 membered saturated heterocyclic ring having 1-3 heteroatoms independently selected from nitrogen, oxygen, or sulfur. In some embodiments, Ring D is an optionally substituted 5-6 membered saturated heterocyclic ring having 1-2 heteroatoms independently selected from nitrogen, oxygen, or sulfur.

In some embodiments, Ring D is an optionally substituted 4-7 membered partially unsaturated heterocyclic ring having 1-3 heteroatoms independently selected from nitrogen, oxygen, or sulfur. In some embodiments, Ring D is an optionally substituted 5-6 membered partially unsaturated heterocyclic ring having 1-2 heteroatoms independently selected from nitrogen, oxygen, or sulfur.

In some embodiments, Ring D is an optionally substituted 7-10 membered bicyclic saturated heterocyclic ring having 1-5 heteroatoms independently selected from nitrogen, oxygen, or sulfur. In some embodiments, Ring D is an optionally substituted 8-10 membered bicyclic saturated heterocyclic ring having 1-2 heteroatoms independently selected from nitrogen, oxygen, or sulfur.

In some embodiments, Ring D is an optionally substituted 7-10 membered bicyclic partially unsaturated heterocyclic ring having 1-5 heteroatoms independently selected from nitrogen, oxygen, or sulfur. In some embodiments, Ring D is an optionally substituted 8-10 membered bicyclic partially unsaturated heterocyclic ring having 1-2 heteroatoms independently selected from nitrogen, oxygen, or sulfur.

In some embodiments, Ring D is an optionally substituted 8-10 membered bicyclic heteroaryl ring having 1-5 heteroatoms independently selected from nitrogen, oxygen, or sulfur. In some embodiments, Ring D is an optionally substituted 8 membered bicyclic heteroaryl ring having 1-3 heteroatoms independently selected from nitrogen, oxygen, or sulfur. In some embodiments, Ring D is an optionally substituted 9 membered bicyclic heteroaryl ring having 1-3 heteroatoms independently selected from nitrogen, oxygen, or sulfur. In some embodiments, Ring D is an optionally substituted 10 membered bicyclic heteroaryl ring having 1-3 heteroatoms independently selected from nitrogen, oxygen, or sulfur.

In some embodiments, each $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from C$_{1-20}$ aliphatic, C$_{1-20}$ heteroaliphatic having 1-3 heteroatoms independently selected from nitrogen, oxygen, or sulfur.

In certain embodiments, at least one $R^z$ is independently halogen.

In certain embodiments, at least one $R^z$ is independently selected from —OR, —N(R')$_2$, —NR'C(O)R', —NR'C(O)OR', —NR'C(O)N(R')$_2$, —NR'SO$_2$R', —NR'SO$_2$N(R')$_2$, or —NR'OR'.

In certain embodiments, each $R^z$ is independently optionally substituted C$_{1-20}$ aliphatic. In certain embodiments, each $R^z$ is independently optionally substituted C$_{1-10}$ aliphatic. In certain embodiments, each $R^z$ is independently optionally substituted C$_{1-5}$ aliphatic. In certain embodiments, $R^z$ is alkyl. In certain embodiments, each $R^z$ is independently selected from methyl, ethyl, propyl, or butyl. In certain embodiments, each $R^z$ is isopropyl.

In certain embodiments, each $R^z$ is independently optionally substituted C$_{1-20}$ heteroaliphatic having 1-3 heteroatoms independently selected from nitrogen, oxygen, or sulfur.

In some embodiments, —Ar is of the formula:

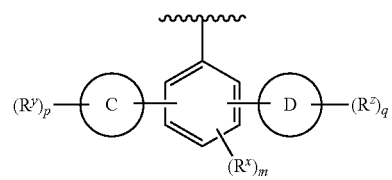

wherein each of $R^x$, m, Ring C, $R^y$, p, Ring D, $R^z$, and q are as defined above and described herein.

In some embodiments, —Ar is of the formula:

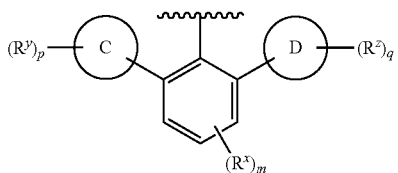

wherein each of $R^x$, m, Ring C, $R^y$, p, Ring D, $R^z$, and q are as defined above and described herein.

In some embodiments, —Ar is of the formula:

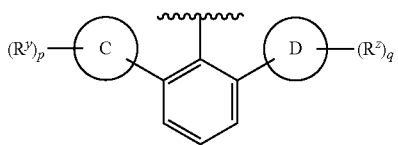

wherein each of Ring C, $R^y$, p, Ring D, $R^z$, and q are as defined above and described herein.

In some embodiments, —Ar is of the formula:

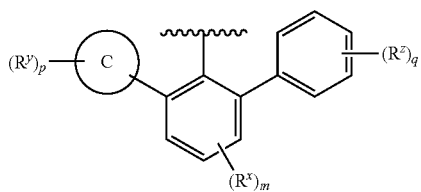

wherein each of $R^x$, m, Ring C, $R^y$, p, $R^z$, and q are as defined above and described herein.

In some embodiments, —Ar is of the formula:

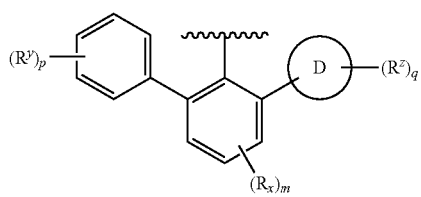

wherein each of $R^x$, m, Ring C, $R^y$, p, Ring D, $R^z$, and q are as defined above and described herein.

In some embodiments, —Ar is of the formula:

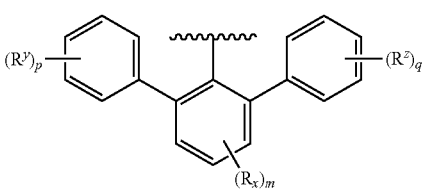

wherein each of $R^x$, m, $R^y$, p, $R^z$, and q are as defined above and described herein.

In some embodiments, —Ar is of the formula:

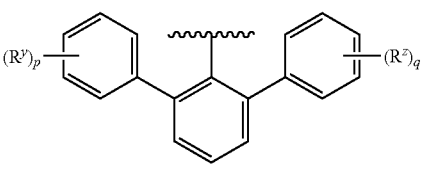

wherein each of $R^y$, p, $R^z$, and q are as defined above and described herein.

In some embodiments, —Ar is of the formula:

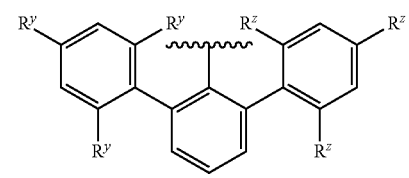

wherein each of $R^y$ and $R^z$ are as defined above and described herein. In certain embodiments wherein —Ar is as depicted above, each $R^y$ and each $R^z$ is independently selected from optionally substituted $C_{1-20}$ aliphatic. In certain embodiments wherein —Ar is as depicted above, each $R^y$ and each $R^z$ is independently selected from optionally substituted $C_{1-10}$ aliphatic. In certain embodiments wherein —Ar is as depicted above, each $R^y$ and each $R^z$ is independently selected from optionally substituted alkyl. Exemplary $R^y$ and $R^z$ groups include methyl, ethyl, propyl, and butyl.

In certain embodiments, —Ar has the following structure:

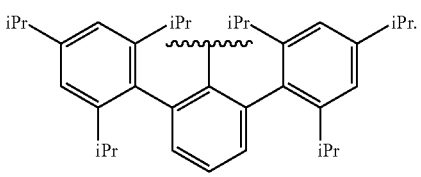 [SMILES: *c1c(-c2c(C(C)C)cc(C(C)C)cc2C(C)C)cccc1-c1c(C(C)C)cc(C(C)C)cc1C(C)C]

As defined generally above, $R^5$ is halogen, —$OR^6$, —$N(R')_2$, —NR'C(O)R', —NR'C(O)OR', —NR'C(O)N(R')_2$, —NR'SO_2R', —NR'SO_2N(R')_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur.

In some embodiments, $R^5$ is halogen. In other embodiments, $R^5$ is —$OR^6$, —$N(R')_2$, —NR'C(O)R', —NR'C(O)OR', —NR'C(O)N(R')_2$, —NR'SO_2R', —NR'SO_2N(R')_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur, wherein $R^5$ is coordinated to M via a nitrogen.

In certain embodiments, $R^5$ is —N(R')$_2$. In some embodiments, $R^5$ are —N(R')$_2$, wherein one R is hydrogen and the other is optionally substituted $C_{1-20}$ aliphatic.

In other embodiments, $R^5$ is —N(R')$_2$, wherein the two R' groups are taken together with the nitrogen to form an optionally substituted 3-8 membered saturated, partially unsaturated, or aryl ring having 0-3 heteroatoms not including the N atom from N(R')$_2$ independently selected from nitrogen, oxygen, or sulfur, wherein $R^5$ is coordinated to M via a nitrogen. In some embodiments, the two R' groups are taken together with the nitrogen to form an optionally substituted 5-membered heteroaryl ring having 0-3 nitrogen atoms not including the N atom from N(R')$_2$. Such rings include optionally substituted pyrrol-1-yl, pyrazol-1-yl, imidazol-1-yl, and triazol-1-yl. In some embodiments, such rings are unsubstituted pyrrol-1-yl, pyrazol-1-yl, imidazol-1-yl, and triazol-1-yl.

In some embodiments, $R^5$ is an optionally substituted 5-6 membered monocyclic heteroaryl ring having at least one nitrogen and 0-3 heteroatoms independently selected from nitrogen, oxygen, or sulfur. In some embodiments, $R^5$ is an optionally substituted group selected from pyrrolyl, pyrazolyl, imidazolyl, triazolyl, oxazolyl, isoxazoly, oxadiazoyl, thiazolyl, and thiazolyl. In some embodiments, $R^5$ is an unsubstituted group selected from pyrrolyl, pyrazolyl, imidazolyl, triazolyl, oxazolyl, isoxazoly, oxadiazoyl, thiazolyl, and thiazolyl. In some embodiments, $R^5$ is unsubstituted pyrrolyl. In some embodiments, $R^5$ is unsubstituted pyrrolyl.

In other embodiments, $R^5$ is an optionally substituted 8-10 membered bicyclic heteroaryl ring having at least one nitrogen and 0-4 heteroatoms independently selected from nitrogen, oxygen, or sulfur. In some embodiments, $R^5$ is an optionally substituted group selected from indolyl, benzimidazolyl, and indazolyl. In some embodiments, $R^5$ is an unsubstituted group selected from indolyl, benzimidazolyl, and indazolyl.

In certain embodiments, $R^5$ is an optionally substituted group selected from

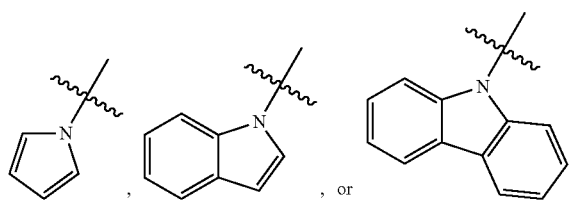 [SMILES: *n1cccc1 ; *n1ccc2ccccc21 ; *n1c2ccccc2c2ccccc21]

, or wherein each ∫ represents the point of attachment to the metal. In some embodiments, $R^5$ is an unsubstituted group selected from

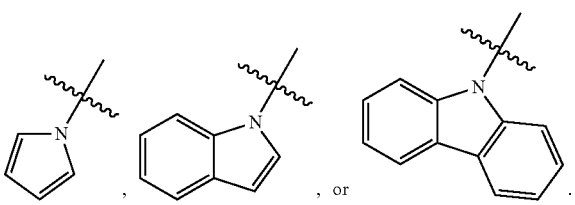 [SMILES: *n1cccc1 ; *n1ccc2ccccc21 ; *n1c2ccccc2c2ccccc21]

, or .

As defined generally above, $R^6$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, $R^6$ is optionally substituted $C_{1-20}$ aliphatic. In some embodiments, $R^6$ is unsubstituted $C_{1-20}$ aliphatic. In some embodiments, $R^6$ is optionally substituted $C_{1-20}$ heteroaliphatic having 1-3 heteroatoms independently selected from nitrogen, oxygen, or sulfur. In some embodiments, $R^6$ is unsubstituted $C_{1-20}$ heteroaliphatic having 1-3 heteroatoms independently selected from nitrogen, oxygen, or sulfur.

In some embodiments, $R^6$ is optionally substituted phenyl. In some embodiments, $R^6$ is unsubstituted phenyl.

In some embodiments, $R^6$ is an optionally substituted 3-7 membered saturated carbocyclic ring. In some embodiments, $R^6$ is an optionally substituted 5-6 membered saturated carbocyclic ring.

In some embodiments, $R^6$ is an optionally substituted 3-7 membered partially unsaturated carbocyclic ring. In some embodiments, $R^6$ is an optionally substituted 5-6 membered partially unsaturated carbocyclic ring.

In some embodiments, $R^6$ is an optionally substituted 8-10 membered bicyclic saturated ring. In some embodiments, $R^6$ is an optionally substituted 8-10 membered bicyclic partially unsaturated ring. In some embodiments, $R^6$ is an optionally substituted 10 membered bicyclic aryl ring. In some embodiments, $R^6$ is an unsubstituted 10 membered bicyclic aryl ring.

In some embodiments, $R^6$ is an optionally substituted a 5-6 membered monocyclic heteroaryl ring having 1-4 heteroatoms independently selected from nitrogen, oxygen, or sulfur. In some embodiments, $R^6$ is an optionally substituted a 5-6 membered monocyclic heteroaryl ring having 1-2 heteroatoms independently selected from nitrogen, oxygen, or sulfur.

In some embodiments, $R^6$ is an optionally substituted a 5 membered monocyclic heteroaryl ring having 1-4 heteroatoms independently selected from nitrogen, oxygen, or sulfur. In some embodiments, $R^6$ is an optionally substituted a 5 membered monocyclic heteroaryl ring having 1-2 heteroatoms independently selected from nitrogen, oxygen, or sulfur.

In some embodiments, $R^6$ is an optionally substituted a 6 membered monocyclic heteroaryl ring having 1-4 heteroatoms independently selected from nitrogen, oxygen, or sulfur. In some embodiments, $R^6$ is an optionally substituted a 6 membered monocyclic heteroaryl ring having 1-2 heteroatoms independently selected from nitrogen, oxygen, or sulfur.

In some embodiments, $R^6$ is an optionally substituted 4-7 membered saturated heterocyclic ring having 1-3 heteroatoms independently selected from nitrogen, oxygen, or sulfur. In some embodiments, $R^6$ is an optionally substituted 5-6 membered saturated heterocyclic ring having 1-3 heteroatoms independently selected from nitrogen, oxygen, or sulfur. In some embodiments, $R^6$ is an optionally substituted 4-7 membered partially unsaturated heterocyclic ring having 1-3 heteroatoms independently selected from nitrogen, oxygen, or sulfur. In some embodiments, $R^6$ is an optionally substituted 5-6 membered partially unsaturated heterocyclic ring having 1-3 heteroatoms independently selected from nitrogen, oxygen, or sulfur.

In some embodiments, $R^6$ is an optionally substituted 7-10 membered bicyclic saturated heterocyclic ring having 1-5 heteroatoms independently selected from nitrogen, oxygen, or sulfur. In some embodiments, $R^6$ is an optionally substituted 7-10 membered bicyclic saturated heterocyclic ring having 1-2 heteroatoms independently selected from nitrogen, oxygen, or sulfur. In some embodiments, $R^6$ is an optionally substituted 7-10 membered bicyclic partially unsaturated heterocyclic ring having 1-5 heteroatoms independently selected from nitrogen, oxygen, or sulfur. In some embodiments, $R^6$ is an optionally substituted 7-10 membered bicyclic partially unsaturated heterocyclic ring having 1-2 heteroatoms independently selected from nitrogen, oxygen, or sulfur.

In some embodiments, $R^6$ is an optionally substituted 8-10 membered bicyclic heteroaryl ring having 1-5 heteroatoms independently selected from nitrogen, oxygen, or sulfur. In some embodiments, $R^6$ is an optionally substituted 8-10 membered bicyclic heteroaryl ring having 1-3 heteroatoms independently selected from nitrogen, oxygen, or sulfur.

As defined and described above and herein, each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand.

In some embodiments, two —$OR^7$ are the same. In some embodiments, two —$OR^7$ are different.

In some embodiments, at least one $R^7$ is independently optionally substituted phenyl. In some embodiments, at least one $R^7$ is independently optionally substituted $C_{1-20}$ aliphatic. In some embodiments, at least one $R^7$ is independently $C_{1-20}$ aliphatic substituted with one or more halogen. In some embodiments, at least one $R^7$ is independently $C_{1-20}$ aliphatic substituted with one or more —F. In some embodiments, at least one $R^7$ is independently tertiary $C_{1-20}$ aliphatic substituted with one or more —F. In some embodiments, at least one $R^7$ is independently tertiary $C_{1-20}$ alkyl substituted with one or more —F. In some embodiments, at least one $R^7$ is independently selected from tert-butyl, —$C(CF_3)_2(Me)$ and —$C(CF_3)_3$.

In some embodiments, each $R^7$ is independently optionally substituted phenyl. In some embodiments, each $R^7$ is independently optionally substituted $C_{1-20}$ aliphatic. In some embodiments, each $R^7$ is independently $C_{1-20}$ aliphatic substituted with one or more halogen. In some embodiments, each $R^7$ is independently $C_{1-20}$ aliphatic substituted with one or more —F. In some embodiments, each $R^7$ is independently tertiary $C_{1-20}$ aliphatic substituted with one or more —F. In some embodiments, each $R^7$ is independently tertiary $C_{1-20}$ alkyl substituted with one or more —F. In some embodiments, each $R^7$ is independently selected from tert-butyl, —$C(CF_3)_2(Me)$ and —$C(CF_3)_3$.

In some embodiments, —$OR^7$ is an asymmetric ligand. In some embodiments, —$OR^7$ is a symmetric ligand. In certain embodiments, —$OR^7$ is a silyl-protected BINOL derivative.

In some embodiments, —$OR^7$ is an optionally substituted group selected from:

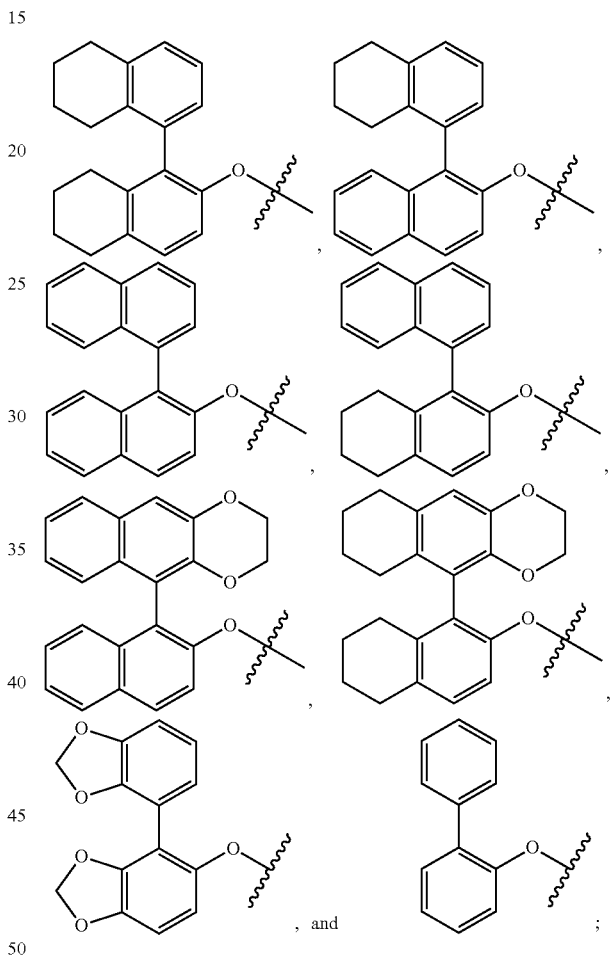

wherein each $⌇$ represents the point of attachment to the metal, M.

In certain embodiments, $R^7$ is optionally substituted —Ar', wherein Ar' is as defined above and described herein.

As defined above and described herein, Ar' is of the following formula:

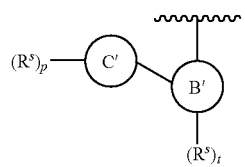

wherein:
t is 0-4;
p is 0-6;
each Ring B' and Ring C'' is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and
each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR';
wherein each R' is independently as defined above and described herein.

In some embodiments, t is 0. In some embodiments, t is 1. In some embodiments, t is 2. In some embodiments, t is 3. In some embodiments, t is 4.

In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, t is 0-4 as valency permits. In some embodiments, p is 0-6 as valency permits.

In some embodiments, Ring B' is optionally substituted phenyl.

In some embodiments, Ring B' is a group selected from:

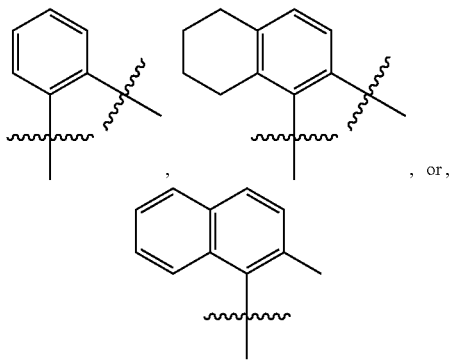

wherein each ⌇ independently represents the point of attachment to Ring C' or oxygen; wherein Ring B' is optionally substituted with 0-4 $R^s$; and wherein each of Ring C' and $R^s$ is independently as defined above and described herein.

In some embodiments, Ring B' is of the following formula:

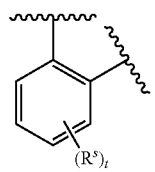

wherein each of $R^s$ and t is independently as defined above and described herein In some embodiments, Ring B' is an optionally substituted a 3-7 membered saturated carbocyclic ring. In some embodiments, Ring B' is an optionally substituted a 5-6 membered saturated carbocyclic ring. In some embodiments, Ring B' is an optionally substituted a 3-7 membered partially unsaturated carbocyclic ring. In some embodiments, Ring B' is an optionally substituted a 5-6 membered partially unsaturated carbocyclic ring.

In some embodiments, Ring B' is an optionally substituted 8-10 membered bicyclic saturated carbocyclic ring. In some embodiments, Ring B' is an optionally substituted 8-10 membered bicyclic partially unsaturated carbocyclic ring. In some embodiments, Ring B' is an optionally substituted 10 membered bicyclic aryl ring.

In some embodiments, Ring B' is an optionally substituted 5-6 membered monocyclic heteroaryl ring having 1-4 heteroatoms independently selected from nitrogen, oxygen, or sulfur. In some embodiments, Ring B' is an optionally substituted 5-6 membered monocyclic heteroaryl ring having 1-2 heteroatoms independently selected from nitrogen, oxygen, or sulfur.

In some embodiments, Ring B' is an optionally substituted 5 membered monocyclic heteroaryl ring having 1-4 heteroatoms independently selected from nitrogen, oxygen, or sulfur. In some embodiments, Ring B' is an optionally substituted 5 membered monocyclic heteroaryl ring having 1-2 heteroatoms independently selected from nitrogen, oxygen, or sulfur.

In some embodiments, Ring B' is an optionally substituted 6 membered monocyclic heteroaryl ring having 1-4 heteroatoms independently selected from nitrogen, oxygen, or sulfur. In some embodiments, Ring B' is an optionally substituted 6 membered monocyclic heteroaryl ring having 1-2 heteroatoms independently selected from nitrogen, oxygen, or sulfur.

In some embodiments, Ring B' is an optionally substituted 4-7 membered saturated heterocyclic ring having 1-3 heteroatoms independently selected from nitrogen, oxygen, or sulfur. In some embodiments, Ring B' is an optionally substituted 5-6 membered saturated heterocyclic ring having 1-2 heteroatoms independently selected from nitrogen, oxygen, or sulfur.

In some embodiments, Ring B' is an optionally substituted 4-7 membered partially unsaturated heterocyclic ring having 1-3 heteroatoms independently selected from nitrogen, oxygen, or sulfur. In some embodiments, Ring B' is an optionally substituted 5-6 membered partially unsaturated heterocyclic ring having 1-2 heteroatoms independently selected from nitrogen, oxygen, or sulfur.

In some embodiments, Ring B' is an optionally substituted 7-10 membered bicyclic saturated heterocyclic ring having 1-5 heteroatoms independently selected from nitrogen, oxygen, or sulfur. In some embodiments, Ring B' is an optionally substituted 8-10 membered bicyclic saturated heterocyclic ring having 1-2 heteroatoms independently selected from nitrogen, oxygen, or sulfur.

In some embodiments, Ring B' is an optionally substituted 7-10 membered bicyclic partially unsaturated heterocyclic ring having 1-5 heteroatoms independently selected from nitrogen, oxygen, or sulfur. In some embodiments, Ring B' is an optionally substituted 8-10 membered bicyclic partially unsaturated heterocyclic ring having 1-2 heteroatoms independently selected from nitrogen, oxygen, or sulfur.

In some embodiments, Ring B' is an optionally substituted 8-10 membered bicyclic heteroaryl ring having 1-5 heteroatoms independently selected from nitrogen, oxygen, or sulfur. In some embodiments, Ring B' is an optionally substituted 8 membered bicyclic heteroaryl ring having 1-3 heteroatoms independently selected from nitrogen, oxygen, or sulfur. In some embodiments, Ring B' is an optionally substituted 9 membered bicyclic heteroaryl ring having 1-3 heteroatoms independently selected from nitrogen, oxygen, or sulfur. In some embodiments, Ring B' is an optionally substituted 10 membered bicyclic heteroaryl ring having 1-3 heteroatoms independently selected from nitrogen, oxygen, or sulfur.

In some embodiments, Ring C' is optionally substituted phenyl.

In some embodiments, Ring C' is a group selected from:

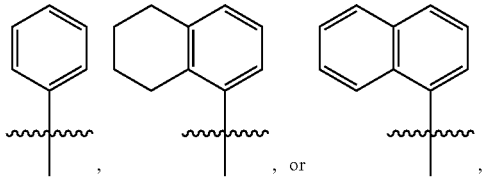

, or wherein each ⫶ represents the point of attachment to Ring B'; wherein Ring C' is optionally substituted with 0-6 $R^s$; and wherein each of Ring B' and $R^s$ is independently as defined above and described herein.

In some embodiments, Ring C" is of the following formula:

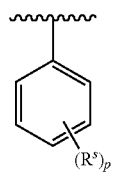

$(R^s)_p$ wherein $R^y$ and p is independently as defined above and described herein.

In certain embodiments, Ring C' is of the following formula:

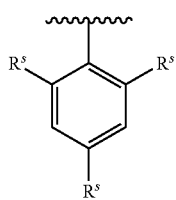

wherein $R^y$ is as defined above and described herein.

In certain embodiments, Ring C' is of the following structure:

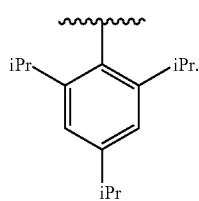 [SMILES: *c1c(C(C)C)cc(C(C)C)cc1C(C)C]

In some embodiments, Ring C' is an optionally substituted a 3-7 membered saturated carbocyclic ring. In some embodiments, Ring C' is an optionally substituted a 5-6 membered saturated carbocyclic ring. In some embodiments, Ring C' is an optionally substituted a 3-7 membered partially unsaturated carbocyclic ring. In some embodiments, Ring C' is an optionally substituted a 5-6 membered partially unsaturated carbocyclic ring.

In some embodiments, Ring C' is an optionally substituted 8-10 membered bicyclic saturated carbocyclic ring. In some embodiments, Ring C' is an optionally substituted 8-10 membered bicyclic partially unsaturated carbocyclic ring. In some embodiments, Ring C' is an optionally substituted 10 membered bicyclic aryl ring.

In some embodiments, Ring C' is an optionally substituted 5-6 membered monocyclic heteroaryl ring having 1-4 heteroatoms independently selected from nitrogen, oxygen, or sulfur. In some embodiments, Ring C' is an optionally substituted 5-6 membered monocyclic heteroaryl ring having 1-2 heteroatoms independently selected from nitrogen, oxygen, or sulfur.

In some embodiments, Ring C' is an optionally substituted 5 membered monocyclic heteroaryl ring having 1-4 heteroatoms independently selected from nitrogen, oxygen, or sulfur. In some embodiments, Ring C' is an optionally substituted 5 membered monocyclic heteroaryl ring having 1-2 heteroatoms independently selected from nitrogen, oxygen, or sulfur.

In some embodiments, Ring C' is an optionally substituted 6 membered monocyclic heteroaryl ring having 1-4 heteroatoms independently selected from nitrogen, oxygen, or sulfur. In some embodiments, Ring C' is an optionally substituted 6 membered monocyclic heteroaryl ring having 1-2 heteroatoms independently selected from nitrogen, oxygen, or sulfur.

In some embodiments, Ring C' is an optionally substituted 4-7 membered saturated heterocyclic ring having 1-3 heteroatoms independently selected from nitrogen, oxygen, or sulfur. In some embodiments, Ring C' is an optionally substituted 5-6 membered saturated heterocyclic ring having 1-2 heteroatoms independently selected from nitrogen, oxygen, or sulfur.

In some embodiments, Ring C' is an optionally substituted 4-7 membered partially unsaturated heterocyclic ring having 1-3 heteroatoms independently selected from nitrogen, oxygen, or sulfur. In some embodiments, Ring C' is an optionally substituted 5-6 membered partially unsaturated heterocyclic ring having 1-2 heteroatoms independently selected from nitrogen, oxygen, or sulfur.

In some embodiments, Ring C' is an optionally substituted 7-10 membered bicyclic saturated heterocyclic ring having 1-5 heteroatoms independently selected from nitrogen, oxygen, or sulfur. In some embodiments, Ring C' is an optionally substituted 8-10 membered bicyclic saturated heterocyclic ring having 1-2 heteroatoms independently selected from nitrogen, oxygen, or sulfur.

In some embodiments, Ring C' is an optionally substituted 7-10 membered bicyclic partially unsaturated heterocyclic ring having 1-5 heteroatoms independently selected from nitrogen, oxygen, or sulfur. In some embodiments, Ring C' is an optionally substituted 8-10 membered bicyclic partially unsaturated heterocyclic ring having 1-2 heteroatoms independently selected from nitrogen, oxygen, or sulfur.

In some embodiments, Ring C' is an optionally substituted 8-10 membered bicyclic heteroaryl ring having 1-5 heteroatoms independently selected from nitrogen, oxygen, or sulfur. In some embodiments, Ring C' is an optionally substituted 8 membered bicyclic heteroaryl ring having 1-3 heteroatoms independently selected from nitrogen, oxygen, or sulfur. In some embodiments, Ring C' is an optionally substituted 9 membered bicyclic heteroaryl ring having 1-3 heteroatoms independently selected from nitrogen, oxygen, or sulfur. In some embodiments, Ring C' is an optionally substituted 10 membered bicyclic heteroaryl ring having 1-3 heteroatoms independently selected from nitrogen, oxygen, or sulfur.

In some embodiments, each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In certain embodiments, at least one $R^s$ is independently halogen. In certain embodiments, at least one $R^s$ is independently —F. In certain embodiments, at least one $R^s$ is independently —Cl. In certain embodiments, at least one $R^s$ is independently —Br. In certain embodiments, at least one $R^s$ is independently —I.

In certain embodiments, at least one $R^s$ is independently selected from R', —OR', —SR', —S(O)R', —S(O)$_2$R', —OSi(R')$_3$, or —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In certain embodiments, at least one $R^s$ is R', wherein R' is as defined above and described herein. In some embodiments, at least one $R^s$ is optionally substituted $C_{1-6}$ aliphatic. In some embodiments, at least one $R^s$ is optionally substituted $C_{1-6}$ alkyl. In some embodiments, at least one $R^s$ is optionally substituted $C_{1-6}$ haloalkyl. In some embodiments, at least one $R^s$ is optionally substituted $C_{1-6}$ haloalkyl, wherein one substituent is —F. In some embodiments, at least one $R^s$ is optionally substituted $C_{1-6}$ haloalkyl, wherein two or more substituents are —F. In certain embodiments, at least one $R^s$ is selected from methyl, ethyl, propyl, or butyl. In certain embodiments, at least one $R^s$ is isopropyl. In certain embodiments, at least one $R^s$ is —CF$_3$.

In some embodiments, at least one $R^s$ is hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, at least one $R^s$ is —OSi(R')$_3$, wherein each R is independently as defined above and described herein.

In some embodiments, at least one $R^s$ is —OR', wherein each R is independently as defined above and described herein.

In some embodiments, at least one $R^s$ is selected from —SR', —S(O)R', —S(O)$_2$R', wherein each R' is independently as defined above and described herein.

As generally defined above and herein, each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, each R is independently optionally substituted $C_{1-6}$ aliphatic. In some embodiments, each R' is independently optionally substituted $C_{1-6}$ alkyl. In some embodiments, each R' is independently optionally substituted $C_{1-6}$ haloalkyl. In some embodiments, each R' is independently optionally substituted $C_{1-6}$ haloalkyl, wherein one substituent is —F. In some embodiments, each R' is independently optionally substituted $C_{1-6}$ haloalkyl, wherein two or more substituents are —F. In certain embodiments, at least one R' is independently selected from methyl, ethyl, propyl, or butyl. In certain embodiments, at least one $R^s$ is isopropyl. In certain embodiments, at least one R' is —CF$_3$.

In some embodiments, at least one R' is hydrogen. In some embodiments, at least one R' is independently selected from an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, at least one R' is optionally substituted $C_{1-6}$ aliphatic. In some embodiments, at least one R' is optionally substituted phenyl. In some embodiments, at least one R' is optionally substituted 3-7 membered saturated or partially unsaturated carbocyclic ring. In some embodiments, at least one R' is optionally substituted 8-10 membered bicyclic saturated, partially unsaturated or aryl ring. In some embodiments, at least one R' is optionally substituted 5-6 membered monocyclic heteroaryl ring having 1-4 heteroatoms independently selected from nitrogen, oxygen, or sulfur. In some embodiments, at least one R' is optionally substituted 4-7 membered saturated or partially unsaturated heterocyclic ring having 1-3 heteroatoms independently selected from nitrogen, oxygen, or sulfur. In some embodiments, at least one R' is optionally substituted 7-10 membered bicyclic saturated or partially unsaturated heterocyclic ring having 1-5 heteroatoms independently selected from nitrogen, oxygen, or sulfur. In some embodiments, at least one R' is optionally substituted 8-10 membered bicyclic heteroaryl ring having 1-5 heteroatoms independently selected from nitrogen, oxygen, or sulfur.

In some embodiments, at least one —OR⁷ is an asymmetric ligand. In some embodiments, at least one —OR⁷ is a symmetric ligand. In certain embodiments, at least one —OR⁷ is a silyl-protected BINOL derivative.
In some embodiments, each —OR⁷ is independently is an optionally substituted group selected from:
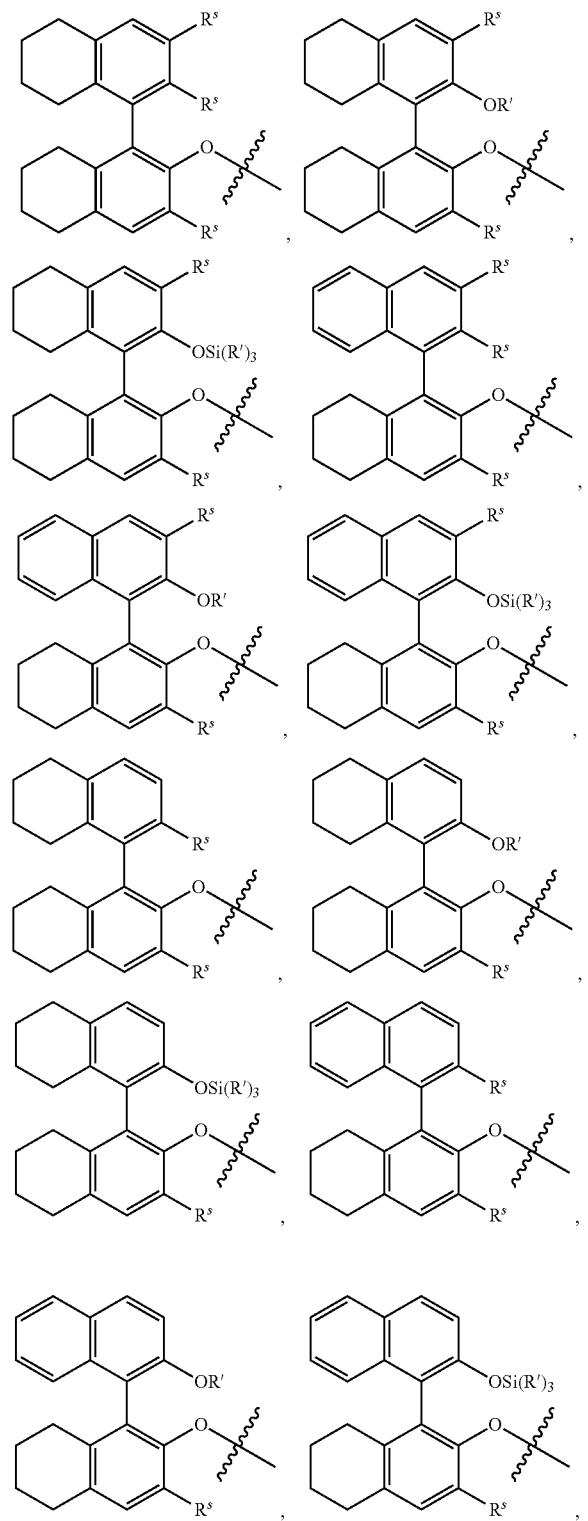
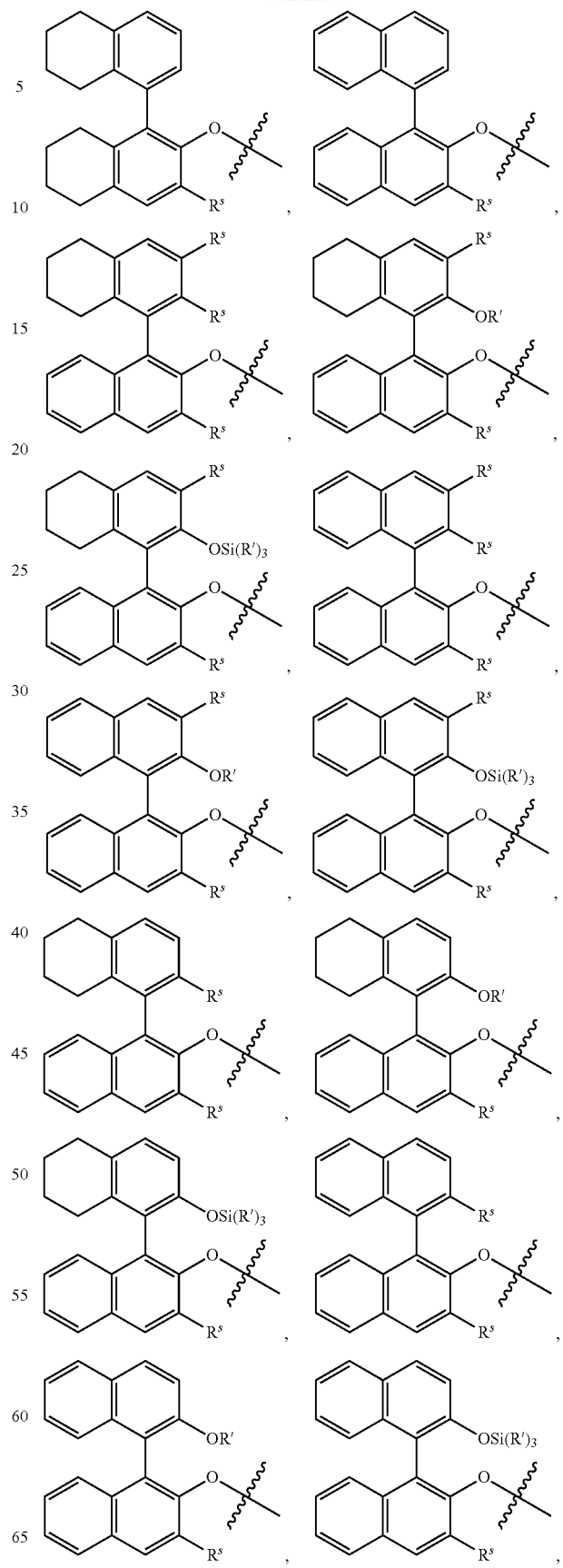

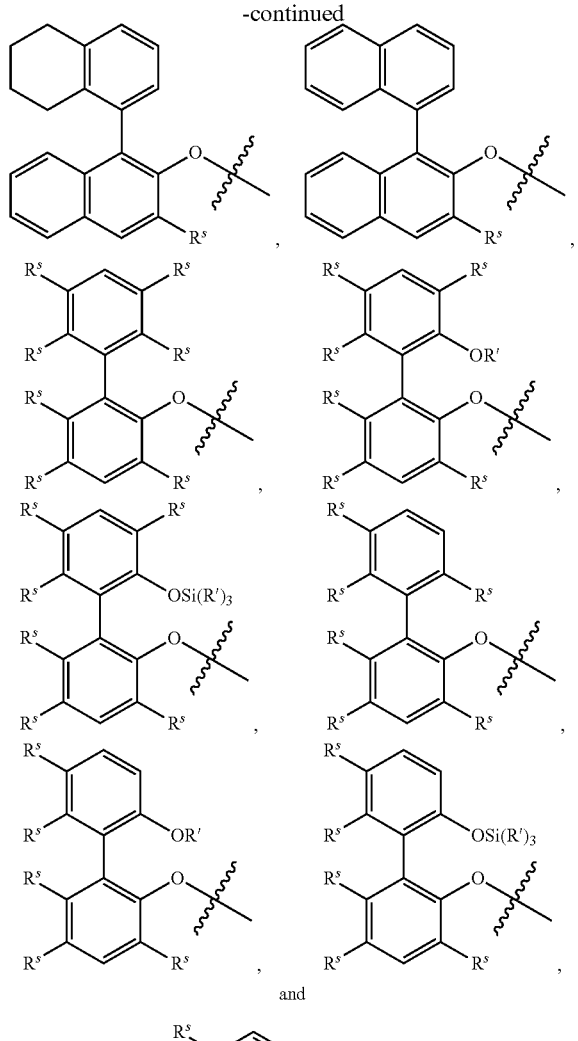
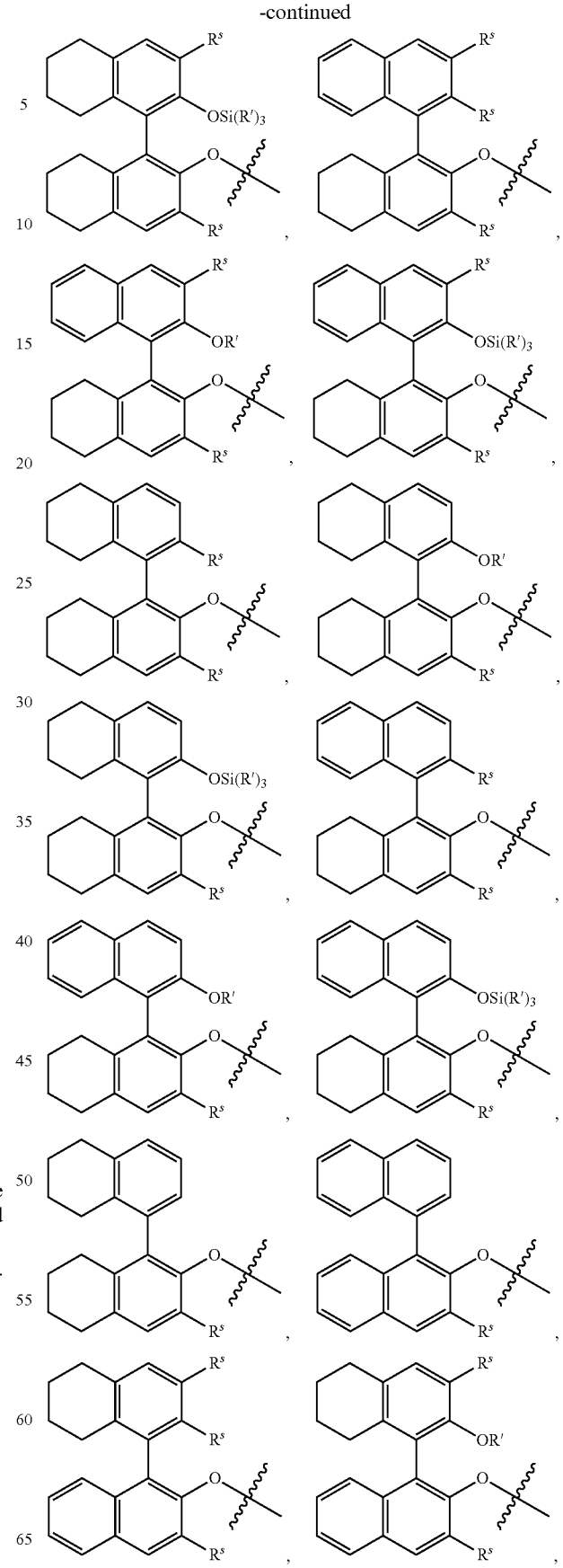
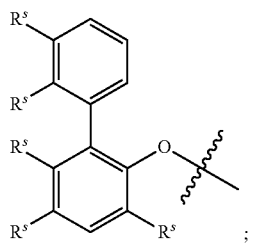
wherein each *s* represents the point of attachment to the metal, M, and each of $R^s$ and R' is independently as defined above and described herein.
In some embodiments, at least one —$OR^7$ is independently an optionally substituted group selected from:
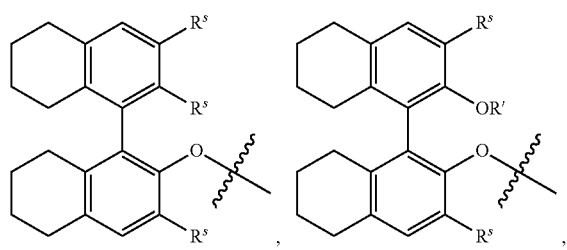

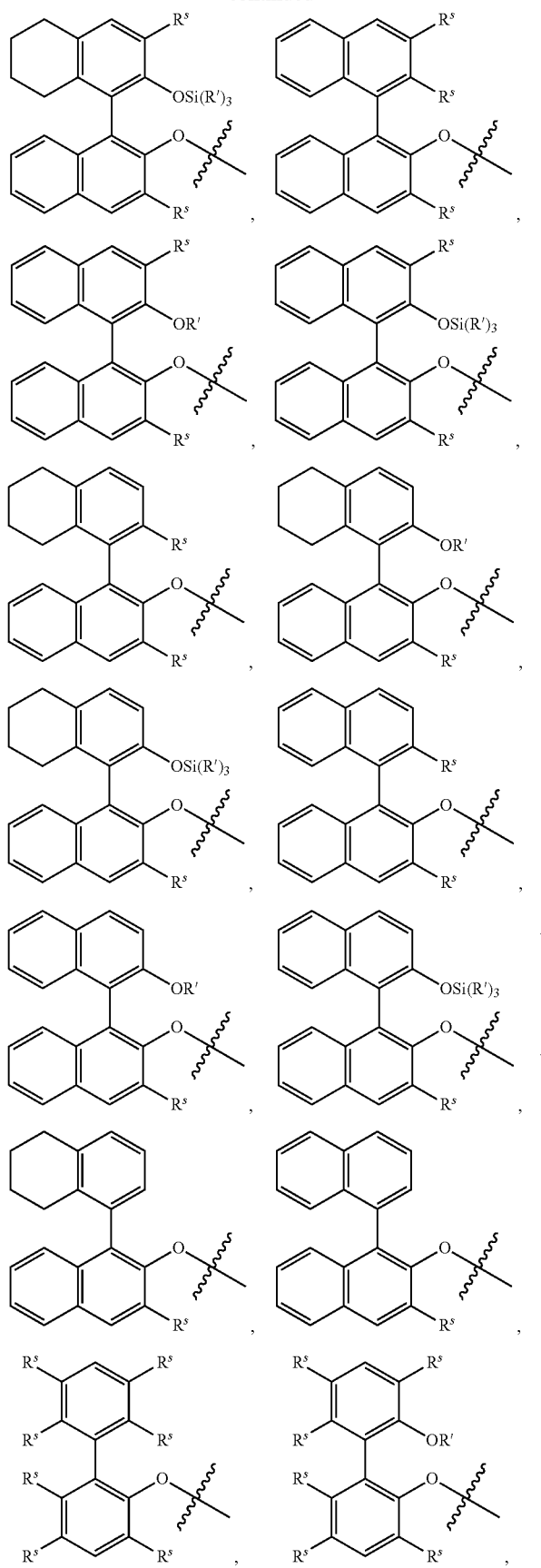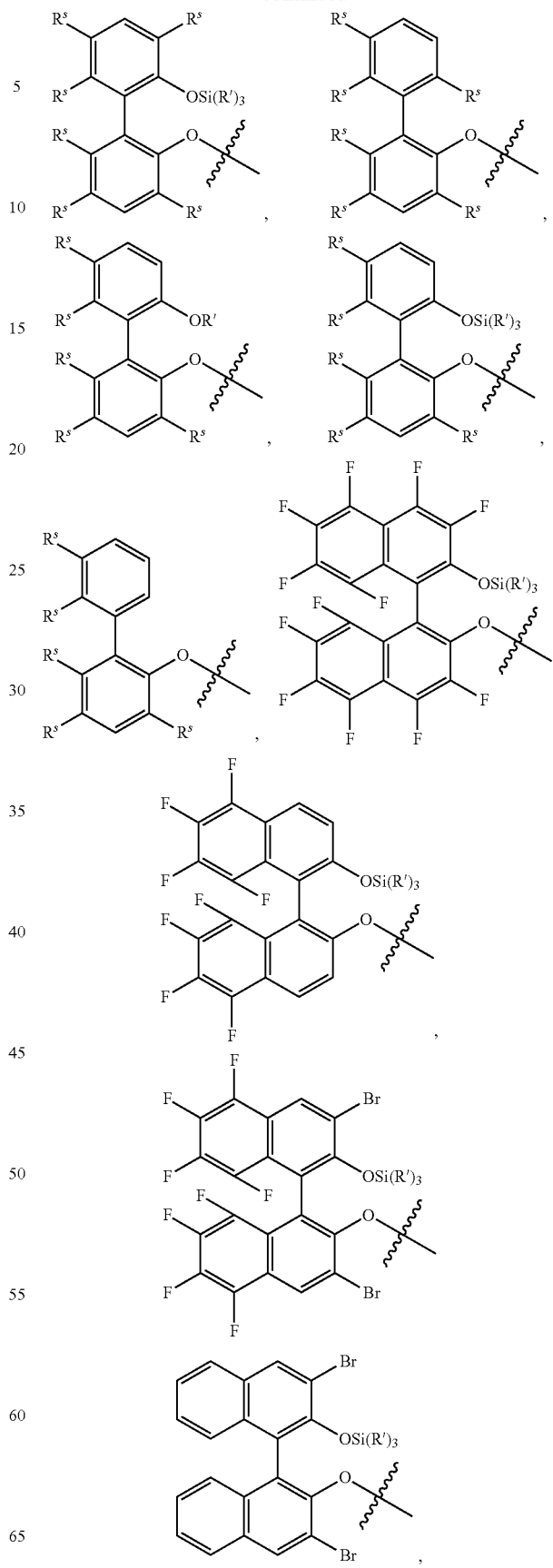

-continued
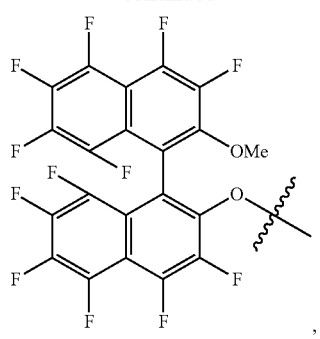,
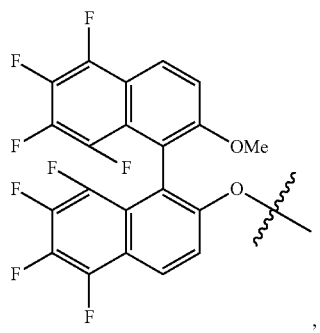,
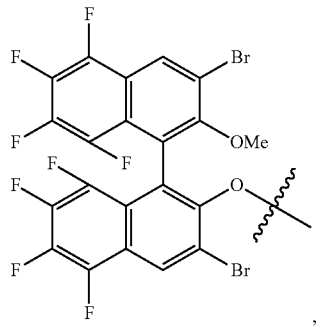,
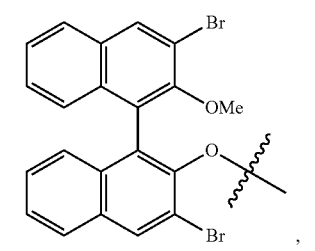,
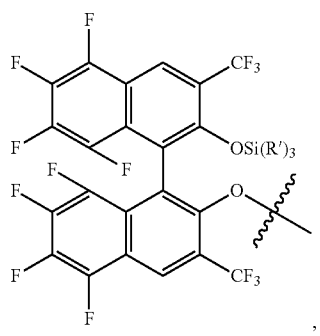,
-continued
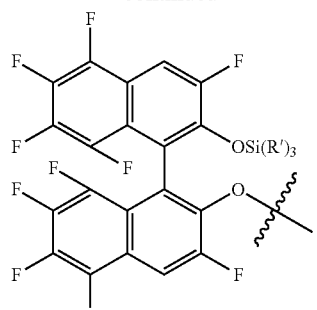,
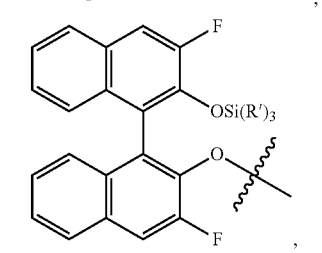,
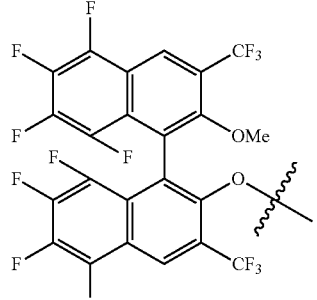,
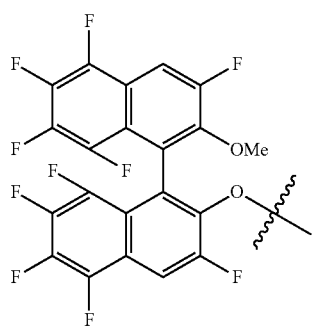,
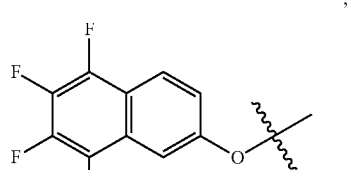 and
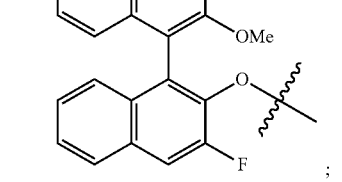;

wherein:
    each $\mathcal{S}$ represents the point of attachment to the metal, M;
    each of $R^s$ and $R'$ is independently as defined above and described herein; and
    one or more $R^s$ are —F.

In some embodiments, two $R^7$ are optionally taken together with the oxygen atoms they are bound to form a bidentate ligand. In some embodiments, two $R^7$ are taken together with the oxygen atoms they are bound to form a bidentate ligand.

In some embodiments, two $R^7$ are taken together with the oxygen atoms they are bound to form a bidentate ligand having one of the following structures:

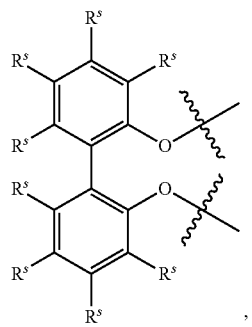
,

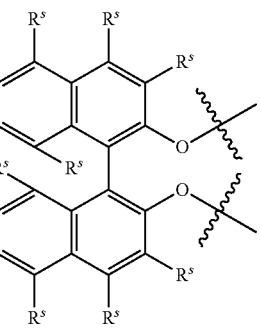
, and

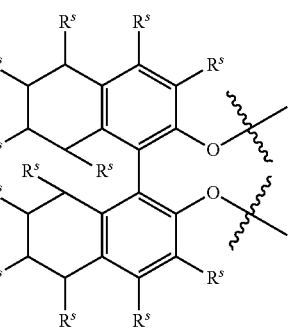
;

wherein:
    each $\mathcal{S}$ represents the point of attachment to the metal, M; and
    each $R^s$ is independently as defined above and described herein.

In some embodiments, two $R^7$ are taken together with the oxygen atoms they are bound to form a bidentate ligand having one of the following structures:

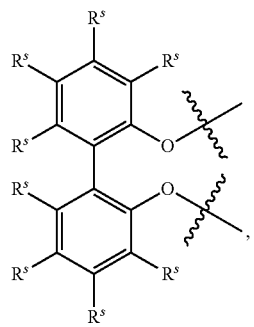
,

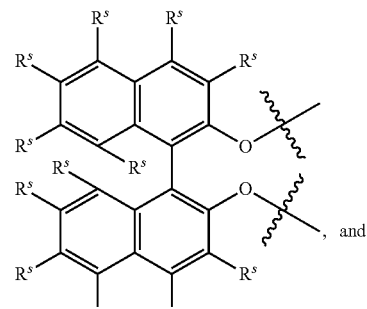
, and

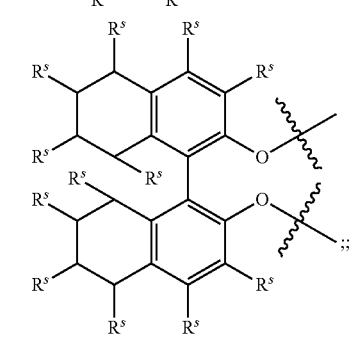
;;

wherein:
    each $\mathcal{S}$ represents the point of attachment to the metal, M;
    each $R^s$ is independently as defined above and described herein; and
    one or more $R^s$ are —F.

In some embodiments, two $R^7$ are taken together with the oxygen atoms they are bound to form a bidentate ligand having one of the following structures:

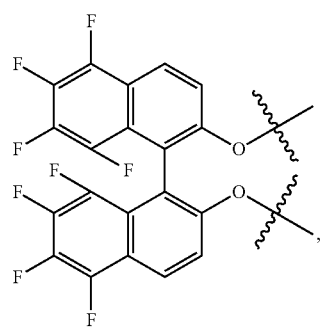
,

-continued

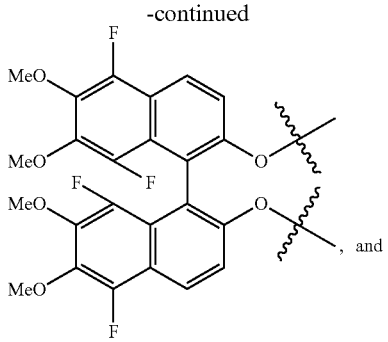
, and

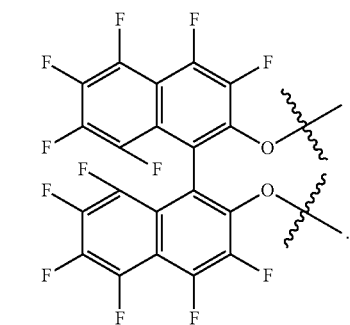
.

As generally defined above and herein, $R^8$ is $R^1$, or phenyl optionally substituted with one to five $R^9$, wherein each of $R^1$ and $R^9$ is independently as defined above and described herein.

In some embodiments, $R^8$ is $R^1$, wherein $R^1$ is as defined above and described herein. In some embodiments, $R^8$ is phenyl optionally substituted with one to five $R^9$, wherein each $R^9$ is independently as defined above and described herein.

In some embodiments, $R^8$ is adamantyl. In some embodiments, $R^8$ is tert-butyl.

As generally defined above and herein, each $R^9$ is independently halogen or $R^1$, wherein $R^1$ is independently as defined above and described herein.

In some embodiments, at least one $R^9$ is halogen. In some embodiments, at least one $R^9$ is —F. In some embodiments, at least one $R^9$ is —Cl. In some embodiments, at least one $R^9$ is —Br. In some embodiments, at least one $R^9$ is —I.

In some embodiments, at least one $R^9$ is $R^1$, wherein $R^1$ is optionally substituted $C_{1-20}$ aliphatic. In some embodiments, at least one $R^9$ is optionally substituted $C_{1-20}$ alkyl. In some embodiments, at least one $R^9$ is optionally substituted straight chain $C_{1-20}$ alkyl. In some embodiments, at least one $R^9$ is optionally substituted secondary $C_{1-20}$ alkyl. In some embodiments, at least one $R^9$ is optionally substituted $C_{1-20}$ cycloalkyl. In some embodiments, at least one $R^9$ is optionally substituted tertiary $C_{1-20}$ alkyl. In some embodiments, at least one $R^9$ is tert-butyl. In some embodiments, at least one $R^9$ is adamantyl. In some embodiments, at least one $R^9$ is optionally substituted $C_{1-20}$ aliphatic containing a quaternary carbon.

In some embodiments, $R^9$ is $R^1$ wherein $R^1$ is optionally substituted with on or more —F. In some embodiments, $R^9$ is —$CF_3$. In some embodiments, $R^9$ is —$C_2F_5$.

In some embodiments, $R^8$ is an optionally substituted group selected from:

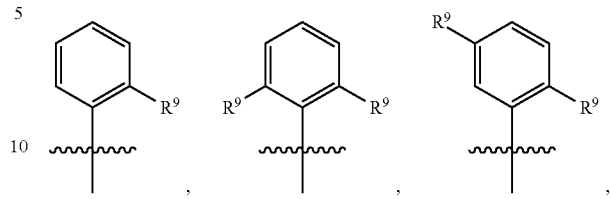
, , ,

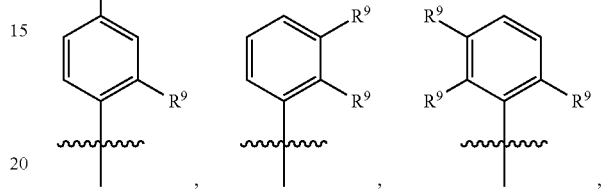
, , ,

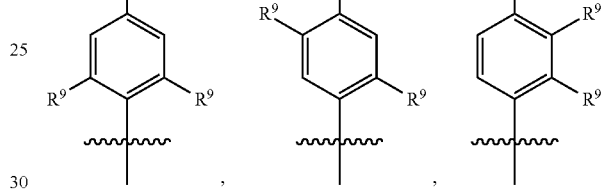
, , ,

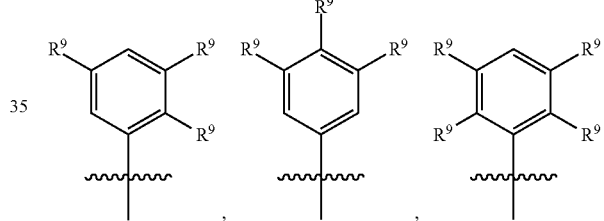
, , ,

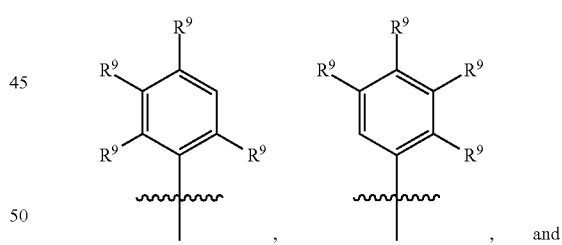
, and

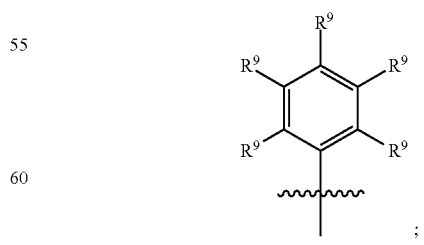
;

wherein each $\xi$ represents the point of attachment to the nitrogen atom, and each $R^9$ is independently as defined above and described herein.

In some embodiments, $R^8$ is an optionally substituted group selected from:

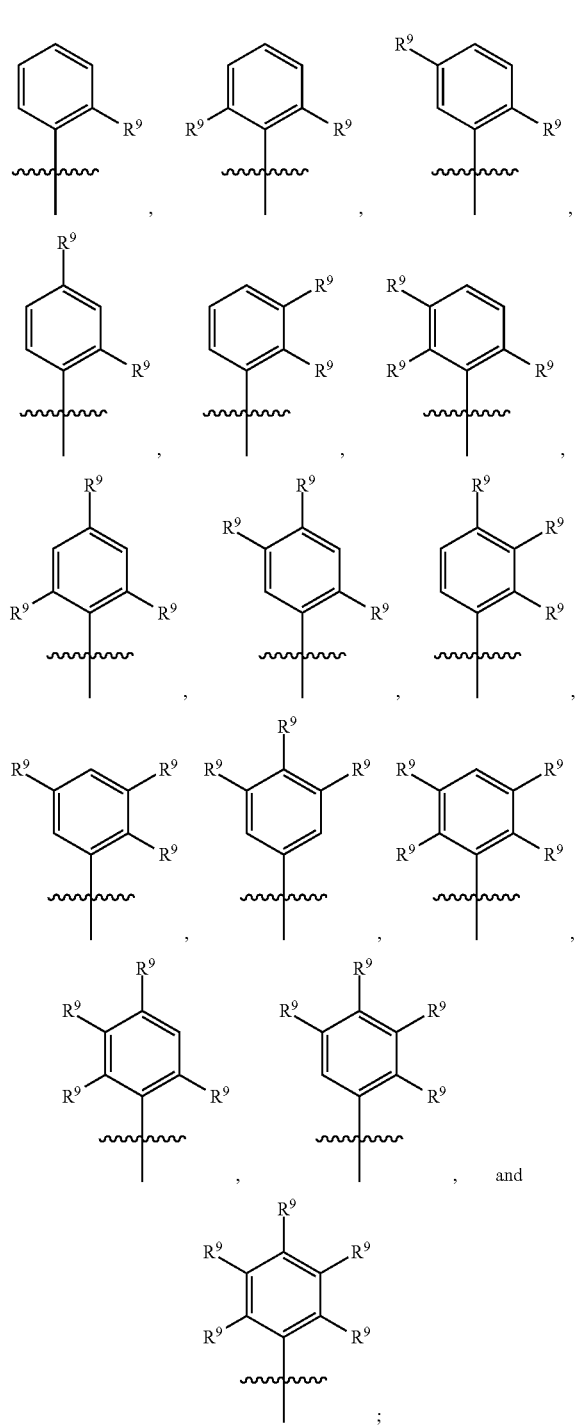

wherein:
  each ⌇ represents the point of attachment to the nitrogen atom, and each $R^9$ is independently as defined above and described herein; and
  one ore more $R^9$ are —F.

In some embodiments, M of formula II-c is molybdenum.
In some embodiments, M of formula II-c is tungsten.

In some embodiments, $R^8$ is:

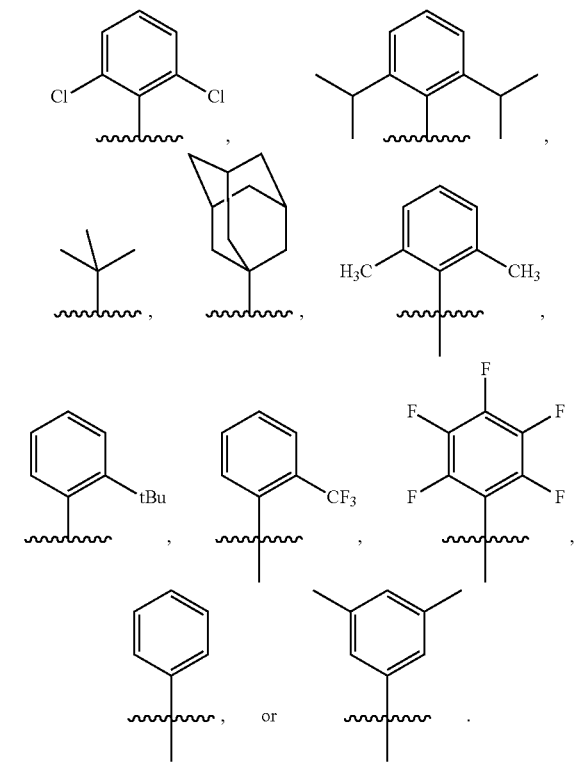

In some embodiments, $R^8$ is

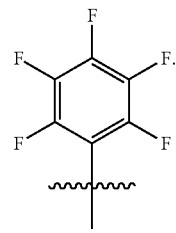

In some embodiments, one of the stereoisomers of a metal complex of formula II-a, II-b, or II-c is used in preparing a compound of formula I or formula I-a. In some embodiments, two or more of the stereoisomers of a metal complex of formula II-a, II-b, or II-c is used in preparing a compound of formula I or formula I-a. In some embodiments, one enantiomer of a metal complex of formula II-a, II-b, or II-c is used in preparing a compound of formula I or formula I-a. In some embodiments, one enantiomer of a metal complex of formula II-a, II-b, or II-c is used in preparing a compound of formula I or formula I-a. In some embodiments, a metal complex of formula II-a, II-b, or II-c for use in preparing a compound of formula I or formula I-a is stereochemically pure. In some embodiments, a metal complex of formula II-a, II-b, or II-c for use in preparing a compound of formula I or formula I-a is a mixture of stereoisomers. In some embodiments, a metal complex of formula II-a, II-b, or II-c for use in preparing a compound of formula I or formula I-a is a mixture of enantiomers. In some embodiments, a metal complex of formula II-a, II-b, or II-c for use in preparing a compound of formula I or formula I-a is a mixture of diastereomers. In some embodiments, a metal complex of formula II-a, II-b, or II-c for use in preparing a compound of formula I or formula I-a is racemic.

In some embodiments, a metal complex of formula II-a for use in preparing a compound of formula I or formula I-a is as depicted below:

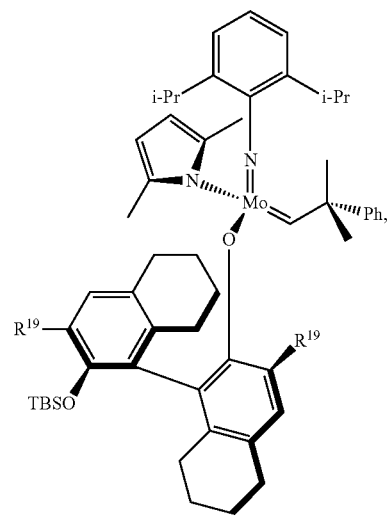

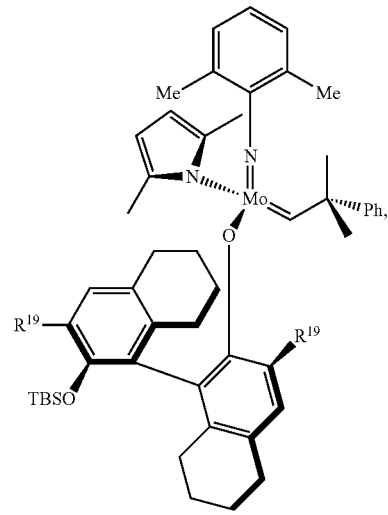

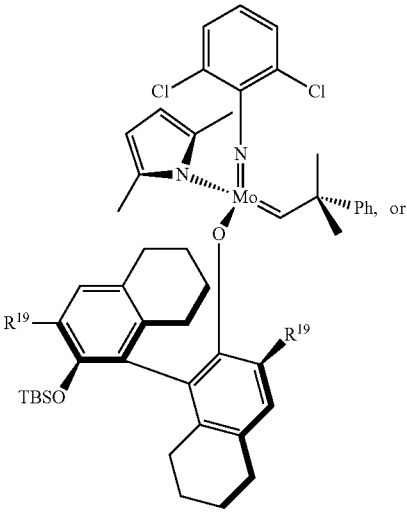

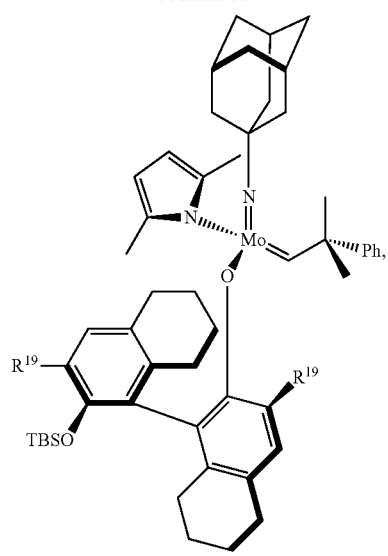

wherein each $R^{19}$ is independently F, Cl, Br, or I. In certain embodiments, $R^{19}$ is Br. In some embodiments, a metal complex is as depicted above, wherein Mo is replaced with W.

In some embodiments, a metal complex of formula II-a for use in preparing a compound of formula I or formula I-a is as depicted below:

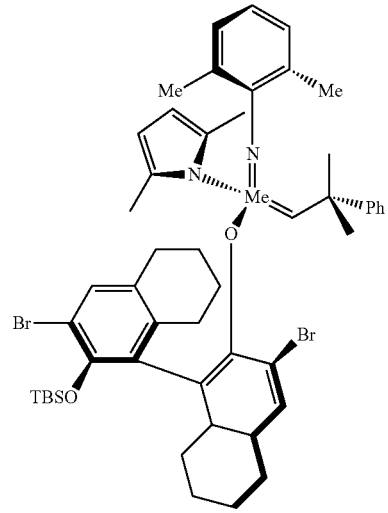

131

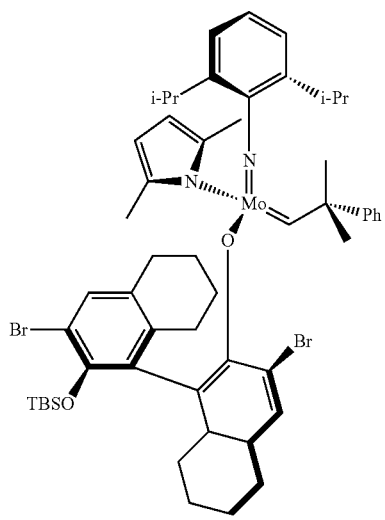

132

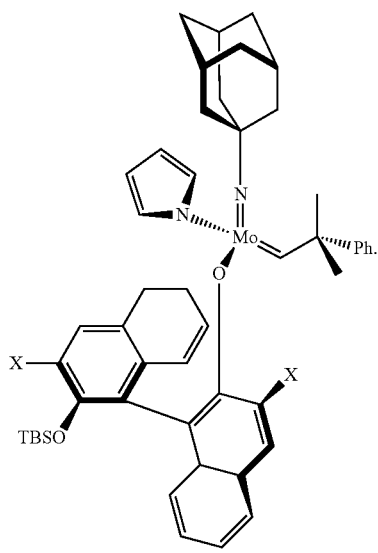

wherein each X is independently Br or I. In some embodiments, a metal complex is as depicted above, wherein Mo is replaced with W.

In some embodiments, a complex of formula II-a for use in preparing a compound of formula I or formula I-a is as depicted below:

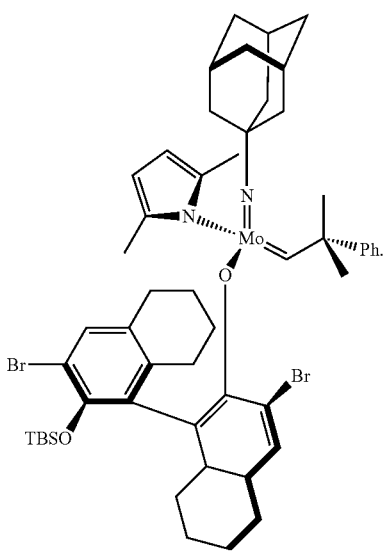

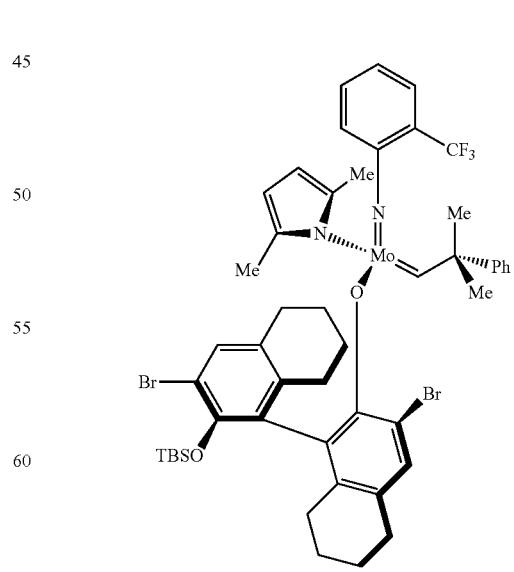

In some embodiments, a metal complex is as depicted above, wherein Mo is replaced with W.

In some embodiments, a metal complex of formula II-a for use in preparing a compound of formula I or formula I-a is as depicted below:

133
-continued
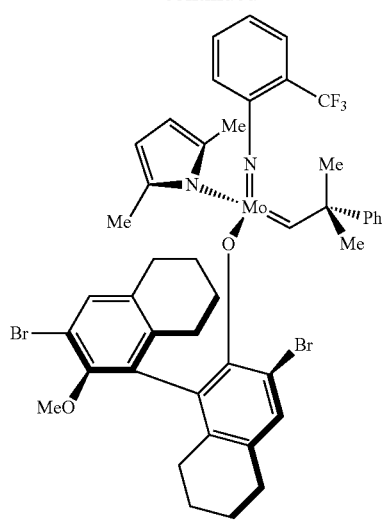
134
-continued
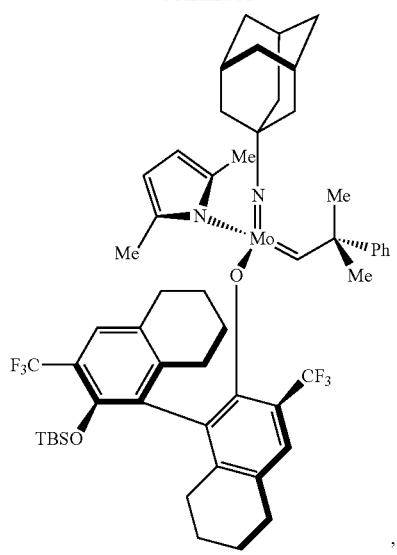
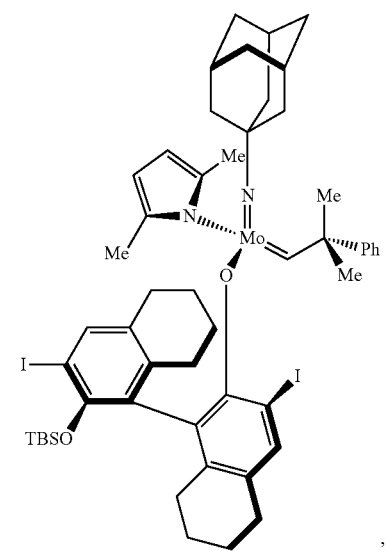
(binol)
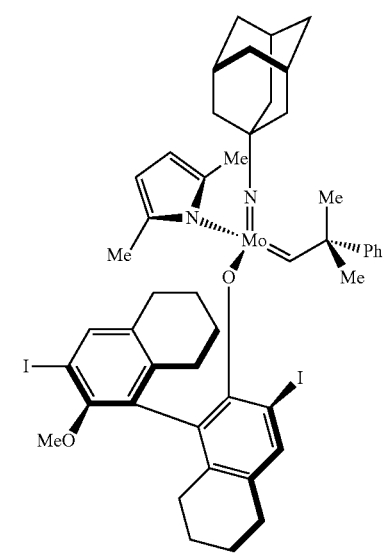

135
-continued
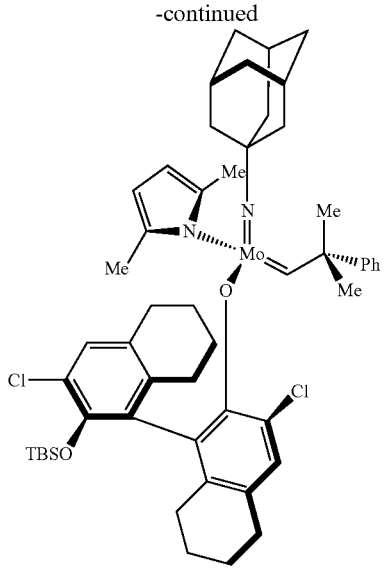
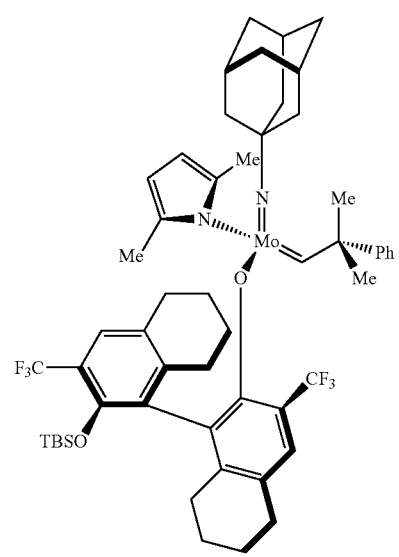
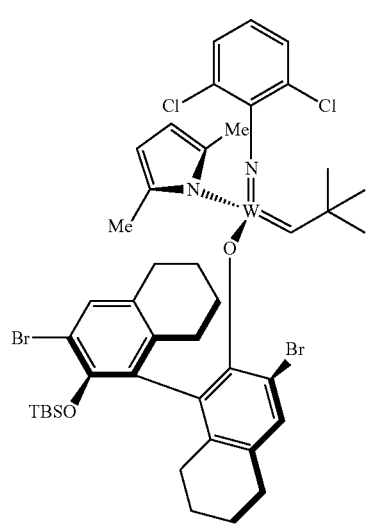
136
-continued
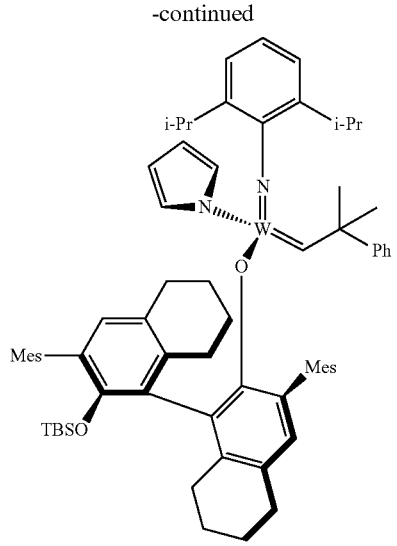
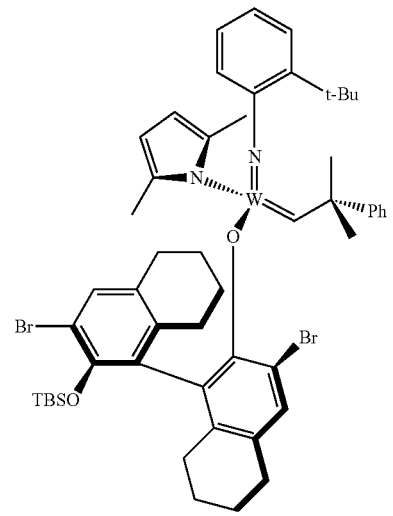
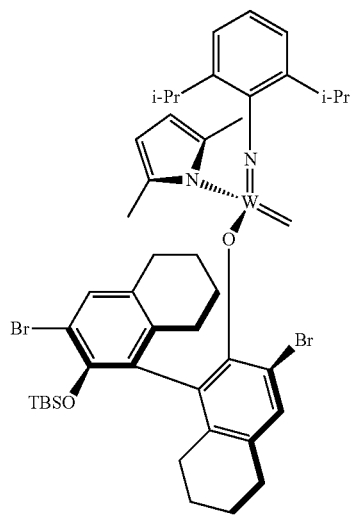

137
-continued
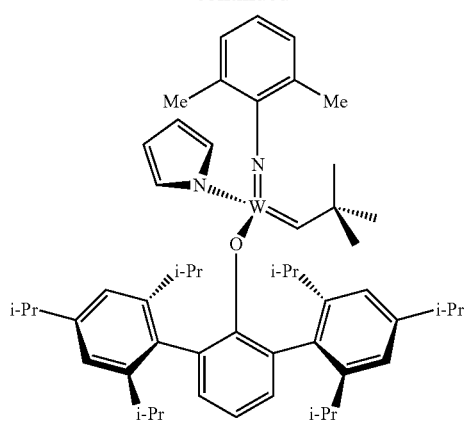
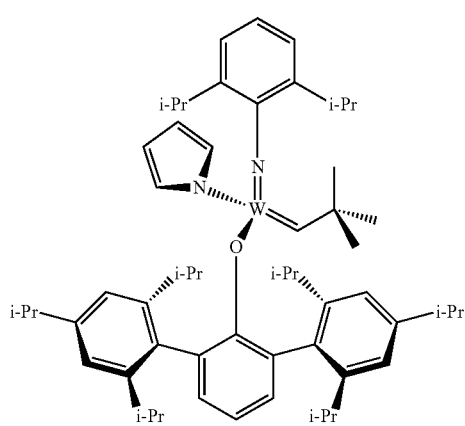
138
-continued
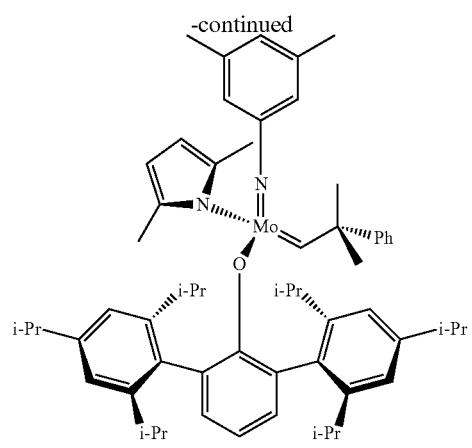
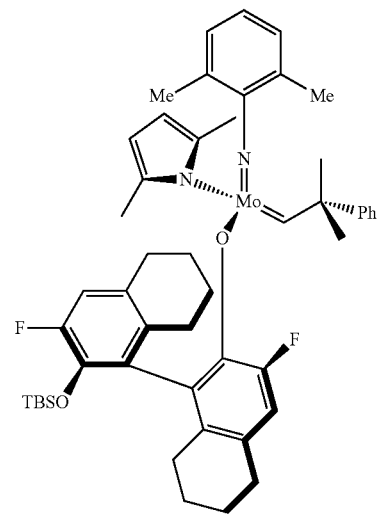
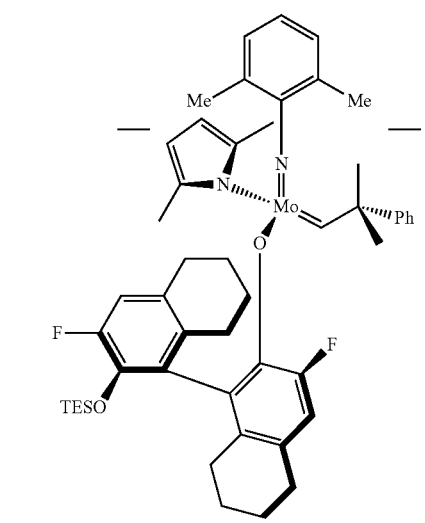
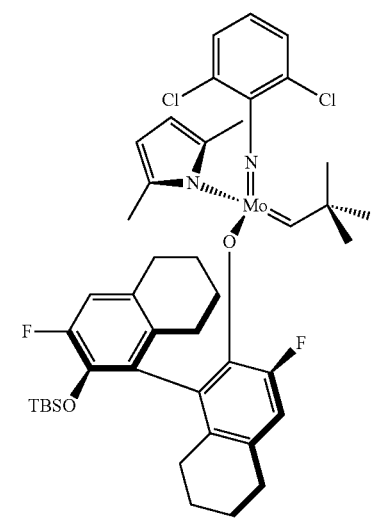

139

-continued

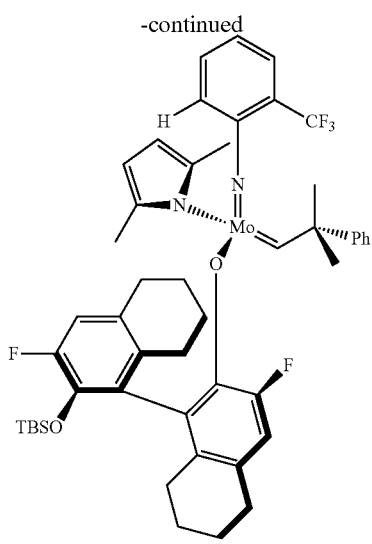

140

-continued

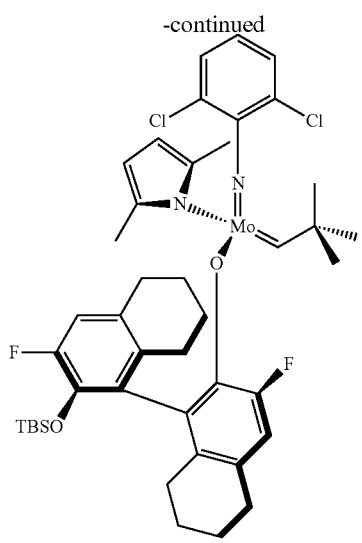

or

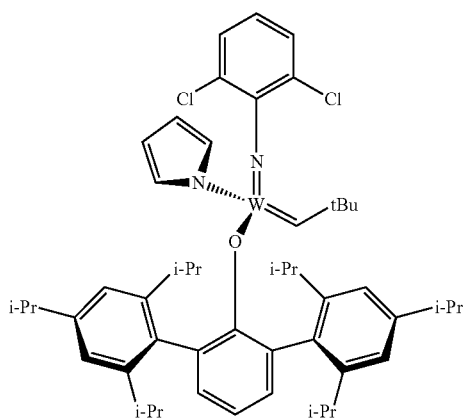

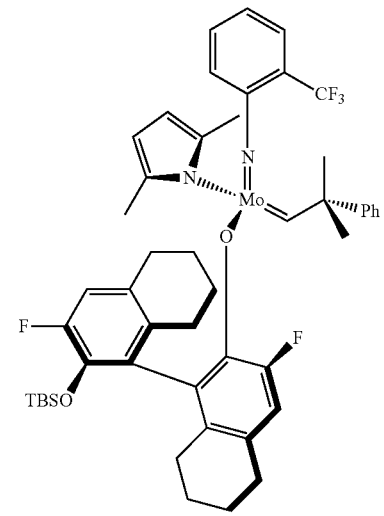

;

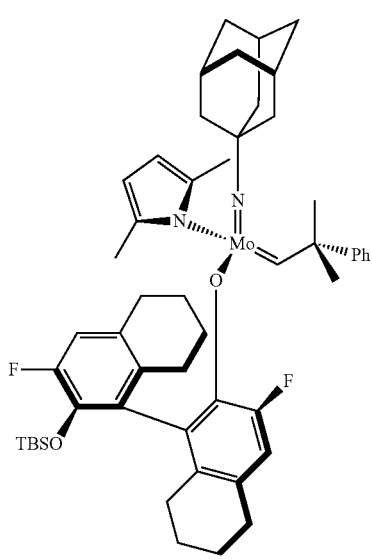

wherein Mes is 2,4,6-trimethyl phenyl, and wherein each X is independently Br, I, or CF₃. It would be apparent to one of skill in the art that the above-depicted silyl groups (e.g., TES and TBSO) can be replaced with any other silyl group known in the art to function as an oxygen protecting group. Alternatively, one of skill in the art would also appreciate that a lower alkyl group can replace the above-depicted silyl groups to afford an alkoxy substituent such as, e.g., —OMe (also depicted above). Exemplary other such alkoxy groups derived from replacing the above-depicted silyl group with an optionally substituted aliphatic group are also contemplated by the present invention.

In some embodiments, a complex of formula II-b is as depicted below:
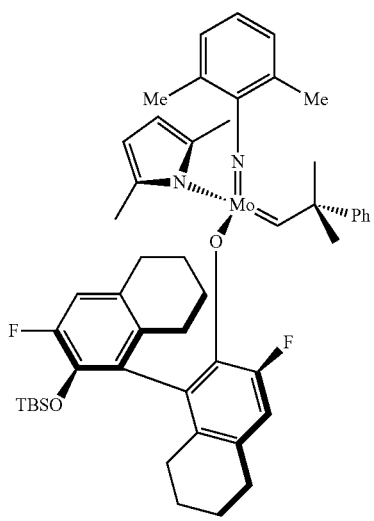
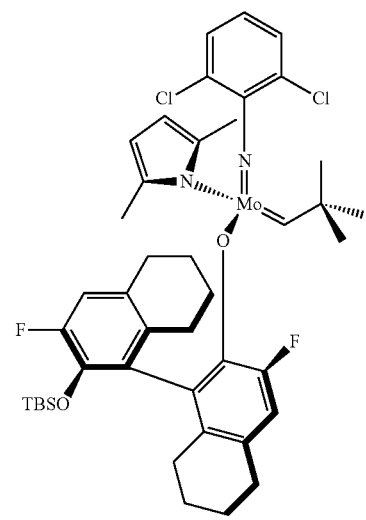
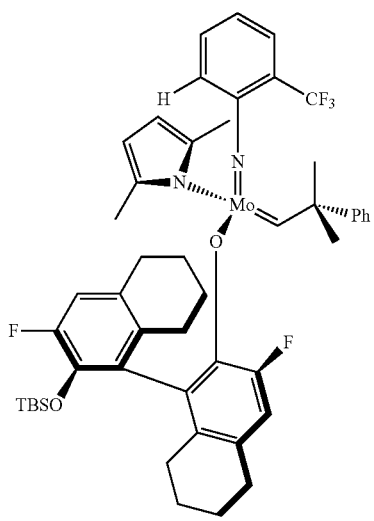
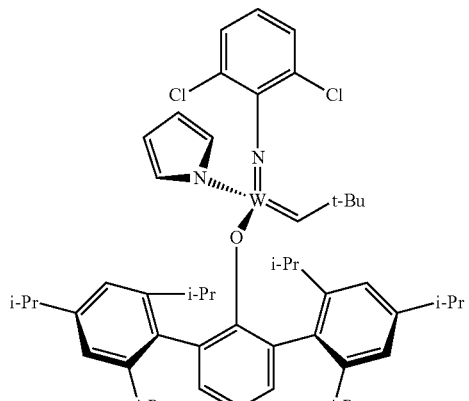
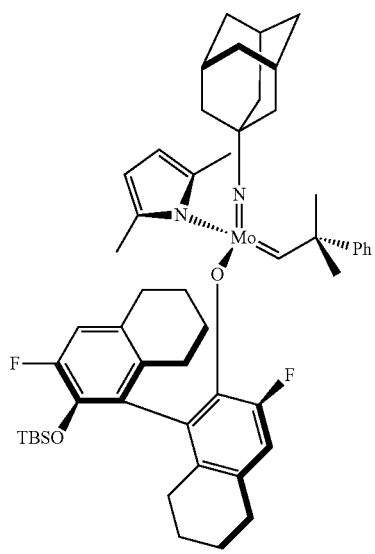
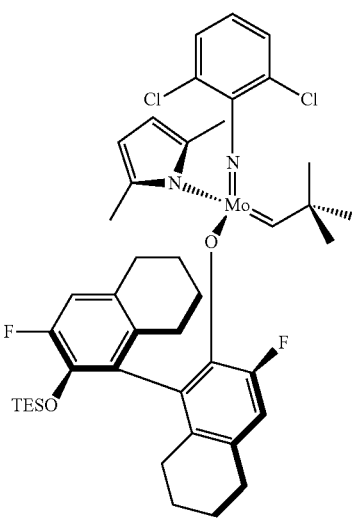
or

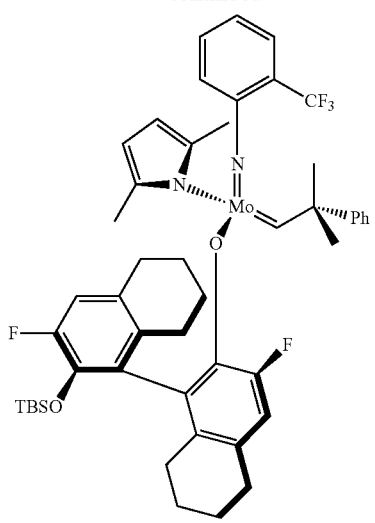
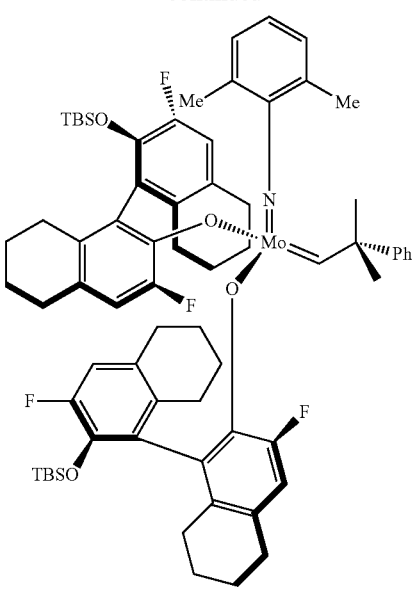
In some embodiments, a complex of formula II-b for use in preparing a compound of formula I or formula I-a is as depicted below:
11
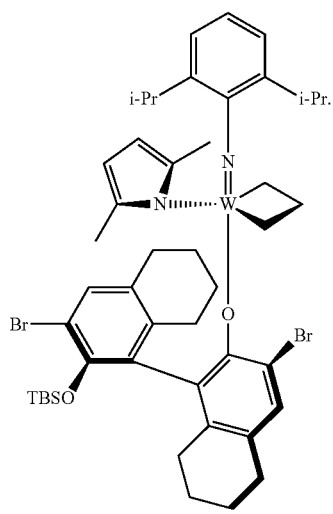
In some embodiments, a complex of formula II-c for use in preparing a compound of formula I or formula I-a is as depicted below:
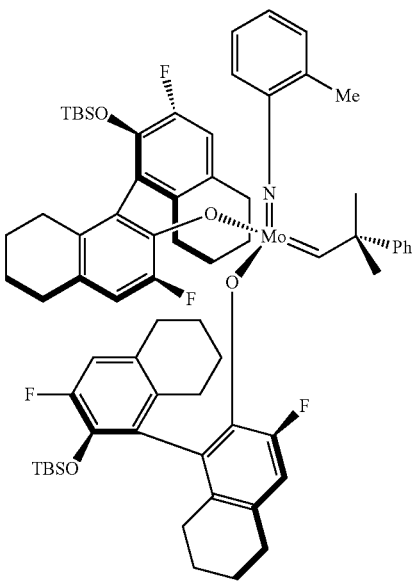
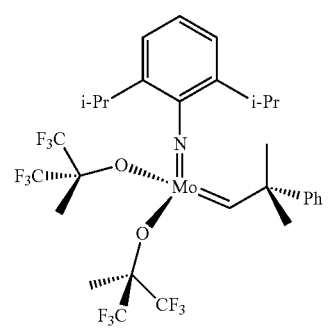

145
-continued
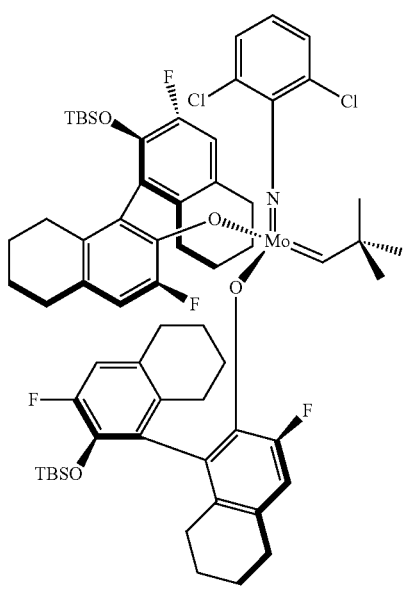
146
-continued
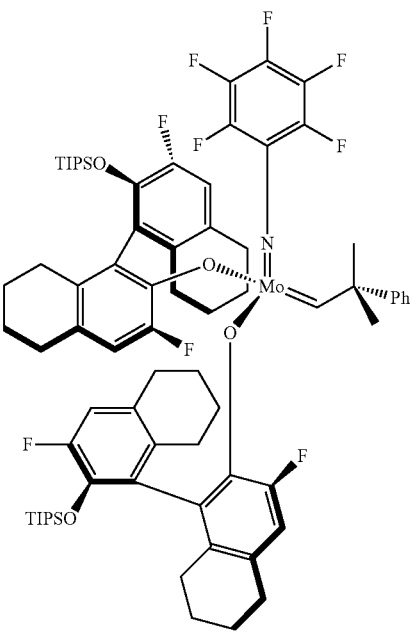
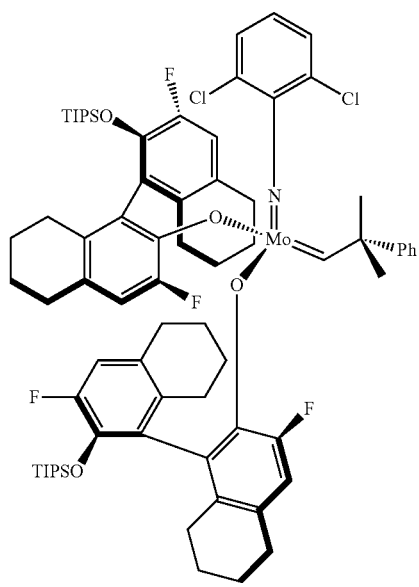
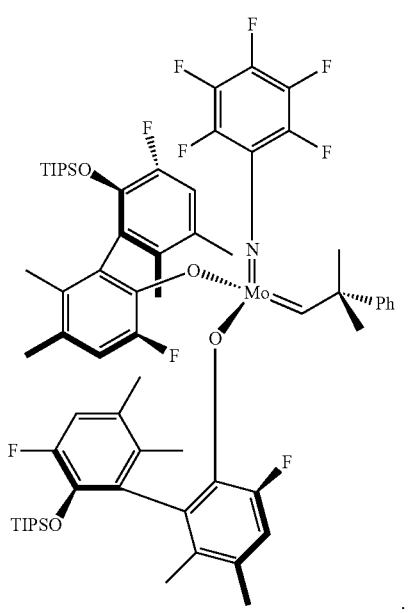

In some embodiments, a complex of formula II-c is as depicted below:
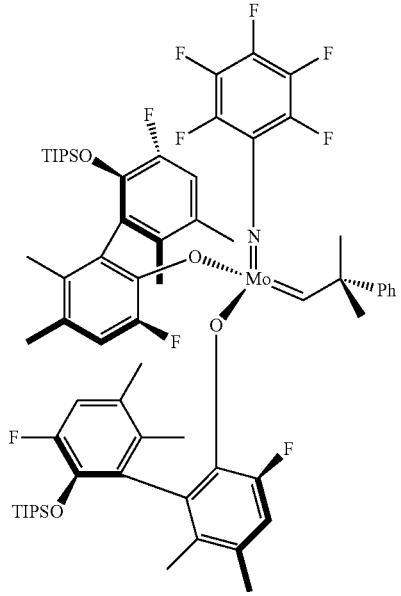
-continued
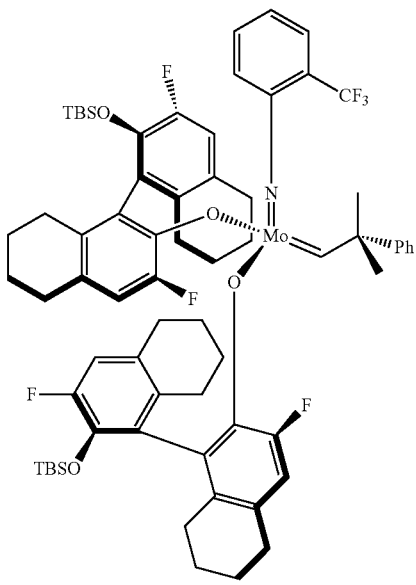
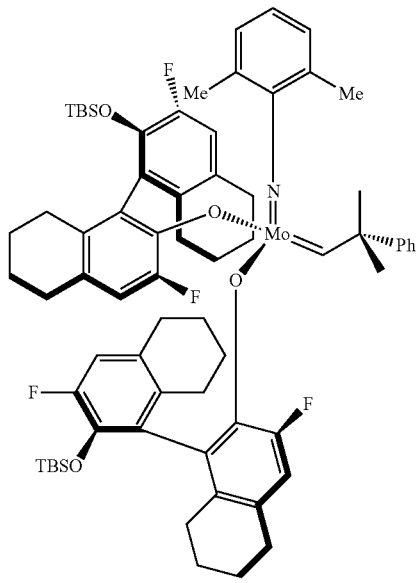

-continued

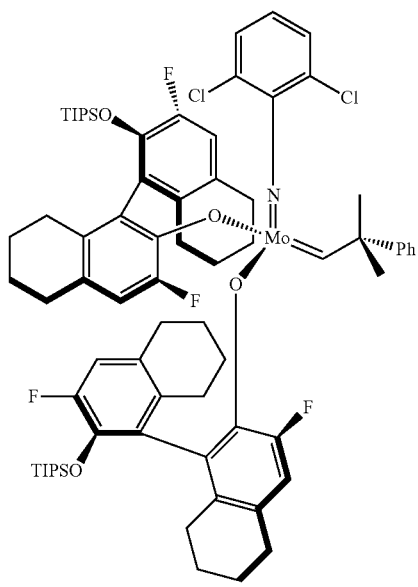

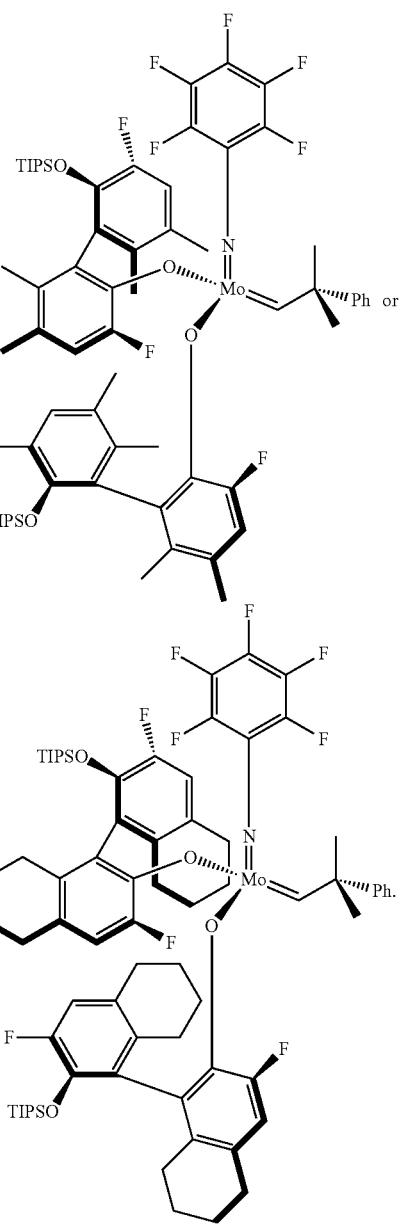

In some embodiments, a complex of formula II-c is:

Exemplary other such metal complexes for use in preparing a compound of formula I are as depicted below:
Novel Metal Complexes of the Present Invention In some embodiments, the present invention provides novel metal complexes for use in the synthesis of macrocyclic z-alkenes.

In some embodiments, a provided metal complex is of either of formula III-a or III-b:

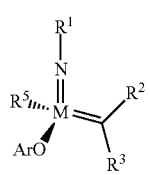

III-a

-continued

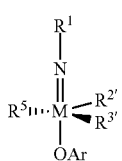

III-b wherein each of M, $R^1$, $R^2$, $R^{2'}$, $R^3$, $R^{3'}$, —Ar, and $R^5$ are as defined above and described in embodiments herein with regard to formula II-a and II-b. One of skill in the art will recognize that metal complexes of formula III-a depicted above are a subset of formula II-a. Likewise, metal complexes of formula III-b depicted above are a subset of formula II-b. Accordingly, the present invention contemplates metal complexes of either of formula III-a or formula III-b comprising any of the various embodiments described above and herein, which embodiments, in combination, comprise a novel metal complex.

In some embodiments, the present invention provides a metal complex of either of formula III-a or III-b, wherein —Ar is of any of the embodiments described above and herein. In certain embodiments, —Ar is as depicted below:

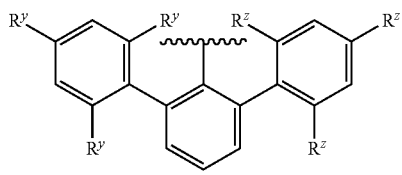

wherein each of $R^y$ and $R^z$ are as defined above and described herein. In certain embodiments wherein —Ar is as depicted above, each $R^y$ and each $R^z$ is independently selected from optionally substituted $C_{1-20}$ aliphatic. In certain embodiments wherein —Ar is as depicted above, each $R^y$ and each $R^z$ is independently selected from optionally substituted $C_{1-10}$ aliphatic. In certain embodiments wherein —Ar is as depicted above, each $R^y$ and each $R^z$ is independently selected from optionally substituted alkyl. Exemplary $R^y$ and $R^z$ groups include methyl, ethyl, propyl, and butyl.

In certain embodiments, a provided metal complex is of formula III-a or III-b, wherein —Ar has the following structure:

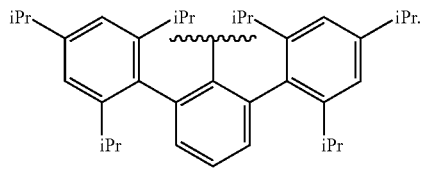

In certain embodiments, a provided metal complex of formula III-a has the following structure:

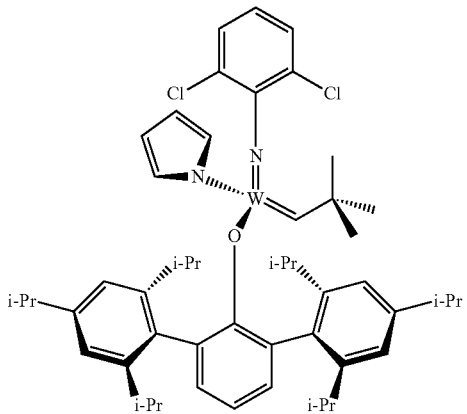

In some embodiments, a metal complex is as depicted above, wherein W is replaced with Mo.

In some embodiments, a complex of formula II-b is as depicted below:

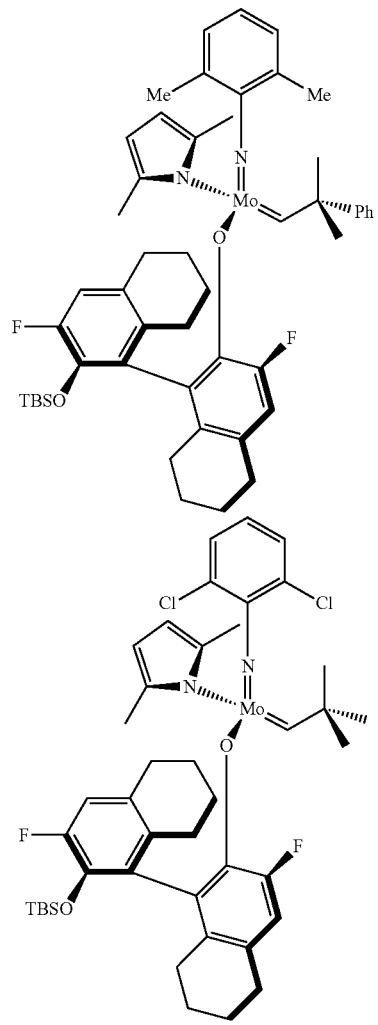

153
-continued
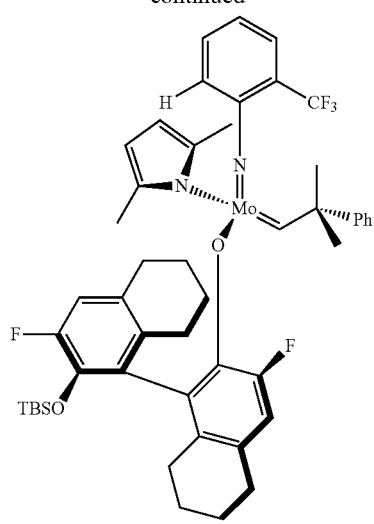
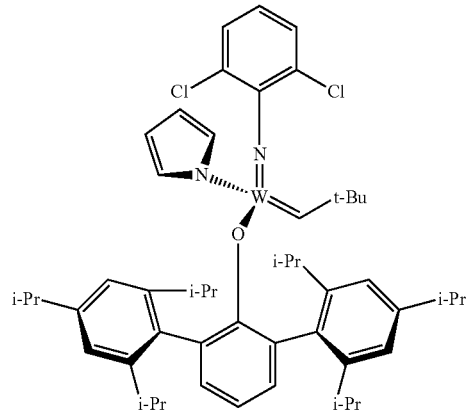
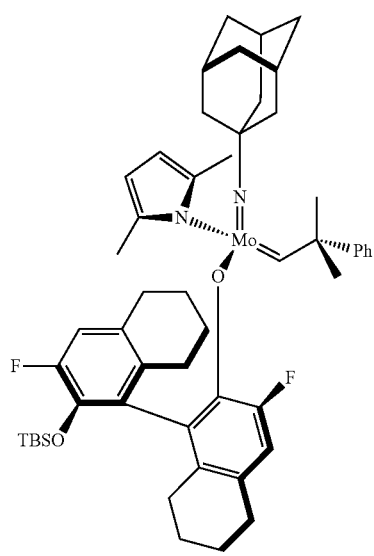
154
-continued
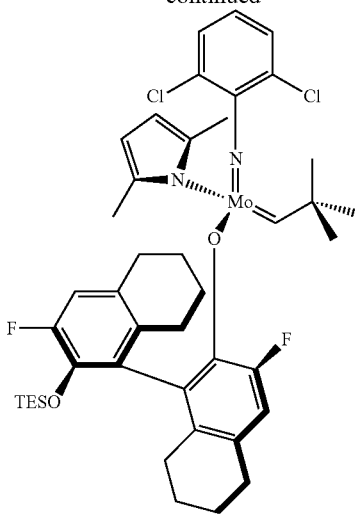
or
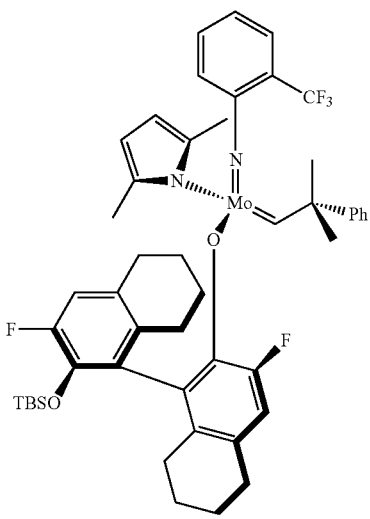
;
In some embodiments, a provided metal complex is of formula II-c:
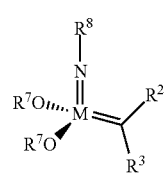
II-c
wherein each of M, $R^2$, $R^3$, $R^7$ and $R^8$ is independently as defined above and described herein.

In some embodiments, a provided metal complex is of formula II-c:

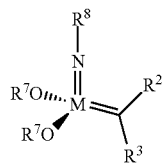

wherein M is molybdenum; and wherein each of $R^2$, $R^3$, $R^7$ and $R^8$ is independently as defined above and described herein.

In some embodiments, $R^8$ in formula II-c is optionally substituted phenyl wherein one or more substituents is —F. In some embodiments, $R^8$ is

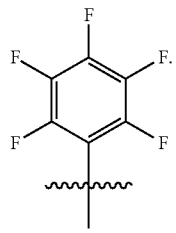

In some embodiments, $R^8$ in formula II-c is an optionally substituted group selected from:

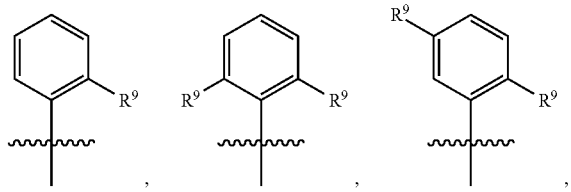

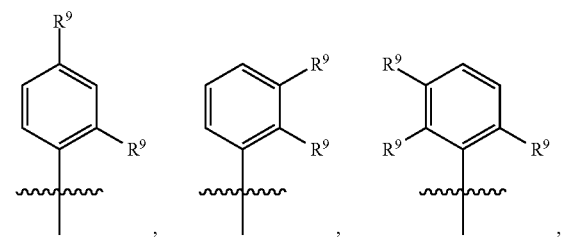

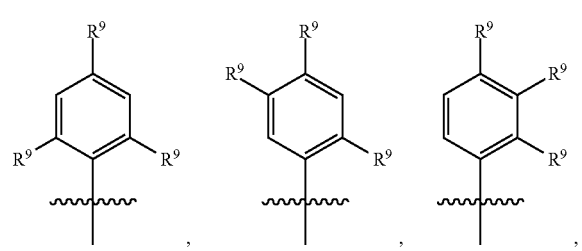

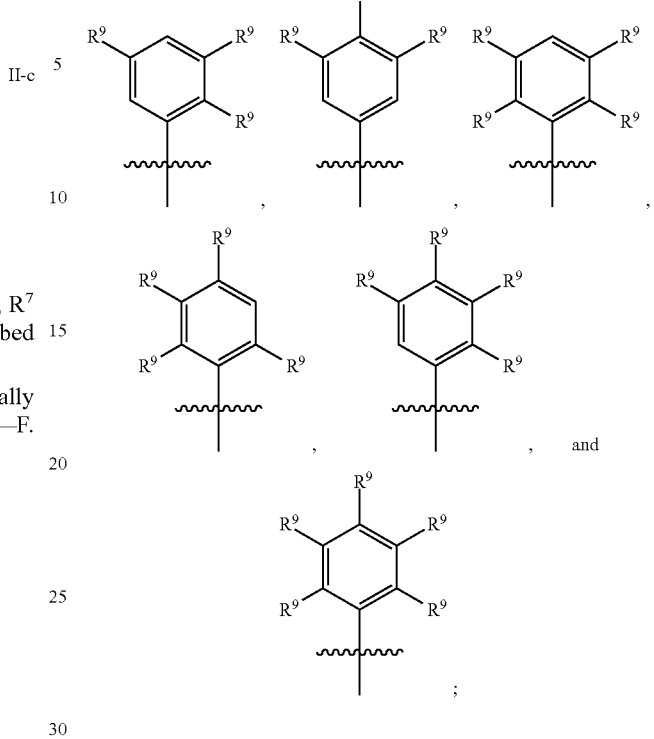

wherein:
each $\boldsymbol{\mathcal{S}}$ represents the point of attachment to the nitrogen atom, and each $R^9$ is independently as defined above and described herein; and
one ore more $R^9$ are —F.

In some embodiments, $R^2$ in formula II-c is —$C(CH_3)_3$ and $R^3$ in formula II-c is hydrogen. In some embodiments, $R^2$ in formula II-c is —$C(CH_3)_2Ph$ and $R^3$ in formula II-c is hydrogen.

In some embodiments, each —$OR^7$ in formula II-c is independently an optionally substituted group selected from:

wherein:

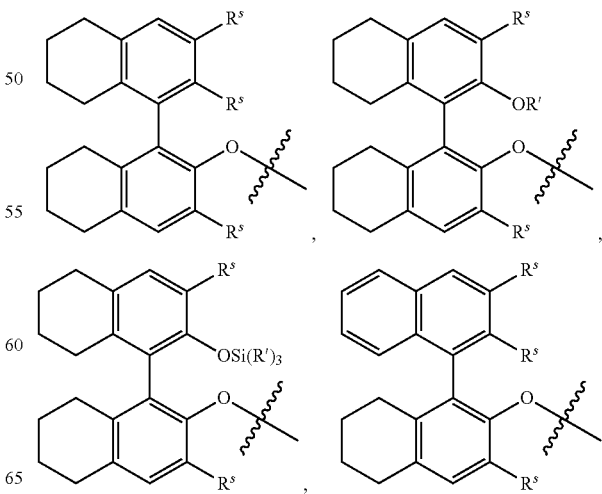

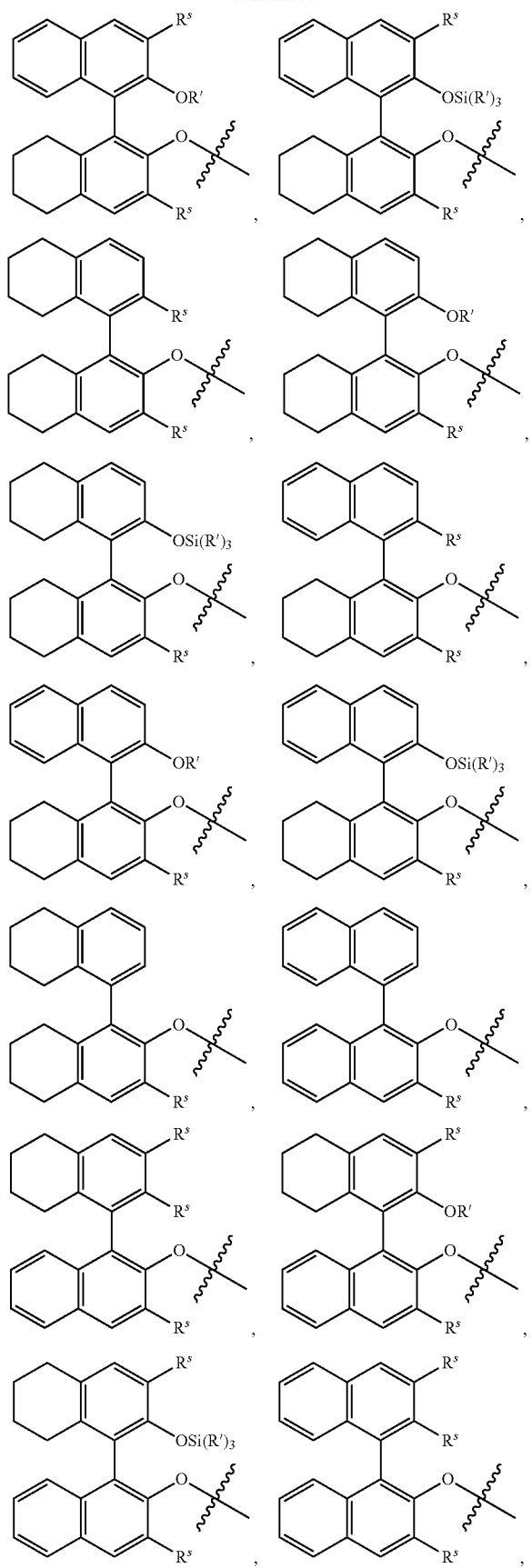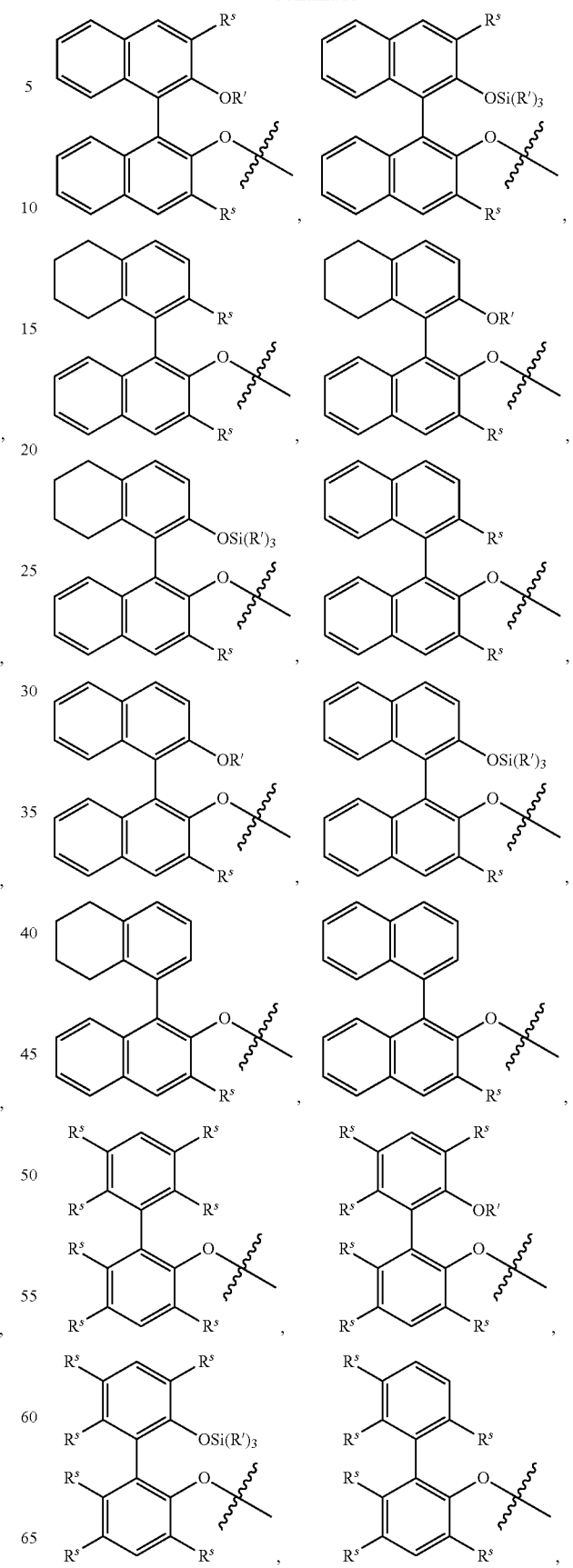

-continued

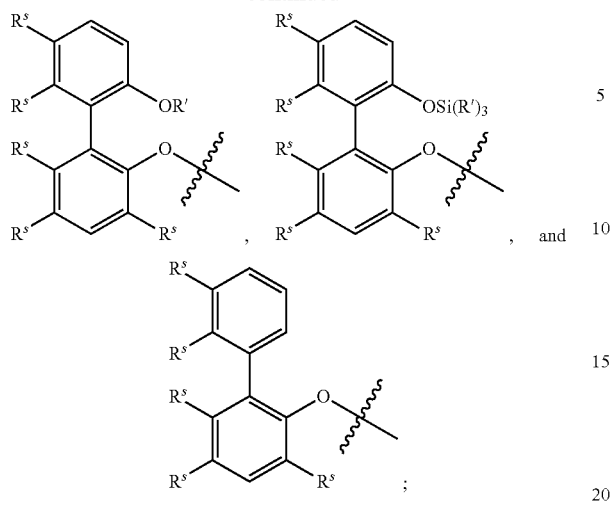

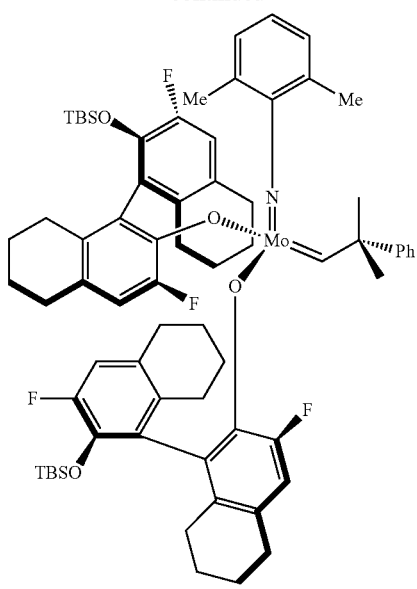

each $s$ represents the point of attachment to the metal, M;

each of $R^s$ and $R'$ is independently as defined above and described herein; and one or more $R^s$ are —F.

In some embodiments, each $R^7$ is independently optionally substituted phenyl. In some embodiments, each $R^7$ is independently optionally substituted $C_{1-20}$ aliphatic. In some embodiments, each $R^7$ is independently $C_{1-20}$ aliphatic substituted with one or more halogen. In some embodiments, each $R^7$ is independently $C_{1-20}$ aliphatic substituted with one or more —F. In some embodiments, each $R^7$ is independently tertiary $C_{1-20}$ aliphatic substituted with one or more —F. In some embodiments, each $R^7$ is independently tertiary $C_{1-20}$ alkyl substituted with one or more —F. In some embodiments, each $R^7$ is independently selected from tert-butyl, —C(CF$_3$)$_2$(Me) and —C(CF$_3$)$_3$.

In some embodiments, a complex of formula II-c is as depicted below:

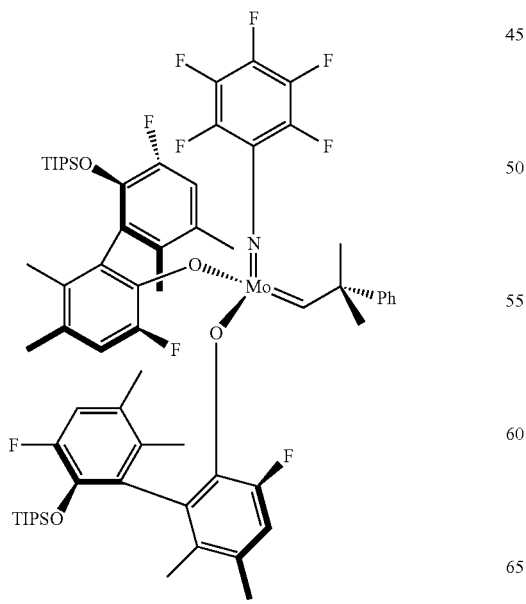

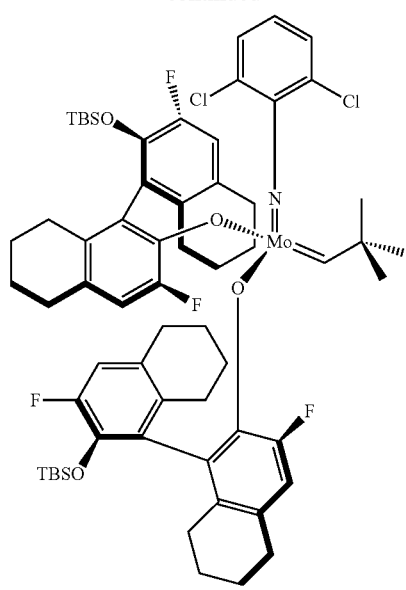
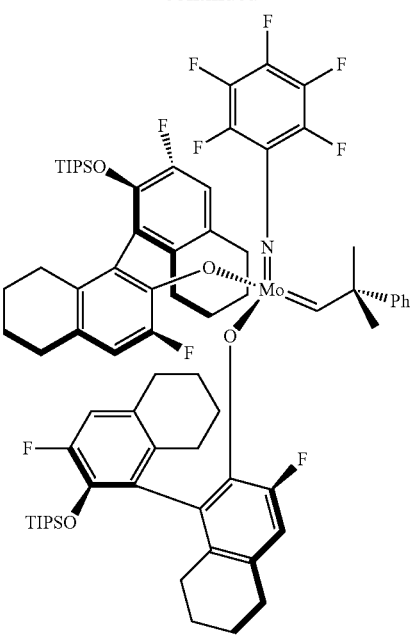
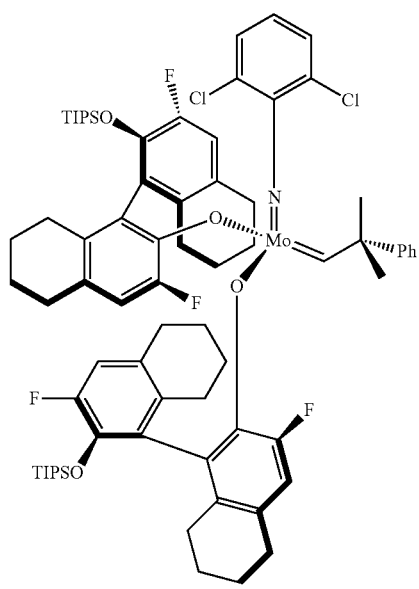
In some embodiments, a complex of formula II-c is:
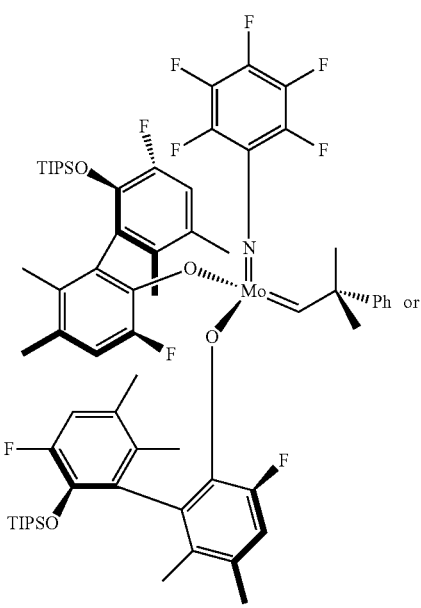

-continued

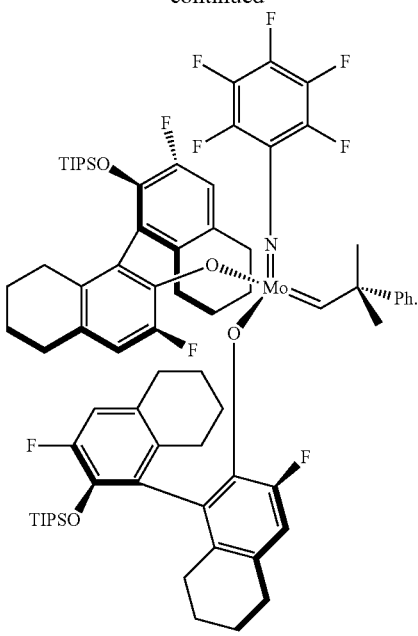

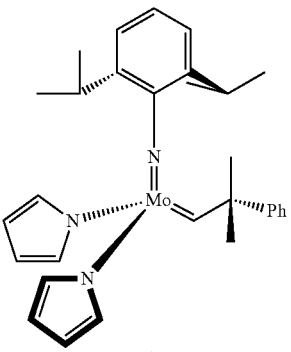

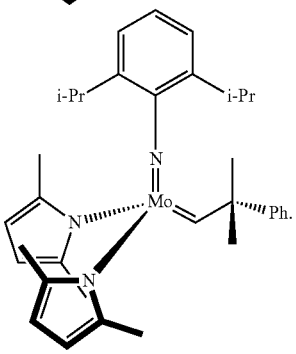

Conditions

As described above, the present invention provides a method comprising reacting a suitable diene with a stereogenic-at-metal catalyst of formula II-a, II-b or II-c under suitable conditions to form a compound of formula I or formula I-a:

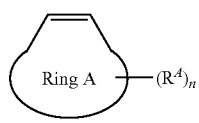

I

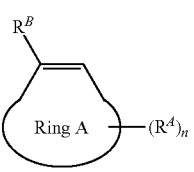

I-a

In some embodiments, a stereogenic at metal catalyst is a metal complex of formula II-a, II-b or II-c and is generated from a synthetically accessible or commercially available metal complex and one or more suitable ligands. In certain embodiments, generation of a metal complex of formula II-a, II-b or II-c occurs in situ. In some embodiments, the metal complex of formula II-a, II-b or II-c is made using a metal complex of either of the following structures:

In certain embodiments, the Mo metal center of the metal complex of formula II-a, II-b or II-c is replaced with a W metal center. Methods of making metal complexes of formula II-a, II-b or II-c are described in further detail herein in the Exemplification.

In some embodiments, one or more suitable ligands are provided under suitable conditions so as to generate a metal complex of formula II-a, II-b or II-c for use in a provided method. In some embodiments, a ligand is provided in a molar ratio of about 10:1, 9:1, 8:1, 7:1, 6:1, 5:1, 4:1, 3:1, 2:1, or 1:1 relative to the metal complex. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal complex. In certain embodiments, a ligand is provided in a molar ratio of about 1:1 relative to the metal complex. One of skill in the art will appreciate that the optimal molar ratio of ligand to metal complex will depend on, inter alia, whether the ligand is mono- or bidentate.

In some embodiments, a provided method requires an amount of catalyst such that the loading is from about 0.01 mol % to about 20 mol % of catalyst relative to substrate (i.e., a suitable diene). In certain embodiments, the catalyst is used in an amount of between about 0.1 mol % to about 10 mol %. In certain embodiments, the catalyst is used in an amount of between about 0.1 mol % to about 5 mol %. In certain embodiments, the catalyst is used in an amount of between about 0.1 mol % to about 3 mol %. In certain embodiments, the catalyst is used in an amount of about 3 mol %, 4 mol %, 5 mol %, 6 mol %, 7 mol %, 8 mol %, 9 mol %, or 10 mol %.

Suitable conditions for performing a provided method generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, tetrahydrofuran (THF), or dioxanes, or mixtures thereof. In certain embodiments, one or more solvents are deuterated. In some embodiments, a single solvent is used. In certain embodiments, the solvent is benzene or toluene. In certain embodiments, the solvent is dichloromethane.

In some embodiments, mixtures of two or more solvents are used, and in some cases may be preferred to a single solvent. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Methods of the present invention typically employ ambient reaction temperatures. In some embodiments, a suitable reaction temperature is about 15° C., about 20° C., about 25° C., or about 30° C. In some embodiments, a suitable reaction temperature is from about 15° C. to about 25° C. In certain embodiments, a suitable reaction temperature is about 20° C., 21° C., 22° C., 23° C., 24° C., or 25° C.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr.

In some embodiments, a method of the present invention requires an amount of solvent such that the concentration of the reaction is between about 0.01 M and about 1 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.05 M. In some embodiments, the concentration of the reaction is about 0.1 M.

In some embodiments, a method of the present invention requires a reaction time of about 1 minute to about 1 day. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1 hour. In certain embodiments, the reaction time is about 2, 3, 4, 5, 6, 7, 8, 9, 10, 11, or 12 hours. In some embodiments, the reaction time is about 12 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 30 minutes. In some embodiments, the reaction time is about 1, 1.5, 2, 2.5, or 3 hours.

In some embodiments, a method of the present invention produces a product having a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

Compositions of the Present Invention

In some embodiments, a method of the present invention (i.e. a ring-closing metathesis reaction) provides a composition comprising an alkene-containing macrocyclic compound enriched in the Z configuration. Thus, the present invention provides compositions which comprise an alkene-containing macrocyclic compound enriched in the Z configuration. As used herein, the phrase "enriched in the Z configuration" refers to a composition wherein at least about 50% of the double bond produced in the metathesis reaction has a Z configuration. In some embodiments, a provided composition enriched in the Z configuration is characterized in that at least 55% of the double bond produced in the metathesis reaction has a Z configuration. In some embodiments, a provided composition enriched in the Z configuration is characterized in that at least 60% of the double bond produced in the metathesis reaction has a Z configuration. In some embodiments, a provided composition enriched in the Z configuration is characterized in that at least 65% of the double bond produced in the metathesis reaction has a Z configuration. In some embodiments, a provided composition enriched in the Z configuration is characterized in that at least 70% of the double bond produced in the metathesis reaction has a Z configuration. In some embodiments, a provided composition enriched in the Z configuration is characterized in that at least 75% of the double bond produced in the metathesis reaction has a Z configuration. In some embodiments, a provided composition enriched in the Z configuration is characterized in that at least 80% of the double bond produced in the metathesis reaction has a Z configuration. In some embodiments, a provided composition enriched in the Z configuration is characterized in that at least 85% of the double bond produced in the metathesis reaction has a Z configuration. In some embodiments, a provided composition enriched in the Z configuration is characterized in that at least 90% of the double bond produced in the metathesis reaction has a Z configuration. In some embodiments, a provided composition enriched in the Z configuration is characterized in that at least 91%, 92%, 93%, 94%, 95%, 96%, 97%, 98%, or 99% of the double bond produced in the metathesis reaction has a Z configuration. In some embodiments, a provided composition enriched in the Z configuration is characterized in that at least 99.1%, 99.2%, 99.3%, 99.4%, 99.5%, 99.6%, 99.7%, 99.8%, or 99.9% of the double bond produced in the metathesis reaction has a Z configuration.

EXEMPLIFICATION

General

Unless otherwise noted, all reactions were performed with distilled and degassed solvents under an atmosphere of dry $N_2$ in oven- (135° C.) or flame-dried glassware with standard dry box or vacuum line techniques. All the substrates were dried by azeotropic distillation with $C_6H_6$ prior to use in reactions with Mo and W-based complexes. Substrate 3 (Furstner, A.; Langemann, K. Synthesis 1997, 792-803), 4 (Meng, D.; Bertinato, P.; Balog, A.; Su, D.-S.; Kamenecka, T.; Sorensen, E. J.; Danishefsky, S. J. J. Am. Chem. Soc. 1997, 119, 10073-10092), 13 (Furstner, A.; Langemann, K. J. Org. Chem. 1996, 61, 3942-3943), precursor to 15 (Furstner, A.; Langemann, K. Synthesis 1997, 792-803) and 18 (Jakubec, P.; Cockfield, D. M.; Dixon, D. J. J. Am. Chem. Soc. 2009, 131, 16632-16633) were synthesized according to the previously reported procedures. Infrared (IR) spectra were recorded on a Bruker FTIR Alpha (ATR Mode) spectrometer, $v_{max}$ in $cm^{-1}$. Bands are characterized as broad (br), strong (s), medium (m), or weak (w). $^1H$ NMR spectra were recorded on a Varian Unity INOVA 400 (400 MHz) spectrometer. Chemical shifts are reported in ppm from tetramethylsilane with the solvent resonance resulting from incomplete deuterium incorporation as the internal standard ($CDCl_3$: δ 7.26 ppm, $C_6D_6$: δ 7.16 ppm, $CD_3OD$: δ 3.31 ppm). Data are reported as follows: chemical shift, integration, multiplicity (s=singlet, d=doublet, q=quartet, br=broad, m=multiplet), and coupling constants (Hz). $^{13}C$ NMR spectra were recorded on a Varian Unity INOVA 400 (100 MHz) spectrometer with complete proton decoupling. Chemical shifts are reported in ppm from tetramethylsilane with the solvent resonance as the internal standard ($CDCl_3$: δ 77.16 ppm, $CD_3OD$: δ 49.00 ppm). High-resolution mass spectrometry was performed on a Micromass LCT ESI-MS (positive mode) at the Boston College Mass Spectrometry Facility. Z:E ratios of 5, 7, yuzu lactone, 14, 15, 16, and epilachnene were determined by $^1H$ NMR; Z:E ratios of 17 and ambrettolide (Furstner, A.; Guth, O.; Rumbo, A.; Seidel, G. J. Am. Chem. Soc. 1999, 121, 11108-11113) was determined by $^{13}C$ NMR. The stereochemistry of the macrocyclic alkenes was proofed by comparison with reported data (yuzu lactone (Furstner, A.; Guth, O.; Rumbo, A.; Seidel, G. J. Am. Chem. Soc. 1999, 121, 11108-11113), 14 (Furstner, A.; Langemann, K. J. Org. Chem. 1996, 61, 3942-3943), 15 (Furstner, A.; Langemann, K. Synthesis 1997, 792-803), epilachnene (Furstner, A.; Langemann, K. Synthesis 1997, 792-803)); the stereochemistry 16 was determined based on nOe study; the stereochemical proof of 7 and 17 was determined based on the crystal structure of the major isomer. Optical rotations were measured on a Rudolph Research Analytical Autopol IV Polarimeter.

Vacuum Pumps:

Edwards RV8 two stage rotary vane pump generates a vacuum of 1.0 torr at point of connection to the reaction vessel. KNF Laboport N840.3FTP diaphragm vacuum pump generates a vacuum of 7.0 torr at point of connection to the reaction vessel.

Solvents:

Solvents were purged with argon and purified under a positive pressure of dry Ar by a modified Innovative Technologies purification system. Toluene (Fisher), dichloromethane (Fisher) and benzene (Aldrich) were passed successively through activated copper and alumina columns; benzene (Aldrich), and pentane (Fisher; n-Pentane was allowed to stir over concentrated $H_2SO_4$ for three days, washed with water, followed by a saturated aqueous solution of $NaHCO_3$, dried over $MgSO4$, and filtered before use in a solvent purification system.) were passed successively through activated Cu and alumina columns. Tetrahydrofuran (Fisher) was purified by distillation from sodium benzophenone ketyl immediately prior to use. N,N-Dimethylformamide (Acros; extra dry with molecular sieves) was used as received. All work-up and purification procedures were carried out with reagent grade solvents (purchased from Doe & Ingalls) under air atmosphere.

Metal-Based Complexes:

Mo-based bis(alkoxide) complex 1 was prepared according to a previously reported procedure (Schrock, R. R.; Murdzek, J. S.; bazan, G. C.; Robbins, J.; DiMare, M.; O'Regan, M. J. Am. Chem. Soc. 1990, 112, 3875-3886). Mo or W monopyrrolide-monoaryloxide complexes 8a, 8b and 9 (Malcolmson, S. J.; Meek, S. J.; Sattely, E. S.; Schrock, R. R.; Hoveyda, A. H. Nature 2008, 456, 933-937) were prepared in situ according to published procedures from Mo bis(pyrrolide) complexes A, B and C ((a) Hock, A. S.; Schrock, R. R.; Hoveyda, A. H. J. Am. Chem. Soc. 2006, 128, 16373-16375. (b) Singh, R.; Czekelius, C.; Schrock, R. R.; Müller, P. M.; Hoveyda, A. H. Organometallics 2007, 26, 2528-2539); 10 and 12 (Jiang, A. J.; Zhao, Y.; Schrock, R. R.; Hoveyda, A. H. J. Am. Chem. Soc. 2009, 131, 16630-16631) were prepared and purified according to previously disclosed procedures (Jiang, A. J.; Simpson, J. H.; Müller, P.; Schrock, R. R. J. Am. Chem. Soc. 2009, 131, 7770-7780). Mo monopyrolide-monoaryloxide metallacyclobutane complexe 11 was prepared and purified according to the reported procedure (Jiang, A. J.; Simpson, J. H.; Müller, P.; Schrock, R. R. J. Am. Chem. Soc. 2009, 131, 7770-7780). Ru-based carbene complexes 2a-d were obtained from Materia, Inc. and purified by silica gel column chromatography and recrystallization (dichloromethane/pentane) prior to use. Unless otherwise noted, all Mo and W complexes were handled under an inert atmosphere of $N_2$ in a dry box. Chart 1. Mo Bis-Pyrrolide Complexes and Chiral Enantiomerically Pure Alcohol.

A

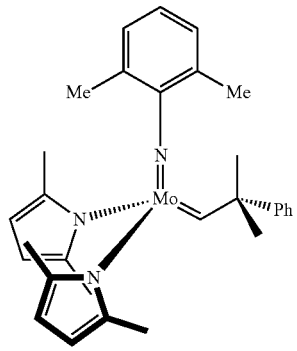

-continued

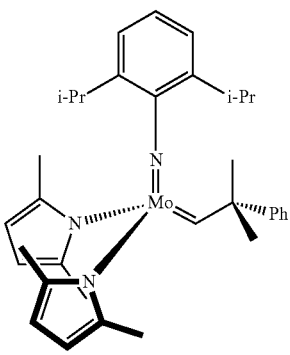
B

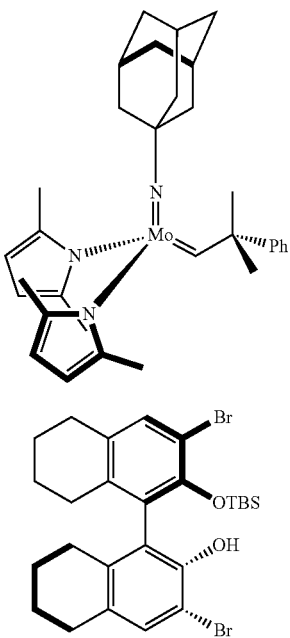
C

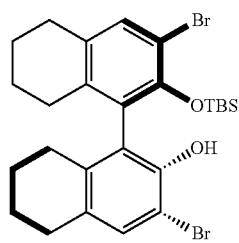
D

Reagents:

Acetic anhydride was purchased from Aldrich and used as received.

Azobisisobutyronitrile (AIBN) was purchased from Janssen Chimica and used as received.

$d_6$-Benzene was purchased from Cambridge Isotope Laboratories and distilled from Na into activated 4 Å molecular sieves prior to use.

6-Bromo-1-hexene was purchased from Fluorochem and used as received.

tert-Butyldimethylsilyl trifluoromethanesulfonate (TBSOTf) was purchased from TCI and used as received.

But-3-en-1-amine was purchased from Alfa Aesar and used as received.

But-3-en-1-ol was purchased from Aldrich and used as received.

(+)-Camphorsulfonic acid was purchased from Aldrich and used as received.

d-Chloroform was purchased from Cambridge Isotope Laboratories and passed through basic alumina then stored in activated 4 Å molecular sieves prior to use.

Dec-9-en-1-ol was purchased from Aldrich and used as received.

Dec-9-enoic acid was purchased from Aldrich and used as received.

Diisobutylaluminium hydride (DIBAL-H) was purchased from Strem and used as received.

Dimethyl sulfoxide (DMSO) was purchased from Acros and distilled over $CaH_2$ and dried over 4 Å activated molecular sieves prior to use.

Di-tert-Butyl dicarbonate was purchased from Alfa Aesar and used as received.

4-(N,N-Dimethylamino)pyridine (DMAP) was purchased from Aldrich and used as received.

N,N-Dimethylformaamide (DMF) was purchased from Acros and dried over 4 Å activated molecular sieves prior to use.

1-Ethyl-3-(3-dimethylaminopropyl)carbodiimide hydrochloride (EDC) was purchased from Aldrich and used as received.

Formaldehyde (37% solution in water) was purchased from Fisher Scientific and used as received.

Hex-5-enoic acid was purchased from Aldrich and used as received.

Hydrogen fluoride-pyridine complex was purchased from Aldrich and used as received.

1-Hydroxy-benzotriazole (HOBT) was purchased from Advance Tech. and used as received.

2-Iodoxybenzoic acid (IBX) was purchased from Aldrich and used as received.

Lithium triethylborohydride (1.0 M solution in THF) was purchased from Aldrich and used as received.

2,6-Lutidine was purchased from Aldrich and distilled over $CaH_2$ prior to use.

Mesitylene was purchased from Aldrich and used as received.

Methanol was purchased from Aldrich and dried over 4 Å activated molecular sieves prior to use.

$d_4$-Methanol was purchased from Cambridge Isotope Laboratories and used as received.

Methyl triphenylphosphonium bromide was purchased from Alfa Aesar and used as received.

Oct-7-enoic acid was purchased from Aldrich and used as received.

Oxalyl chloride was purchased from Acros and distilled over $CaH_2$ prior to use.

Potassium tert-butyloxide was purchased from Alfa Aesar and used as received.

Tributyltin hydride was purchased from Alfa Aesar and used as received.

Triethylamine was purchased from Aldrich and distilled over $CaH_2$ prior to use.

Trifluoroacetic acid was purchased from Aldrich and used as received.

p-Toluenesulfonic acid (PTSA) was purchased from Aldrich and used as received.

Undec-10-enoic acid was purchased from Aldrich and used as received.

Undec-10-en-1-amine was purchased from GFS Chemical and used as received.

Z-Selective RCM for Synthesis of Sparsely Substituted Macrocycles

We began by examining the ability of different molybdenum and tungsten alkylidenes to promote the RCM of diene 13 to afford sixteen-membered ring carboxylic ester 14 (Table 1); a previous attempt involving the use of ruthenium carbene 2a led to the formation of the ring with 77% E selectivity (4.0 mol %, 22° C., 30 h) (Xu, Z. et al. Applications of Zr-catalyzed carbomagnesation and Mo-catalyzed macrocyclic ring-closing metathesis in asymmetric synthesis. Enantioselective total synthesis of Sch 38516 (fluvirucin B). *J. Am. Chem. Soc.* 119, 10302-10316 (1997)). Preliminary calculations revealed that E-14 is 1.2 kcal/mol lower in energy than its Z isomer, suggesting that, at equilibrium, there would exist an approximately 88:12 mixture enriched in the E isomer. As demonstrated by the data summarized in entries 1-5, E-14 was indeed formed preferentially with complexes 1 or 2c-d; reduced pressure, a strategy used to lower ethylene concentration and minimize isomerization, did not improve efficiency or selectivity (cf. entries 1 vs. 2, and 4 vs. 5). In sharp contrast, Z-14 was generated with moderate preference when RCM is performed with molybdenum monopyrrolides 8a-b (entries 6-8). Adamantylimido 9 delivers 85% Z selectivity when RCM was performed under 7.0 torr of pressure (62% yield; entry 10); stereoselectivity increases to 92% Z with 1.2 mol % catalyst loading (entry 11; vs. 3.0 mol % in entry 10) but with similar efficiency, presumably because isomerization of the cyclic Z alkene was reduced with the catalyst being less available.

Reaction with tungsten alkylidene 10 lead to similarly high yield and stereochemical control (62% and 91% Z; entry 13), with the derived metallacyclobutane 11 delivering a more efficient (73% yield) RCM that proceeded with an equal degree of Z-selectivity (90%). There was exceptional stereoselectivity with dichloroimido W alkylidene 12 (95% Z; entry 15, Table 1). This reaction proceeded to 14% conversion.

TABLE 1

Initial Examination of the Stereogenic-at-Mo & W Complexes as Catalysts for RCM of diene 13 to generate sixteen-membered macrocycle Z-14

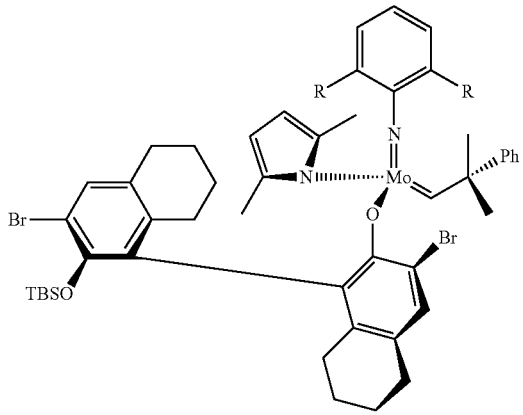

8a R = Me
8b R = i-Pr

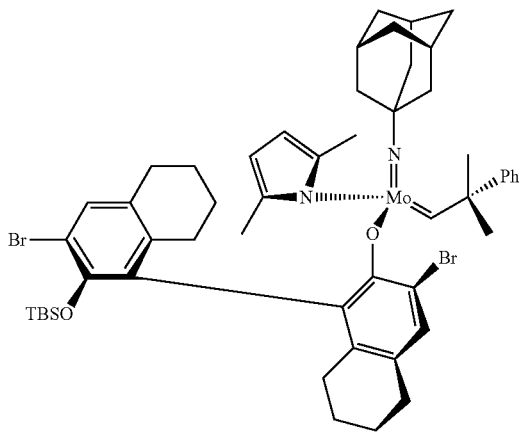

9

TABLE 1-continued
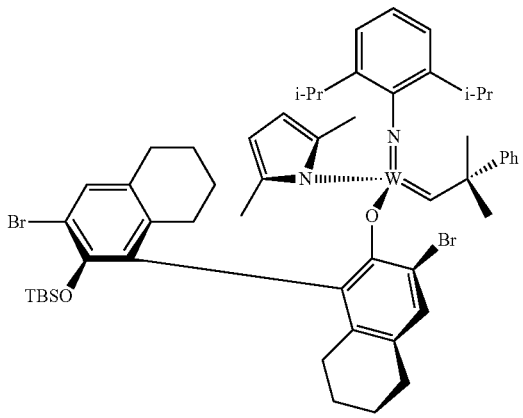
10
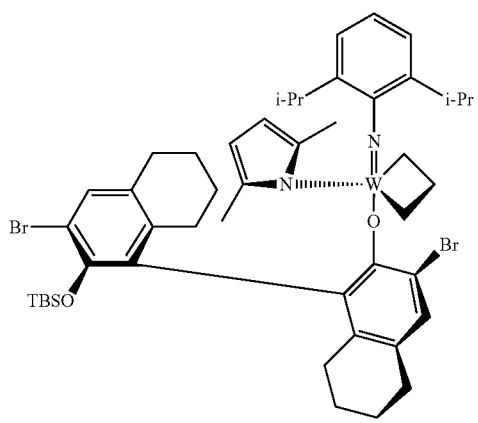
11
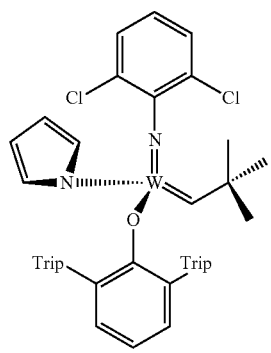
Trip = 2,4,6-(i-Pr)$_3$C$_6$H$_2$
12
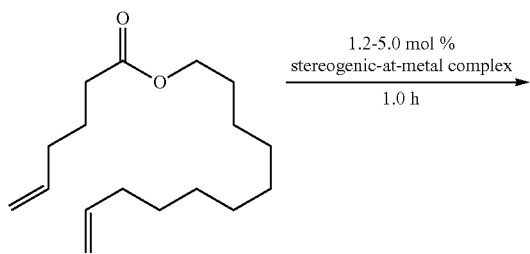 [SMILES: C=CCCCCCCCCCOC(=O)CCCC=C]
13

TABLE 1-continued

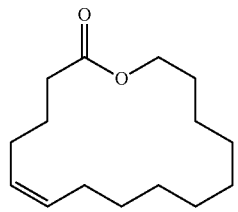 [SMILES: O=C1CCC/C=C\CCCCCCCCCO1]

14

| Entry no. | Metal Complex | Catalyst Loading† | Conditions | Conv. (%)§; Yield (%)§§ | Z:E§ |
|---|---|---|---|---|---|
| 1 | 1 | 5.0 | ambient | 85; 60 | 22:78 |
| 2 | 1 | 5.0 | 7.0 torr | 96; 58 | 21:79 |
| 3 | 2c | 5.0 | ambient | 75; 61 | 21:79 |
| 4 | 2d | 5.0 | ambient | 71; 59 | 20:80 |
| 5 | 2d | 5.0 | 7.0 torr | 95; 76 | 21:79 |
| 6 | 8a | 5.0 | ambient | 56; 45 | 70:30 |
| 7 | 8a | 5.0 | 7.0 torr | 97; 56 | 77:23 |
| 8 | 8b | 5.0 | 7.0 torr | 91; 55 | 72:28 |
| 9 | 9 | 3.0 | ambient | 55; 45 | 85:15 |
| 10 | 9 | 3.0 | 7.0 torr | 80; 62 | 85:15 |
| 11 | 9 | 1.2 | 7.0 torr | 75; 56 | 92:8 |
| 12 | 10 | 5.0 | ambient | 56; 46 | 80:20 |
| 13 | 10 | 5.0 | 7.0 torr | 80; 62 | 91:9 |
| 14 | 11 | 5.0 | 7.0 torr | 91; 73 | 90:10 |
| 15 | 12 | 5.0 | 7.0 torr | 14; 10 | 95:5 |

The reactions were carried out in purified toluene under an atmosphere of nitrogen gas or under vacuum as noted; reaction in entry 3 was performed in $CH_2Cl_2$ at 40° C.; see below for details.
†Complexes 1, 2c and 10-12 were prepared and then used, whereas alkylidenes 8a-b and 9 were synthesized in situ from the corresponding bis-pyrrolide and aryl alcohol, which proceeds in >98% yield for 8a-b but in 60% (±2%) yield in the case of 9 (thus, catalyst loading for the latter complex is 3.0 mol %). See below for details
§Conversion and Z:E ratios measured by analysis of 400 MHz $^1$H NMR spectra of unpurified mixtures; the variance of values are estimated to be <±2%.
§§Yield of isolated product after purification; the variance of values are estimated to be <±5%.

Macrocyclic esters or amides of different ring sizes were synthesized through the use of molybdenum or tungsten alkylidenes 9-11 with unprecedented Z selectivity and with efficiency levels that render the method of notable utility (Table 2); the disparity between the percent conversion and yield was largely due to adventitious oligomerization. Three of the macrocycles are natural products: the thirteen-membered camphor- and minty-smelling yuzu lactone (entries 1-4, Table 2), fifteen-membered aza-macrolide epilachnene (entries 13-14, see also Scheme 1), secreted by the Mexican bean beetle as part of its pupae defense mechanism (Rossini, C., González, A., Farmer, J., Meinwald J. & Eisner, T. Antiinsectan activity of epilachnene, a defensive alkaloid from pupae of Mexican bean beetles (*Epilachna varivestis*). *J. Chem. Ecol.* 26, 391-397 (2000)), and seventeen-membered musk-odored ambrettolide (entries 19-22). For comparison purposes and to underline the unique ability of the mono-pyrrolide alkylidenes to deliver high Z selectivity, the data regarding the RCM promoted by molybdenum alkylidene 1 and ruthenium carbene 2c are also presented in Table 2; in all cases, substantial amounts of the E alkenes were formed and, at times, with a significant preference (93% E in entries 5-6, Table 2). With complexes 9 and 11, moderate Z selectivity (69-73% Z) was achieved in the formation of thirteen-membered yuzu lactone versus the 93:7 Z:E ratio obtained with sixteen-membered ring 17. Such findings are congruent with the ability of the more strained rings to undergo ring-opening, thereby promoting alkene isomerization; when the RCM leading to yuzu lactone with complex 9 was analyzed after 10 minutes (20% conv.), Z-selectivity is 82% (vs. 69% after one hour). Accordingly, ring-opening/isomerization was more efficient and E selectivity was higher when 1 or 2c are used to synthesize yuzu lactone (83-85% E, entries 1-2) than when the less strained 17 was the desired product (34-44% E, entries 15-16, Table 2).

TABLE 2

Synthesis of macrocyclic esters and amides through catalytic Z-selective RCM

| Entry no. | Macrocyclic Z Alkene | Catalyst; Loading | Conv. (%)§; Yield (%)§§ | Z:E§ |
|---|---|---|---|---|
| 1 | | 1; 5 mol % | 92; 30 | 17:83 |
| 2 | | 2c; 5 mol % | 93; 46 | 15:85 |
| 3 | | 9; 3 mol % | 63; 49 | 69:31 |
| 4 | | 11; 5 mol% | 74; 46 | 73:27 | yuzu lactone

TABLE 2-continued

Synthesis of macrocyclic esters and amides through catalytic Z-selective RCM

| Entry no. | Macrocyclic Z Alkene | Catalyst; Loading | Conv. (%)§; Yield (%)§§ | Z:E§ |
|---|---|---|---|---|
| 5 | 15 (macrocyclic lactone) | 1; 5 mol % | 97; 67 | 7:93 |
| 6 | | 2c; 5 mol % | 98; 74 | 7:93 |
| 7 | | 9; 3 mol % | 74; 50 | 80:20 |
| 8 | | 11; 5 mol % | 82; 54 | 82:18 |
| 9 | 16 (macrocyclic lactam) | 1; 5 mol % | 96; 56 | 21:79 |
| 10 | | 2c; 5 mol % | 98; 68 | 15:85 |
| 11 | | 9; 3 mol % | 72; 50 | 95:5 |
| 12 | | 11; 5 mol % | <20; ND | ND |
| 13 | epilachnene | 9; 1.2 mol % | 76; 70 | 91:9 |
| 14 | | 11; 3 mol % | 88; 76 | 87:13 |
| 15 | 17 | 1; 5 mol % | 93; 53 | 56:44 |
| 16 | | 2c; 5 mol % | 98; 60 | 68:34 |
| 17 | | 9; 3 mol % | 81; 69 | 93:7 |
| 18 | | 11; 5 mol % | <20; ND | ND |
| 19 | ambrettolide | 1; 5 mol % | 95; 65 | 23:77 |
| 20 | | 2c; 5 mol % | 95; 61 | 24:76 |
| 21 | | 9; 3 mol % | 85; 77 | 91:9 |
| 22 | | 11; 5 mol % | 90; 78 | 88:12 |

The reactions were carried out in purified toluene for one hour under an atmosphere of nitrogen gas (with complexes 1 and 2c) or under vacuum (with complexes 9 and 11), as noted; reactions with Ru complex 2c were performed in $CH_2Cl_2$ at 40° C. (1.0 h). See below for details.
§Conversion and Z:E ratios measured by analysis of 400 MHz $^1H$ NMR spectra of unpurified mixtures; the variance of values are estimated to be <±2%.
§§Yield of isolated product after purification; the variance of values are estimated to be <±2%.
ND = not determined.

Z-Selective RCM for Syntheses of Epothilones A & C

Epothilones, which contain a sixteen-membered ring macrolactone, are naturally occurring potent tubulin polymerization and microtubule stabilizing agents that have been investigated extensively during the past fifteen years. Biological studies have shown that the geometry of the macrocyclic alkene influences the activity of this celebrated family of molecules. Moreover, the Z macrocyclic alkene of epothilone C is needed for the desired stereochemical outcome in the epoxidation process, delivering epothilone A; the proper epoxide stereochemistry is essential for biological activity (Altmann, K. H. et al. The total synthesis and biological assessment of trans-epothilone A. Helv. Chim. Acta 85, 4086-4110 (2002)).

To probe the capacity of the molybdenum and tungsten mono-pyrrolides to promote a Z-selective RCM en route to epothilones, we first prepared diene 4 largely based on a sixteen-step sequence developed previously (Meng, D. et al. Total synthesis of epothilones A and B. *J. Am. Chem. Soc.* 119, 10073-10092 (1997)). Treatment of 4 with 10 mol % Mo-based arylimido alkylidene 8a lead to 57% conversion to macrocyclic alkene 5 within three hours, but there was only a slight preference for the Z isomer (64% Z; entry 1, Table 3). When adamantylimido 9 was employed under the same conditions (entry 2, Table 3), efficiency and stereoselectivity improve (87% conv. in 1.5 h and 85% Z), presumably as a result of a more easily accessible metal center and a larger size differential between the aryloxide and the alkylimido unit; use of reduced pressure lead to only a limited enhancement of percent conversion and stereoselectivity (entry 3 vs. 2). The efficiency and Z selectivity with which the RCM in the presence of tungsten arylimido 11 proceeded are similar to those observed with the corresponding molybdenum variants (entry 4, Table 3). However, when ring closure was carried out with tungsten alkylidene 12, which bears a 2,6-dichlorophenylimido and a more sizeable 2,5-di-[2,4,6-(i-Pr)$_3$]-phenoxy ligand (vs. aryloxides in 8-11), there was 77% conversion to macrolactone 5 within 2.5 hours, and RCM stereoselectivity improves to 96% Z (entry 5, Table 3). Under reduced pressure (entry

TABLE 3

Z-Selective Catalytic RCM for Stereoselective Total Syntheses of Epothilones A and C

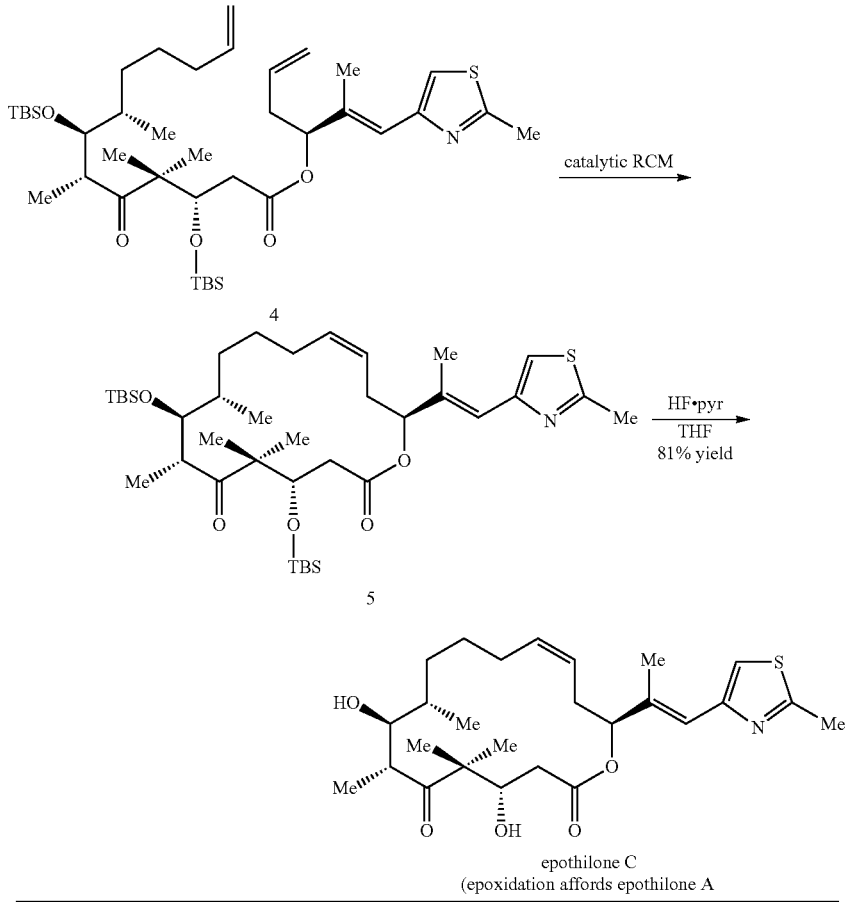

| Entry no. | Catalyst; Loading | Conditions; Concentration | Time | Conv. (%)§; Yield (%)§§ | Z:E§ |
|---|---|---|---|---|---|
| 1 | 8a; 10 mol % | 1.0 torr; 1.0 mM | 3.0 h | 57; ND | 64:36 |
| 2 | 9; 10 mol % | ambient; 1.0 mM | 1.5 h | 87; ND | 85:15 |
| 3 | 9; 10 mol % | 1.0 torr; 1.0 mM | 1.5 h | 91; ND | 90:10 |
| 4 | 11; 10 mol % | ambient; 1.0 mM | 2.5 h | 72; ND | 79:21 |
| 5 | 12; 10 mol % | ambient; 1.0 mM | 2.5 h | 77; ND | 96:4 |
| 6 | 12; 10 mol % | 1.0 torr; 1.0 mM | 2.5 h | 97; 85 | 96:4 |
| 7 | 12; 5.0 mol % | 1.0 torr; 0.01 mM | 2.0 h | 98; 86 | 96:4 |
| 8 | 12; 3.0 mol % | 1.0 torr; 0.05 mM | 3.0 h | 97; 63 | 97:3 |

The reactions were carried out in purified benzene under an atmosphere of nitrogen gas or in toluene under vacuum, as noted, see below for details.
§Conversion and Z:E ratios measured by analysis of 500 MHz $^1$H NMR spectra of unpurified mixtures; the variance of values are estimated to be ≤±2%.
§§Yield of isolated product after purification; the variance of values are estimated to be ≤±2%.
THF = tetrahydrofuran; ND = not determined.

6, Table 3) the reaction proceeded to near completion in the same amount of time (97% conv., 2.5 h), allowing the desired macrocycle to be isolated in 85% yield (96% Z). As the findings summarized in entry 7 of Table 3 illustrate, with the reaction mixture ten times more concentrated (0.01 M), 5 mol % of 12 is sufficient for a highly efficient and Z-selective RCM (86% yield, 96% Z). When 3.0 mol % of the same alkylidene was used and the solution is fifty times more concentrated (0.05 M), the desired product (5) was obtained in 63% yield and 97% Z selectivity (entry 8, Table 3); as before, the wider differential between percent conversion and the yield values (97% and 63%, respectively) was largely the result of adventitious oligomerization, likely facilitated by the increased concentration of the substrate. The higher stereoselectivities furnished by the tungsten catalysts underline a notable advantage of these catalysts: while exhibiting attenuated activity, they are also less likely to react with the macrocyclic alkene to cause generation of the E isomers. Thus, tungsten monopyrrolide 12 offered the desired balance of reactivity such that there was efficient RCM but little or no further reaction with the Z alkene. Macrolactone 5, as depicted in Table 3, was converted to epothilone C in 81% yield upon removal of the two silyl ethers. Stereoselective epoxidation of epothilone C afforded epothilone A. Nagata, T., Nakagawa, M. & Nishida, A. The first total synthesis of nakadomarin A. *J. Am. Chem. Soc.* 125, 7484-7485 (2003) (Ono, K., Nakagawa, M. & Nishida, A. Asymmetric total synthesis of (−)-nakadomarin A. *Angew. Chem. Int. Ed,* 43, 2020-2023 (2004)).

Z-Selective RCM for Synthesis of Macrocyclic Moiety of Nakadomarin A

The above findings raise the question as to whether the problem of catalytic Z-selective synthesis of the fifteen-membered ring alkene moiety of nakadomarin A (cf. FIG. 1), an exceptionally potent anti-cancer and anti-microbial agent isolated in only minute quantities (Schrock, R. R. & Hoveyda, A. H. Molybdenum and tungsten imido alkylidene complexes as efficient olefin metathesis catalysts. *Angew. Chem. Int. Edn* 42, 4592-4633 (2003); Fürstner, A. & Langemann, K. Macrocycles by ring-closing metathesis. *Synthesis* 792-803 (1997)).

This can be addressed through the use of monopyrrolide complexes. As the data in entries 1-2 of Table 4 illustrate, in contrast to sterically demanding arylimido molybdenum alkylidene 8b, which delivers 10% conversion to 7, a precursor to the natural product, the more accessible adamantylimido 9 readily transformed 6 to the pentacyclic structure with 69:31 Z:E ratio. Similar to the RCM with 8b, reaction with tungsten alkylidene 10 did not proceed as readily (entry 3, Table 4), which is likely due to inefficient rate of initiation. When metallacyclobutane 11, a convenient precursor to the more reactive methylidene, was employed, RCM is rendered notably more facile (95% conv., 69% yield; entry 4, Table 4); Z selectivity, however, is reduced (55%). Thus, tungsten alkylidene 12, emerged as the source of an efficient and uniquely stereoselective catalyst: as illustrated in entry 5 of Table 4, tetracyclic diene 6 was used to synthesize the desired pentacyclic 7 in 90% yield after purification and with a remarkable 97% Z selectivity (performed on 107 mg of the substrate).

What is especially striking is that under conditions (i.e., 0.1 M; entry 7, Table 4) that are usually used to accomplish the far simpler catalytic RCM processes of smaller rings (e.g., five- or six-membered rings), where competitive homocoupling is unlikely, cyclization through olefin metathesis surprisingly proceeded to furnish the desired macrocycle in 52% yield and 94% Z selectivity. It is noteworthy that when RCM of 6 was carried out at 0.1 M concentration, reduced pressure was no longer necessary; otherwise, 7 was obtained in a lower yield and with reduced selectivity (39% and 90% Z under 7.0 torr, entry 6, Table 4).

TABLE 4

Z-Selective Catalytic RCM Reactions for Stereoselective Synthesis of Nakadomarin A

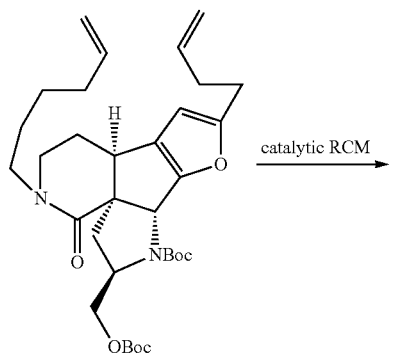

TABLE 4-continued

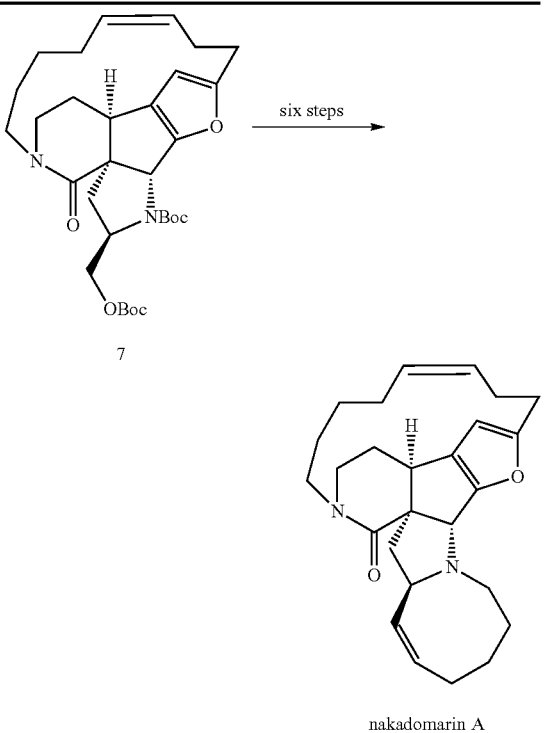

nakadomarin A

| Entry no. | Catalyst; Loading | Conditions; Concentration | Time | Conv. (%)§; Yield (%)§§ | Z:E† |
|---|---|---|---|---|---|
| 1 | 8b; 5.0 mol % | 7.0 torr; 5.0 mM | 2.0 h | 10; ND | ND |
| 2 | 9; 6.0 mol % | 7.0 torr; 5.0 mM | 2.0 h | 95; 71 | 69:31 |
| 3 | 10; 5.0 mol % | 7.0 torr; 5.0 mM | 2.0 h | 26; ND | ND |
| 4 | 11; 5.0 mol % | 7.0 torr; 5.0 mM | 2.0 h | 95; 69 | 55:45 |
| 5 | 12; 5.0 mol % | 7.0 torr; 5.0 mM | 2.0 h | 98; 90 | 97:3 |
| 6 | 12; 5.0 mol % | 7.0 torr; 0.1 M | 0.5 h | >98; 39 | 90:10 |
| 7 | 12; 5.0 mol % | ambient; 0.1 M | 2.0 h | 95; 52 | 94:6 |

The reactions were carried out in purified benzene under an atmosphere of nitrogen gas or under vacuum, as noted. The stereochemical identity of 7 was determined by X-ray crystallography. See below for details.
§Conversion and Z:E ratios measured by analysis of 400 MHz $^1$H NMR spectra of unpurified mixtures; the variance of values are estimated to be <±2%.
§§Yield of isolated product after purification; the variance of values are estimated to be <±5%.
Boc = tert-Butoxycarbamate; ND = not determined.

Since at higher concentration of diene 6, homocoupling increases, it is likely that the ethylene formed as the byproduct increased the availability of the highly reactive methylidene, which reacted with the acyclic disubstituted alkene of the homocoupled product to regenerate the monomeric RCM substrate; such a process increased the efficiency with which the targeted fifteen-membered ring is generated. Moreover, ethylene can react with the alkylidene derived from the homocoupled byproduct to regenerate the methylidene and inhibit its RCM, leading to the formation of a 30-membered ring structure. The above scenario, and the fact that Z selectivity remains high at 0.1 M concentration (94% Z), implies that the tungsten methylidene reacted with the acyclic alkene of the homocoupled triene preferably (vs. the cyclic alkene of 7). Without wishing to be bound by theory, the lower stereoselectivity observed under vacuum (90:10 vs. 94:6 Z:E, entries 6-7) may be because some macrocyclic product is obtained from reaction of a terminal alkylidene with the internal Z or E disubstituted olefin of a homocoupled molecule, formation of which is less prevalent at ambient pressure; such a process might well be less selective than that involving a terminal alkene of a monomeric diene. It is thus the accumulation of several subtle reactivity preferences that surprisingly culminate in the metathesis reaction being performed with complex 12 at 0.1 M concentration to occur efficiently and with high Z selectivity.

Late-Stage Z-Selective RCM and Total Synthesis of Nakadomarin a

The total synthesis of nakadomarin A might was accomplished through late-stage RCM; such an approach presents additional challenges and further underlines the reliability of the catalytic method. One possible route involves the more demanding RCM (vs. 6→7) of cyclooctene-containing 18 (Fürstner, A. & Langemann, K. Macrocycles by ring-closing metathesis. *Synthesis* 792-803 (1997)).

Figure 2:
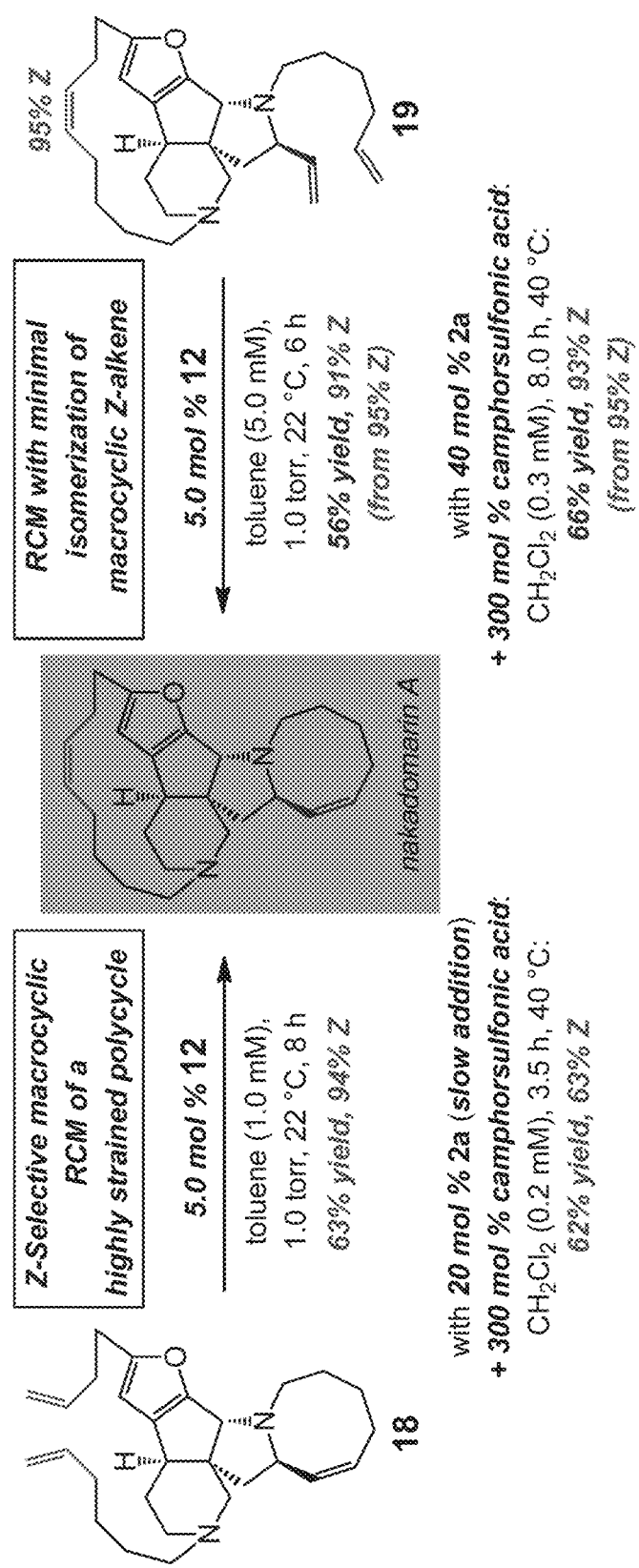
FIG. 2. Two different approaches towards total synthesis of potent anti-cancer and anti-microbial nakadomarin A realized through late-stage tungsten-catalyzed RCM of pentacyclic precursors 18 and 19 and comparison with optimal results delivered by Ru catalysts. The conversion of the relatively strained pentacyclic 18 can be performed with tungsten complex 12 to afford the natural product in 63% yield and 94% Z selectivity; this is in stark contrast to previous attempts, the best of which involves the use of 20 mol % of a Ru carbene added slowly to a highly dilute solution (0.2 mM) and that affords significantly lower stereoselectivity (63% Z). Similarly, conversion of macrocyclic 19 to the natural product proceeds with minimal loss of stereochemical purity and is substantially more efficient than the most efficient transformation possible with previously reported catalysts (5.0 mol % vs. 40 mol % loading).

The higher ring strain within the pentacyclic diene substrate retards the rate of ring closure and lowers the barrier to adventitious rupture of the macrocyclic alkene or, although less likely, of the eight-membered ring. Thus, past attempts at achieving transformation of 18 to nakadomarin A, as also shown in FIG. 2, have involved the less reactive ruthenium carbene 2a (vs. 2b-c) so that post-RCM isomerization of the macrocyclic alkene is minimized. Use of such a reluctant catalyst, however, translates to high catalyst loadings and elevated temperatures (20 mol %, 40° C.) as well as extremely dilute conditions (0.2 mM), since it is unlikely that homocoupled byproducts can be reverted back to the monomeric dienes or directly converted to the desired macrocycle. Additionally, the presence of substantial quantities (300 mol %) of camphorsulfonic acid, a strong Brønsted acid, is needed in the Ru-catalyzed RCM for achieving 63% Z selectivity (otherwise, slight excess of E alkene is obtained) (Fürstner, A. & Langemann, K. Macrocycles by ring-closing metathesis. *Synthesis* 792-803 (1997).

In stark contrast, treatment of 18 with 5.0 mol % 12 at room temperature for eight hours lead to the formation of nakadomarin A in 63% yield and 94% Z selectivity. Another difficult RCM process involves conversion of pentacyclic 19, synthesized from 7 (see below), to nakadomarin A (FIG. 2). The challenge in this approach relates to achieving the formation of the strained hexacyclic natural product without promoting isomerization of the macrocyclic Z alkene. As shown in FIG. 2, 19 was converted to nakadomarin A in 56% yield and 91% Z selectivity. Catalytic RCM of 19 was slower that that of 18; as a result, a higher solution concentration was needed (5.0 vs. 1.0 mM) for complete conversion (50% conv. at 1.0 mM), which likely resulted in a small loss of stereochemical purity of the macrocyclic alkene (91% vs. 95% Z). For comparison, the same transformation required 40 mol % of ruthenium complex 2a. Another notable aspect of W-catalyzed processes versus those promoted by 20-40 mol % of ruthenium complex 2a is the facility with which pure nakadomarin A is secured.

When 2a was used, the reaction mixture contains significant amounts of tricyclohexylphosphine oxide, which cannot be easily removed by chromatography. Accordingly, treatment with 1.0 N HCl to double-protonate the amine sites of the alkaloid and render it soluble in the aqueous phase, was required; subsequent separation of the phosphine oxide-containing organic layer and basification of the aqueous phase leads to regeneration of nakadomarin A, which was further purified by passing through silica gel (see the Supplementary Information for details). With tungsten complex 12, routine chromatography was all that is needed for obtaining a pure sample of nakadomarin A (94-95% Z) obtained from RCM (no acid treatment or aqueous extraction).

The ability of molybdenum and tungsten mono-pyrrolides to promote Z-selective macrocyclic ring formation substantially enhances the general utility of a catalytic method that is of great significance to the field of chemical synthesis. Successful applications to total syntheses of epothilones A and C as well as nakadomarin A, leading to a near doubling of the overall efficiency with which these notable biologically active natural products can be accessed, highlight the reliability of the protocols described above. Our findings illustrate that, in planning a multi-step route for the preparation of a complex molecule, molybdenum or tungsten alkylidenes can indeed be relied upon to deliver the desired outcome at the late stages of a total synthesis. We demonstrate that, as the result of the appropriate reactivity exhibited by the tungsten catalysts, which promote RCM without significant isomerization and allow for the recovery of adventitious homocoupled byproduct through reaction with ethylene, catalytic ring closures affording the two natural products can be performed under commonly used reaction concentrations. It is indeed the finely balanced activity profile furnished by the tungsten alkylidenes—a class of organometallic complexes rarely utilized in stereoselective catalytic olefin metathesis—that is one of the more noteworthy outcomes of our investigations.

The impact of catalytic Z-selective RCM is not limited to the macrocyclic structures examined in this study; there are numerous other total syntheses (Fürstner, A., Stelzer, F., Rumbo, A. & Krause, H. Total synthesis of the turrianes and evaluation of their DNA-cleaving properties. Che. Eur. J. 8, 1856-1871 (2002); She, J., Lampe, J. W., Polianski, A. B. & Watson, P. S. Examination of the olefin-olefin ring-closing metathesis to prepare latrunculin B. Tetrahedron Lett. 50, 298-301 (2009); Smith, B. J. & Sulikowski, G. A. Total synthesis of (±)-haliclonacyclamine C. *Angew. Chem. Int. Edn* 49, 1599-1602 (2010)) of complex and biologically active molecules that would significantly benefit from the strategies disclosed above. The ability to access macrocycles should be applicable to synthesis of a wide array of Z-alkenes that reside within ten- to eighteen-membered rings or even larger cyclic structures that are contain carbon-based as well as various heteroatom substituents (i.e., O-, N-, or S-based or a combination thereof). The advances detailed herein are expected to have a wide-ranging and immediate impact on the synthesis of a large number of macrocyclic molecules that are of interest for research in medicine, biology and materials research.

Preparation of Mo Monoalkoxide-Monopyrrolide Complexes

Chart 2. In Situ Generated Mo Monoalkoxide-Monopyrrolide Complexes.

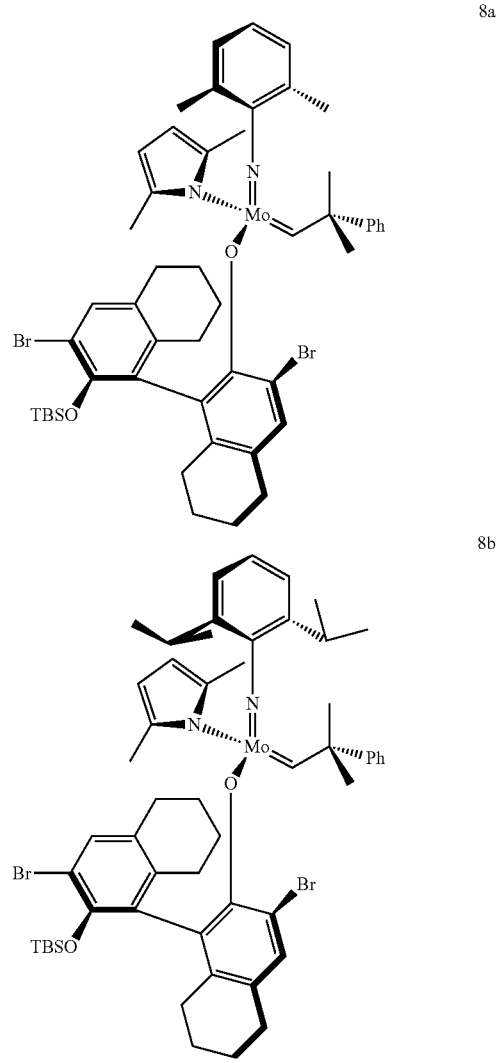

9

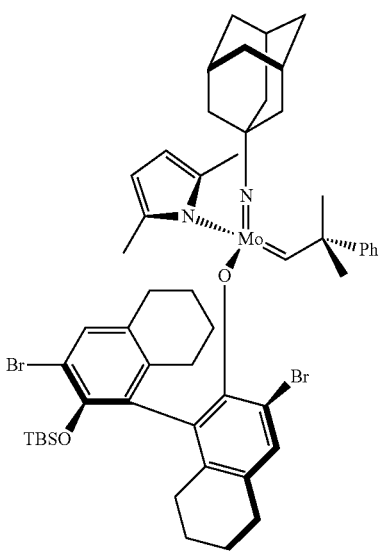

General Procedure:

In an N$_2$-filled glovebox, a 4-mL vial with magnetic stir bar was charged with Mo bispyrrolide complex C (8.6 mg, 15.2 μmol), chiral alcohol D (8.5 mg, 15.2 μmol), and C$_6$D$_6$ (760 up. The vial was tightly capped and the mixture was allowed to stir for 1 hour, at which time it was transferred to an NMR tube (screw cap NMR) by a pipette. The NMR tube was capped and sealed with Teflon tape. (Please note that for in situ-generated complexes, only the diagnostic signals of the α-carbon of the syn-alkylidenes are reported. $^1$H NMR (400 MHz, C$_6$D$_6$): δ 12.94 (1H, s), 12.74 (1H, s), 12.46 (1H, s), 12.38 (1H, s); dr=3:1 (entry 1, Table 1).

Representative Procedure for Preparation of Mo Complex 9 (Prepared and Used In Situ):

In an N$_2$-filled glovebox, a 4-mL vial containing a magnetic stir bar was charged with C (6.0 mg, 10.5 μmol), chiral alcohol D (6.0 mg, 10.5 μmol), and C$_6$H$_6$ (500 μL, 0.02 M), causing the mixture to turn orange. The vial was capped and the mixture was allowed to stir for 1 hour at 22° C., after which the catalyst solution was transferred to the reaction mixture by a syringe (dried at 65° C. under vacuum).

Synthesis of Macrocyclic Alkenes by Z-Selective Ring-Closing Metathesis (RCM)

General Procedure for Catalytic Ring-Closing Metathesis (RCM) Reactions with Mo or W-Based Catalyst:

In an N$_2$-filled glovebox, an oven-dried 35-mL vial with a magnetic stir bar was charged with the diene substrate. A stock solution of the complex in C$_6$H$_6$ (or toluene), prepared as mentioned above, was added to the solution of substrate in toluene (0.005 M) by syringe. The resulting mixture was allowed to stir for 2-3 min to allow complete initiation of the catalyst, and connected to a 7 torr vacuum generated from a rotavap pump by a vacuum adapter. The resulting solution was allowed to stir for the required period of time under vacuum; toluene was added a few times to maintain the appropriate concentration. The reaction was then quenched by exposure to air and concentrated in vacuo (percent conversion determined by 400 MHz $^1$H NMR analysis). Purification was performed by silica gel chromatography.

General Procedure for Catalytic Ring-Closing Metathesis (RCM) Reactions with Ru-Based Catalyst:

A flame-dried 50-mL round bottom flask with a magnetic stir bar, attached with a reflux condenser, was charged with a solution of diene substrate in dichloromethane or toluene. Ru-based carbene, was weighed and dissolved in the corresponding solvent. The solution of the catalyst was then added to the substrate by a syringe. The resulting mixture was allowed to stir at 40° C. for the required period of time. The reaction was then quenched by the addition of excess ethyl vinyl ether and allowed to stir for two hours. Then the mixture was concentrated in vacuo (percent conversion determined by 400 MHz $^1$H NMR analysis). Purification was performed by silica gel chromatography.

Representative Procedure for Preparation of the Ester Containing Diene Substrates:

A 100 mL round-bottom flask with a magnetic stir bar was charged with a carboxyl acid and an alcohol. The mixture was dissolved in dichloromethane and allowed to stir at room temperature; 1-ethyl-3-(3-dimethylaminopropyl) carbodiimide hydrochloride (1.1 equivalent) and 4-(N,N-dimethylamino)pyridine (0.1 equivalent) was added. After stirred for 12 hours, brine was added to quench the reaction. Layers partitioned and aqueous layer was washed twice with dichloromethane. Combined organic layers dried over sodium sulfate and concentrated in vacuo. The crude mixture was purified by silica gel chromatography.

Representative Procedure for Preparation of the Amide Containing Diene Substrates:

A 100 mL round-bottom flask with a magnetic stir bar was charged with a carboxyl acid and an amine. The mixture was dissolved in dichloromethane and allowed to stir at room temperature; Hunig's base (2 equivalent), 1-ethyl-3-(3-dimethylaminopropyl) carbodiimide hydrochloride (1.1 equivalent) and 1-hydroxy-benzotriazole (1.1 equivalent) was added. After stirred for 12 hours, brine was added to quench the reaction. Layers partitioned and aqueous layer was washed twice with dichloromethane. Combined organic layers dried over sodium sulfate and concentrated in vacuo. The unpurified mixture was purified by silica gel chromatography.

Z-Selective Macrocyclic Ring-Closing Metathesis (RCM)

But-3-en-1-yl dec-9-enoate (Precursor to Yuzu Lactone)

Following the aforementioned procedure, diene was prepared from dec-9-enoic acid and but-3-en-1-ol. The resulting yellow oil was purified by silica gel chromatography (30:1 hexanes: diethyl ether) to afford the desired product as a colorless oil. IR (neat): 3077 (m), 2927 (s), 2855 (s), 1737 (s), 1641 (m), 1458 (m), 1418 (m), 1353 (m), 1243 (s), 1170 (s), 1115 (m), 992 (s), 912 (s), 725 (m), 635 (m); $^1$H NMR (400 MHz, CDCl$_3$): δ 5.86-5.74 (2H, m), 5.14-4.91 (4H, m), 4.12 (2H, t, J=6.8 Hz), 2.38 (2H, ddt, J=13.6, 6.8, 1.4 Hz), 2.29 (2H, t, J=7.6 Hz), 2.06-2.01 (2H, m), 1.63-1.59 (2H, m), 1.39-1.26 (8H, m); $^{13}$C NMR (100 MHz, CDCl$_3$): δ 174.0, 139.3, 134.2, 117.3, 114.3, 63.4, 34.5, 33.9, 33.3, 29.2, 29.2, 29.1, 29.0, 25.1; HRMS (ESI$^+$) [M+H]$^+$ calcd for C$_{14}$H$_{25}$O$_2$: 225.1855. found: 225.1855.

N-(But-3-en-1-yl)undec-10-enamide (Precursor to 16)

Figure 3B:
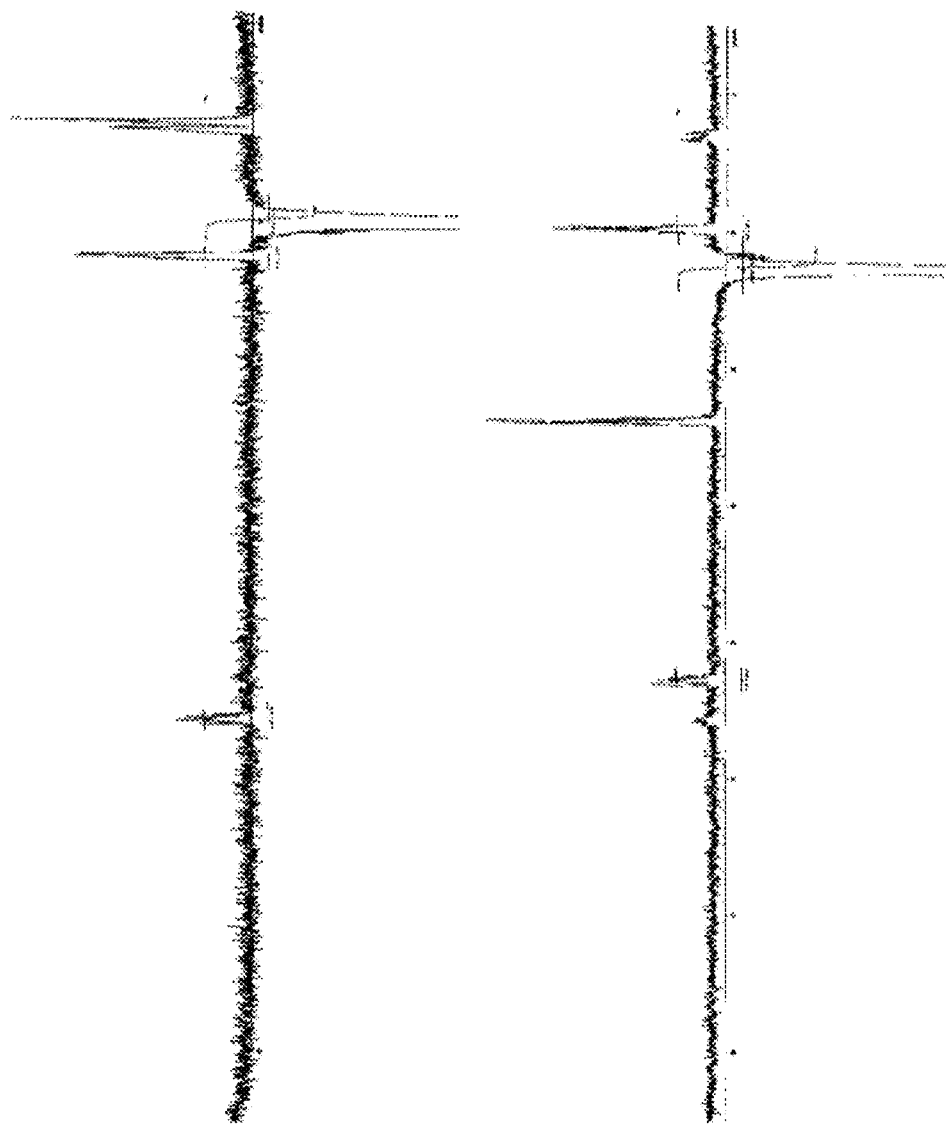
Figure 3B:
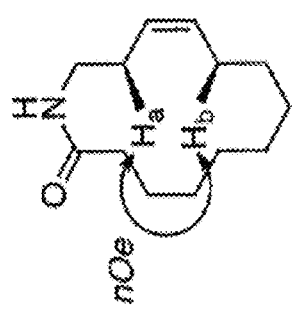

Following the aforementioned procedure, diene was prepared from undec-10-enoic acid and but-3-en-1-amine. The resulting yellow solid was purified by silica gel chromatography (5:1 hexanes: ethyl acetate) to afford the desired product as a white solid. IR (neat): 3296 (br, s), 3078 (m), 2925 (s), 2854 (s), 1640 (s), 1548 (s), 1437 (s), 1359 (m), 1271 (m), 1151 (m), 991 (s), 909 (s), 722 (m), 634 (m); $^1$H NMR (400 MHz, CDCl$_3$): δ 5.85-5.71 (2H, m), 5.45 (1H, s, br), 5.12-4.91 (4H, m), 3.33 (2H, dt, J=6.8, 6.4 Hz), 2.25 (2H, ddd, J=13.6, 6.8, 0.8 Hz), 2.14 (2H, t, J=7.6 Hz), 2.06-2.00 (2H, m), 1.65-1.57 (2H, m), 1.38-1.24 (10H, m); $^{13}$C NMR (100 MHz, CDCl$_3$): δ 173.2, 139.3, 135.5, 117.3, 114.3, 38.4, 37.0, 34.0, 33.9, 29.5, 29.4, 29.4, 29.2, 29.0, 25.9; HRMS (ESI$^+$) [M+H]$^+$ calcd for C$_{15}$H$_{28}$N$_1$O$_1$: 238.2171. found: 238.2167. For proof of stereochemistry, see FIG. 3.

N-(Undec-10-en-1-yl)hex-5-enamide (Precursor to 17)

Following the aforementioned procedure, diene was prepared from hex-5-enoic acid and undec-10-en-1-amine. The resulting yellow solid was purified by silica gel chromatography (5:1 hexanes: ethyl acetate) to afford the desired product as a white solid. IR (neat): 3291 (br, s), 3078 (m), 2924 (s), 2853 (s), 1640 (s), 1550 (s), 1438 (s), 1369 (m), 1257 (m), 991 (s), 908 (s), 722 (m), 634 (m); $^1$H NMR (400 MHz, CDCl$_3$): δ 5.86-5.73 (2H, m), 5.39 (1H, s, br), 5.05-4.91 (4H, m), 3.23 (2H, dt, J=13.2, 7.2, 6.6 Hz), 2.16 (2H, t, J=7.4 Hz), 2.12-2.00 (4H, m), 1.78-1.70 (2H, m), 1.50-1.46 (2H, m), 1.38-1.27 (12H, m); $^{13}$C NMR (100 MHz, CDCl$_3$): δ 172.8, 139.3, 138.1, 115.4, 114.3, 39.6, 36.2, 33.9, 33.3, 29.8, 29.6, 29.5, 29.4, 29.2, 29.1, 27.1, 24.9; HRMS (ESI$^+$) [M+H]$^+$ calcd for C$_{17}$H$_{32}$N$_1$O$_1$: 266.2484. found: 266.2491.

Dec-9-en-1-yl oct-7-enoate (Precursor to Ambrettolide)

Following the aforementioned procedure, diene was prepared from oct-7-enoic acid and dec-9-en-1-ol. The resulting yellow oil was purified by silica gel chromatography (50:1 hexanes: diethyl ether) to afford the desired product as a colorless oil. IR (neat): 3077 (m), 2926 (s), 2855 (s), 1736 (s), 1641 (m), 1462 (m), 1417 (m), 1351 (m), 1255 (s), 1168 (s), 1113 (m), 1076 (m), 993 (s), 909 (s), 734 (m), 632 (m); $^1$H NMR (400 MHz, CDCl$_3$): δ 5.86-5.75 (2H, m), 5.02-4.91 (4H, m), 4.05 (2H, t, J=6.8 Hz), 2.29 (2H, t, J=7.6 Hz), 2.08-2.01 (4H, m), 1.67-1.59 (4H, m), 1.42-1.27 (14H, m); $^{13}$C NMR (100 MHz, CDCl$_3$): δ 174.0, 139.2, 138.9, 114.5, 114.3, 64.5, 34.4, 33.9, 33.7, 29.5, 29.3, 29.1, 29.0, 28.8, 28.7, 28.6, 26.0, 25.0; HRMS (ESI$^+$) [M+H]$^+$ calcd for C$_{18}$H$_{33}$O$_2$: 281.2481. found: 281.2475.

(Z)-oxacyclohexadec-6-en-2-one (14)

Following the aforementioned procedure for Mo-catalyzed RCM, the resulting crude mixture was purified by silica gel chromatography (50:1 hexanes: diethyl ether) to afford the macrocyclic alkene 14 as a colorless oil (56% yield, Z:E=92:8). IR (neat): 3003 (m), 2927 (s), 2856 (s), 1735 (s), 1459 (m), 1349 (m), 1239 (m), 1206 (m), 1167 (m), 1144 (m), 1045 (m), 715 (m); $^1$H NMR (400 MHz, CDCl$_3$): δ 5.40-5.31 (2H, m), 4.15 (2H, dd, J=5.2, 5.2 Hz), 2.35 (2H, dd, J=6.6, 6.6 Hz), 2.13-2.01 (4H, m), 1.75-1.61 (4H, m), 1.44-1.27 (12H, m); $^{13}$C NMR (100 MHz, CDCl$_3$): δ 174.0, 131.2, 129.0, 64.5, 34.3, 28.0, 27.9, 27.4, 27.0, 26.9, 26.8, 26.6, 26.2, 25.6, 25.5; HRMS (ESI$^+$) [M+H]$^+$ calcd for C$_{15}$H$_{27}$O$_2$: 239.2011. found: 239.2010.

(Z)-oxacyclotridec-10-en-2-one (Yuzu Lactone)

Following the aforementioned procedure for W-catalyzed RCM, the resulting crude mixture was purified by silica gel chromatography (30:1 hexanes: diethyl ether) to afford the macrocyclic alkene as a colorless oil (46% yield, Z:E=73: 27). IR (neat): 2927 (s), 2857 (s), 1733 (s), 1448 (s), 1351 (m), 1254 (m), 1231 (m), 1185 (m), 1146 (m), 1011 (m), 968 (m), 864 (m), 783 (m); $^1$H NMR (400 MHz, CDCl$_3$): δ 5.60-5.31 (2H, m), 4.24 (1.5H, dd, J=5.2, 5.2 Hz), 4.15 (0.5H, dd, J=5.4, 5.4 Hz), 2.45-2.28 (4H, m), 2.10 (1.4H, dd, J=12.4, 5.4 Hz), 2.03 (0.6H, dd, J=11.6, 6.8 Hz), 1.71-1.62 (2H, m), 1.53-1.16 (8H, m); $^{13}$C NMR (100 MHz, CDCl$_3$): (Z isomer) δ 174.9, 132.4, 127.3, 64.3, 35.5, 29.9, 27.7, 27.4, 26.1, 26.0, 24.7, 23.7; HRMS (ESI$^+$) [M+H]$^+$ calcd for C$_{12}$H$_{21}$O$_2$: 197.1542. found: 197.1536.

(Z)-oxacyclotetradec-11-en-2-one (15)

Following the aforementioned procedure for W-catalyzed RCM, the resulting crude mixture was purified by silica gel chromatography (50:1 hexanes: diethyl ether) to afford the macrocyclic alkene 15 as a colorless oil (54% yield, Z:E=82: 18). IR (neat): 3006 (m), 2929 (s), 2859 (s), 1733 (s), 1457 (m), 1383 (m), 1284 (s), 1173 (m), 1142 (m), 1084 (m), 1053 (m), 1003 (m), 716 (m); $^1$H NMR (400 MHz, CDCl$_3$): δ 5.57-5.34 (2H, m), 4.23 (1.7H, dd, J=5.2, 5.2 Hz), 4.13 (0.3H, dd, J=5.6, 5.6 Hz), 2.43-2.33 (4H, m), 2.04-2.01 (2H, m), 1.65-1.62 (2H, m), 1.38-1.25 (10H, m); $^{13}$C NMR (100 MHz, CDCl$_3$): (Z isomer) δ 174.1, 132.5, 127.2, 63.9, 33.5, 27.9, 27.7, 26.3, 26.2, 25.7, 25.6, 25.4, 23.7; HRMS (ESI$^+$) [M+H]$^+$ calcd for C$_{13}$H$_{23}$O$_2$: 211.1698. found: 211.1699.

(Z)-azacyclotetradec-11-en-2-one (16)

Following the aforementioned procedure for Mo-catalyzed RCM, the resulting crude mixture was purified by silica gel chromatography (2:1 hexanes: ethyl acetate) to afford the macrocyclic alkene 16 as a white solid (50% yield, Z:E=95:5). IR (neat): 3285 (br, s), 3070 (m), 3003 (m), 2924 (s), 2861 (s), 1637 (s), 1549 (s), 1461 (m), 1436 (s), 1362 (m), 1264 (s), 1180 (m), 1024 (m), 723 (s), 598 (m); $^1$H NMR (400 MHz, CDCl$_3$): δ 5.65-5.57 (2H, m), 5.33-5.26 (1H, m), 3.42-3.38 (2H, m), 2.29-2.24 (2H, m), 2.20-2.16 (2H, m), 2.04-1.97 (2H, m), 1.71-1.65 (2H, m), 1.36-1.29 (10H, m); $^{13}$C NMR (100 MHz, CDCl$_3$): δ 172.9, 133.6, 127.2, 38.4, 35.2, 28.2, 28.1, 26.4, 26.0, 26.0, 25.3, 24.8, 24.4; HRMS (ESI$^+$) [M+H]$^+$ calcd for C$_{13}$H$_{24}$N$_1$O$_1$: 210.1858. found: 210.1860.

(Z)-5-propyl-1-oxa-4-azacyclopentadec-10-en-15-one (Epilachnene)

Following the aforementioned procedure for Mo-catalyzed RCM, the resulting crude mixture was purified by silica gel chromatography (17:2:1 hexanes: ethyl acetate: triethyl amine) to afford the macrocyclic alkene as a colorless oil (70% yield, Z:E=91:9). IR (neat): 2953 (s), 2927 (br, s), 2855 (s), 1736 (s), 1460 (s), 1382 (m), 1239 (m), 1207 (s), 1181 (s), 1050 (m), 1021 (m), 697 (m); $^1$H NMR (400 MHz, CDCl$_3$): δ 5.39 (1H, dd, J=14.4, 8.0 Hz), 5.30-5.24 (1H, m), 4.37-4.31 (1H, m), 3.96 (1H, ddd, J=11.2, 4.8, 2.4 Hz), 2.98 (1H, ddd, J=14.4, 8.0, 2.8 Hz), 2.77 (1H, ddd, J=14.0, 6.0, 2.0 Hz), 2.46-2.31 (3H, m), 2.22-2.00 (4H, m), 1.86-1.79 (1H, m), 1.74-1.66 (1H, m), 1.49-1.09 (11H, m), 0.90 (3H, t, J=6.8 Hz); $^{13}$C NMR (100 MHz, CDCl$_3$): δ 173.8, 131.5, 129.6, 63.5, 56.4, 45.8, 38.4, 34.3, 32.3, 29.0, 27.6, 25.9, 25.7, 24.3, 19.3, 14.6; HRMS (ESI$^+$) [M+H]$^+$ calcd for C$_{16}$H$_{30}$N$_1$O$_2$: 268.2276. found: 268.2264.

(Z)-azacyclohexadec-6-en-2-one (17)

Following the aforementioned procedure for Mo-catalyzed RCM, the resulting crude mixture was purified by silica gel chromatography (2:1 hexanes: ethyl acetate) to afford the macrocyclic alkene 17 as a white solid (69% yield, Z:E=93:7). IR (neat): 3295 (br, s), 3082 (m), 3003 (m), 2926 (s), 2854 (s), 1639 (s), 1554 (s), 1483 (s), 1356 (m), 1270 (m), 1154 (m), 705 (m); $^1$H NMR (400 MHz, CDCl$_3$): δ 5.45 (1H, br, s), 5.38-5.30 (2H, m), 3.34 (2H, dt, J=6.0, 5.6 Hz), 2.22-2.19 (2H, m), 2.12-2.01 (4H, m), 1.76-1.69 (2H, m), 1.52-1.46 (2H, m), 1.42-1.26 (12H, m); $^{13}$C NMR (100 MHz, CDCl$_3$): δ 173.0, 130.8, 129.1, 39.1, 36.5, 29.1, 27.8, 27.5, 27.4, 26.7, 26.5, 26.3, 26.0, 25.8, 25.7; HRMS (ESI$^+$) [M+H]$^+$ calcd for C$_{15}$H$_{28}$N$_1$O$_1$: 238.2169. found: 238.2171. The Z:E ratio of 17 is determined by NMR spectrum.

(Z)-oxacycloheptadec-8-en-2-one (Ambrettolide)

Following the aforementioned procedure for Mo-catalyzed RCM, the resulting crude mixture was purified by silica gel chromatography (50:1 hexanes: diethyl ether) to afford the macrocyclic alkene as a colorless oil (77% yield, Z:E=91:9). IR (neat): 3002 (m), 2926 (s), 2855 (s), 1736 (s), 1460 (s), 1385 (m), 1354 (m), 1256 (s), 1119 (m), 1070 (m), 968 (m), 842 (m), 720 (m), 696 (m); $^1$H NMR (400 MHz, CDCl$_3$): δ 5.32 (2H, t, J=4.6 Hz), 4.13 (2H, t, J=5.4 Hz), 2.32 (2H, t, J=6.4 Hz), 2.09-2.01 (4H, m), 1.67-1.59 (4H, m), 1.43-1.23 (14H, m); $^{13}$C NMR (100 MHz, CDCl$_3$): δ 174.1, 130.3, 130.2, 63.8, 34.7, 29.5, 28.9, 28.8, 28.6, 28.6, 28.5, 27.8, 27.1, 26.9, 25.5, 25.4; HRMS (ESI$^+$) [M+H]$^+$ calcd for C$_{16}$H$_{29}$O$_2$: 253.2168. found: 253.2170. The Z:E ratio of ambrettolide is determined by NMR spectrum.

Synthesis of Epothilone C (3S,6R,7S,8S)-(S,E)-2-Methyl-1-(2-methylthiazol-4-yl)hexa-1,5-dien-3-yl 3,7-bis((tert-butyldimethylsilyl)oxy)-4,4,6,8-tetramethyl-5-oxotridec-12-enoate A solution of (3S,6R,7S,8S)-(S,E)-2-methyl-1-(2-methylthiazol-4-yl)hexa-1,5-dien-3-yl 3-((tert-butyldimethylsilyl)oxy)-7-hydroxy-4,4,6,8-tetramethyl-5-oxotridec-12-enoate (Nicolaou, K. C.; He, Y.; Vourloumis, D.; Vallberg, H.; Roschangar, F.; Sarabia, F.; Ninkovic, S.; Yang, Z.; Trujillo, J. I. *J. Am. Chem. Soc.* 1997, 119, 7960-7973) in DCM at −50° C. was treated with 2,6-lutidine (1.82 mL, 15.7 mmol) followed by TBSOTf (3.60 mL, 15.7 mmol). The reaction mixture was stirred at the same temperature for 0.5 h, quenched by NH$_4$Cl (sat.) and extracted with DCM (3×). The combined organic layers were dried (MgSO$_4$), filtered and concentrated under reduced pressure. Purification by chromatography on SiO$_2$ (hexanes:ethyl ether=100:2 to 10:1) followed by the second chromatography (hexanes: diethyl ether=100:4 to 100:6 to 10:1) afforded 0.281 g (73%) of the title compound as a colorless oil.

The physical and spectral data were identical to those previously reported for the title compound. IR (neat) 3076 (w), 2954 (m), 2929 (m), 2886 (m), 2856 (m), 1736 (m), 1696 (m), 1641 (w), 1505 (w), 1471 (w), 1385 (s), 1292 (w), 1259 (m), 1177 (m), 1084 (m); $^1$H NMR (400 MHz, CDCl$_3$): 6.95 (1H, s), 6.90 (1H, s), 5.85-5.65 (1H, m), 5.30 (1H, t, J=6.8 Hz), 5.13-4.91 (4H, m), 4.34 (1H, dd, J=6.0, 3.6 Hz), 3.73 (1H, dd, J=6.8, 2.4 Hz), 3.15 (1H, dq, J=14.0, 6.8 Hz), 2.70 (3H, s), 2.56-2.43 (3H, m), 2.39 (1H, dd, J=16.8, 6.0 Hz), 2.07 (3H, d, J=4.0 Hz), 2.05-1.98 (2H, m), 1.50-1.29 (3H, m), 1.24 (3H, s), 1.19-1.06 (2H, m), 1.06-1.02 (6H, m), 0.89 (3H, d, J=6.8 Hz), 0.89 (9H, s), 0.87 (9H, s), 0.15 (3H, s), 0.05 (3H, s), 0.03 (6H, s); $^{13}$C NMR (100 MHz, CDCl$_3$): 217.9, 171.4, 164.8, 152.7, 139.2, 137.0, 133.6, 121.3, 118.0, 116.6, 114.6, 78.9, 77.8, 74.3, 53.6, 45.5, 40.5, 39.1, 37.8, 34.6, 30.7, 27.3, 26.4, 26.3, 23.4, 20.6, 19.5, 18.7, 18.4, 17.9, 15.6, 14.8, −3.7, −3.9, −4.3, −4.8; HRMS (ESI$^+$) [M+H]$^+$ calcd for C$_{40}$H$_{72}$NO$_5$SSi$_2$: 734.4670. found: 734.4652.

(4S,7R,8S,9S,16S,Z)-4,8-Bis((tert-butyldimethylsilyl)oxy)-5,5,7,9-tetramethyl-16-((E)-1-(2-methylthiazol-4-yl)prop-1-en-2-yl)oxacyclohexadec-13-ene-2,6-dione In an N$_2$-filled glovebox, diene (36.9 mg, 50.2 μmol, azeotroped with benzene 3×) in a 100-mL round bottom flask was dissolved in toluene (50 ml) and treated with a solution of the tungsten complex (0.126 mL, 0.02 M in benzene, 2.51 μmol). The flask was capped with a septum fitted with two 20-gauge needles and a vacuum adapter. The reaction mixture was exposed to vacuum (1 torr) and stirred at 22° C. for 3.5 h. Additional toluene was added during the reaction (after 2 h) to compensate for solvent loss due to vacuum. The reaction mixture was then quenched by the addition of ethyl ether and concentrated under reduced pressure. Purification on SiO$_2$ (hexanes:diethyl ether 20:1) afforded 30.3 mg (85%, Z:E=96:4) of the title compound as a colorless solid.

The physical and spectral data were identical to those previously reported for the title compound (Quintard, D.; Bertrand, P.; Bachmann, C.; Gesson, J. P. *Eur. J. Org. Chem.* 2004, 4762-4770; Schinzer, D.; Bauer, A.; Bohm, O. M.; Limberg, A.; Cordes, M. *Chem. Eur. J.* 1999, 5, 2483-2491). IR (neat): 2955 (m), 2924 (s), 2854 (m), 1743 (m), 1697 (w), 1462 (m), 1378 (w), 1254 (m), 1182 (w), 1158 (w), 1097 (w), 1066 (w), 1019 (w); $^1$H NMR (400 MHz, CDCl$_3$): 6.96 (1H, s), 6.57 (1H, s) [diagnostic E isomer signal: 6.53 (1H, s)], 5.53 (1H, dt, J=11.2, 4.2 Hz), 5.42-5.23 (1H, m), 5.02 (1H, d, J=10.2 Hz), 4.03 (1H, dd, J=10.2, 1.2 Hz), 3.89 (1H, d, J=8.4 Hz), 3.05-2.96 (1H, m), 2.82 (1H, dd, J=16.2, 1.2 Hz), 2.79-2.70 (2H, m), 2.70 (3H, s), 2.67 (1H, dd, J=16.2, 10.2 Hz), 2.40-2.33 (1H, m), 2.11 (3H, d, J=1.2 Hz), 2.10-2.06 (1H, m), 1.90-1.82 (1H, m), 1.62-1.46 (3H, m), 1.30-1.00 (1H, m), 1.19 (3H, s), 1.14 (3H, s), 1.09 (3H, d, J=6.6 Hz), 0.95 (3H, d, J=6.6 Hz), 0.94 (9H, s), 0.84 (9H, s), 0.12 (3H, s), 0.10 (3H, s), 0.07 (3H, s), −0.10 (3H, s); $^{13}$C NMR (100 MHz, CDCl$_3$): 215.2, 174.5, 164.8, 152.7, 138.8, 135.3, 123.0, 119.7, 116.3, 79.8, 79.5, 76.6, 53.6, 48.2, 39.1, 38.1, 32.0, 31.6, 29.4, 28.6, 26.6, 26.4, 25.2, 24.4, 19.4, 19.3, 18.9, 18.8, 17.9, 15.5, −3.0, −3.1, −3.5, −5.5. HRMS (ESI$^+$) [M+H]$^+$ calcd for C$_{38}$H$_{67}$NO$_5$SSi$_2$: 706.4357. found: 706.4348.

Epothilone C

A solution of (4S,7R,8S,9S,16S,Z)-4,8-Bis((tert-butyldimethylsilyl)oxy)-5,5,7,9-tetramethyl-16-((E)-1-(2-methylthiazol-4-yl)prop-1-en-2-yl)oxacyclohexadec-13-ene-2,6-dione (26.2 mg, 37.1 μmol) in THF (3.6 ml) in a plastic vial was treated with HF-pyridine complex (70% HF, 1.09 mL). The reaction mixture was stirred at 22° C. for 36 h, diluted with DCM and quenched by NaHCO$_3$ (sat.). The aqueous layer was extracted with DCM (2×). The combined organic layers were dried (MgSO$_4$) and concentrated under reduced pressure. Purification on SiO$_2$ (hexanes: diethyl ether 2:1 to 1:1) afforded 15.2 mg (81%, Z:E=95:5) of epothilone C as a colorless solid together with 2.6 mg of mono-desilylated product.

The physical and spectral data were identical to those previously reported for epothilone C (Nicolaou, K. C.; He, Y.; Vourloumis, D.; Vallberg, H.; Roschangar, F.; Sarabia, F.;

Ninkovic, S.; Yang, Z.; Trujillo, J. I. *J. Am. Chem. Soc.* 1997, 119, 7960-7973; Quintard, D.; Bertrand, P.; Bachmann, C.; Gesson, J. P. *Eur. J. Org. Chem.* 2004, 4762-4770; Schinzer, D.; Bauer, A.; Bohm, O. M.; Limberg, A.; Cordes, M. *Chem. Eur. J.* 1999, 5, 2483-2491). IR (neat): 3503 (br), 2928 (s), 1732 (s), 1686 (s), 1506 (m), 1465 (m), 1405 (m), 1376 (m), 1331 (m), 1293 (m), 1249 (m), 1184 (m), 1150 (m), 1090 (m), 1047 (m), 1006 (m); $^1$H NMR (400 MHz, CDCl$_3$): 6.96 (1H, s), 6.59 (1H, s) [diagnostic E isomer signal: 6.56 (1H, s)], 5.49-5.34 (2H, m), 5.29 (1H, dd, J=10.0, 2.0 Hz), 4.22 (1H, d, J=10.4 Hz), 3.74 (1H, dd, J=4.0, 2.0 Hz), 3.22 (1H, br s), 3.14 (1H, dq, J=13.6, 2.4 Hz), 3.02 (1H, br s), 2.74-2.64 (1H, m), 2.70 (3H, s), 2.50 (1H, dd, J=15.2, 11.2 Hz), 2.36 (1H, dd, J=15.2, 2.8 Hz), 2.30-2.15 (2H, m), 2.09 (3H, d, J=1.6 Hz), 2.06-1.98 (1H, m), 1.80-1.1.61 (2H, m), 1.41-1.30 (1H, m), 1.33 (s, 3H), 1.28-1.16 (2H, m), 1.18 (3H, d, J=6.8 Hz), 1.08 (3H, s), 1.00 (3H, d, J=7.2 Hz); $^{13}$C NMR (100 MHz, CDCl$_3$): 220.8, 170.6, 165.2, 152.2, 138.9, 133.6, 125.2, 119.6, 116.0, 78.6, 74.3, 72.5, 53.6, 41.9, 39.5, 38.8, 32.6, 32.0, 27.8, 27.7, 23.0, 19.3, 18.7, 16.1, 15.7, 13.7. HRMS (ESI$^+$) [M+H]$^+$ calcd for C$_{26}$H$_{40}$NO$_5$S: 478.2627. found: 478.2625.

Synthesis of Nakadomarin A.

The route depicted in Chart 3 was used to prepare the RCM substrate required for total synthesis of nakadamarin A.

Nitro Ester Nak-A.

To a solution of methyl ester Nak-A (Kyle, A. F., Dixon, D. J. Submitted to *Chem. Sci* for publication) (8.28 g, 38.83 mmol) and nitro alkene Nak-B (4.95 g, 25.62 mmol) (Jakubec, P.; Cockfield, D. M.; Dixon, D. J. *J. Am. Chem. Soc.* 2009, 131, 16632-16633) in toluene (82 mL) was added organocatalyst$^4$ (4.26 g, 7.77 mmol) in one portion. The reaction was stirred for 3 days at 30° C. before being concentrated in vacuo and purified by column chromatography (7:3 to 3:7 PE: diethyl ether). Nak-C was obtained as a yellow crystalline solid which was further purified by recrystallization from Et$_2$O cooled to −20° C. Further purification of the mother liquors were also required in a similar manner to give the desired compound as a colorless crystalline solid (7.50 g, 72% yield, single diastereoisomer). mp 90-92° C.; IR (neat): 2984 (w), 2935 (w), 1738 (s), 1690 (s), 1554 (s), 1413 (m), 1380 (m), 1278 (m), 1224 (m), 1038 (w), 923 (w), 819 (w); $^1$H NMR (400 MHz, CDCl$_3$): δ 7.30 (1H, d, J=0.8 Hz), 6.03 (1H, d, J=0.8 Hz), 5.78 (1H, ddt, J=17.0, 10.3, 6.6 Hz), 5.06-4.86 (4H, m), 4.07 (1H, dd, J=10.6, 3.8 Hz), 3.94-3.88 (1H, m), 3.82 (3H, s), 3.43-3.30 (2H, m), 2.67 (2H, t, J=7.5 Hz), 2.40-2.31 (2H, m), 2.21-2.17 (2H, m), 1.68 (3H, s), 1.43 (3H, s); $^{13}$C NMR (100 MHz, CDCl$_3$): δ 171.7, 167.3, 157.1, 140.3, 137.0, 119.6, 115.6, 105.0, 91.9, 76.8, 69.9, 63.5, 58.7, 53.4, 38.8, 33.4, 31.9, 27.5, 26.3, 23.3; HRMS (ESI$^+$) [M+Na]$^+$ calcd for C$_{20}$H$_{26}$N$_2$NaO$_7$: 429.1632. found: 429.1637; [α]$_D^{21}$+0.9 (c=0.67, CHCl$_3$).

Chart 3. Synthesis of (−)Nakadamarin A.

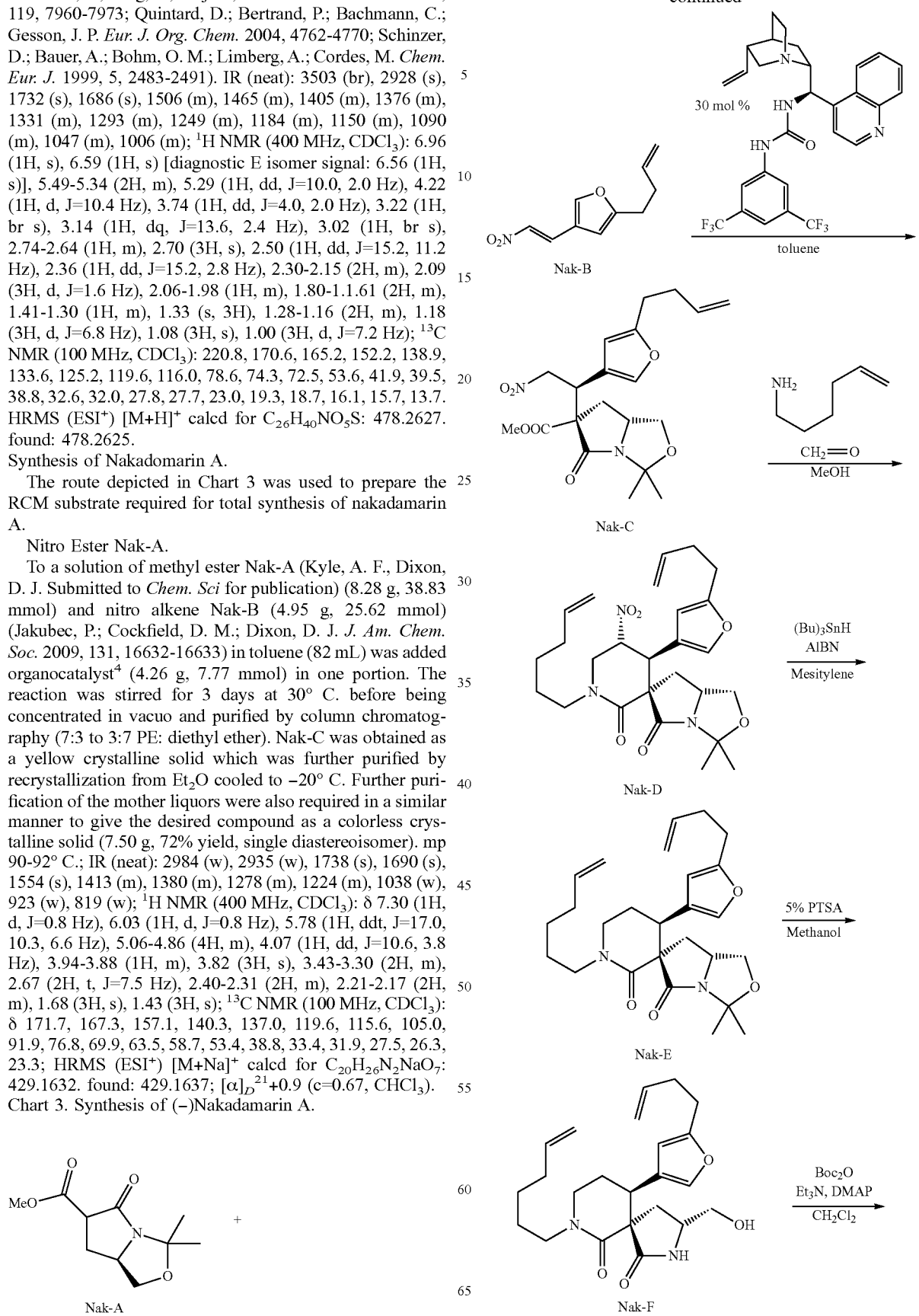

195
-continued
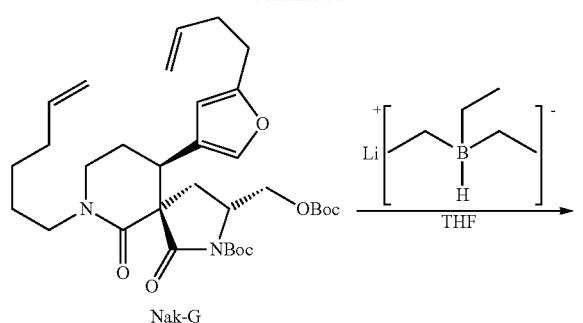
Nak-G
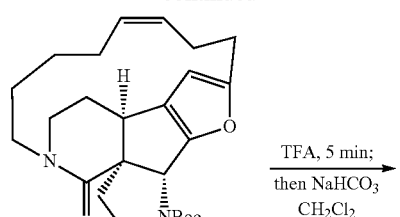
196
-continued
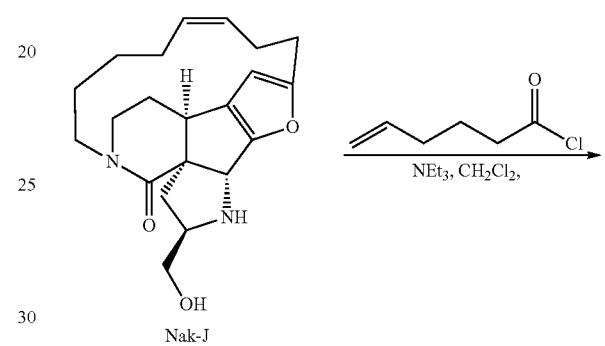
7
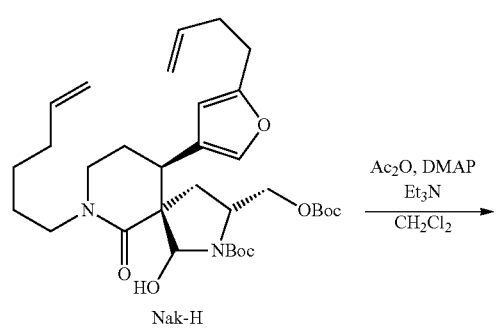
Nak-H
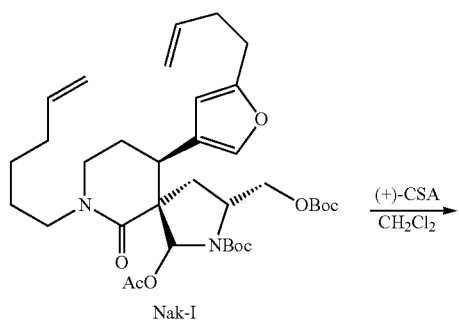
Nak-I
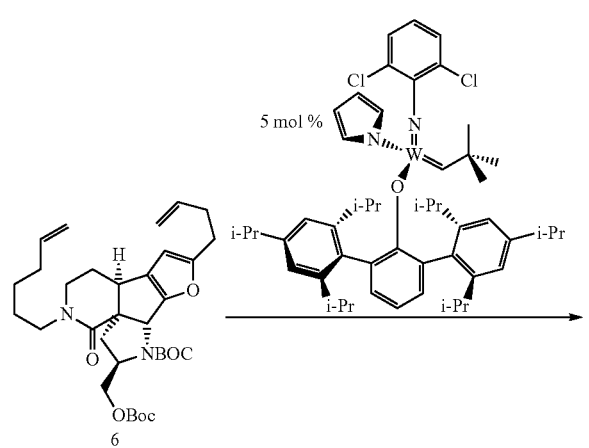
6
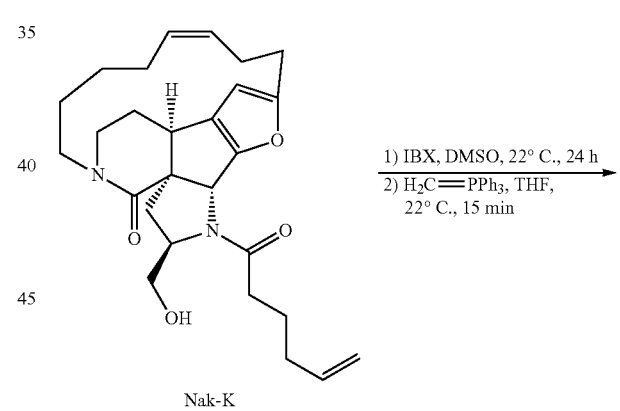
Nak-J
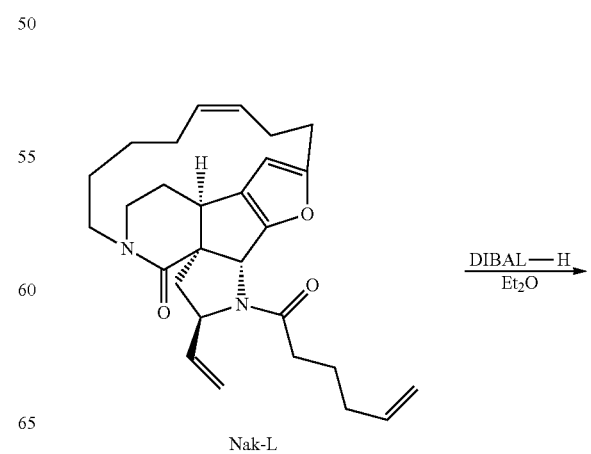
Nak-K
Nak-L

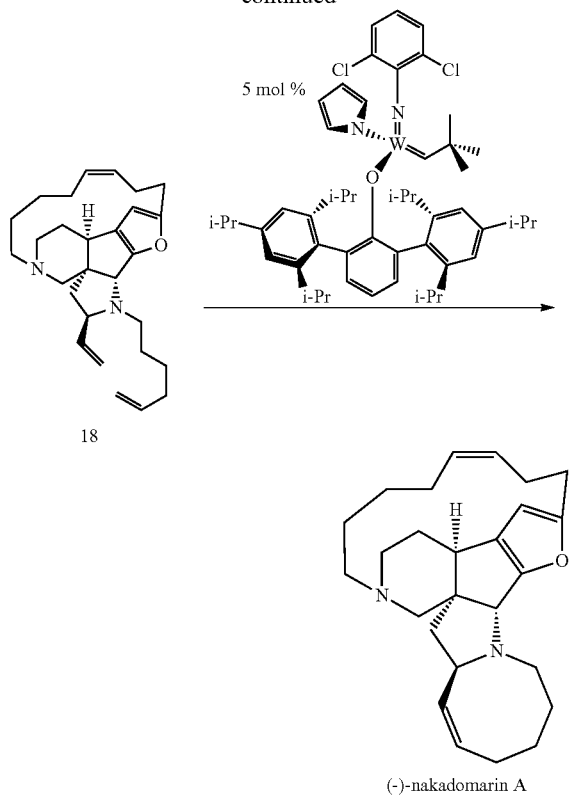

(-)-nakadomarin A

Nitro Lactam Nak-D.

A mixture of 6-bromo-1-hexene (11.40 g, 69.90 mmol) and NaN$_3$ (6.82 g, 104.9 mmol) in DMSO (82 mL) was stirred for two hours. The reaction mixture was poured into water (160 mL) and extracted with diethyl ether (50 mL×3). The combined organic layers were washed with brine and water was added. Triphenylphosphine (36.67 g, 139.8 mmol) was added over ten minutes. The reaction mixture was stirred for 16 hours and then extracted with 1M HCl for three times. The aqueous phase was extracted with diethyl ether and organic extracts were discarded. The aqueous layer was basified with solid sodium hydroxide while cooling in a ice-bath. Extracted with diethyl ether (50 mL×3) and combined organic layers were washed with brine, dried and concentrated. By concentrated with a stream of nitrogen, amine was prepared as a colorless oil. A solution of nitro ester Nak-C (5.30 g, 13.04 mmol), hex-5-en-1-amine (1.94 g, 19.56 mmol) and formaldehyde (37% solution in water) (1.59 g, 1.46 mL, 19.56 mmol) in MeOH (100 mL) was refluxed for 5 h. The solution was cooled to room temperature and concentrated in vacuo before being purified by column chromatography (1:1 to 2:8 PE: diethyl ether) to afford the nitro amide Nak-D as a brown oil (4.15 g, 66% yield). IR (neat): 2982 (w), 2933 (w), 2858 (w), 1693 (s), 1650 (s), 1556 (s), 1411 (m), 1350 (m), 1259 (m), 1134 (w), 916 (w), 821 (w); $^1$H NMR (400 MHz, CDCl$_3$): δ 7.28 (1H, d, J=1.0 Hz), 6.06 (1H, d, J=1.0 Hz), 5.89 (1H, ddd, J=12.0, 9.5, 6.5 Hz), 5.84-5.72 (2H, m), 5.06-4.93 (4H, m), 4.01 (1H, dd, J=12.0, 6.4 Hz), 3.90 (1H, dd, J=8.0, 5.4 Hz), 3.79 (1H, dd, J=12.1, 9.1 Hz), 3.57-3.47 (3H, m), 3.46-3.34 (2H, m), 3.01 (1H, dd, J=13.3, 7.2 Hz), 2.66 (2H, t, J=7.5 Hz), 2.38-2.30 (2H, m), 2.13-2.05 (2H, m), 1.90 (1H, dd, J=13.1, 7.3 Hz), 1.70-1.56 (2H, m), 1.58 (3H, s), 1.47-1.37 (2H, m), 1.35 (3H, s); $^{13}$C NMR (100 MHz, CDCl$_3$): δ 168.4, 167.2, 157.2, 139.9, 138.3, 137.0, 118.8, 115.7, 114.9, 104.9, 91.6, 81.5, 69.7, 62.8, 58.7, 49.4, 48.3, 42.9, 33.3, 31.9, 31.6, 27.6, 26.3, 26.2, 25.8, 23.3; HRMS (ESI$^+$) [M+Na]$^+$ calcd for C$_{26}$H$_{35}$N$_3$NaO$_6$: 508.2418. found: 508.2412; [α]$_D^{21}$ +97.3 (c=0.640, CHCl$_3$).

Spiro-Lactam Nak-E Nitro Amide Nak-D.

(5.60 g, 11.53 mmol) was dissolved in mesitylene (160 mL). To this was added AIBN (0.38 g, 2.31 mmol) and tributyltin hydride (16.78 g, 15.28 mL, 57.65 mmol) and the mixture was degassed by repeated cycles of vacuum/nitrogen purge. The reaction was then heated rapidly to reflux in a pre-heated oil bath for 2.5 h before being cooled to room temperature. The reaction mixture was loaded directly onto silica and the mesitylene and excess tin compounds eluted with petroleum ether before ramping the solvent system (9:1 to 1:8 PE: diethyl ether), to obtain the spiro-lactam Nak-E as a pale yellow oil (2.95 g, 58% yield). IR (neat): 2982 (w), 2932 (w), 2863 (w), 1691 (s), 1638 (s), 1548 (w), 1491 (w), 1442 (w), 1406 (m), 1261 (w), 914 (w); $^1$H NMR (400 MHz, CDCl$_3$): δ 7.24 (1H, br. s), 6.05 (1H, br. s), 5.87-5.74 (2H, m), 5.08-4.91 (4H, m), 3.88 (1H, dd, J=7.7, 5.2 Hz), 3.54-3.31 (6H, m), 2.99 (1H, dd, J=12.8, 7.5 Hz), 2.95-2.87 (2H, m), 2.70-2.63 (2H, m), 2.40-2.32 (2H, m), 2.14-2.03 (2H, m), 1.84 (1H, dd, J=12.6, 7.1 Hz), 1.78-1.71 (1H, m), 1.67-1.53 (5H, m), 1.48-1.36 (2H, m), 1.29 (3H, s); $^{13}$C NMR (100 MHz, CDCl$_3$): δ 169.5, 168.6, 156.2, 138.6, 137.8, 137.2, 124.7, 115.4, 114.6, 105.6, 91.2, 69.9, 63.3, 58.6, 48.3, 47.4, 40.0, 33.4, 33.0, 32.0, 27.6, 26.3, 26.3, 26.0, 25.3, 23.4; HRMS (ESI$^+$) [M+Na]$^+$ calcd for C$_{26}$H$_{36}$N$_2$NaO$_4$: 463.2567. found: 463.2578; [α]$_D^{21}$ +94.1 (c=2.30, CHCl$_3$).

Alcohol Nak-F.

p-Toluenesulfonic acid (PTSA) (0.063 g, 0.33 mmol) was added to a solution of spiro-lactam Nak-E (2.91 g, 6.61 mmol) in methanol (150 mL) and the solution heated at reflux for 4 h. A further addition of PTSA (0.010 g, 0.05 mmol) was required after this time. After heating at reflux for a further 1 h, the solution was cooled to room temperature, concentrated and purified by column chromatography (ethyl acetate to 98:2 ethyl acetate:methanol) to yield Nak-F as a colorless oil (2.11 g, 80% yield). IR (neat): 3406 (m), 3270 (m), 2929 (m), 2858 (m), 1695 (s), 1618 (s), 1494 (w), 1435 (m), 1348 (w), 1272 (m), 1125 (w), 1062 (w), 912 (m), 734 (w); $^1$H NMR (400 MHz, CDCl$_3$): δ 7.22 (1H, d, J=0.8 Hz), 6.28 (1H, br. s), 6.06 (1H, d, J=0.8 Hz), 5.87-5.73 (2H, m), 5.08-4.91 (4H, m), 4.47 (1H, t, J=5.4 Hz), 3.59 (2H, t, J=4.9 Hz), 3.52-3.37 (3H, m), 3.37-3.22 (2H, m), 3.15-3.02 (1H, m), 2.84 (1H, dd, J=13.4, 2.8 Hz), 2.71-2.60 (3H, m), 2.41-2.32 (2H, m), 2.16-2.03 (3H, m), 1.84-1.72 (1H, m), 1.67-1.54 (2H, m), 1.45-1.35 (2H, m); $^{13}$C NMR (100 MHz, CDCl$_3$): δ 175.6, 170.5, 156.2, 138.5, 138.1, 137.4, 124.4, 115.3, 114.7, 105.7, 65.7, 55.6, 52.9, 48.5, 47.6, 40.4, 34.0, 33.4, 32.0, 27.6, 26.3, 26.0, 25.3; HRMS (ESI$^+$) [M+Na]$^+$ calcd for C$_{23}$H$_{32}$N$_2$NaO$_4$: 423.2254. found: 423.2258; [α]$_D^{21}$ +112.0 (c=0.700, CHCl$_3$).

Bis-Boc lactam Nak-G.

To a solution of Nak-F (1.75 g, 4.37 mmol) in CH$_2$Cl$_2$ (75 mL) was added DMAP (0.053 g, 0.43 mmol) and triethylamine (2.21 g, 3.04 mL, 21.86 mmol) before the portionwise addition of di-tert-butyl dicarbonate (4.77 g, 21.86 mmol). The solution was stirred for 15 h at room temperature. The dark yellow solution formed was concentrated and purified by column chromatography (4:1 to 3:7 PE: ethyl acetate), to give the bis-Boc lactam Nak-G as a colorless oil (2.55 g, 97% yield). IR (neat): 2979 (w), 2934 (w), 1781 (m), 1744 (s), 1640 (s), 1491 (w), 1455 (w), 1369 (m), 1278 (s), 1254 (s), 1158 (s), 914 (w), 856 (w); $^1$H NMR (400 MHz, CDCl$_3$):

δ 7.17 (1H, br. s), 5.93 (1H, br. s), 5.85-5.73 (2H, m), 5.06-4.92 (4H, m), 4.44 (1H, dd, J=10.0, 4.4 Hz), 4.19 (1H, dd, J=9.9, 8.6 Hz), 3.82 (1H, "tt", J=8.9, 4.5 Hz), 3.52-3.40 (3H, m), 3.29 (1H, ddd, J=13.1, 8.7, 6.4 Hz), 3.06-2.92 (1H, m), 2.84 (1H, dd, J=13.4, 2.8 Hz), 2.73 (1H, dd, J=13.8, 4.7 Hz), 2.65-2.58 (2H, m), 2.37-2.29 (2H, m), 2.13-2.03 (3H, m), 1.79-1.71 (1H, m), 1.66-1.52 (2H, m), 1.48 (9H, s), 1.46 (9H, s), 1.45-1.36 (2H, m); $^{13}$C NMR (100 MHz, CDCl$_3$): δ 172.8, 167.7, 156.7, 153.1, 149.4, 138.5, 138.3, 137.2, 123.9, 115.4, 114.7, 105.1, 83.3, 82.1, 68.2, 57.0, 53.4, 48.3, 47.4, 41.6, 33.5, 32.0, 31.3, 27.9, 27.8, 27.6, 26.4, 26.1, 25.2; HRMS (ESI$^+$) [M+Na]$^+$ calcd for C$_{33}$H$_{48}$N$_2$NaO$_8$: 623.3303. found: 623.3312; $[\alpha]_D^{21}$+120.0 (c=0.700, CHCl$_3$).

Aminol Nak-H.

To a solution of Nak-G (2.50 g, 4.16 mmol) in THF (105 mL) was added dropwise lithium triethylborohydride (11.20 mL, 11.20 mmol, 1 M solution in THF) at −78° C. and the solution stirred at this temperature for 3 h before being quenched with sat. aq. NH$_4$Cl solution (100 mL). The reaction was allowed to warm to room temperature over 1 h and then diluted with diethyl ether (150 mL). The aqueous layer was extracted and the organics dried (Na$_2$SO$_4$) and concentrated. The crude oil was purified by column chromatography (4:1 to 7:3 PE: ethyl acetate) to yield Nak-H as a colorless oil (2.04 g, 81% yield): The $^1$H-NMR spectrum of the title compound suffers from considerable broadening due to rotamers when run in CDCl$_3$ at 298 K. Attempts to improve this spectrum by collecting the data in toluene-d$_8$ at 363 K resulted in decomposition of the compound. The compound was therefore used in the next step without full characterization.

Diene 6.

To a solution of Nak-H (300 mg, 0.498 mmol) in CH$_2$Cl$_2$ (10 ml) was added triethylamine (0.28 g, 0.39 mL, 2.79 mmol), acetic anhydride (0.29 g, 0.26 mL, 2.79 mmol) and DMAP (3 mg). The reaction was stirred at room temperature for 6 h followed by the addition of a second portion of DMAP (20 mg). The reaction was stirred for 15 h, before being filtered through a silica pad, which was washed with diethyl ether. The filtrate was concentrated and the crude residue was dissolved in CH$_2$Cl$_2$ (10 ml), (+)-camphorsulfonic acid (21 mg, 0.09 mmol) was added and the reaction stirred at room temperature for 1 h. The mixture was concentrated in vacuo and the crude product was purified by column chromatography (9:1 to 6:4 PE: ethyl acetate), to give diene 6 as a colorless oil (268 mg, 92% yield). The $^1$H NMR spectrum of the title compound suffers from broadening due to rotamers when run in CDCl$_3$ at 298 K. The major rotamer has been assigned. IR (neat): 2978 (m), 2931 (m), 1743 (s), 1699 (s), 1640 (s), 1483 (w), 1454 (w), 1380 (s), 1369 (s), 1279 (s), 1255 (s), 1162 (s), 1099 (w), 913 (w), 863 (w); $^1$H NMR (400 MHz, CDCl$_3$): δ 5.91-5.68 (3H, m), 5.08-4.90 (5H, m), 4.72 (1H, dd, J=9.6, 3.5 Hz), 4.35 (1H, "t", J=9.5 Hz), 4.13-4.04 (1H, m), 3.37 (2H, t, J=7.3 Hz), 3.27-3.12 (2H, m), 3.02 (1H, t, J=6.1 Hz), 2.69 (2H, t, J=7.6 Hz), 2.59 (1H, dd, J=13.4, 4.5 Hz), 2.38 (2H, "q", J=7.1 Hz), 2.16-1.99 (4H, m), 1.71-1.60 (1H, m), 1.56-1.43 (20H, m), 1.40-1.30 (2H, m); $^{13}$C NMR (100 MHz, CDCl$_3$): δ 172.2, 161.1, 155.0, 153.9, 153.2, 138.4, 137.3, 128.2, 115.4, 114.8, 102.2, 81.7, 80.0, 67.0, 65.9, 63.9, 56.8, 48.0, 45.1, 43.5, 40.5, 33.4, 32.0, 29.2, 28.5, 28.3, 27.8, 26.7, 26.0; HRMS (ESI$^+$) [M+Na]$^+$ calcd for C$_{33}$H$_{48}$N$_2$NaO$_7$: 607.3354. found: 607.3349; $[\alpha]D^{21}$+28.9 (c=3.40, CHCl$_3$).

Boc Pentacycle 7.

In an N$_2$-filled glovebox, diene (107 mg, 0.186 mmol) in a 100 mL round bottom flask was dissolved in toluene (37 mL) and treated with W complex 12 (9.1 mg, 9.3 μmol, 0.05 equivalent). Then allowed to stir for three minutes, the flask was attached to a 7 torr vacuum system by a vacuum adapter. After stirred at 22° C. for two hours, the reaction mixture was brought outside of the glovebox and exposed to air. The crude mixture was purified by silica gel chromatography (2:1 to 1:2 hexanes: diethyl ether) to afford the macrocyclic alkene 7 as a white solid (94.1 mg, 0.168 mmol, 90% yield, Z:E=97:3). IR (neat): 2978 (s), 2938 (s), 2868 (m), 1742 (s), 1694 (s), 1634 (s), 1488 (m), 1453 (m), 1393 (s), 1367 (s), 1351 (s), 1277 (s), 1254 (s), 1155 (s), 1106 (s), 953 (m), 859 (m), 792 (m), 761 (m), 732 (m); $^1$H NMR (400 MHz, CDCl$_3$): δ 5.82 (1H, s), 5.44 (1H, dd, J=12.2, 5.6 Hz), 5.26 (1H, dd, J=12.0, 5.6 Hz), 4.81-4.72 (2H, m), 4.46 (1H, dt, J=8.8, 2.4 Hz), 4.28-4.25 (1H, m), 4.17 (1H, dd, J=6.6, 5.4 Hz), 3.27 (1H, s), 3.14 (1H, dt, J=7.6, 2.4 Hz), 2.90 (1H, dd, J=8.0, 2.8 Hz), 2.75 (1H, t, J=8.4 Hz), 2.59-2.41 (4H, m), 2.19 (2H, dd, J=8.8, 4.0 Hz), 2.10 (1H, d, J=8.4 Hz), 1.93-1.88 (2H, m), 1.62-1.59 (1H, m), 1.53-1.40 (19H, m), 1.28-1.23 (1H, m), 0.99-0.96 (1H, m), 0.03--0.05 (1H, m); $^{13}$C NMR (100 MHz, CDCl$_3$): δ 171.6, 159.9, 157.0, 154.2, 153.4, 130.5, 128.7, 128.5, 103.0, 82.1, 80.2, 69.0, 67.7, 67.6, 58.3, 46.8, 43.5, 39.5, 36.0, 28.8, 28.3, 27.9, 27.6, 26.6, 26.3, 25.6, 22.3; HRMS (ESI$^+$) [M+H]$^+$ calcd for C$_{31}$H$_{45}$N$_2$O$_7$: 557.3227. found: 557.3218; $[\alpha]_D^{20}$ −63.17 (c=0.640, CHCl$_3$).

Aminol Nak-J.

In a 35-mL vial with a magnetic bar, the macrocyclic alkene (130 mg, 0.233 mmol) was treated with neat trifluoroacetic acid (1.0 mL, excess), and allowed to stir for five minutes at 22° C. Then the acid was removed by vacuum. The resulting yellow oil was treated with sat. aq. NaHCO$_3$ (6 mL) and dichloromethane (6 mL). Layers partitioned and the aqueous layer was extracted with a 4:1 mixture of chloroform/isopropanol (6 mL×3). Combined organic layers was dried and concentrated. The crude mixture was purified by silica gel chromatography (9:1 dichloromethane: methanol) to afford the aminol Nak-J as a white solid (80 mg, 0.225 mmol, 95% yield, Z:E=95:5). IR (neat): 3368 (br, s), 3004 (m), 2925 (s), 2856 (s), 1676 (s), 1604 (s), 1494 (m), 1443 (s), 1361 (m), 1201 (s), 1181 (s), 1131 (s), 1035 (m), 840 (m), 800 (m), 722 (m); $^1$H NMR (400 MHz, CDCl$_3$): δ 5.82 (1H, s), 5.46 (1H, dd, J=14.8, 8.8 Hz), 5.26 (1H, dd, J=16.0, 8.8 Hz), 4.80-4.37 (4H, m), 3.82-3.69 (3H, m), 3.29 (1H, s), 3.08 (1H, dt, J=12.4, 3.6 Hz), 2.91 (1H, dd, J=12.0, 4.0 Hz), 2.82-2.78 (1H, m), 2.62-2.46 (3H, m), 2.32 (1H, dd, J=12.4, 9.6 Hz), 2.16-2.09 (2H, m), 2.00-1.88 (3H, m), 1.64-1.46 (2H, m), 1.30-1.25 (1H, m), 1.05-0.99 (1H, m), 0.06--0.05 (1H, m); $^{13}$C NMR (100 MHz, CDCl$_3$): δ 173.6, 161.7, 155.8, 130.4, 129.6, 128.7, 103.4, 71.7, 69.0, 63.7, 63.0, 46.8, 43.4, 41.1, 37.1, 28.8, 27.6, 26.4, 26.0, 25.3, 23.2; HRMS (ESI$^+$) [M+H]$^+$ calcd for C$_{21}$H$_{29}$N$_2$O$_3$: 357.2178. found: 357.2171; $[\alpha]_D^{20}$ −78.41 (c=0.700, CHCl$_3$).

Alcohol Nak-K.

In a 4-mL vial with a magnetic bar, catalytic amount of DMF (1 drop) was added to 5-hexenoic acid (40 mg, 0.351 mmol) and cooled to 0° C.; oxalyl chloride (53 mg, 0.421 mmol) was added carefully and then stirred for fifteen minutes at 22° C. 1 mL diethyl ether was added and the mixture was filtered through a cotton plug and concentrated with a stream of nitrogen to deliver crude 5-hexenyl chloride. In another 50-mL round bottom flask, aminol (120 mg, 0.337 mmol) and triethyl amine (170 mg, 1.685 mmol) were dissolved in dichloromethane (15 mL) and cooled to −20° C. A pre-cooled solution of 5-hexenyl chloride in dichloromethane was added by syringe. The reaction mixture was allowed to slowly warm to 22° C. in thirty minutes and allowed to stir for three hours. The crude mixture was concentrated by vacuum to yield a yellow oil, which was purified by silica gel chromatography (1:1 hexanes:ethyl acetate to 9:1 ethyl acetate: methanol) to afford the primary alcohol Nak-K as a white solid (84 mg, 0.283 mmol, 84% yield, Z:E=95:5). IR (neat): 3350 (br, m), 2923 (s), 2854 (s), 1628 (s), 1549 (m), 1490 (m), 1440 (s), 1353 (m), 1326 (m), 1218 (m), 1203 (m), 1099 (m), 1080 (m), 911 (m), 805 (m), 750 (m); $^1$H NMR (400 MHz, CDCl$_3$): δ 6.04 (1H, d, J=9.2 Hz), 5.87 (1H, s), 5.84-5.76 (1H, m), 5.46 (1H, dd, J=18.4, 8.8 Hz), 5.26 (1H, dd, J=18.0, 8.0 Hz), 5.07-4.95 (2H, m), 4.91 (1H, s), 4.45 (1H, dt, J=12.8, 4.0 Hz), 4.26-4.19 (1H, m), 3.75-3.62 (2H, m), 3.32 (1H, t, J=2.8 Hz), 3.11 (1H, dt, J=12.0, 4.0 Hz), 2.93 (1H, dd, J=12.4, 4.8 Hz), 2.78-2.67 (1H, m), 2.60-2.39 (5H, m), 2.30-2.11 (5H, m), 2.02-1.89 (3H, m), 1.81-1.43 (4H, m), 1.33-1.22 (1H, m), 1.05-0.95 (1H, m), −0.01−−0.12 (1H, m); $^{13}$C NMR (100 MHz, CDCl$_3$): δ 174.8, 171.2, 161.1, 155.4, 138.2, 130.5, 130.5, 128.5, 115.2, 103.6, 68.9, 68.2, 66.6, 66.4, 46.8, 43.2, 39.2, 35.1, 34.5, 33.4, 28.7, 27.5, 26.5, 26.3, 25.4, 24.3, 22.3; HRMS (ESI$^+$) [M+H]$^+$ calcd for C$_{27}$H$_{37}$N$_2$O$_4$: 453.2753. found: 453.2739; [α]$_D^{20}$ −48.67 (c=0.260, CHCl$_3$).

Triene Nak-L.

In a 50-mL round bottom flask with a magnetic bar, 2-iodoxybenzoic acid (413 mg, 1.473 mmol) was added to a solution of alcohol (148 mg, 0.327 mmol) in 20 mL DMSO. The reaction mixture was allowed to stir for 24 hours at 22° C. Then the mixture was poured into sat. aq. NaHCO$_3$ solution (60 mL) and extracted with diethyl ether (4×60 mL). The combined organic layers were washed with water (30 mL), dried and concentrated to give the crude aldehyde as a yellow oil, which was used directly for the next step without purification. In another 50-mL round bottom flask, KOt-Bu (172 mg, 1.537 mmol) was added to MePPh$_3$Br (700 mg, 1.962 mmol) in toluene (10 mL). The resulting mixture was placed in a sonication bath until a homogenous bright yellow solution formed. The reaction mixture was stirred at 22° C. for one and a half hour. The crude aldehyde was dissolved in THF (10 mL) and the solution was rapidly added to the freshly prepared Ylide solution. After 15 minutes, the reaction mixture was concentrated; 30 mL water and 30 mL ethyl acetate was added. Layers partitioned and aqueous layer was washed three times with ethyl acetate (30 mL). Combined organic layers was dried and concentrated by vacuum to yield a colorless oil, which was purified by silica gel chromatography (3:2 to 2:3 hexanes: ethyl acetate) to afford the triene Nak-L as a white foam (122 mg, 0.272 mmol, 83% yield, Z:E=95:5). IR (neat): 2934 (s), 2863 (s), 1633 (s), 1488 (m), 1440 (s), 1406 (s), 1355 (s), 1287 (m), 1206 (m), 1168 (m), 992 (m), 953 (m), 912 (m), 732 (m); $^1$H NMR (400 MHz, CDCl$_3$): δ 5.96-5.68 (3H, m), 5.48 (1H, dd, J=18.0, 9.2 Hz), 5.28 (1H, dd, J=16.4, 8.8 Hz), 5.20-4.89 (5H, m), 4.67-4.44 (2H, m), 3.34 (1H, s), 3.21-3.12 (1H, m), 3.00-2.69 (2H, m), 2.59-2.32 (5H, m), 2.20-1.92 (7H, m), 1.79-1.43 (5H, m), 1.34-1.18 (1H, m), 1.06-0.98 (1H, m), 0.04−−0.08 (1H, m); $^{13}$C NMR (100 MHz, CDCl$_3$): rotamers: δ 173.1, 172.5, 171.5, 171.3, 160.6, 160.1, 157.6, 156.0, 140.3, 139.6, 138.6, 138.6, 130.5, 130.3, 129.9, 129.1, 128.6, 128.2, 115.5, 114.9, 114.9, 113.9, 103.5, 103.0, 70.4, 68.3, 67.6, 67.0, 63.5, 63.3, 46.9, 43.4, 39.9, 39.6, 39.1, 38.3, 34.5, 34.4, 33.4, 33.3, 28.8, 28.7, 27.5, 27.2, 26.6, 26.4, 26.2, 25.5, 25.3, 24.3, 24.2, 22.4, 22.2; HRMS (ESI$^+$) [M+H]$^+$ calcd for C$_{28}$H$_{37}$N$_2$O$_3$: 449.2804. found: 449.2790; [α]$_D^{20}$ −76.61 (c=0.110, CHCl$_3$).

Diamine 18.

In a 25-mL round bottom flask with a magnetic bar, DIBAL (159 µL, 0.893 mmol) was added to a solution of amide (20 mg, 44.6 µmol) in 5 mL diethyl ether at 0° C. and allowed to stir for four hours. Then a second portion of DIBAL (159 µL, 0.893 mmol) was added and the reaction mixture was allowed to warm to 22° C. and stir for two hours. Sat. aq. Rochelle salt (5 ml) was added at −78° C. and the mixture was warmed to 22° C. and allowed to stir for six hours. Layers partitioned and aqueous layer was washed three times with diethyl ether (10 mL). Combined organic layers was dried and concentrated by vacuum to yield a colorless oil, which was purified by neutral alumina chromatography (10:1 to 2:1 hexanes: diethyl ether) to afford the diamine 18 as a colorless oil (14 mg, 33.3 µmol, 75% yield, Z:E=95:5). IR (neat): 3075 (m), 3003 (m), 2921 (s), 2856 (s), 2974 (s), 1641 (s), 1556 (m), 1445 (s), 1385 (m), 1359 (m), 1342 (m), 1172 (s), 1129 (s), 1100 (m), 1084 (m), 992 (s), 910 (s), 857 (m), 793 (m), 726 (m); $^1$H NMR (400 MHz, CDCl$_3$): δ 5.94-5.83 (1H, m), 5.78 (1H, s), 5.69-5.60 (1H, m), 5.48 (1H, dd, J=18.0, 8.0 Hz), 5.26 (1H, dd, J=18.4, 7.6 Hz), 5.14-4.94 (4H, m), 4.16 (1H, s), 3.14-3.08 (1H, m), 3.00 (1H, d, J=10.8 Hz), 2.78-2.70 (2H, m), 2.65-2.43 (4H, m), 2.41 (1H, dt, J=11.6, 3.2 Hz), 2.32-2.09 (6H, m), 2.00-1.84 (3H, m), 1.77 (1H, ddd, J=14.0, 7.2, 2.4 Hz), 1.70-1.53 (3H, m), 1.50-1.38 (2H, m), 1.36-1.25 (2H, m), 1.08-0.96 (2H, m), 0.94-0.78 (2H, m); $^{13}$C NMR (100 MHz, CDCl$_3$): δ 160.6, 156.2, 140.9, 139.5, 133.6, 131.7, 128.1, 116.8, 114.2, 103.3, 71.0, 66.8, 62.6, 59.6, 58.4, 49.9, 45.1, 42.7, 41.4, 33.8, 28.9, 28.3, 27.9, 27.7, 27.2, 26.5, 26.3, 22.3; HRMS (ESI$^+$) [M+H]$^+$ calcd for C$_{28}$H$_{41}$N$_2$O: 421.3219. found: 421.3207; [α]$_D^{20}$ −30.14 (c=0.067, MeOH).

Nakadomarin A.

In an N$_2$-filled glovebox, diamine 18 (8.0 mg, 19.0 µmol) in a 8-mL vial was dissolved in toluene (3.8 mL) and treated with a stock solution of W complex 12 (93 µL, 0.95 µmol, 1 mg/mL, 0.05 equivalent). Then allowed to stir for three minutes, the vial was capped with a septa (with a needle through) and attached to a 1 torr vacuum system by a vacuum adapter. After stirred at 22° C. for eight hours, the reaction mixture was brought outside of the glovebox and exposed to air. The crude mixture was purified by silica gel chromatography (19:1 diethyl ether: ammonium hydroxide) to afford nakadomarin A as a white foam (4.2 mg, 10.7 µmol, 56% yield, Z:E=91:9). The physical and spectral data were identical to those previously reported (Ono, K.; Nakagawa, M.; Nishida, A. *Angew. Chem. Int. Ed.* 2004, 43, 2020-2023; Jakubec, P.; Cockfield, D. M.; Dixon, D. J. *J. Am. Chem. Soc.* 2009, 131, 16632-16633; Nilson, M. G.; Funk, R. L. *Org. Lett.* 2010, 12, 4912-4915). IR (neat): 3005 (m), 2923 (s), 2856 (s), 2790 (s), 2742 (s), 1444 (s), 1357 (m), 1330 (m), 1309 (m), 1276 (m), 1238 (m), 1196 (m), 1132 (s), 1080 (m), 953 (m), 937 (s), 725 (m); $^1$H NMR (400 MHz, CD$_3$OD): δ 5.86 (1H, s), 5.79 (1H, dd, J=17.6, 9.4 Hz), 5.51-5.40 (2H, m), 5.28-5.21 (1H, m), 3.92 (1H, s), 3.74-3.69 (1H, m), 3.08-2.98 (1H, m), 3.03 (1H, d, J=12.4 Hz), 2.83 (1H, br, s), 2.80-2.68 (2H, m), 2.64-2.57 (2H, m), 2.52-2.44 (1H, m), 2.40 (1H, dd, J=11.6, 3.6 Hz), 2.34-2.26 (3H, m), 2.18-1.95 (4H, m), 1.90 (2H, dd, J=12.4, 4.8 Hz), 1.81 (1H, ddd, J=14.0, 7.2, 2.6 Hz), 1.74-1.56 (4H, m), 1.47 (1H, dd, J=12.4, 10.0 Hz), 1.42-1.27 (2H, m), 1.11-1.00 (2H, m), 0.92-0.88 (1H, m); $^{13}$C NMR (100 MHz, CD$_3$OD): δ 162.3, 156.7, 135.1, 134.4, 132.2, 131.6, 129.3, 104.7, 74.7, 63.6, 60.7, 59.3, 58.2, 50.9, 46.1, 43.5, 43.1, 29.5, 29.2, 29.2, 28.8, 27.2, 27.1, 26.0, 26.0, 23.0; HRMS (ESI$^+$) [M+H]$^+$ calcd for C$_{26}$H$_{37}$N$_2$O: 393.2906. found: 293.2899; [α]$_D^{20}$ −73.59 (c=0.040, methanol).

Nakadomarin A.

A flame-dried 150-mL round bottom flask with a magnetic stir bar, attached with a reflux condenser, was charged with a solution of diamine 18 (10.0 mg, 23.8 µmol) and (+)- camphorsulfonic acid (17 mg, 71.4 μmol, 3.0 equivalent) in dichloromethane (10 mL). The resulting mixture was allowed to stir for 10 minutes and then diluted with dichloromethane (73 mL). 1$^{st}$-generation Grubbs catalyst (5.9 mg, 7.6 μmol, 0.3 equivalent) was weighed and dissolved in dichloromethane (4 mL). The solution of the catalyst was then added to the substrate by a syringe. The resulting mixture was allowed to stir at 40° C. for 5 hours. Then another portion of the Ru carbene (1.9 mg, 1.9 μmol, 0.1 equivalent) was dissolved in dichloromethane (2 mL) and then added to the reaction. The reaction was then allowed to stir at 40° C. for 3 hours and quenched by the addition of 1 M aq. HCl (10 mL). Layers partitioned and organic layer extracted by 1 M aq. HCl (10 mL×3). The aqueous extracts were combined, cooled to 0° C. and pH was adjusted to 14 by the addition of sat. aq. NaOH. The aqueous mixture was washed with diethyl ether (10 mL×3) and dichloromethane (10 mL×3). The combined organic extracts were dried, filtered and concentrated in vacuo to give a colorless oil. Purification was performed by silica gel chromatography (19:1 diethyl ether: ammonium hydroxide) to afford nakadomarin A as a white foam (6.1 mg, 14.0 μmol, 66% yield, Z:E=93:7).

Proof of Stereochemistry.

Figure 4:
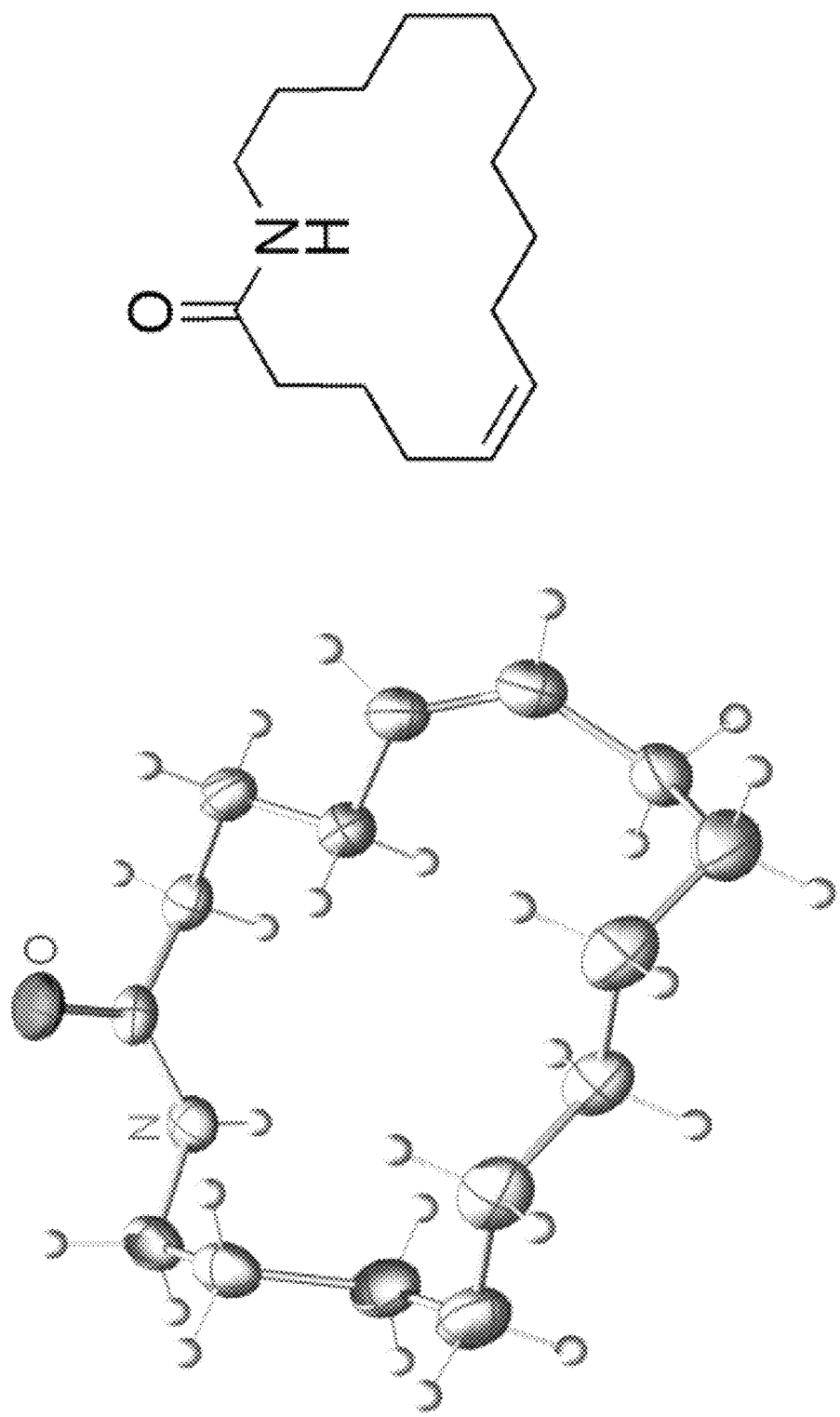
FIG. 4. X-ray structure of 17.
Figure 5:
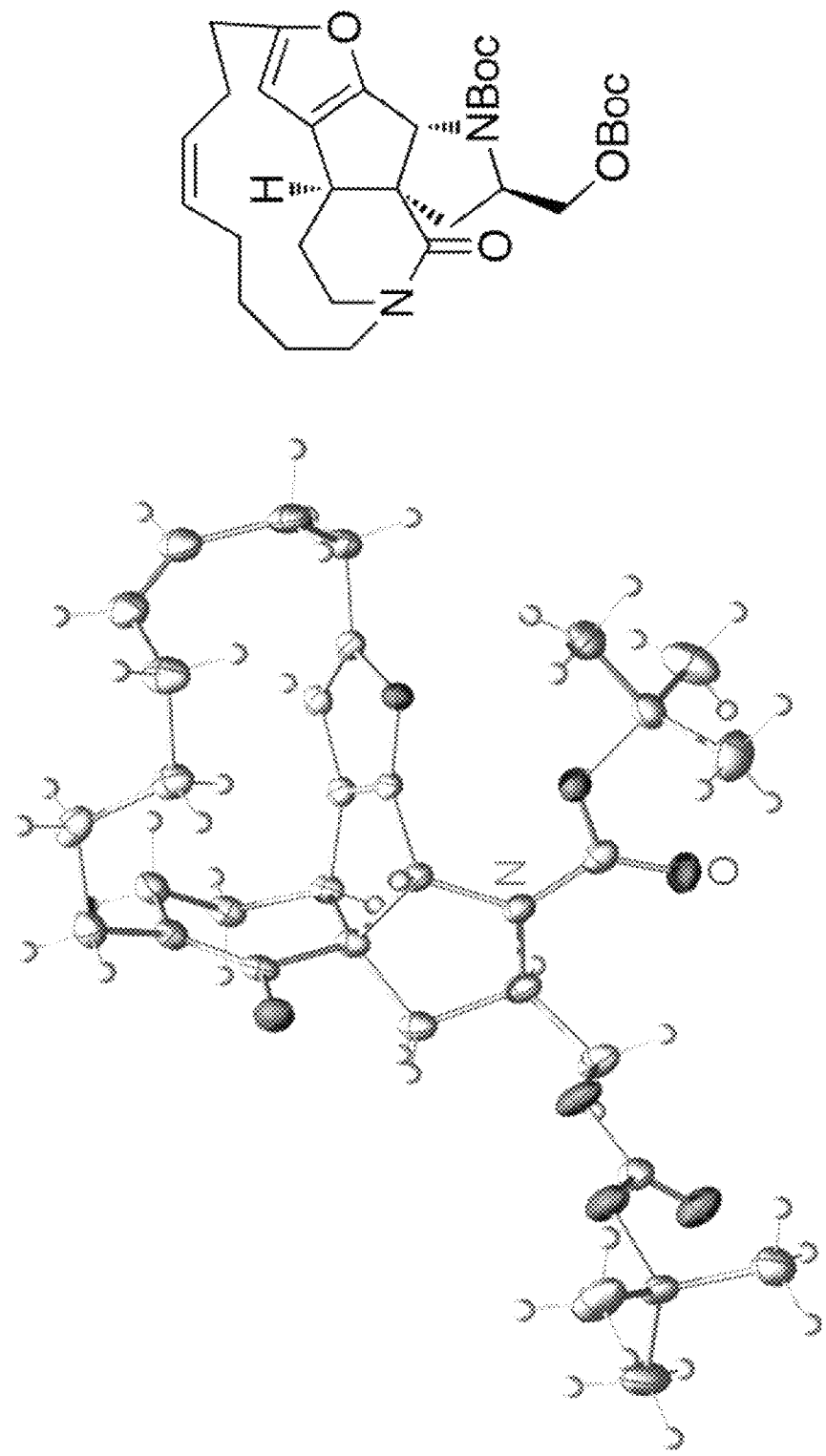
FIG. 5. X-ray structure of 7.

The identity of the major isomer of 17 and 7 from Mo or W-catalyzed macrocyclic RCM was established through X-ray crystallography (FIGS. 4 and 5, Tables 5 and 6).

TABLE 5

Crystal data and structure refinement for $C_{15}H_{27}NO$ (17).

| | |
|---|---|
| Identification code | C15H27NO |
| Empirical formula | C15 H27 N O |
| Formula weight | 237.38 |
| Temperature | 143(2)K |
| Wavelength | 0.71073≈ |
| Crystal system | Orthorhombic |
| Space group | P b c a |
| Unit cell dimensions | a = 17.3448(8)≈  α = 90∞. |
| | b = 9.6231(5)≈  β = 90∞. |
| | c = 17.7549(8)≈  γ = 90∞. |
| Volume | 2963.5(2)≈$^3$ |
| Z | 8 |
| Density (calculated) | 1.064 Mg/m$^3$ |
| Absorption coefficient | 0.065 mm$^{-1}$ |
| F(000) | 1056 |
| Crystal size | 0.22 × 0.04 × 0.03 mm$^3$ |
| Theta range for data collection | 2.29 to 25.00∞. |
| Index ranges | −20 <= h <= 20, −11 <= k <= 11, −21 <= l <= 21 |
| Reflections collected | 39195 |
| Independent reflections | 2612 [R(int) = 0.0652] |
| Completeness to theta = 25.00∞ | 99.9% |
| Absorption correction | Semi-empirical from equivalents |
| Max. and min. transmission | 0.9980 and 0.9858 |
| Refinement method | Full-matrix least-squares on F$^2$ |
| Data/restraints/parameters | 2612/1/157 |
| Goodness-of-fit on F$^2$ | 1.014 |
| Final R indices [I > 2 sigma(I)] | R1 = 0.0377, wR2 = 0.0717 |
| R indices (all data) | R1 = 0.0695, wR2 = 0.0828 |
| Extinction coefficient | na |
| Largest diff. peak and hole | 0.140 and −0.155 e.≈$^{-3}$ |

TABLE 6

Crystal data and structure refinement for $C_{31}H_{44}N_2O_7$ (7).

| | |
|---|---|
| Identification code | C31H44N2O7 |
| Empirical formula | C31 H44 N2 O7 |
| Formula weight | 556.68 |
| Temperature | 100(2)K |
| Wavelength | 1.54178≈ |
| Crystal system | Monoclinic |
| Space group | P 2(1) |
| Unit cell dimensions | a = 10.342(3)≈  α = 90∞. |
| | b = 9.907(3)≈  β = 93.895(12)∞. |
| | c = 14.462(5)≈  γ = 90∞. |
| Volume | 1478.2(8)≈$^3$ |
| Z | 2 |
| Density (calculated) | 1.251 Mg/m$^3$ |
| Absorption coefficient | 0.716 mm$^{-1}$ |
| F(000) | 600 |
| Crystal size | 0.20 × 0.12 × 0.05 mm$^3$ |
| Theta range for data collection | 3.06 to 67.47∞. |
| Index ranges | −12 <= h <= 12, −11 <= k <= 11, −17 <= l <= 10 |
| Reflections collected | 15917 |
| Independent reflections | 5100 [R(int) = 0.0382] |
| Completeness to theta = 67.47∞ | 98.0% |
| Absorption correction | Semi-empirical from equivalents |
| Max. and min. transmission | 0.9651 and 0.8701 |
| Refinement method | Full-matrix least-squares on F$^2$ |
| Data/restraints/parameters | 5100/1/367 |
| Goodness-of-fit on F$^2$ | 1.097 |
| Final R indices [I > 2 sigma(I)] | R1 = 0.0293, wR2 = 0.0787 |
| R indices (all data) | R1 = 0.0778, wR2 = 0.0915 |
| Absolute structure parameter | 0.02(14) |
| Extinction coefficient | na |
| Largest diff. peak and hole | 0.365 and −0.302 e.≈$^{-3}$ |

Synthesis of Z-Trisubstituted Alkenes Through Stereoselective Ring-Closing Metathesis (RCM) Reactions. Application to Total Synthesis of Epothilones B and D Many biologically active macrocycles contain a C—C double bond through which various other derivatives might be prepared; the stereochemical identity of the alkene or the resulting moieties can be critical to the beneficial properties of such molecules. Catalytic ring-closing metathesis (RCM) is a protocol that is employed widely for the synthesis of large unsaturated rings; however, cyclizations typically proceed without control of alkene stereoselectivity—a shortcoming is particularly costly with complex structures when RCM is performed after a long sequence of transformations. A solution to achieving high Z selectivity in RCM reactions that afford disubstituted or more substituted alkenes is highly desirable. Here, we introduce a new class of catalysts that promoted macrocyclic RCM reactions through Z-selective synthesis of trisubstituted alkenes.

Catalytic alkene ring-closing metathesis (RCM) is indispensable to the preparation of cyclic structure (Hoveyda, A. H.; Zhugralin, A. R. Nature 2007, 450, 243-251); it is used extensively in the synthesis of a variety of biologically active molecules (Deiters, A.; Martin, S. F. Chem. Rev. 2004, 104, 2199-2238; Nicolaou, K. C.; Bulger, P. G.; Sarlah, D. Angew. Chem., Int. Ed. 2005, 44, 4490-4527; Gradillas, A.; Perez-Castells, J. Angew. Chem., Int. Ed. 2006, 45, 6086-6101; Gradillas, A.; Pérez-Castells, J. in Metathesis in Natural Product Synthesis (Cossy, J.; Arsenyadis, S.; Meyer, C.; Eds); Wiley-VCH, 2010.). RCM is broadly employed in accessing large rings; this is in spite of the lack of a reliably stereoselective variant, availability of which would substantially enhance the value of this important class of reactions. The absence of stereochemical control, without wishing to be limited by any theory, may originate from the outcome of a catalytic ring closure being mostly dependent on the energetic attributes of the product stereoisomers (vs dictated by the catalyst used). With small- or medium-rings, Z alkenes are generated exclusively; this is not the case with sizeable rings, since, frequently, either the energy difference between the two isomeric alkenes is insufficient for achieving high stereoselectivity by thermodynamic control, or, if one isomer is adequately lower in energy, the catalyst is unable to promote facile equilibration. An example of such lack of stereoselectivity can be found in relation to numerous attempts that have been made towards the total syntheses of an important class of important biologically active macrocycles, namely epothilones. Before invention disclosed above and herein, all attempts to prepare the 16-membered core through an RCM approach have resulted in a virtually equal mixture of alkene isomers (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073-10092; Nicolaou, K. C.; He, Y.; Vourloumis, D.; Vallberg, H.; Roschangar, F.; Sarabia, F.; Ninkovic, S.; Yang, Z.; Trujillo, J. I. *J. Am. Chem. Soc.* 1997, 119, 7960-7973; Schinzer, D.; Limberg, A.; Bauer, A.; Bohm, O. M.; Cordes, M. *Angew. Chem., Int. Ed.* 1997, 36, 523-524; Sinha, S. C.; Sun, J.; Miller, G. P.; Wartmann, M.; Lerner, R. A. *Chem. Eur. J.* 2001, 7, 1691-1702).

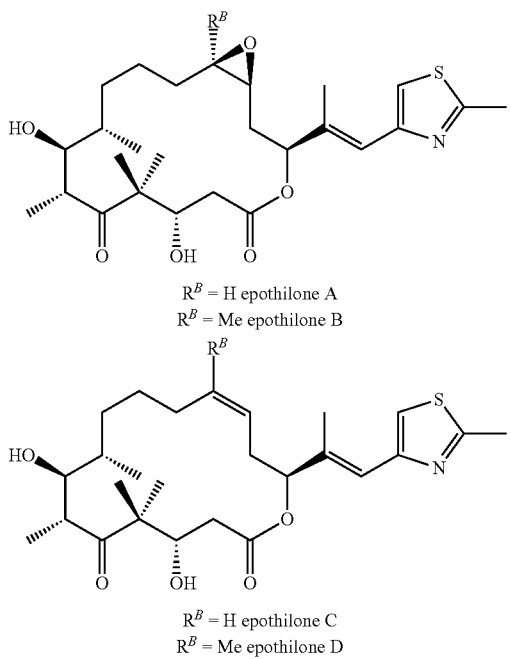

$R^B$ = H epothilone A
$R^B$ = Me epothilone B $R^B$ = H epothilone C
$R^B$ = Me epothilone D In 2009, we reported the first examples of highly Z- and enantioselective olefin metathesis processes; specifically, we demonstrated that a variety of aryl olefins undergo efficient ring-opening/cross-metathesis reactions with a series of relatively strained bicyclic alkenes, catalyzed by stereogenic-at-Mo adamantylimido complexes (Ibrahem, I.; Yu, M.; Schrock, R. R.; Hoveyda, A. H. *J. Am. Chem. Soc.* 2009, 131, 3844-3845). More recently, we showed that such transformations may be performed with enol ether cross partners (Yu, M.; Ibrahem, I.; Hasegawa, M.; Schrock, R. R.; Hoveyda, A. H. *J. Am. Chem. Soc.* 2012, 134, DOI: 10.1021/ja210946z). Additionally, we have shown that mono-pyrrolidemonoaryloxide Mo complexes promote Z-selective homo-coupling (Jiang, A. J.; Zhao, Y.; Schrock, R. R.; Hoveyda, A. H. *J. Am. Chem. Soc.* 2009, 131, 16630-16631; Marinescu, S. C.; Schrock, R. R.; Müller, P.; Takase, M. K.; Hoveyda, A. H. *Organometallics* 2011, 30, 1780-1782) and cross-metathesis (Meek, S. J.; O'Brien, R. V.; Llaveria, J.; Schrock, R. R.; Hoveyda, A. H. *Nature* 2011, 471, 461-466) reactions of terminal olefins. In another critical development, we discovered that the corresponding W-based monopyrrolide are most effective in catalyzing macrocyclic RCM reactions that involve two terminal alkenes with high efficiency as well as exceptional Z selectivity; applications to total syntheses of biologically active natural products epothilones A and C as well as nakadomarin A highlighted the significance of the advance (Yu, M.; Wang, C.; Kyle, A. F.; Jakubec, P.; Dixon, D. J.; Schrock, R. R.; Hoveyda, A. H. *Nature* 2011, 479, 88-93). It was with this background that we selected epothilones B and D, containing and derived from epoxidation of a trisubstituted alkene, respectively, as prominent targets that might allow us to extend the scope of these newly developed complexes and, ultimately, aid in further catalyst development.

Epothilones belong to a family of 16-membered macrolides first isolated from the myxobacterium strain *Sorangium cellulosum* 90 (Hoefle, G.; Bedorf, N.; Steinmetz, H.; Schomburg, D.; Gerth, K.; Reichenbach, H. *Angew. Chem., Int. Ed. Engl.* 1996, 35, 1567-1569). Their anticancer activity, coupled with a mechanism of action similar to that of paclitaxel, has spurred an intense race for their total synthesis and structural modification (For selected reviews, see: (a) Nicolaou, K. C.; Roschangar, F.; Vourloumis, D. *Angew. Chem., Int. Ed.* 1998, 37, 2014-2045. (b) Rivkin, A.; Chou, T.-C.; Danishefsky, S. J. *Angew. Chem., Int. Ed.* 2005, 44, 2838-2850. (c) Altmann, K. H.; Pfeiffer, B.; Arsenyadis, S.; Pratt, B. A.; Nicolaou, K. C. *ChemMedChem* 2007, 2, 396-423). One attractive strategy for formation of the macrocycle is the ring-closing metathesis at the Δ12,13 alkene. Indeed, several of the early examples of successful total syntheses of epothilones depended on a macrocyclic RCM approach (Yang, Z.; He, Y.; Vourloumis, D.; Vallberg, H.; Nicolaou, K. C. *Angew. Chem., Int. Ed.* 1997, 36, 166-168; Schinzer, D.; Limberg, A.; Bauer, A.; Bohm, O. M.; Cordes, M. *Angew. Chem., Int. Ed.* 1997, 36, 523-524). Despite extensive efforts to optimize reaction conditions and protecting groups in substrates, there is essentially no selectivity in favor of the desired Z isomer (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073-10092; Nicolaou, K. C.; He, Y.; Vourloumis, D.; Vallberg, H.; Roschangar, F.; Sarabia, F.; Ninkovic, S.; Yang, Z.; Trujillo, J. I. *J. Am. Chem. Soc.* 1997, 119, 7960-7973). Consequently, other macrocyclization strategies, such as macrolactonization and intramolecular aldol reaction (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073-10092; Nicolaou, K. C.; Ninkovic, S.; Vourlomis, D.; He, Y.; Vallberg, H.; Finlay, M. R. V.; Yang, Z. *J. Am. Chem. Soc.* 1997, 119, 7974-7991; Balog, A.; Harris, C.; Savin, K.; Zhang, X-G.; Chou, T. C.; Danishefsky, S. J. *Angew. Chem., Int. Ed.* 1998, 37, 2675-2678. (c) Schinzer, D.; Bauer, A. *Chem. Eur. J.* 1999, 5, 2492-2500), have been explored as an alternative; such alternative strategies, however, necessitate significantly longer routes compared to synthesis schemes that include catalytic RCM.

One solution to obtaining macrocyclic Z alkenes was presented by Fürstner and co-workers and involves catalytic alkyne metathesis followed by partial hydrogenation of the resulting cyclic C—C triple bond (Fürstner, A.; Mathes, C.; Lehmann, C. W. *Chem. Eur. J.* 2001, 7, 5299-5317). Another possible solution was introduced recently, where a silyl-substituted alkene, installed through hydrosilation of an alkyne, is involved in a stereoselective macrocyclic RCM; subsequent protodesilylation afford the desired Z disubstituted olefin (Wang, Y.; Jimenez, M.; Hansen, A. S.; Raiber, E.-A.; Schreiber, S. L.; Young, D. W. *J. Am. Chem. Soc.* 2011, 133, 9196-9199). One inherent disadvantage associated with both approaches is that additional steps are required to prepare the alkyne. Moreover, the alkyne metathesis/hydrogenation sequence is limited to the preparation of disubstituted alkenes, ruling out the syntheses of epothilones B and D. The latter RCM strategy, the utility of which is yet to be illustrated in a total synthesis setting, requires an additional crosscoupling step to install the third substituent on the macrocyclic alkene.

An efficient and general approach to trisubstituted alkenes of epothilones would involve a Z-selective RCM. Herein, we present such a solution to this important problem.

We faced substantial difficulties regarding the observed levels of activity as well as the degrees of Z selectivity in the course of our initial catalyst screening studies in connection with the macrocyclic RCM leading to trisubstituted alkene of epothilone D (X1→X2, Scheme X1). We found that the use of the well-established achiral Mo alkylidene X3 leads to relatively high efficiency to afford macrocycle X2 in 79% yield but as a 45:55 mixture of Z:E olefin isomers (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073-10092; May, S. A.; Grieco, P. A. *Chem. Commun.* 1998, 1597-1598). Reactions performed with Mo-based monoaryloxide-monopyrrolide complexes X4 and X5 (Scheme X1) proved to be inefficient, affording the macrocycle with minimal stereoselectivity; furthermore, the major component of the product mixture proved to be derived from the product resulting from cross-metathesis of the monosubstituted alkenes in X1 to afford "homo-coupled" product. When the derived W-based complex X6 (Scheme X1), optimal in macrocyclic RCM reactions involving two monosubstituted alkenes and leading to disubstituted macrocyclic alkenes, was used, none of the desired product could be detected. To ensure that such lack of activity is not as a result of slow catalyst initiation, the complex was pre-treated with diallyl ether (to generate the active methylidene); such a strategy proved to be ineffective (<2% conv to macrocycle). Ru catalysts are ineffective as well; for example, reaction with 20 mol % second-generation Grubbs complex (40° C., 24 h) leads to 65% conv to X2, generated as an equal mixture of alkene stereoisomers.

Scheme X1. Initial Screening of Mo and W Complexes to Promote Formation of 2 through Macrocyclic RCM The reaction:

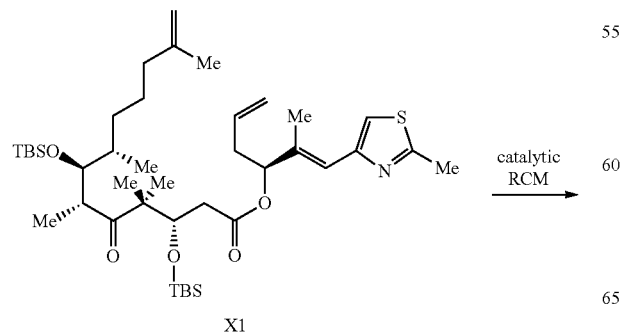

X1

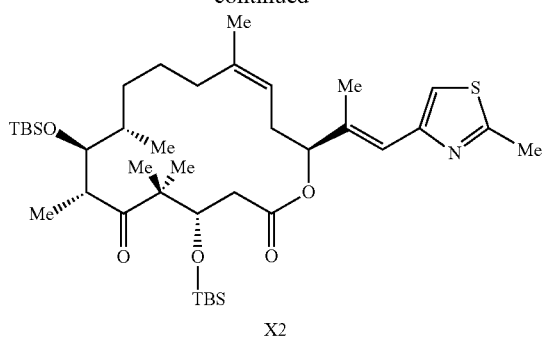

X2

Effectiveness of some of the most effective complexes at the time:

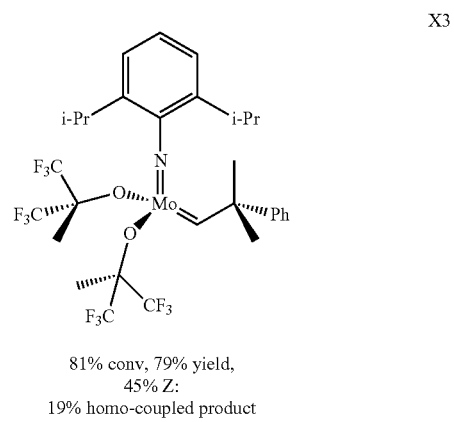

X3

81% conv, 79% yield,
45% Z:
19% homo-coupled product

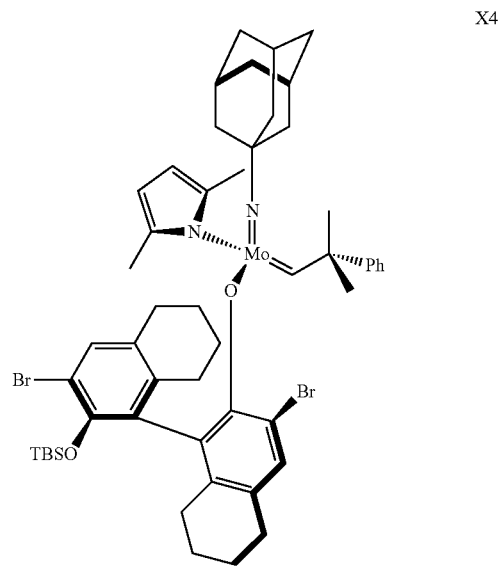

X4

7% conv, yield nd, 59% Z: 18% homo-coupled product
at 50° C.:
17% conv, yield nd, 75% Z. 35% homo-coupled product

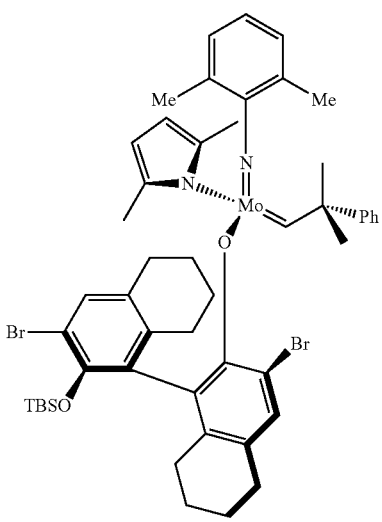

X5

13% conv, yield nd, 61% Z: 16% homo-coupled product at 50° C.:
30% conv. yield nd, 68% Z. 18% homo-coupled product

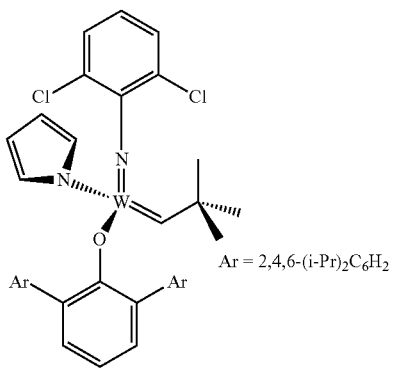

< 2% conv

Notes: Reactions performed with 20 mol % complex at 22° C. for 24 h, unless otherwised noted. nd = not determined.

To identify a more active RCM catalyst that delivers the Z trisubstituted alkene of epothilone D, we turned modification of the modular structure of the Mo-based alkylidene complexes. The significant majority of the screening data described above involved modifications of the imido groups on the metal complexes. We then decided to replace the aryloxide's Br with a smaller and more electron-withdrawing fluoride. Without the intention to be bound by theory, the increased electronegativity of the fluorides was believed to lead to an increase in catalyst activity, since higher Lewis acidity at the transition metal could lead to it more effectively coordinating with the more highly substituted (and thus more sterically hindered) alkene. Moreover, without wishing to be bound by theory, we surmised that the relatively smaller halogen (F vs Cl or Br) would allow the alkylidene complex to accommodate a hindered disubstituted alkene more effectively.

Accordingly, examination of a range of chiral Mo-based alkylidenes, based on the non-limiting principles delineated above, led us to establish that, as shown in Scheme X2, F-containing complex X7 provided a significant improvement in conversion to the desired product (60% cony). Catalytic RCM in the presence of complexes X8 and X9, bearing electron-withdrawing fluorines at the imido ligand, gave rise to even higher efficiency (86-90% cony; Scheme X2). Importantly, through analysis of the $^1$H NMR spectra of the mixtures of bispyrrolides and F-containing aryl alcohols, we were able to determine our attempts to access monopyrrolides X7-X9 in situ had resulted in the formation of various amounts of the derived bis-aryloxides. Without wishing to be bound by theory, we surmised that, despite being substantially more sizeable than a pyrrolide, the second aryloxide can lead to an improvement in reactivity by electronic activation of the Mo-based catalyst. That is, without intention to be limited by theory, we realized it is feasible that the majority of the catalytic activity shown in Scheme X2 is due to the bis-aryloxides, which, in some cases, are only present in small amounts (<10% in the case of X7).

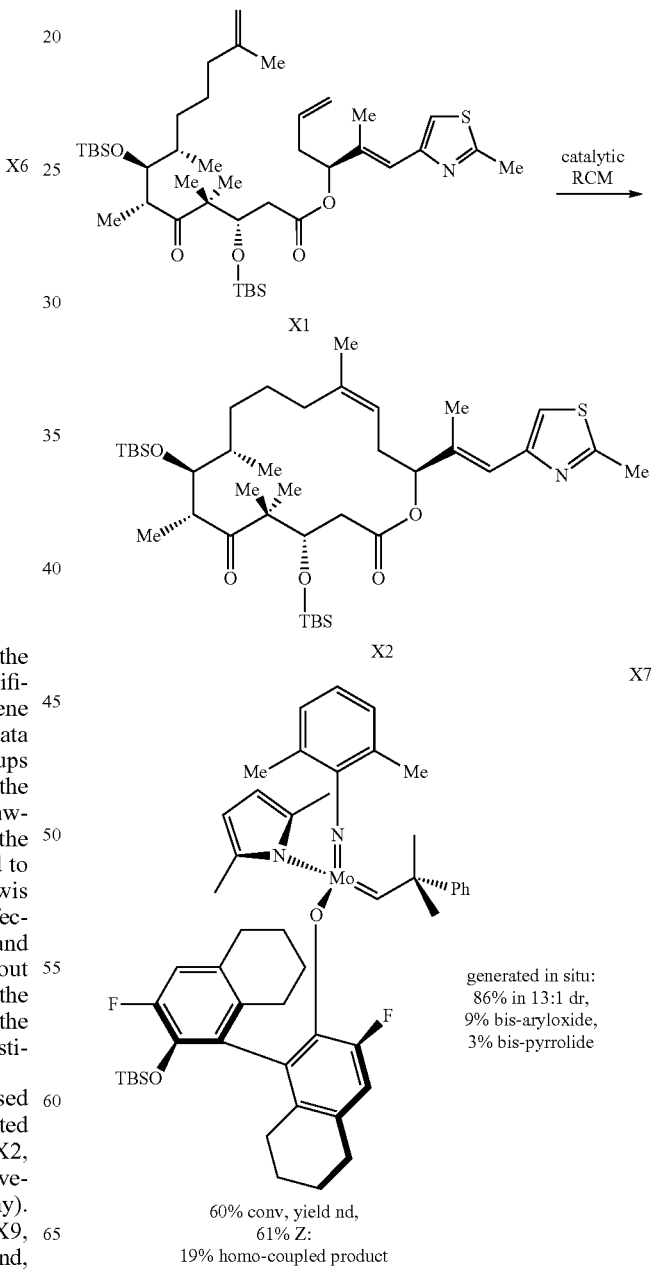

Scheme X2. Examination of Mo Complexes Bearing Various F-Substituted Ligands

60% conv, yield nd,
61% Z:
19% homo-coupled product generated in situ:
86% in 13:1 dr,
9% bis-aryloxide,
3% bis-pyrrolide

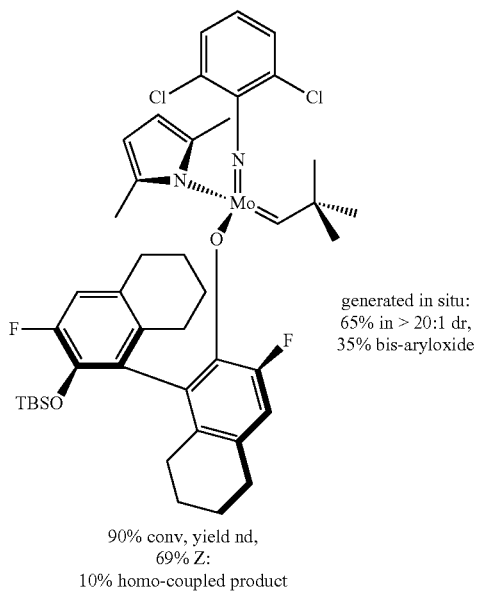

X8 generated in situ:
65% in > 20:1 dr,
35% bis-aryloxide

90% conv, yield nd,
69% Z:
10% homo-coupled product

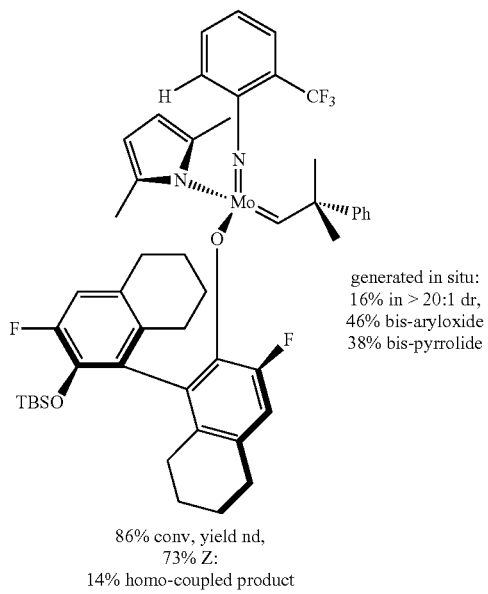

X9 generated in situ:
16% in > 20:1 dr,
46% bis-aryloxide
38% bis-pyrrolide

86% conv, yield nd,
73% Z:
14% homo-coupled product

Notes: Reactions performed with 20 mol % complex at 22° C. for 24 h. Catalyst preparation in situ = treatment of the corresponding bis-pyrrolide with one equiv of aryl alcohol. TBS = t-butyldimethylsilyl. nd = not determined.

Without wishing to be bound by theory, to confirm the possibility that it might indeed be the bis-aryloxide complexes that are responsible for the hike in catalytic activity as well as the observed Z selectivity, chiral (but nonstereogenic-at-Mo) complexes X10 and X11 (Scheme X3) were prepared; the requisite alkylidenes were synthesized by mixing one equivalent of the corresponding bispyrrolides with two equivalents of the phenols, and did not contain any detectable amounts of monopyrrolide-monoaryloxide [as determined by analysis of the 400 MHz 1H NMR spectra of the reaction mixtures; ~2% bispyrrolide (inactive) detected in certain instances)]. We thus found that, remarkably, bis-aryloxide X10 exhibits substantially higher catalytic activity than the mixture of monopyrrolide-monoaryloxide and bisaryloxide generated in our attempts to prepare a sample of complex X9 (see Scheme X3). Such a discovery is in sharp contrast to our previous observation on the apparent lack of reactivity of the bis-aryloxide complexes that contain an adamantyl imido group (vs an arylimido unit, Ibrahem, I.; Yu, M.; Schrock, R. R.; Hoveyda, A. H. J. Am. Chem. Soc. 2009, 131, 3844-3845). Substitution of partially hydrogenated aryloxides with the corresponding fully unsaturated variant (X11, Scheme X3) leads to a catalyst that is slightly less effective in promoting the macrocyclic RCM process. To improve Z selectivity, we outfitted the aryloxide ligand with a larger silyl group (vs t-butyldimethylsilyl; complexes X12 and X13, Scheme X3); such structural modification led to a slight increase in Z-E ratio along with a diminution in reactivity. Replacing the rather bulky trifluoromethylaryl imido group with a smaller pentafluoroaryl imido group (complexes X14 and X15, Scheme X3) resulted in only a slight improvement in Z selectivity. The next significant improvement came from the use of biphenoxide ligand (versus one derived from a binaphthol): a remarkable 82% yield and 86% Z selectivity was obtained when X16 was used. The critical significance of electronic activation of the Mo complexes in achieving high efficiency is evident in the marked lowering of activity exhibited by complex X17.

Scheme X3. Z-Selective Synthesis of a Trisubstituted Alkene Macrocyclic RCM: Catalyst Screening

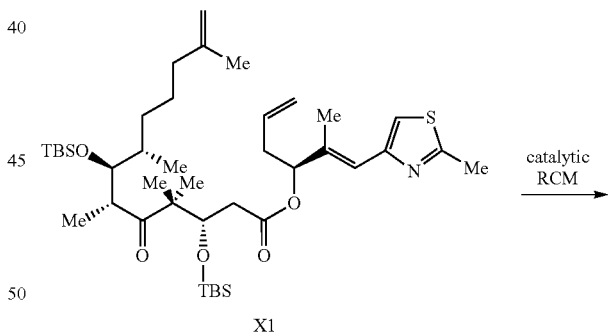

X1

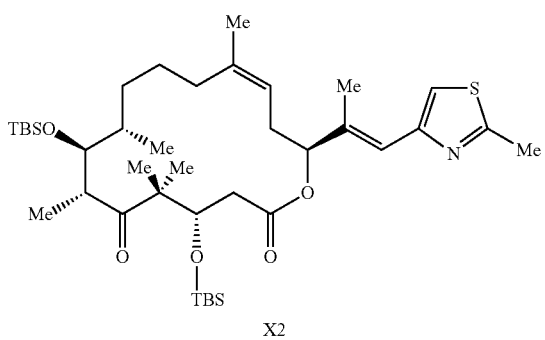

X2

-continued
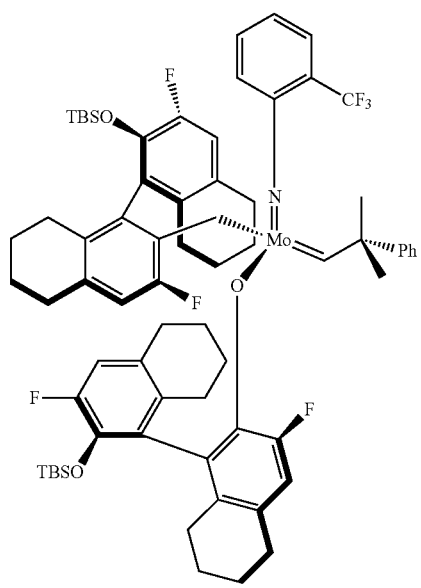
X10
92% conv, yield nd,
70% Z:
8% homo-coupled product
-continued
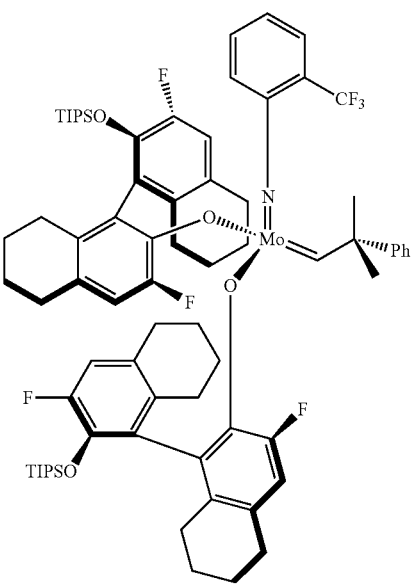
X12
75% conv, yield nd,
79% Z:
21% homo-coupled product
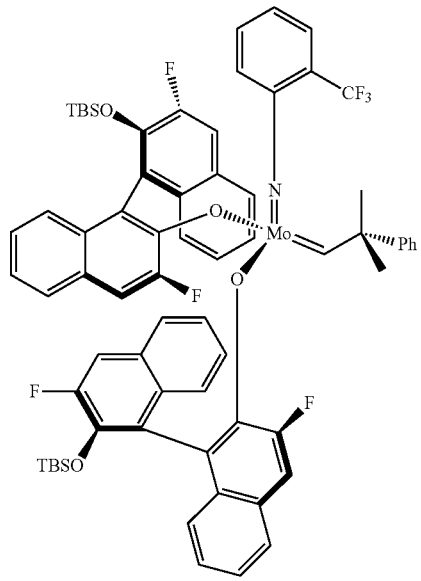
X11
75% conv, yield nd,
74% Z:
19% homo-coupled product
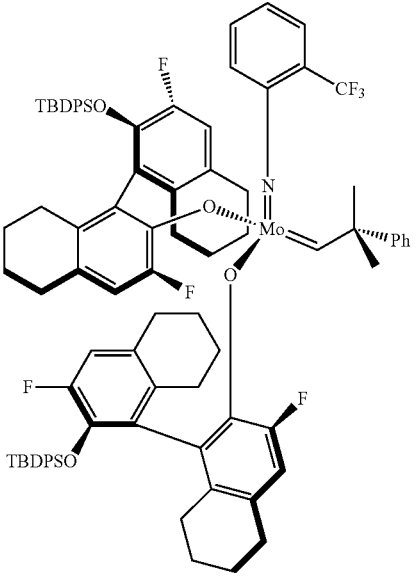
X13
78% conv, yield nd,
81% Z:
22% homo-coupled product 215
-continued

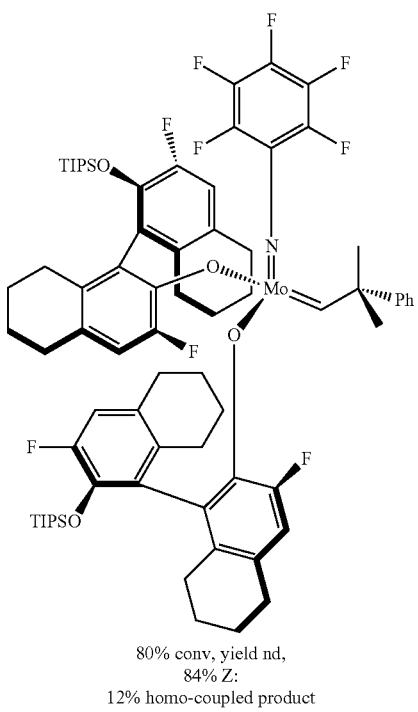

X14

80% conv, yield nd,
84% Z:
12% homo-coupled product

X15

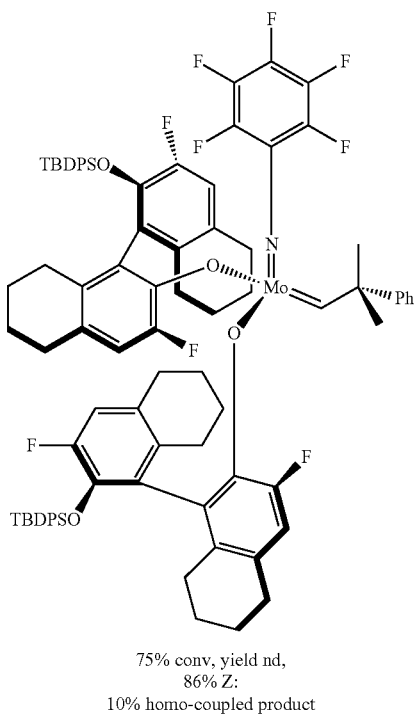

75% conv, yield nd,
86% Z:
10% homo-coupled product

216
-continued

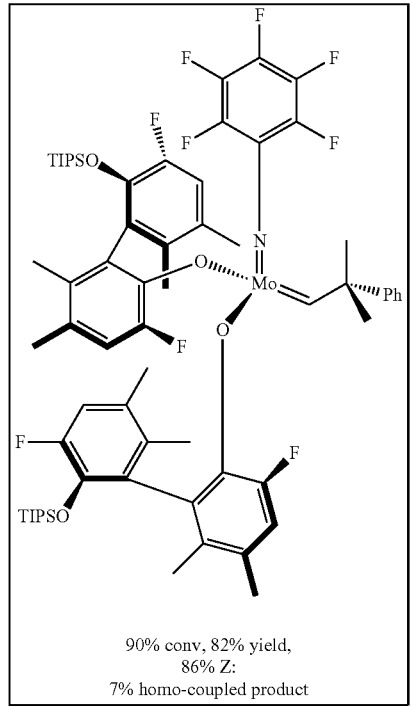

X16

90% conv, 82% yield,
86% Z:
7% homo-coupled product

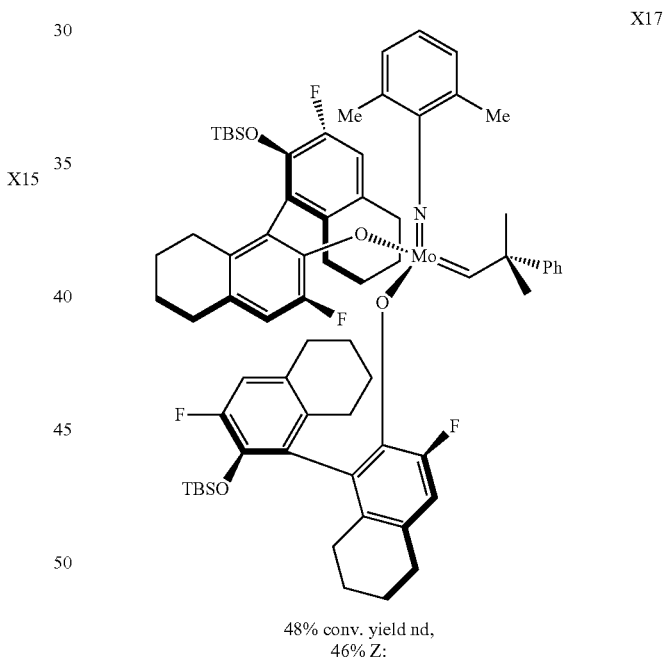

X17

48% conv. yield nd,
46% Z:
25% homo-coupled product

Notes: Reactions performed with 20 mol % complex at 22° C. for 24 h. TBS = t-butyldimethylsilyl; TIPS = tri-(i-propyl)silyl; TBDPS = t-butyldiphenylsilyl.

Appreciable activity and similar or higher Z selectivity can be achieved at lower catalyst loadings. For example, when 10 mol % X10 is used, there is 76% conversion to X2, which is formed cleanly with 76% Z selectivity (vs 92% cony and 70% Z). We find that lower catalyst loadings are easily feasible, particularly with reactions performed at larger scale (e.g., multigram) (Meek, S. J.; O'Brien, R. V.; Llaveria, J.; Schrock, R. R.; Hoveyda, A. H. *Nature* 2011, 471, 461-466).

The Mo-based bis-aryloxides are complementary to monopyrrolide-monoaryloxide complexes: the two systems are optimal in promoting Z-selective RCM of tri- and disubstituted macrocyclic RCM, respectively; the reverse is not true. That is, as monopyrrolides do not initiate efficient formation of trisubstituted cyclic alkenes, the new bis-aryloxides, while catalyzing rapid formation of the less substituted cyclic alkenes, they do so without control of stereoselectivity. For example, macrocyclic RCM of the less substituted analog of X1, which affords the precursor to epothilones A and C, proceeds to >98% conversion within one hour in the presence of 10 mol % bis-aryloxide X10 (Scheme X2), but the product is generated as a 37:63 mixture of Z:E isomers. We have already reported that complexes such as the W-based monopyrrolide X6 (Scheme X1) deliver the disubstituted alkene with >90% Z selectivity.

We have made the unexpected discovery that Mo-based bisaryloxides that carry small and electron-withdrawing F atoms at their aryloxide as well as imido units can give rise to high levels of activity and Z selectivity in macrocyclic RCM reactions that lead to the formation of trisubstituted alkenes. There are numerous other important potential applications (For example, see: (a) Toró, A.; Deslongchamps, P. *J. Org. Chem.* 2003, 68, 6847-6852. (b) Xie, J.; Ma, Y.; Horne, D. A. *Chem. Commun.* 2010, 46, 4770-4772) in the field of RCM that require the synthesis of trisubstituted alkenes in a stereoselective fashion; accordingly, the findings detailed above are expected to have a substantial and wide ranging impact on the preparation of a substantial number of biologically active molecules.

Representative Experimental Procedure

In an $N_2$-filled glovebox, a solution of diene X1 (4.2 mg, 5.6 μmol) in benzene (5.6 mL) was treated with a solution of Mo complex X16 (0.010 M in $C_6D_6$, 0.11 mL, 1.1 μmol). The reaction vessel was loosely capped to allow ethylene gas to vent off. The mixture was allowed to stir at 22° C. for 24 h, after which the reaction was quenched by the addition of wet diethyl ether and concentrated under reduced pressure. Purification by silica gel chromatography (hexanes: $Et_2O$ 100:1 to 20:1) afforded 3.3 mg (82%, Z:E=86:14) of X2 (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073-10092; Nicolaou, K. C.; Ninkovic, S.; Vourlomis, D.; He, Y.; Vallberg, H.; Finlay, M. R. V.; Yang, Z. *J. Am. Chem. Soc.* 1997, 119, 7974-7991) as a colorless solid. 1H NMR of both E and Z isomers, diagnostic signals (400 MHz, CDCl3): δ 6.56 (0.86H, app d, J=0.8 Hz, Z isomer), 6.53 (0.14H, s, E isomer).

In some embodiments, certain ligands were synthesized as described in Chen, Yu; Yekta, Shahla; Martyn, L. J. P.; Zheng, Juan; Yudin, A. K. *Org. Lett.* 2000, 2, 3433-3436; Yudin, A. K.; Martyl, L. J. P.; Pandiaraju, Subramanian; Zheng, Juan; Lough, Alan *Org. Lett.* 2000, 2, 41-44; and Morrison, D. J.; Riegel, S. D.; Piers, W. E.; Parvez, Masood; McDonald, Robert *Chem. commun.* 2006, 2875-2877.

Some of the results are presented in Table 7.

TABLE 7

Selected catalyst screening results.

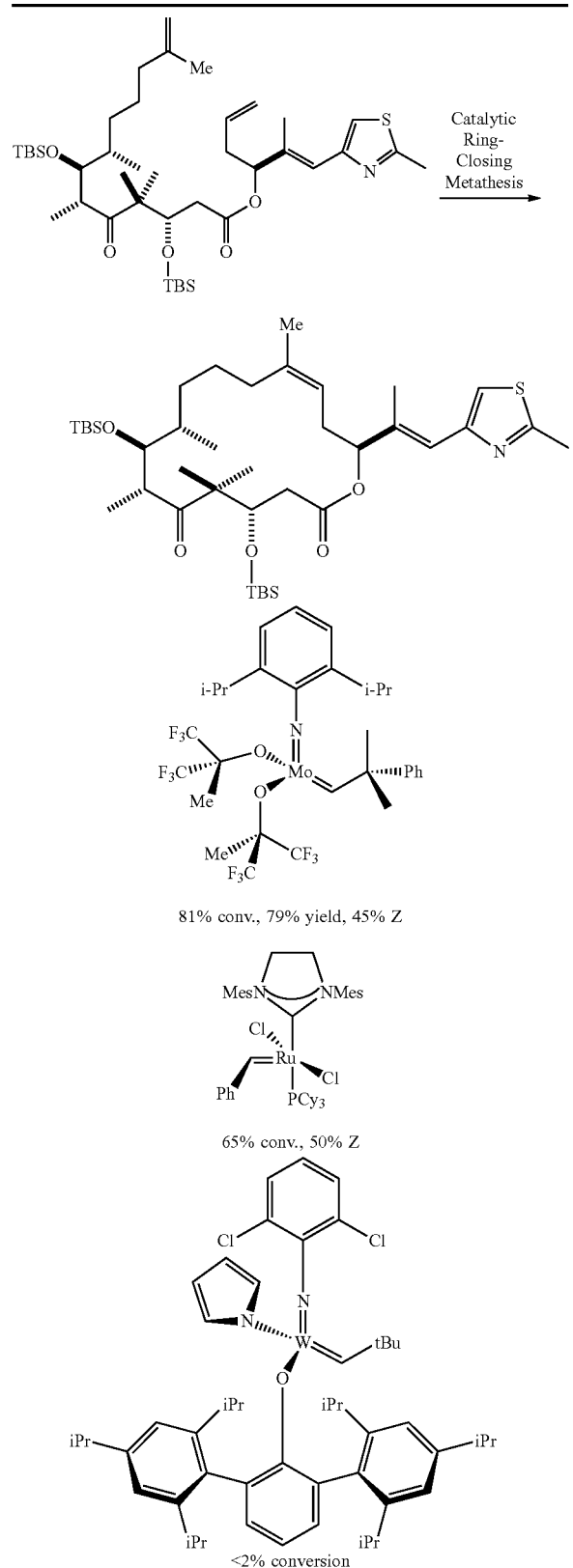

TABLE 7-continued

Selected catalyst screening results.

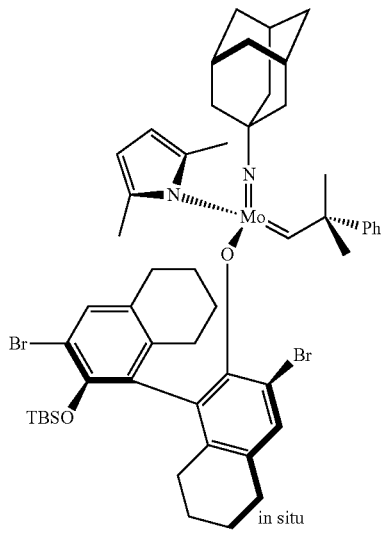

22° C.,
7% conv, 59% Z
18% homo-coupled product
50° C.,
17% conv, 75% Z
35% homo-coupled product

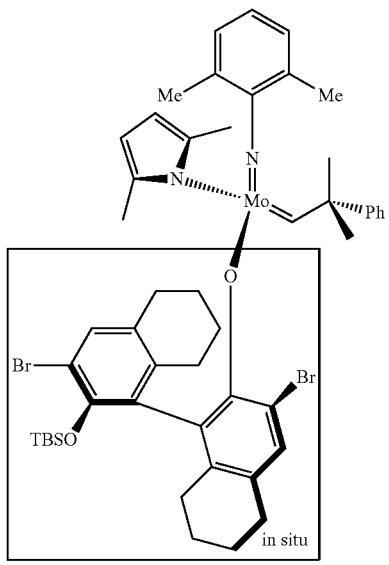

22° C.
13% conv, 61% Z
16% homo-coupled product
50° C.
30% conv, 68% Z
18% homo-coupled product TABLE 7-continued Selected catalyst screening results.

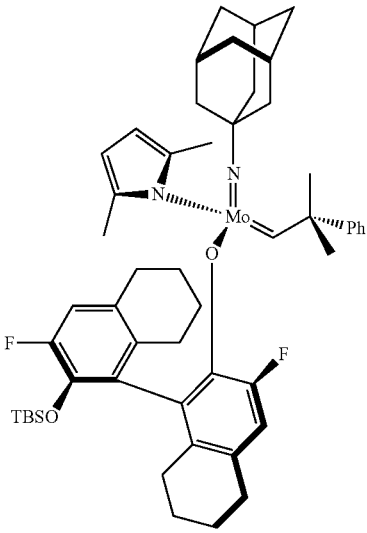

in situ
5% MAP, >98:<2 dr
44% bis-aryloxide
51% bis-pyrolide
20 mol %, 1.0 mM, PhMe,
open vessel, 24 h;
22° C., benzene
7% conv, 50% Z
9% homo-coupled product

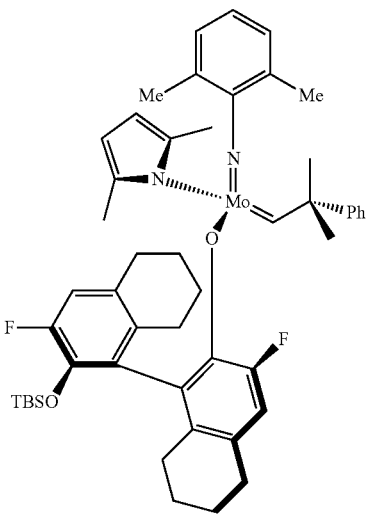

in situ
86% MAP, 13:1 dr
9% bis-aryloxide
3% bis-pyrolide
20 mol %, 1.0 mM, PhMe,
open vessel, 24 h;
22° C., benzene:
60% conv, 61% Z
19% homo-coupled product TABLE 7-continued Selected catalyst screening results.

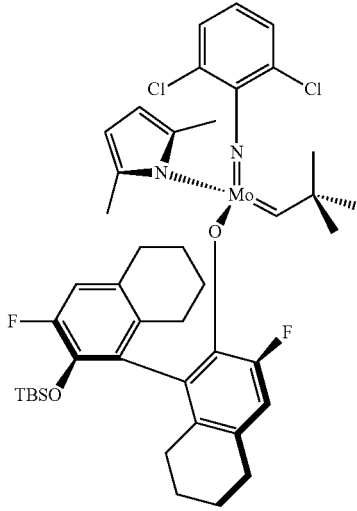

in situ
65% MAP, >98:<2 dr
35% bis-aryloxide
<2% bis-pyrolide
20 mol %, 1.0 mM, PhMe,
open vessel, 24 h;
22° C., benzene
90% conv, 69% Z
10% homo-coupled product

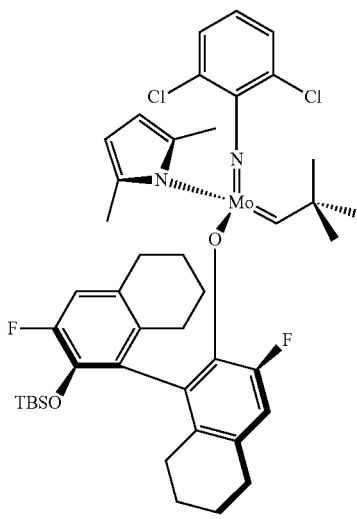

in situ
56% MAP, 8:1 dr
36% bis-aryloxide
<2% bis-pyrolide
20 mol %, 1.0 mM, PhMe,
open vessel, 24 h;
22° C., benzene:
89% conv, 57% Z
11% homo-coupled product TABLE 7-continued Selected catalyst screening results.

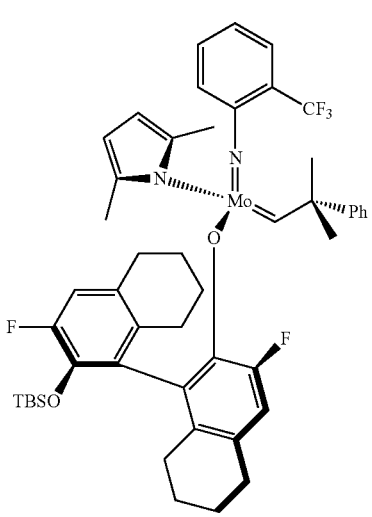

in situ
16% MAP, >98:<2 dr
46% bis-aryloxide
40% bis-pyrolide
20 mol %, 1.0 mM, PhMe,
open vessel, 24 h;
22° C., benzene:
86% conv, 73% Z
14% homo-coupled product

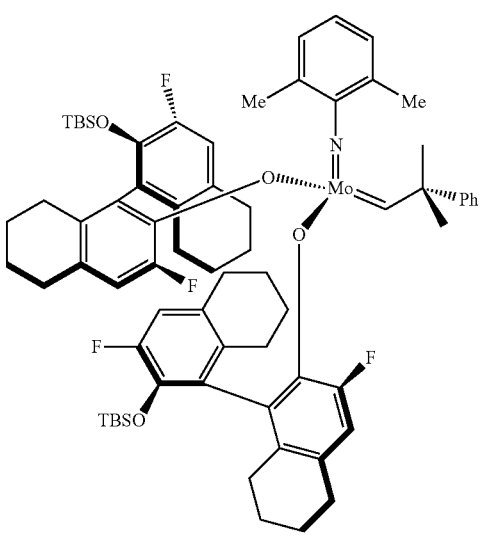

in situ
98% bis-aryloxide
2% of ?
48% conv, 46% Z
25% homo-coupled product

TABLE 7-continued

Selected catalyst screening results.

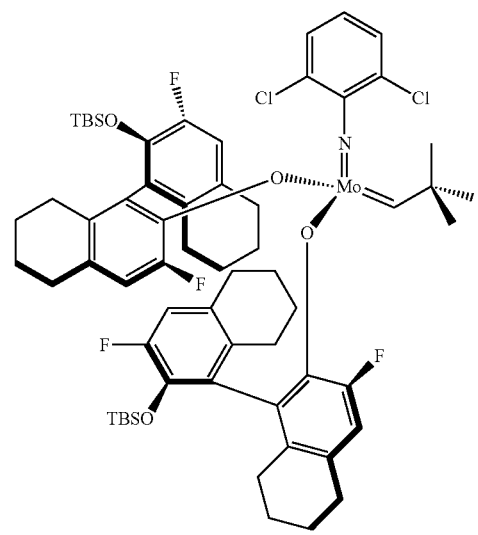

in situ
98% bis-aryloxide
2% bis-pyrrolide
92% conv, 70% Z,
8% homo-coupled product

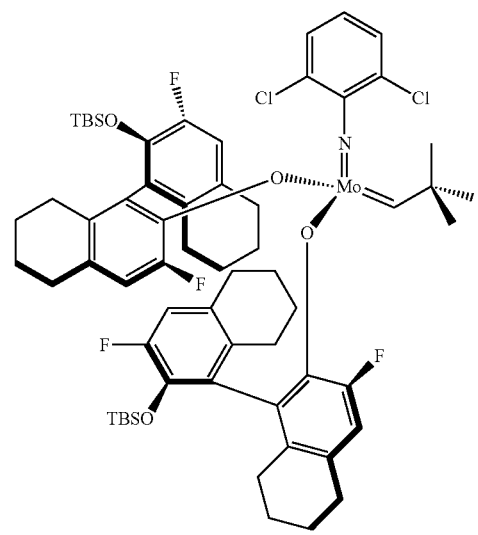

in situ
93% bis-aryloxide
7% MAP
89% conv, 70% Z
11% homo-coupled product

TABLE 7-continued

Selected catalyst screening results.

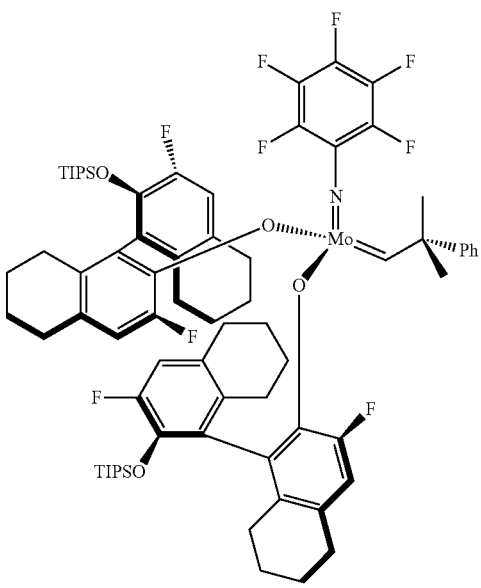

in situ
92% bis-aryloxide
5% bispyrrolide
3% MAP
75% conv, 79% Z,
21% homo-coupled product

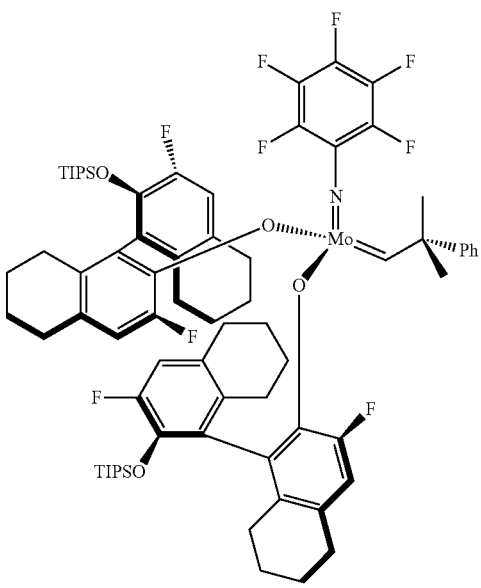

in situ
98% bis-aryloxide
2% bispyrrolide
80% conv, 84% Z,
12% homo-coupled product TABLE 7-continued Selected catalyst screening results.

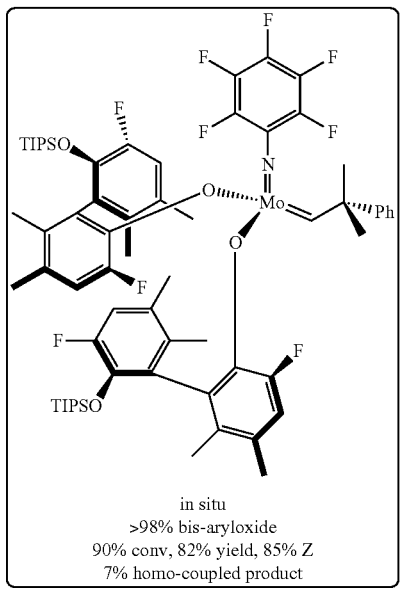

in situ
>98% bis-aryloxide
90% conv, 82% yield, 85% Z
7% homo-coupled product

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

What is claimed is:

1. A metal complex of formula II-c:

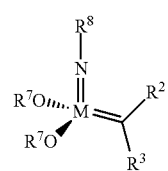

II-c wherein:
M is molybdenum or tungsten;
$R^8$ is $R^1$, or phenyl optionally substituted with one to five $R^9$;
each $R^9$ is independently halogen or $R^1$;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;
each $R^7$ is independently optionally substituted —Ar';
Ar' is of the following formula:

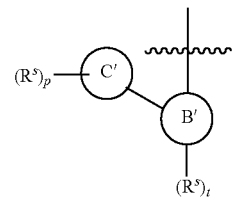

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and
each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR';
each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:
  two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;
wherein at least one $R^s$ is —F, and the metal complex is other than

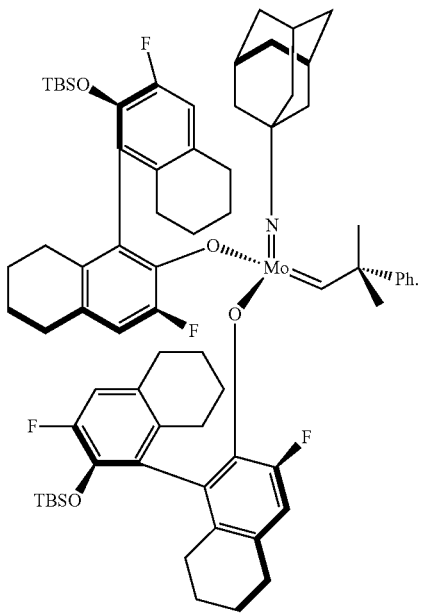

2. The metal complex of claim 1, wherein:
$R^8$ is substituted phenyl, wherein one or more substituents are —F.
3. A metal complex of formula II-c:

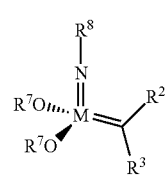

wherein:
M is molybdenum or tungsten;
$R^8$ is phenyl substituted with one to five $R^9$, wherein at least one $R^9$ is —F;
each $R^9$ is independently halogen or $R^1$;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;
each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms to which they are attached to form a bidentate ligand;
Ar' is of the following formula:

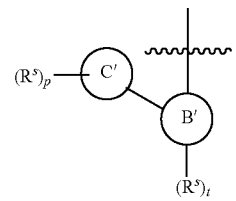

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —N(R')$_2$, —NR'C(O)R', —NR'C(O)OR', —NR'C(O)N(R')$_2$, —NR'SO$_2$R', —NR'SO$_2$N(R')$_2$, or —NR'OR';

each R' is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

4. The metal complex of claim 1, wherein $R^8$ is phenyl substituted with one to five $R^9$, wherein at least one $R^9$ is halogen or —CF$_3$.

5. The metal complex of claim 3, wherein $R^8$ is

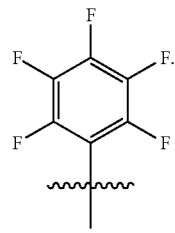

6. The metal complex of claim 3, wherein each $R^7$ is independently Ar', wherein at least one $R^s$ is —F.

7. The metal complex of claim 3, wherein at least one —OR$^7$ is an asymmetric ligand.

8. The metal complex of claim 3, wherein at least one —OR$^7$ is an optionally substituted group selected from

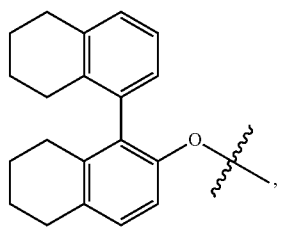

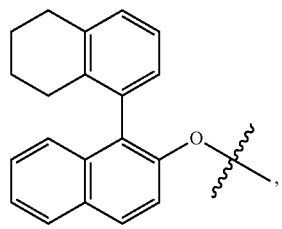

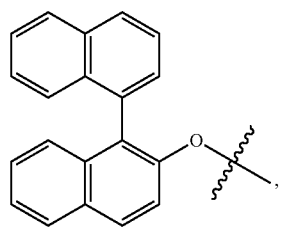

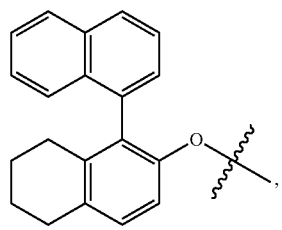

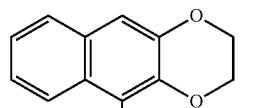

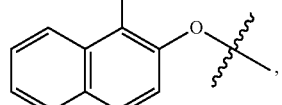

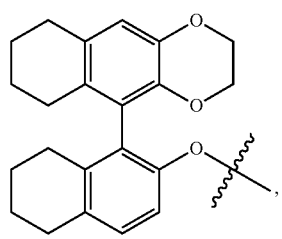

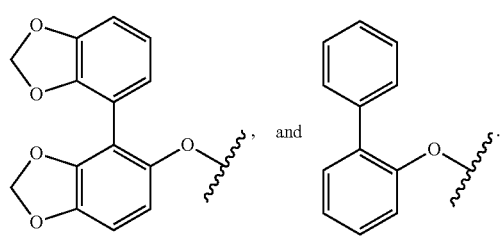 [SMILES: *Oc1ccc2c(c1-c1cccc3c1OCO3)OCO2 ; *Oc1ccccc1-c1ccccc1]

9. The metal complex of claim 3, wherein at least one —OR$^7$ is independently an optionally substituted group selected from:

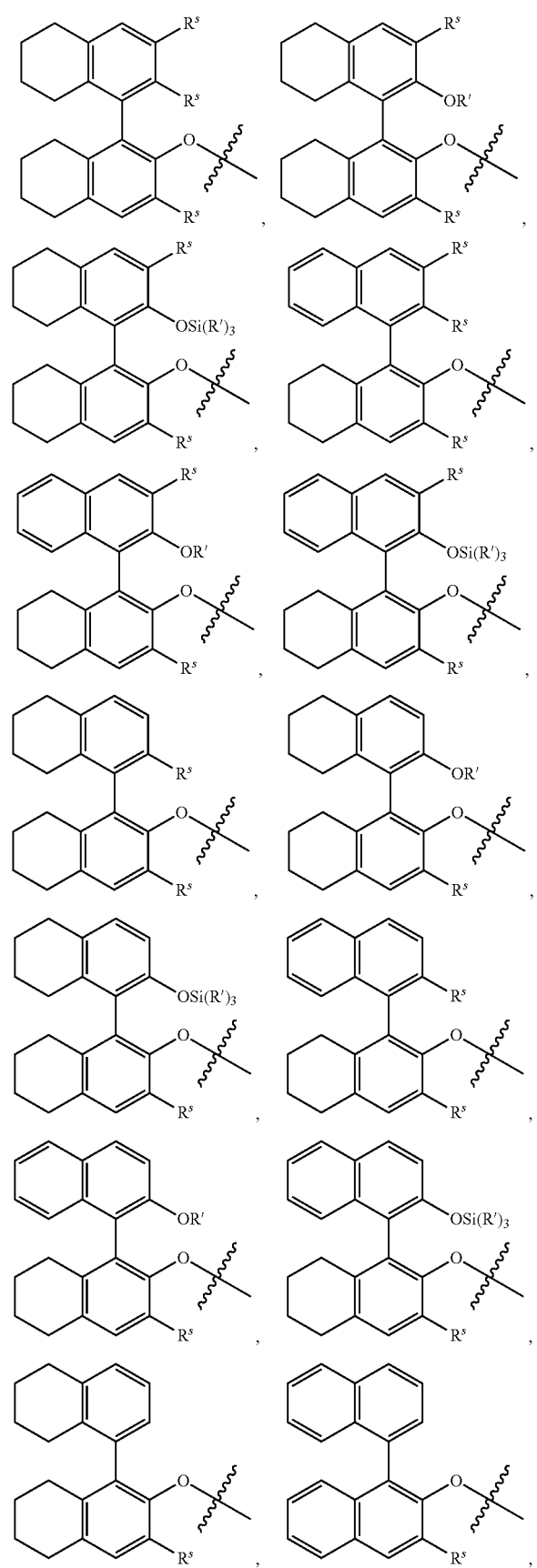
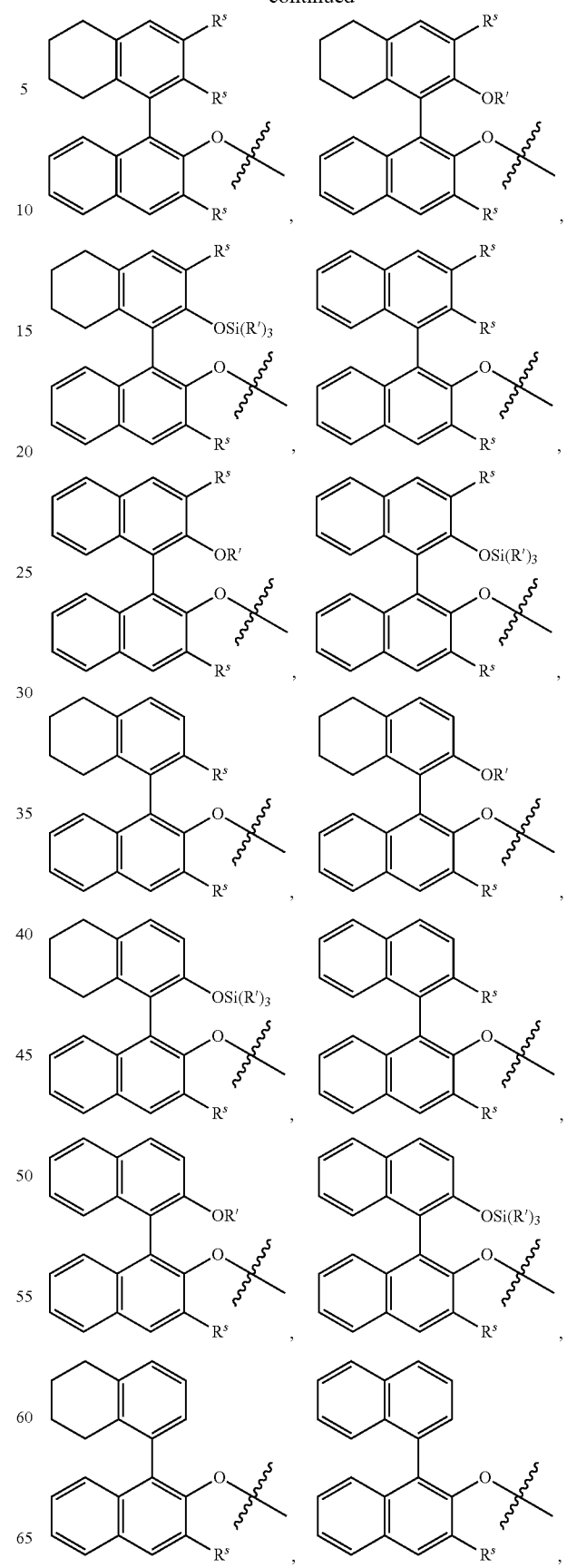

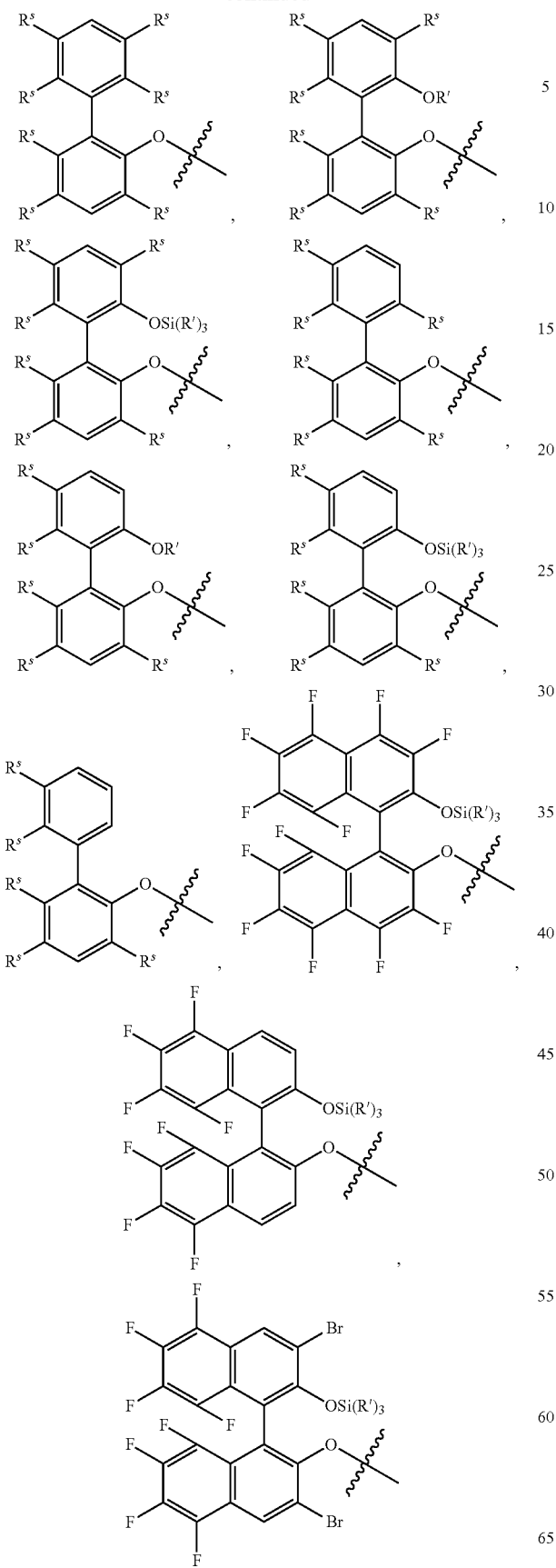
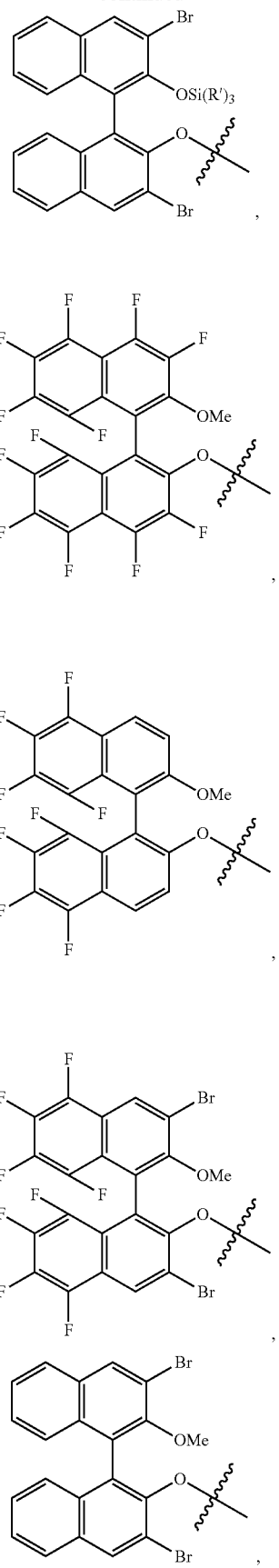

-continued
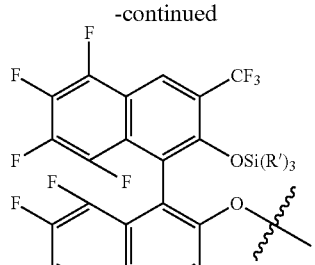
,
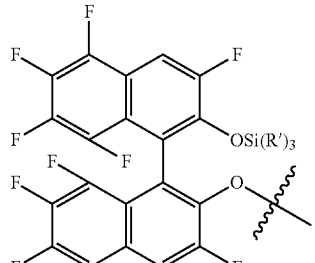
,
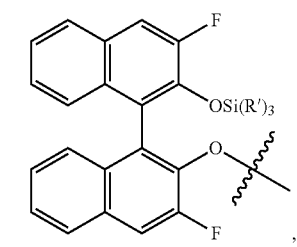
,
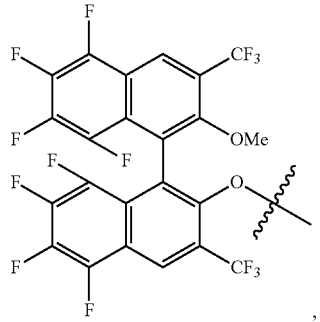
,
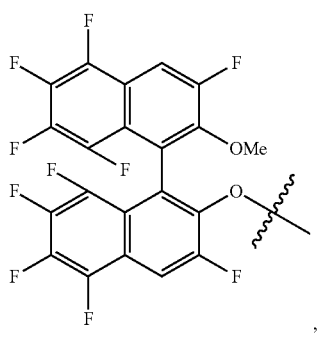
,
-continued
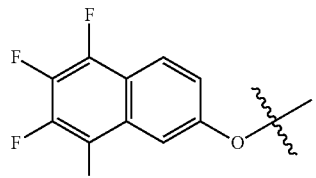
and
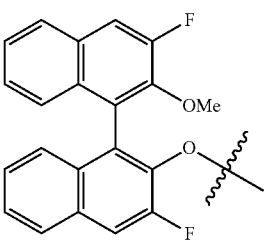
;
wherein one or more $R^s$ are —F.
10. The metal complex of claim 1, wherein each —$OR^7$ is independently an optionally substituted group selected from
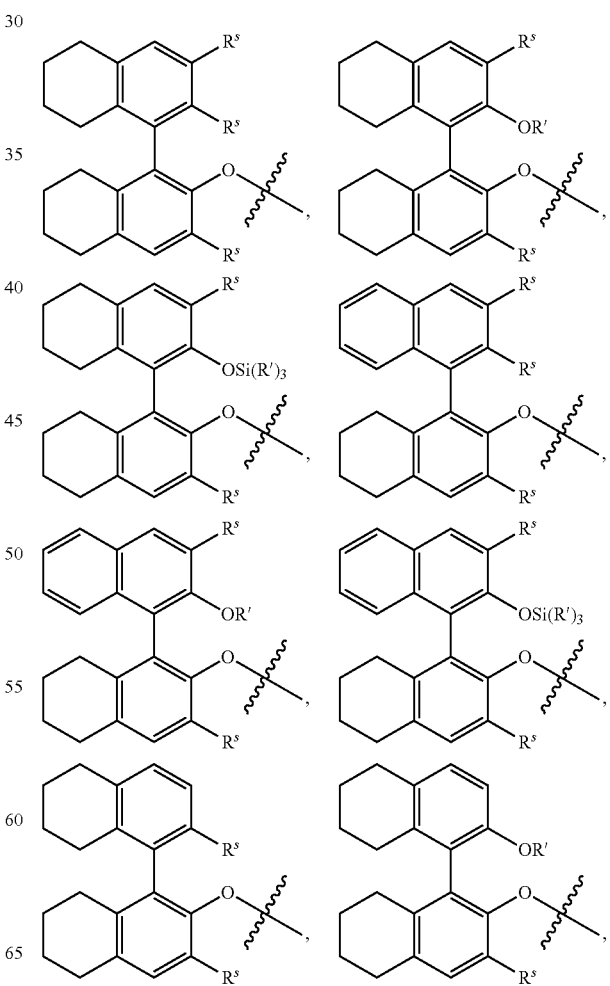

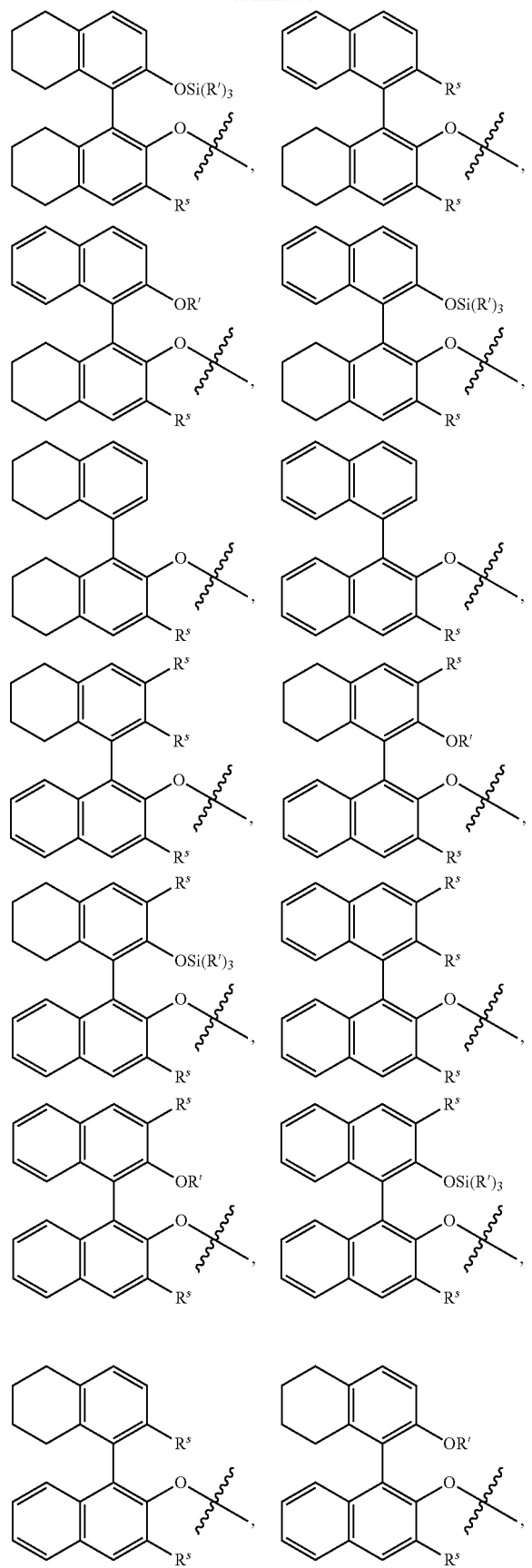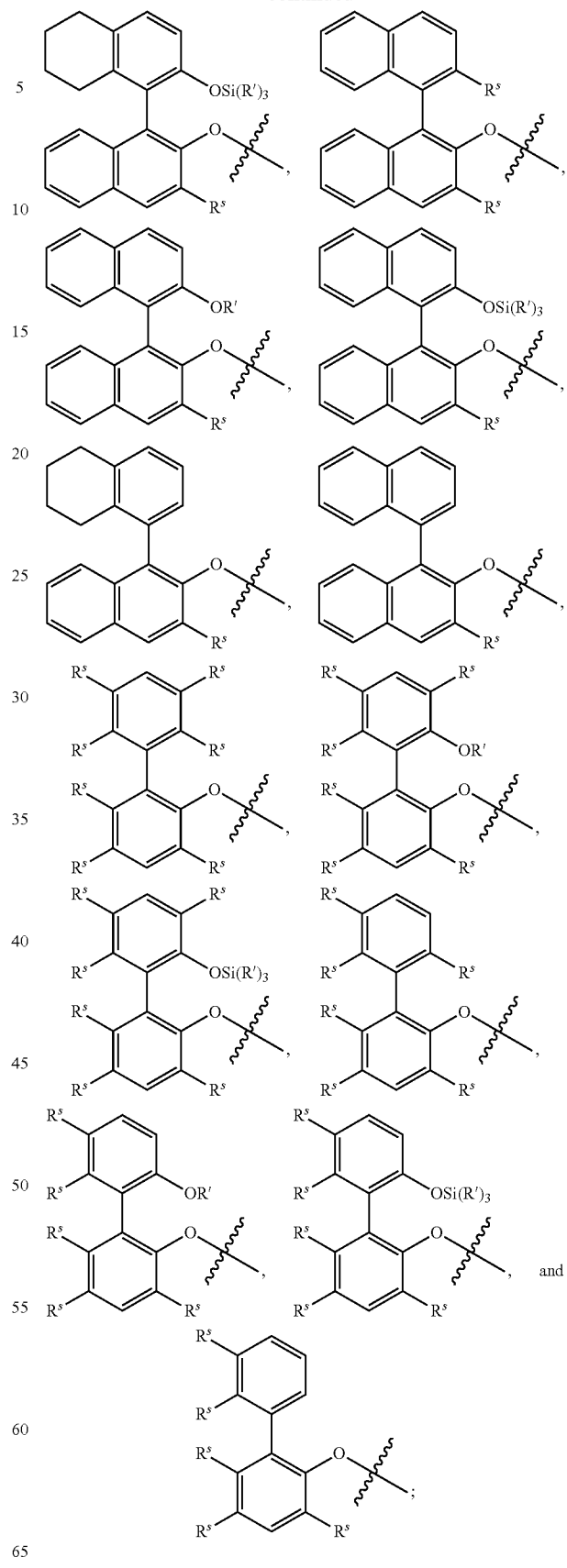
wherein one or more $R^s$ are —F.

11. The metal complex of claim 1, wherein:
M is molybdenum;
$R^8$ is substituted phenyl, wherein one or more substituents are —F.
12. The metal complex of claim 1, wherein the metal complex is selected from:
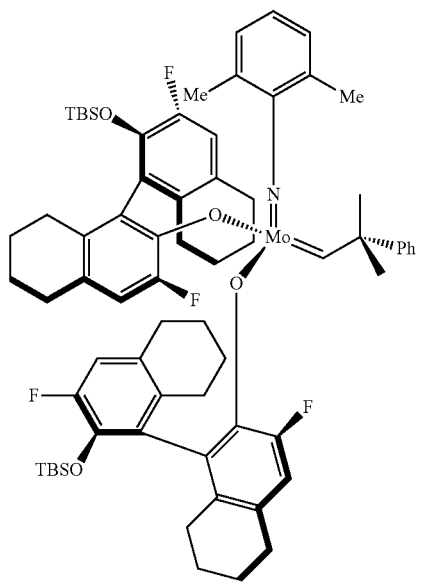
,
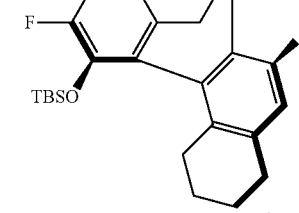
,
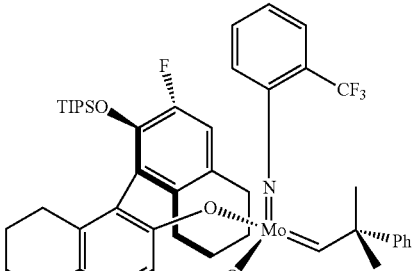
,
-continued
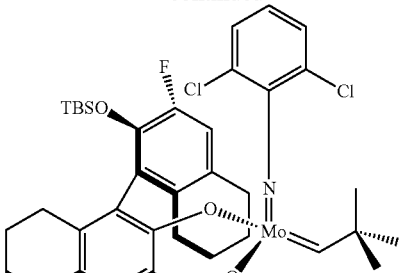
,
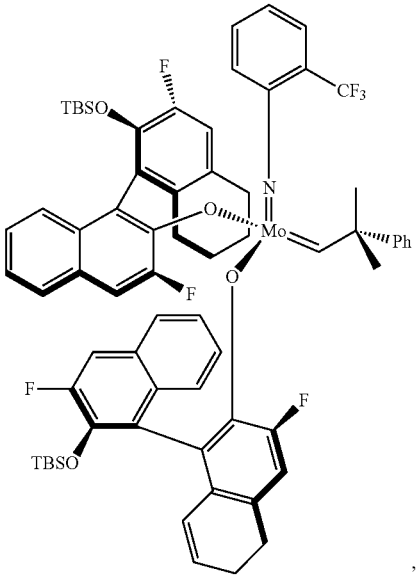
,
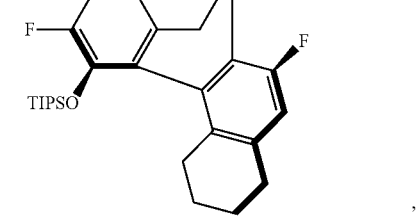
, 241
-continued
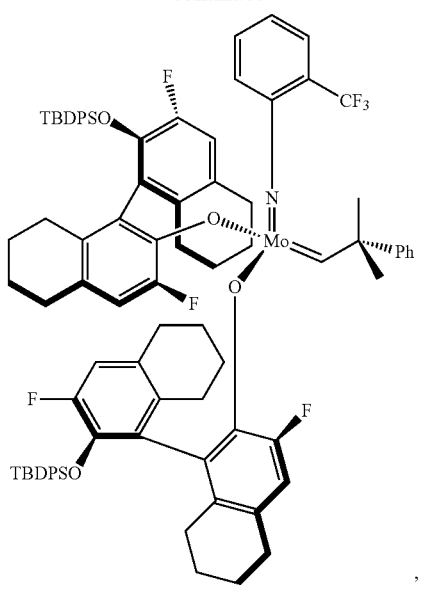
,
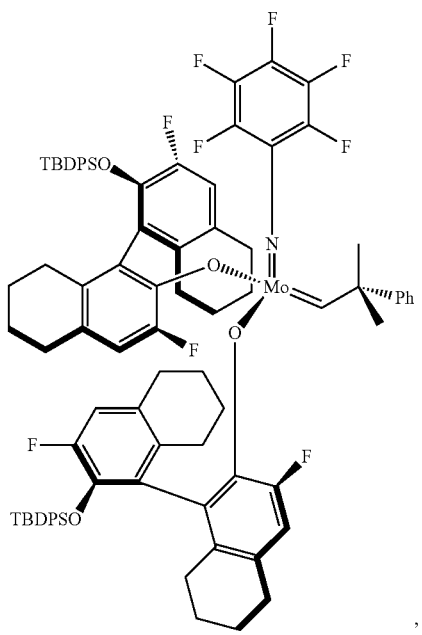
,
242
-continued
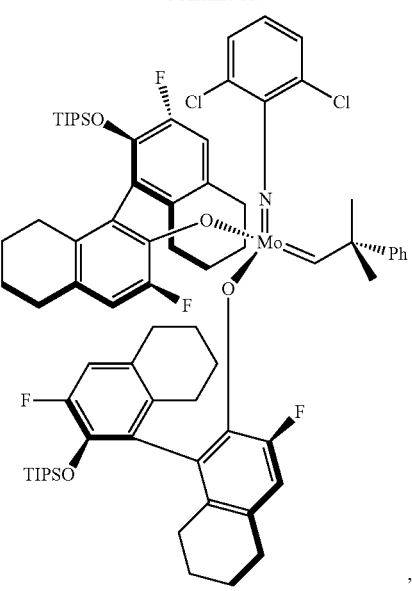
,
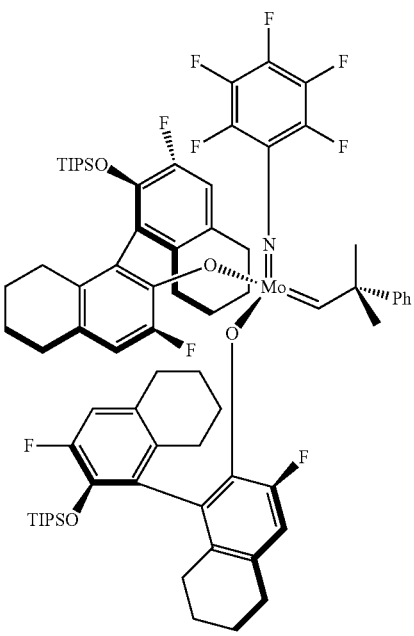
, and

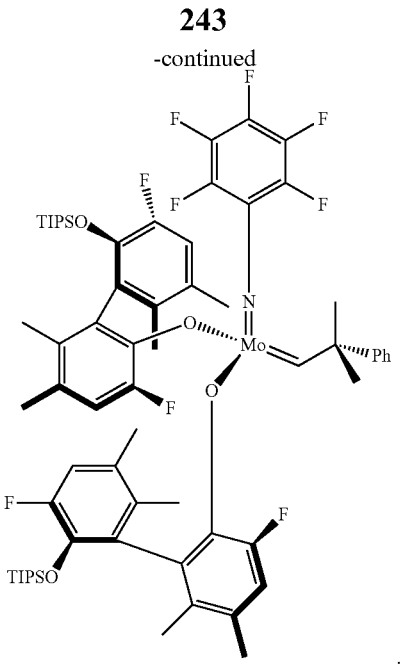

13. A composition comprising a metal complex of claim 1, wherein 35 mol % or more of the M-containing compounds in the composition are a metal complex of claim 1.

14. The composition of claim 13, wherein the metal complex of claim 1 is a complex of claim 2.

15. The composition of claim 13, wherein the metal complex of claim 1 is a complex of claim 4.

16. The metal complex of claim 11, wherein $R^8$ is

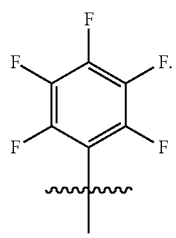

17. The composition of claim 13, wherein the metal complex of claim 1 is a complex of claim 11.

18. The metal complex of claim 6, wherein M is molybdenum.

19. The composition of claim 13, wherein the metal complex of claim 1 is a complex of claim 16.

20. The metal complex of claim 16, wherein each $-OR^7$ is independently selected from:

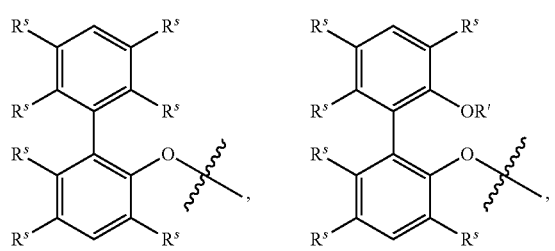

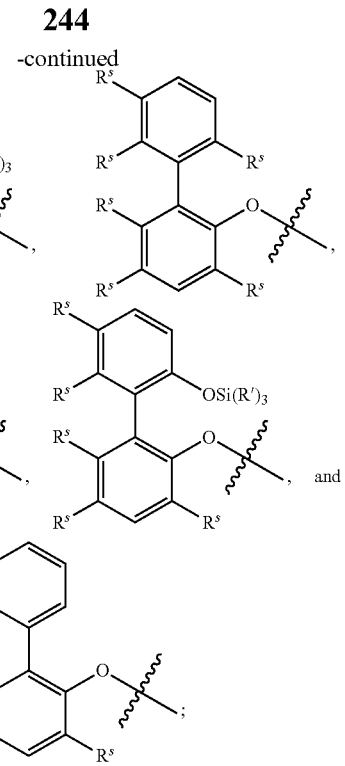

wherein one or more $R^s$ are —F.

21. A composition comprising a metal complex of formula II-c:

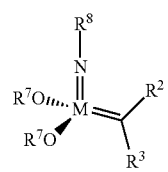

II-c wherein:

M is molybdenum or tungsten;

$R^8$ is $R^1$, or phenyl optionally substituted with one to five $R^9$;

each $R^9$ is independently halogen or $R^1$;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')

$_2$, —C(O)N(R')$_2$, —NR'C(O)R', or —NR'SO$_2$R', provided that R$^2$ and R$^3$ are not simultaneously hydrogen;

each R$^7$ is independently optionally substituted —Ar';

Ar' is of the following formula:

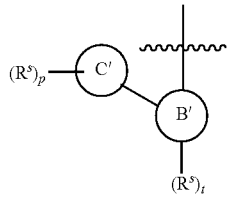

wherein:

t is 0-4;

p is 0-6;

each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each R$^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR';

each R' is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;

wherein the molar ratio of ligand —OR$^7$ to M is about 10:1, 9:1, 8:1, 7:1, 6:1, 5:1, 4:1, 3:1 or 2:1 within the composition.

22. The composition of claim 21, wherein the molar ratio of ligand —OR$^7$ to M is about 2:1 within the composition.

23. The composition of claim 21, wherein R$^8$ is phenyl substituted with one to five R$^9$, wherein at least one R$^9$ is halogen or —CF$_3$.

24. The composition of claim 21, wherein R$^8$ is substituted phenyl, wherein one or more substituents are —F.

25. The composition of claim 21, wherein at least one R$^s$ is —F.

26. The composition of claim 25, wherein:

M is molybdenum;

R$^8$ is substituted phenyl, wherein one or more substituents are —F; and at least one R$^s$ is —F.

27. The composition of claim 25, wherein each —OR$^7$ is independently an optionally substituted group selected from

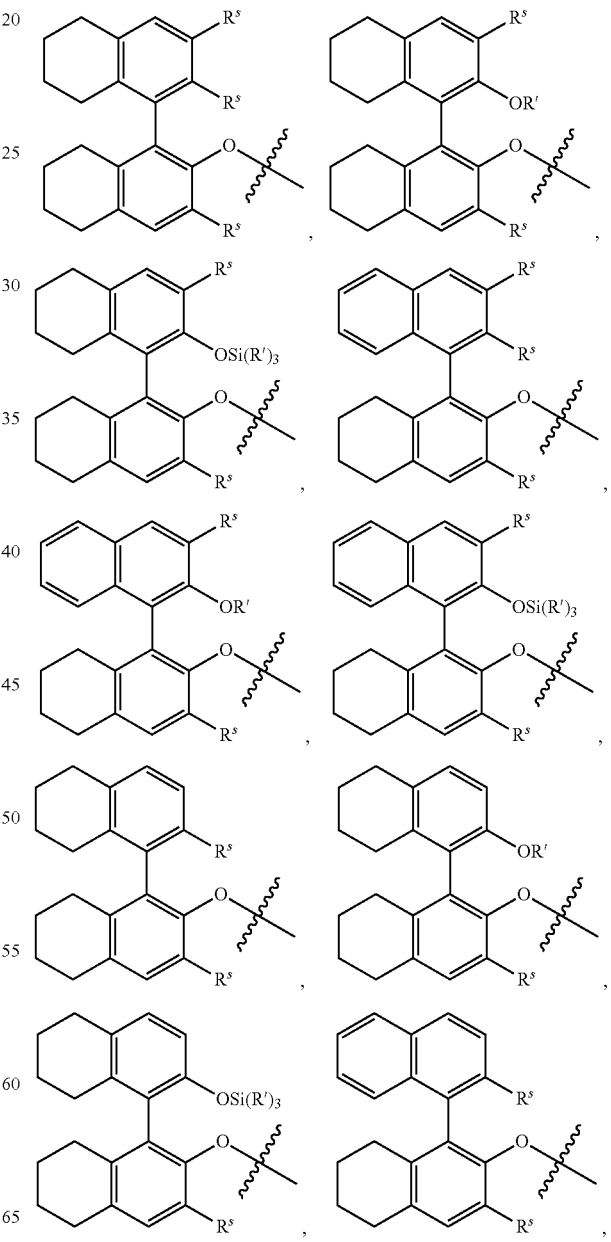

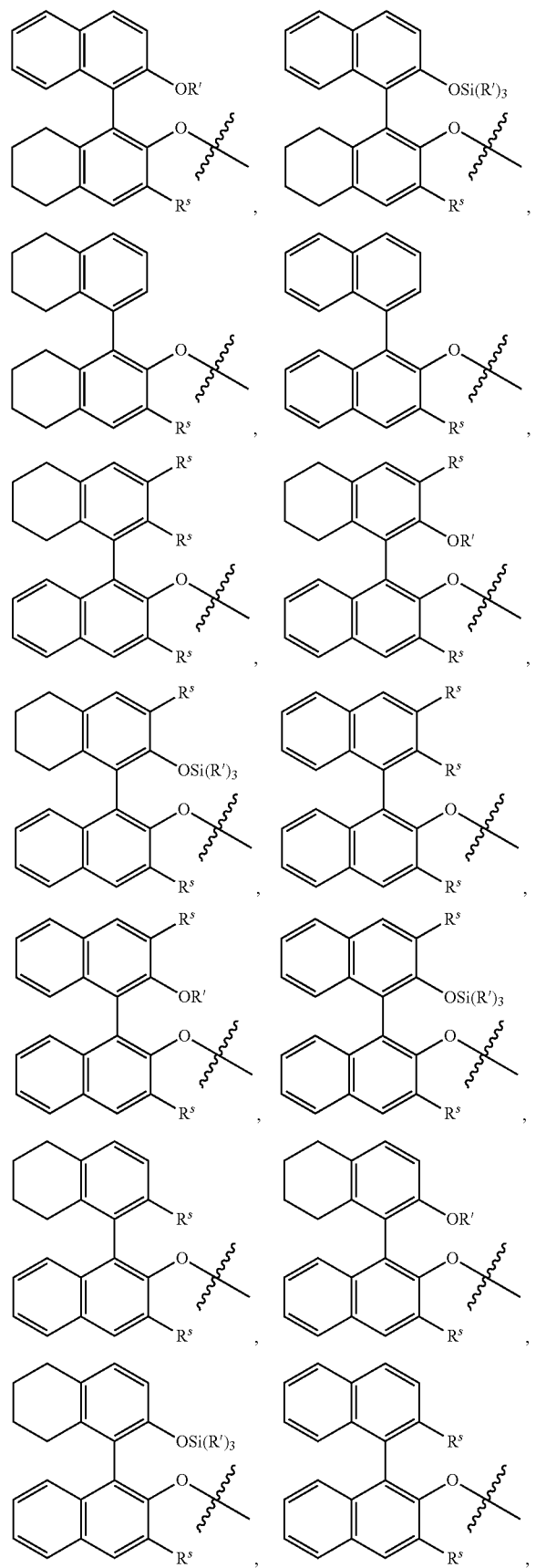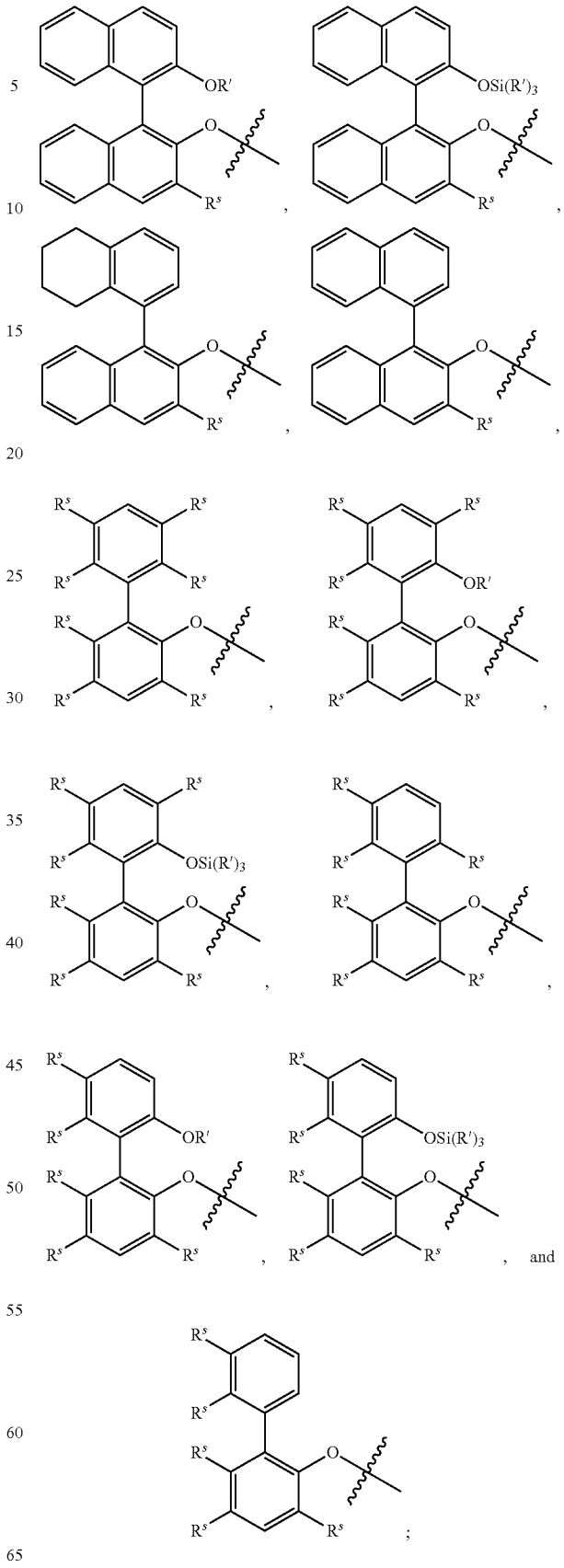
wherein one or more $R^s$ are —F.

28. The composition of claim 26, wherein $R^8$ is
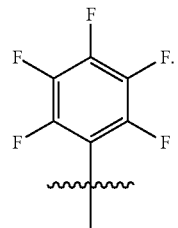
* * * * *